(12) United States Patent
Ogawa et al.

(10) Patent No.: US 7,067,179 B1
(45) Date of Patent: Jun. 27, 2006

(54) FUSED RING COMPOUND

(75) Inventors: Shinji Ogawa, Saitama (JP); Tatsuo Kawara, Tokyo (JP); Sadao Takehara, Sakura (JP); Hiroyuki Ohnishi, Saitama (JP); Kiyofumi Takeuchi, Tokyo (JP); Haruyoshi Takatsu, Tokyo (JP); Gerwald Grahe, Berlin (DE); Rainer Bruno Frings, Berlin (DE); Christine Fugger, Berlin (JP); Cornelia Pithart, Berlin (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 0 days.

(21) Appl. No.: 10/030,185

(22) PCT Filed: Sep. 10, 1999

(86) PCT No.: PCT/JP99/04917

§ 371 (c)(1),
(2), (4) Date: Feb. 1, 2002

(87) PCT Pub. No.: WO01/10803

PCT Pub. Date: Feb. 15, 2001

(30) Foreign Application Priority Data

Aug. 3, 1999 (JP) ................................. 11/219855

(51) Int. Cl.
| | |
|---|---|
| *C09K 19/32* | (2006.01) |
| *C09K 19/30* | (2006.01) |
| *C07C 13/60* | (2006.01) |
| *C07C 25/22* | (2006.01) |
| *C07C 23/44* | (2006.01) |

(52) U.S. Cl. ............ 428/1.1; 252/299.61; 252/299.62; 252/299.63; 570/183; 570/187

(58) Field of Classification Search ........... 252/299.62, 252/299.63, 299.61; 428/1.1; 570/183, 570/187

See application file for complete search history.

(56) References Cited

U.S. PATENT DOCUMENTS

| | | | |
|---|---|---|---|
| 4,434,073 A | 2/1984 | Sucrow et al. | |
| 4,976,887 A | 12/1990 | Takatoh et al. | |
| 6,793,984 B1 * | 9/2004 | Bremer et al. | ............... 428/1.1 |
| 6,929,834 B1 * | 8/2005 | Klasen-Memmer et al. | . 428/1.1 |
| 2004/0006235 A1 * | 1/2004 | Pauluth et al. | .............. 546/285 |

FOREIGN PATENT DOCUMENTS

| | | |
|---|---|---|
| DE | 3148448 A1 | 7/1983 |
| EP | 0-325 035 | 7/1989 |
| GB | 2377706 | * 2/2003 |
| JP | 58-105925 | 6/1983 |
| JP | 2-694 | 1/1990 |
| JP | 5-125055 | 5/1993 |
| JP | 5-262744 | 10/1993 |
| JP | 10-236992 | 9/1998 |

OTHER PUBLICATIONS

CAPLUS 1969: 481008.*
CAPLUS 1999: 292013.*
G. Kossmehl et al.; Mol. Cryst. Liq. Cryst., vol. 269, pp. 39-53, 1995. See PCT search report.

* cited by examiner

*Primary Examiner*—Shean C Wu
(74) *Attorney, Agent, or Firm*—Armstrong, Kratz, Quintos, Hanson & Brooks, LLP

(57) ABSTRACT

A novel compound represented by the general formula (I), and a nematic liquid crystal composition incorporating the same.

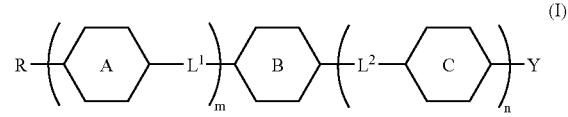

A compound represented by the general formula (I) can be produced industrially extremely easily, as shown in the examples, displays superior compatibility with current general purpose host liquid crystals as a nematic phase, and also shows little crystal precipitation at low temperatures. Moreover, by addition of a small amount of such a compound to a host liquid crystal, the liquid crystal temperature range at low temperatures can be effectively widened without any significant worsening of the various characteristics of the liquid crystal material. Consequently, a compound of the present invention is an extremely useful liquid crystal material which is suitable for various liquid crystal display elements which require a broad operating temperature range.

15 Claims, No Drawings

FUSED RING COMPOUND

TECHNICAL FIELD

The present invention relates to a novel fused ring compound useful as an electro-optical liquid crystal display material, and a liquid crystal composition, and a liquid crystal display using the same.

BACKGROUND ART

Since first appearing as calculator displays, liquid crystal display elements have kept pace with the development of computers, with the demand for increased display size, which was unable to be achieved by TN (Twisted Nematic) mode displays, being met by STN (Supertwisted Nematic) mode displays, and liquid crystal displays are now widely used as the interface between computers and people. Furthermore, active matrix liquid crystal display elements (AM-LCD) in which each pixel is provided with a thin film transistor are able to match the high image quality of CRT displays, and with the additional advantages offered in terms of flatness of the display and reduced energy consumption, they are considered as the displays of the future.

In recent years the demand for portable notebook type computers has increased, and so particularly for the STN-LCD and AM-LCD displays used for such applications, there has also been a demand for displays with characteristics capable of withstanding outdoor use. As a result, characteristics which have been actively sought include a superior contrast at high temperatures, the absence of crystal precipitation or smectic phase formation even at low temperatures, and no deterioration in contrast or display quality even on prolonged exposure to UV light or sunlight. However, conventional liquid crystal compounds and liquid crystal compositions have not always been able to satisfy such demands. The problem of crystal precipitation at low temperatures is particularly serious, and the only way in which to prevent such precipitation is to reduce the amount of liquid crystal compound added, but even materials with superior characteristics are often susceptible to this precipitation problem, and with the conventional, widely used unfused ring type liquid crystal compounds, this remains the most difficult problem to resolve. In other words, amongst unfused ring type liquid crystal compounds, no compound was able to simultaneously satisfy the requirements of a low crystal (or smectic) transition temperature, a high nematic-isotropic transition temperature, a high dielectric anisotropy, and a favorable elastic constant and birefringence.

DISCLOSURE OF INVENTION

The problem which the present invention attempts to resolve is to provide a compound which upon addition to a composition is able to effectively improve the temperature range of the liquid crystal phase, and in particular the stability at low temperatures, and to also provide a liquid crystal composition and a liquid crystal display element with a wide temperature range which utilize such a compound.

In order to resolve the aforementioned problem, the present invention provides a novel compound which is a fused ring compound represented by a general formula (I).

Invention 1: A fused ring compound represented by a general formula (I)

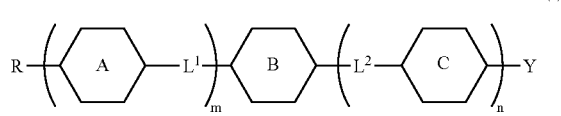

(I)

(wherein, R represents an alkyl group or alkoxyl group of 1 to 16 carbon atoms, an alkenyl group of 2 to 16 carbon atoms, an alkenyloxy group of 3 to 16 carbon atoms, or an alkyl group of 1 to 12 carbon atoms substituted with an alkoxyl group of 1 to 10 carbon atoms, and these groups may be substituted with a halogen, and in those cases in which an asymmetric carbon arises due to substitution or branching, may be either optically active or racemic mixtures; ring A and ring C each represent, independently, a trans-1,4-cyclohexylene group in which a single $CH_2$ structure within the group or 2 or more non-adjacent $CH_2$ structures within the group may be substituted with —O— and/or —S—, a 1,4-phenylene group in which a single CH structure within the group or 2 or more non-adjacent CH structures within the group may be substituted with —N=, a 1,4-cyclohexenylene group, a 1,4-bicyclo(2.2.2)octylene group, a piperidine-1,4-diyl group, a naphthalene-2,6-diyl group, a trans-decahydronaphthalene-trans-2,6-diyl group, or a 1,2,3,4-tetrahydronaphthalene-2,6-diyl group, and these groups may be substituted with a cyano group or a halogen; ring B represents any one of the general formulas (I-1) to (I-9)

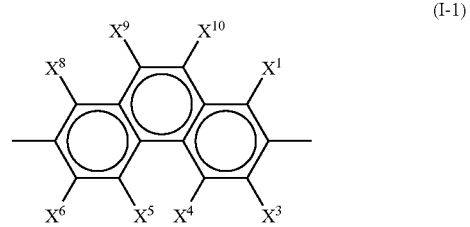

(I-1)

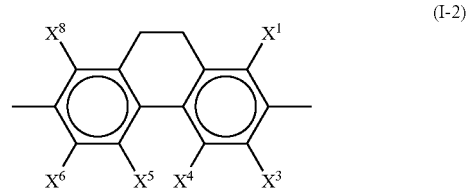

(I-2)

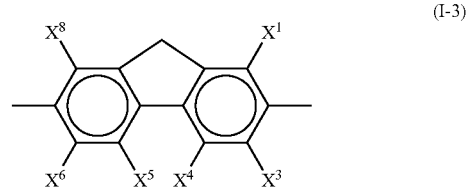

(I-3)

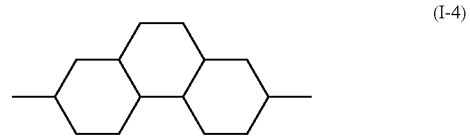

(I-4)

-continued

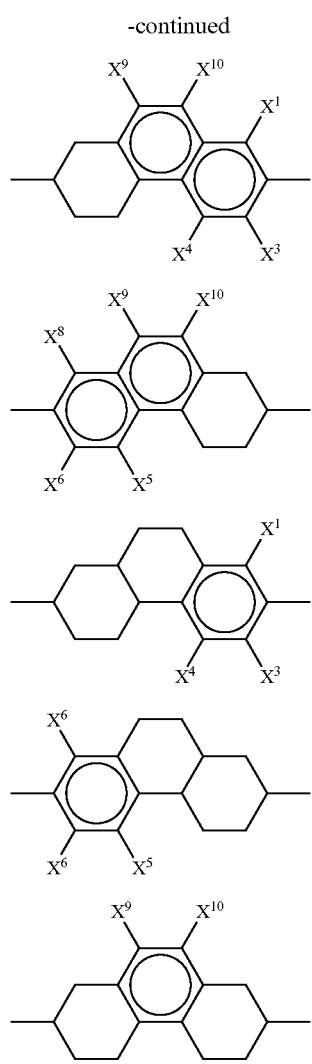

(wherein, $X^1$, $X^3$, $X^4$, $X^5$, $X^6$, $X^8$, $X^9$ and $X^{10}$ each represent, independently, a hydrogen atom, a chlorine atom or a fluorine atom, provided that the following conditions are satisfied:

1. In (I-1) and (I-2), in the case in which at least one of $X^3$, $X^4$, $X^5$ and $X^6$ represents a fluorine atom, and the remainder represent hydrogen atoms, then at least one of $X^1$, $X^8$, $X^9$ and $X^{10}$ represents a chlorine atom or a fluorine atom,
2. In (I-1) and (I-2), in the case in which at least one of $X^1$, $X^8$, $X^9$ and $X^{10}$ represents a fluorine atom, and the remainder represent hydrogen atoms, then at least one of $X^3$, $X^4$, $X^5$ and $X^6$ represents a chlorine atom or a fluorine atom,
3. In (I-3) to (I-9), hydrogen atoms within a ring may be replaced with a cyano group or a halogen); $L^1$ and $L^2$ each represent, independently, —$CH_2CH_2$—, —C≡C—, —$(CH_2)_4$—, —CF=CF—, —$OCH_2$—, —$CH_2O$—, —$OCF_2$—, —$CF_2O$—, —$CO_2$—, —OCO—, —CH=N—N=CH—, —CH=CH—$CH_2$—$CH_2$—, —$CH_2$—$CH_2$—CH=CH— or a single bond; m and n each represent, independently, 0, 1 or 2, although m+n≦2, and in the case in which either m or n is 2, then at least one of $L^1$ or $L^2$, where present, represents a single bond; Y represents a hydrogen atom, a fluorine atom, a chlorine atom, a trifluoromethoxy group, a difluoromethoxy group, a trifluoromethyl group, a 3,3,3-trifluoroethoxy group, a cyano group, a straight chain alkyl group of 1 to 16 carbon atoms, a straight chain alkenyl group of 2 to 16 carbon atoms, a straight chain alkyloxy group of 1 to 12 carbon atoms, or a straight chain alkenyloxy group of 2 to 16 carbon atoms, provided that the following cases are excluded:

1. the case in which ring B represents (I-2), m and n represent 0, R represents an alkyl group and Y represents an alkyl group,
2. the case in which ring B represents (I-3), m and n represent 0, R represents an alkyl group and Y represents an alkoxy group,
3. the case in which ring B represents (I-4), m and n represent 0, R represents an alkyl group and Y represents an alkyl group or a cyano group
4. the case in which ring B represents (I-8), m and n represent 0, R represents an alkyl group and Y represents an alkyl group,
5. the case in which ring B represents (I-4), m represents 0 and n represents 1, ring C represents a 1,4-phenylene group, $L^2$ represents —$CO_2$—, R represents an alkyl group and Y represents an alkyl group, an alkoxy group or a cyano group,
6. the case in which ring B represents (I-4), m represents 0 and n represents 1, ring C represents a 1,4-phenylene group, $L^2$ represents —OCO—, R represents an alkyl group and Y represents an alkoxy group,
7. the case in which ring B represents (I-2), m represents 0 and n represents 1, ring C represents a 1,4-cyclohexylene group, $L^2$ represents —$CO_2$—, R represents an alkyl group and Y represents an alkyl group,
8. the case in which ring B represents (I-1), and $X^9$ and $X^{10}$ represent fluorine atoms, and
9. the case in which ring B represents (I-3), and $X^3$, $X^4$, $X^5$ and $X^6$ simultaneously represent fluorine atoms; and applying similarly to compounds equivalent to those above described using combinations of abbreviations).

Invention 2: A compound according to invention 1, wherein ring A and ring C each represent, independently, a 1,4-phenylene group or a trans-1,4-cyclohexylene group which may be substituted with a fluorine atom.

Invention 3: A compound according to invention 1, wherein $L^1$ and $L^2$ each represent, independently, —OCO—, —$CO_2$—, —$CH_2CH_2$— or a single bond.

Invention 4: A compound according to invention 1, wherein m represents 0, and n represents either 0 or 1.

Invention 5: A compound according to invention 1, wherein $L^1$ and $L^2$ each represent a single bond.

Invention 6: A compound according to invention 1, wherein ring B represents (I-3) or (I-4) which may be substituted with a halogen.

Invention 7: A compound according to invention 1, wherein ring B represents (I-1) or (I-2).

Invention 8: A compound according to invention 1, wherein ring B represents (I-1), and $X^9$ and $X^{10}$ represent hydrogen atoms.

Invention 9: A compound according to invention 1, wherein ring A and ring C each represent, independently, a 1,4-phenylene group or a trans-1,4-cyclohexylene group which may be substituted with a fluorine atom, and ring B represents (I-1), (I-2), (I-3) or (I-4) which may be substituted with a halogen.

Invention 10: A compound according to invention 1, wherein ring A and ring C each represent, independently, a 1,4-phenylene group or a trans-1,4-cyclohexylene group which may be substituted with a fluorine atom, ring B represents (I-1), (I-2), (I-3) or (I-4) which may be substituted with a halogen, and $L^1$ and $L^2$ each represent a single bond.

Invention 11: A compound according to invention 1, wherein ring A and ring C each represent, independently, a 1,4-phenylene group or a trans-1,4-cyclohexylene group which may be substituted with a fluorine atom, ring B represents (I-1), (I-2), (I-3) or (I-4) which may be substituted with a halogen, m represents 0 and n represents 1, and $L^2$ represents a single bond.

Invention 12: A compound according to invention 1, wherein ring A and ring C each represent, independently, a 1,4-phenylene group or a trans-1,4-cyclohexylene group which may be substituted with a fluorine atom, ring B represents (I-1), (I-2), (I-3) or (I-4) which may be substituted with a halogen, m represents 0 and n represents 1, and $L^2$ represents a single bond, and in the case in which ring B represents (I-1)which may be substituted with a halogen, then $X^9$ and $X^{10}$ represent hydrogen atoms.

Invention 13: A compound according to any one of inventions 1 through 12, wherein R represents a straight chain alkyl group of 1 to 12 carbon atoms or a straight chain alkenyl group of 2 to 12 carbon atoms, and Y represents a fluorine atom, a chlorine atom, a trifluoromethoxy group, a trifluoromethyl group, a difluoromethoxy group, a 3,3,3-trifluoroethoxy group or a cyano group.

Invention 14: A liquid crystal composition incorporating at least one compound according to any one of inventions 1 through 13.

Invention 15: A liquid crystal display element utilizing a liquid crystal composition according to invention 14.

Invention 16: An active matrix driven liquid crystal display element utilizing a liquid crystal composition according to invention 14.

Invention 17: A supertwisted nematic liquid crystal display element utilizing a liquid crystal composition according to invention 14.

BEST MODE FOR CARRYING OUT THE INVENTION

The following provides a detailed description of the present invention. A compound of the general formula (I) provided in the present invention is preferably of the form described below.

In general formula (I), R represents an alkyl group or alkoxyl group of 1 to 16 carbon atoms, an alkenyl group of 2 to 16 carbon atoms, an alkenyloxy group of 3 to 16 carbon atoms, or an alkyl group of 1 to 12 carbon atoms substituted with an alkoxyl group of 1 to 10 carbon atoms, and specific examples in the case of an alkyl group include straight chain saturated alkyl groups such as a methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group and an eicosyl group; and branched saturated alkyl groups such as a 1-methylethyl group, 1-methylpropyl group, 2-methylpropyl group, 1,2-dimethylpropyl group, 1-methylbutyl group, 2-methylbutyl group, 3-methylbutyl group, 1,2-dimethylbutyl group, 1,3-dimethylbutyl group, 2,3-dimethylbutyl group, 1-methylpentyl group, 2-methylpentyl group, 3-methylpentyl group, 4-methylpentyl group, 1,2-dimethylpentyl group, 1,3-dimethylpentyl group, 1-methylhexyl group, 2-methylhexyl group, 3-methylhexyl group, 4-methylhexyl group, 5-methylhexyl group, 1,2-dimethylhexyl group, 1,3-dimethylhexyl group, 1-methylheptyl group, 2-methylheptyl group, 3-methylheptyl group, 4-methylheptyl group, 5-methylheptyl group, 6-methylheptyl group, 1,2-dimethylheptyl group, 1,3-dimethylheptyl group, 1-methyloctyl group, 2-methyloctyl group, 3-methyloctyl group, 4-methyloctyl group, 5-methyloctyl group, 6-methyloctyl group, 7-methyloctyl group, 1,2-dimethyloctyl group, 1,3-dimethyloctyl group, 1-methylnonyl group, 2-methylnonyl group, 3-methylnonyl group, 4-methylnonyl group, 5-methylnonyl group, 6-methylnonyl group, 7-methylnonyl group, 8-methylnonyl group, 1,2-dimethylnonyl group, 1,3-dimethylnonyl group, 1-methyldecyl group, 2-methyldecyl group, 3-methyldecyl group, 1,2-dimethyldecyl group, 1,3-dimethyldecyl group, 1-methylundecyl group, 2-methylundecyl group, 3-methylundecyl group, 1,2-dimethylundecyl group, 1,3-dimethylundecyl group, 1-methyldodecyl group, 2-methyldodecyl group, 3-methyldodecyl group, 1,2-dimethyldodecyl group, 1,3-dimethyldodecyl group, 1-methyltridecyl group, 2-methyltridecyl group, 3-methyltridecyl group, 1,2-dimethyltridecyl group and a 1,3-dimethyltridecyl group. Specific examples in the case of an alkoxyl group include straight chain saturated alkoxyl groups such as a methoxy group, ethoxy group, propyloxy group, butyloxy group, pentyloxy group, hexyloxy group, heptyloxy group, octyloxy group, nonyloxy group, decyloxy group, undecyloxy group, dodecyloxy group, tridecyloxy group, tetradecyloxy group, pentadecyloxy group, hexadecyloxy group, heptadecyloxy group, octadecyloxy group, nonadecyloxy group and an eicosyloxy group; and branched saturated alkoxyl groups such as an isopropyloxy group, isobutyloxy group, 1-methylpropyloxy group, 1,2-dimethylpropyloxy group, 1-methylbutyloxy group, 2-methylbutyloxy group, 3-methylbutyloxy group, 1,2-dimethylbutyloxy group, 1,3-dimethylbutyloxy group, 2,3-dimethylbutyloxy group, 1-methylpentyloxy group, 2-methylpentyloxy group, 3-methylpentyloxy group, 4-methylpentyloxy group, 1,2-dimethylpentyloxy group, 1,3-dimethylpentyloxy group, 1-methylhexyloxy group, 2-methylhexyloxy group, 3-methylhexyloxy group, 4-methylhexyloxy group, 5-methylhexyloxy group, 1,2-dimethylhexyloxy group, 1,3-dimethylhexyloxy group, 1-methylheptyloxy group, 2-methylheptyloxy group, 3-methylheptyloxy group, 4-methylheptyloxy group, 5-methylheptyloxy group, 6-methylheptyloxy group, 1,2-dimethylheptyloxy group, 1,3-dimethylheptyloxy group, 1-methyloctyloxy group, 2-methyloctyloxy group, 3-methyloctyloxy group, 4-methyloctyloxy group, 5-methyloctyloxy group, 6-methyloctyloxy group, 7-methyloctyloxy group, 1,2-dimethyloctyloxy group, 1,3-dimethyloctyloxy group, 1-methylnonyloxy group, 2-methylnonyloxy group, 3-methylnonyloxy group, 4-methylnonyloxy group, 5-methylnonyloxy group, 6-methylnonyloxy group, 7-methylnonyloxy group, 8-methylnonyloxy group, 1,2-dimethylnonyloxy group, 1,3-dimethylnonyloxy group, 1-methyldecyloxy group, 2-methyldecyloxy group, 3-methyldecyloxy group, 1,2-dimethyldecyloxy group, 1,3-dimethyldecyloxy group, 1-methylundecyloxy group, 2-methylundecyloxy group, 3-methylundecyloxy group, 1,2-dimethylundecyloxy group, 1,3-dimethylundecyloxy group, 1-methyldodecyloxy group, 2-methyldodecyloxy group, 3-methyldodecyloxy group, 1,2-dimethyldodecyloxy group, 1,3-dimethyldodecyloxy group, 1-methyltridecyloxy group, 2-methyltridecyloxy group, 3-methyltridecyloxy group, 1,2-dimethyltridecyloxy group, and a 1,3-dimethyltridecyloxy group. Specific examples in the case of an alkenyl group include a vinyl group, trans-1-propenyl group, 2-propenyl group, trans-1-butenyl group, trans-2-butenyl group, 3-butenyl group, trans-1-pentenyl group, trans-2-pentenyl group, trans-3-pentenyl group, 4-pentenyl group, trans-1-hexenyl group, trans-2-hexenyl group, trans-3-hexenyl group, trans-4-hexenyl group, 5-hexenyl group, trans-1-heptenyl group, trans-2-heptenyl group, trans-3-heptenyl group, trans-4-heptenyl group, trans-5-heptenyl group, 6-heptenyl group, trans-1-octenyl group, trans-2-octenyl group, trans-3-octenyl group, trans-4-octenyl group, trans-5-octenyl group, trans-6-octenyl group, 7-octenyl group, trans-1-noneyl group, 8-noneyl group, trans-1-decenyl group, 9-decenyl group, trans-1-undecenyl group, 10-undecenyl group, trans-1-dodecenyl group, and a 11-dodecenyl group. Specific examples in the case of an alkenyloxy group include a vinyloxy group, trans-1-propenyloxy group, 2-propenyloxy group, trans-1-butenyloxy group, trans-2-butenyloxy group, 3-butenyloxy group, trans-1-pentenyloxy group, trans-2-pentenyloxy group, trans-3-pentenyloxy group, 4-pentenyloxy group, trans-1-hexenyloxy group, trans-2-hexenyloxy group, trans-3-hexenyloxy group, trans-4-hexenyloxy group, 5-hexenyloxy group, trans-1-heptenyloxy group, trans-2-heptenyloxy group, trans-3-heptenyloxy group, trans-4-heptenyloxy group, trans-5-heptenyloxy group, 6-heptenyloxy group, trans-1-octenyloxy group, trans-2-octenyloxy group, trans-3-octenyloxy group, trans-4-octenyloxy group, trans-5-octenyloxy group, trans-6-octenyloxy group, 7-octenyloxy group, trans-1-noneyloxy group, 8-noneyloxy group, trans-1-decenyloxy group, 9-decenyloxy group, trans-1-undecenyloxy group, 10-undecenyloxy group, trans-1-dodecenyloxy group, and a 11-dodecenyloxy group. Furthermore, these groups may contain a substituted group such as an alkoxyl group of 1 to 10 carbon atoms or a halogen atom or the like, and fluorine atoms are preferred as the halogen atom. Suitable examples include alkoxyl group substituted alkyl groups such as a methoxymethyl group, ethoxymethyl group, propoxymethyl group, butoxymethyl group, pentyloxymethyl group, hexyloxymethyl group, heptyloxymethyl group, 1-methoxyethyl group, 1-ethoxyethyl group, 1-propoxyethyl group, 1-butoxyethyl group, 1-pentyloxyethyl group, 1-hexyloxyethyl group, 1-heptyloxyethyl group, 2-methoxyethyl group, 2-ethoxyethyl group, 2-propoxyethyl group, 2-butoxyethyl group, 2-pentyloxyethyl group, 2-hexyloxyethyl group, 2-heptyloxyethyl group, 1-methoxypropyl group, 1-ethoxypropyl group, 1-propoxypropyl group, 1-butoxypropyl group, 1-pentyloxypropyl group, 1-hexyloxypropyl group, 1-heptyloxypropyl group, 2-methoxypropyl group, 2-ethoxypropyl group, 2-propoxypropyl group, 2-butoxypropyl group, 2-pentyloxypropyl group, 2-hexyloxypropyl group, 2-heptyloxypropyl group, 3-methoxypropyl group, 3-ethoxypropyl group, 3-propoxypropyl group, 3-butoxypropyl group, 3-pentyloxypropyl group, 3-hexyloxypropyl group, 3-heptyloxypropyl group, 4-methoxybutyl group, 4-ethoxybutyl group, 4-propoxybutyl group, 4-butoxybutyl group, 4-pentyloxybutyl group, 4-hexyloxybutyl group, 4-heptyloxybutyl group, 5-methoxypentyl group, 5-ethoxypentyl group, 5-propoxypentyl group, 5-butoxypentyl group, 5-pentyloxypentyl group, 5-hexyloxypentyl group, 5-heptyloxypentyl group, 6-methoxyhexyl group, 6-ethoxyhexyl group, 6-propoxyhexyl group, 6-butoxyhexyl group, 6-pentyloxyhexyl group, 6-hexyloxyhexyl group and a 6-heptyloxyhexyl group; and fluorine substituted alkyl groups such as a fluoromethyl group, difluoromethyl group, trifluoromethyl group, 2-fluoromethyl group, 2,2-difluoroethyl group, 2,2,2-trifluoroethyl group, 1,1,2,2,2-pentafluoroethyl group, 3-fluoropropyl group, 2-fluoropropyl group, 1-fluoropropyl group, 3,3-difluoropropyl group, 3,3,3-trifluoropropyl group, 2,2,3,3-tetrafluoropropyl group, 2,2,3,3,3-pentafluoropropyl group, 1,1,2,2,3,3,3-heptafluoropropyl group, 4-fluorobutyl group, 3-fluorobutyl group, 2-fluorobutyl group, 1-fluorobutyl group, 4,4-difluorobutyl group, 4,4,4-trifluorobutyl group, 3,3,4,4-tetrafluorobutyl group, 3,3,4,4,4-pentafluorobutyl group, 2,2,3,3,4,4,4-heptafluorobutyl group, 5-fluoropentyl group, 4-fluoropentyl group, 3-fluoropentyl group, 2-fluoropentyl group, 1-fluoropentyl group, 5,5-difluoropentyl group, 5,5,5-trifluoropentyl group, 4,4,5,5-tetrafluoropentyl group, 4,4,5,5,5-pentafluoropentyl group, 3,3,4,4,5,5,5-heptafluoropentyl group, 6-fluorohexyl group, 5-fluorohexyl group, 4-fluorohexyl group, 3-fluorohexyl group, 2-fluorohexyl group, 1-fluorohexyl group, 6,6-difluorohexyl group, 6,6,6-trifluorohexyl group, 5,5,6,6,6-pentafluorohexyl group, 4,4,5,5,6,6,6-heptafluorohexyl group, 7-fluoroheptyl group, 6-fluoroheptyl group, 5-fluoroheptyl group, 4-fluoroheptyl group, 3-fluoroheptyl group, 2-fluoroheptyl group, 1-fluoroheptyl group, 7,7-difluoroheptyl group, 7,7,7-trifluoroheptyl group, 6,6,7,7-tetrafluoroheptyl group, 6,6,7,7,7-pentafluoroheptyl group, 5,5,6,6,7,7,7-heptafluoroheptyl group, 8-fluorooctyl group, 7-fluorooctyl group, 6-fluorooctyl group, 5-fluorooctyl group, 4-fluorooctyl group, 3-fluorooctyl group, 2-fluorooctyl group, 1-fluorooctyl group, 8,8-difluorooctyl group, 8,8,8-trifluorooctyl group, 7,7,8,8-tetrafluorooctyl group, 7,7,8,8,8-pentafluorooctyl group and a 6,6,7,7,8,8,8-heptafluorooctyl group. Straight chain alkyl groups of 1 to 12 carbon atoms or straight chain alkenyl groups of 2 to 12 carbon atoms are preferred, straight chain alkyl groups of 1 to 7 carbon atoms or straight chain alkenyl groups of 2 to 7 carbon atoms are even more preferable, and in the case of a straight chain alkenyl group, the structures shown below are particularly desirable.

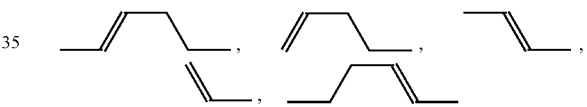

(the structural formulas shown are assumed to link to a ring at the right hand terminal)

Ring A and ring B each represent, independently, a trans-1,4-cyclohexylene group in which a single $CH_2$ structure within the group or 2 or more non-adjacent $CH_2$ structures within the group may be replaced with —O— and/or —S—, a 1,4-phenylene group in which a single CH structure within the group or 2 or more non-adjacent CH structures within the group may be replaced with —N═, a 1,4-cyclohexenylene group, a 1,4-bicyclo(2.2.2)octylene group, a piperidine-1,4-diyl group, a naphthalene-2,6-diyl group, a decahydronaphthalene-2,6-diyl group, or a 1,2,3,4-tetrahydronaphthalene-2,6-diyl group, and specific examples include the types of groups shown below.

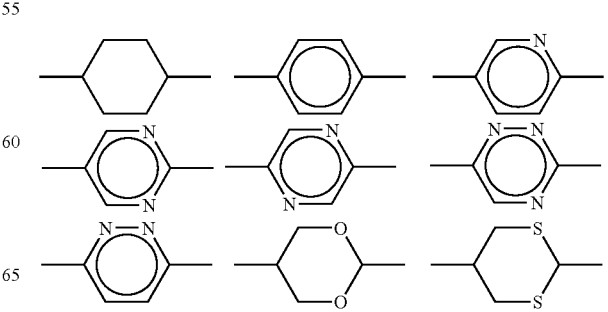

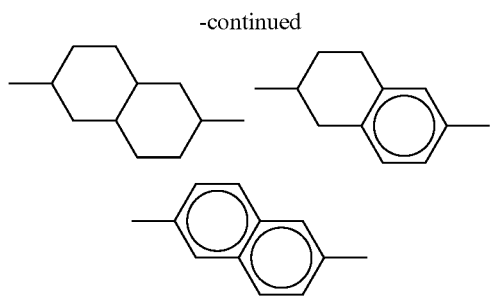

These groups may be substituted with a cyano group or a halogen, although a trans-1,4-cyclohexylene group or a 1,4-phenylene group which may be substituted with a halogen are preferred, and for ring A, a trans-1,4-cyclohexylene group is even more preferable, and for ring C, a 1,4-phenylene group or a trans-1,4-cyclohexylene group are even more preferable, and the structures shown below are particularly preferred.

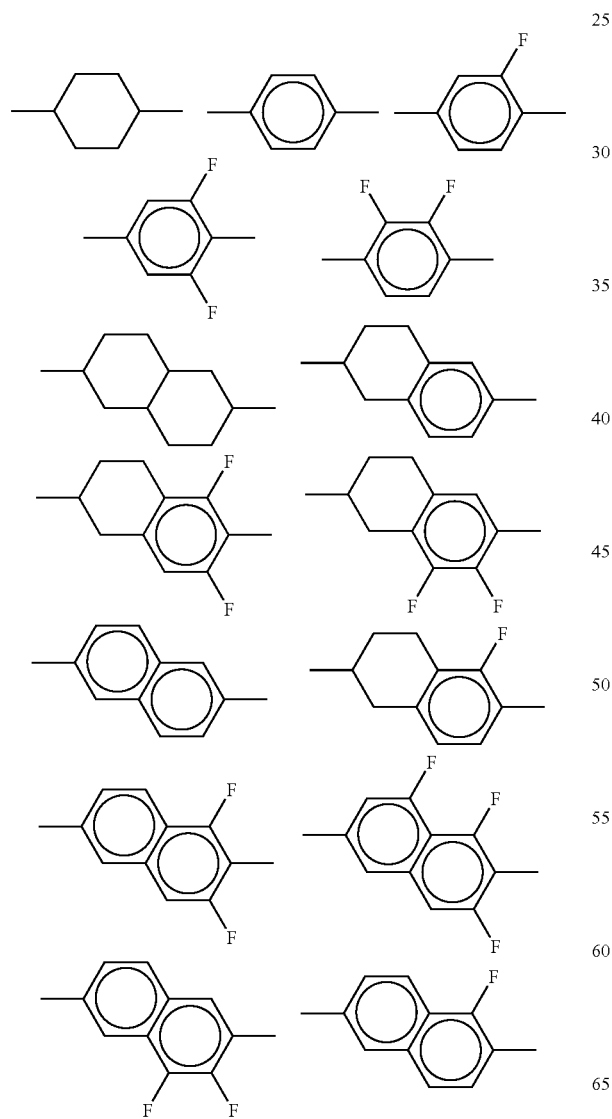

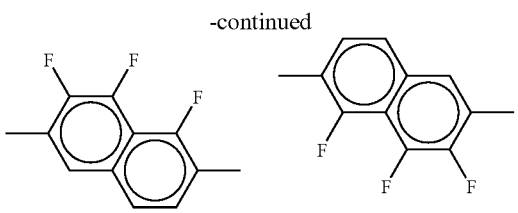

Ring B represents any one of the following structures:

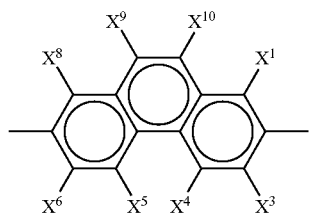
(II-1)

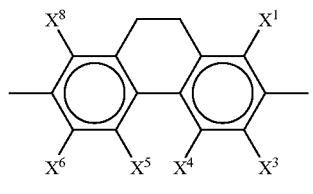
(II-2)

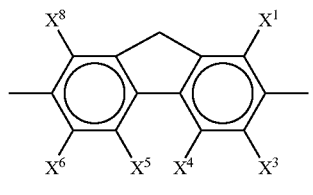
(II-3)

(II-4)

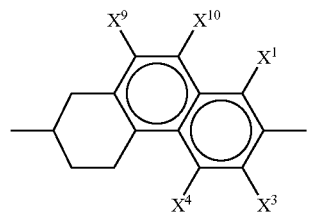
(II-5)

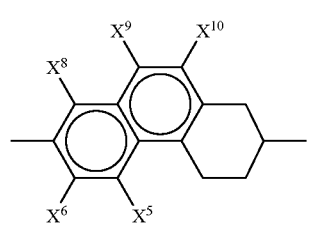
(II-6)

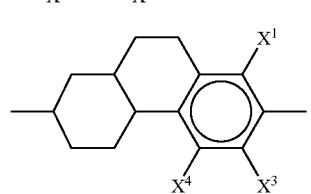
(II-7)

(II-8)

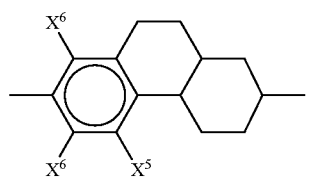

(II-9)

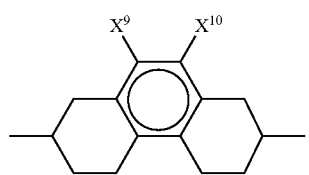

(wherein, $X^1$, $X^3$, $X^4$, $X^5$, $X^6$, $X^8$, $X^9$ and $X^{10}$ each represent, independently, a hydrogen atom, a chlorine atom or a fluorine atom, provided that the following conditions are satisfied:

1. In (II-1) and (II-2), in the case in which at least one of $X^3$, $X^4$, $X^5$ and $X^6$ represents a fluorine atom, and the remainder represent hydrogen atoms, then at least one of $X^1$, $X^8$, $X^9$ and $X^{10}$ represents a chlorine atom or a fluorine atom,
2. In (II-1) and (II-2), in the case in which at least one of $X^1$, $X^8$, $X^9$ and $X^{10}$ represents a fluorine atom, and the remainder represent hydrogen atoms, then at least one of $X^3$, $X^4$, $X^5$ and $X^6$ represents a chlorine atom or a fluorine atom, In (II-3) to (II-9), hydrogen atoms within a ring may be replaced with a cyano group or a halogen), although the following structures are preferred:

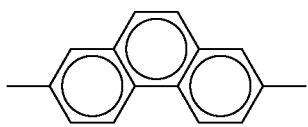

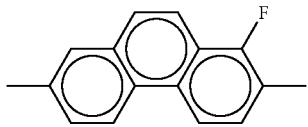

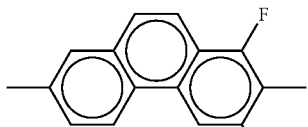

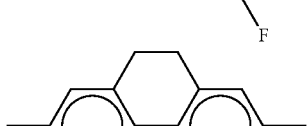

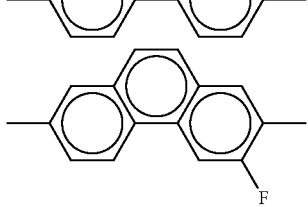

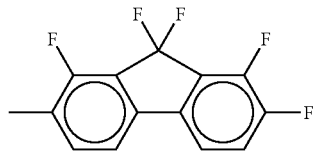

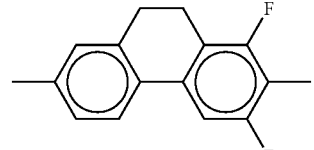

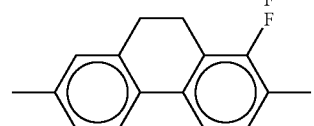

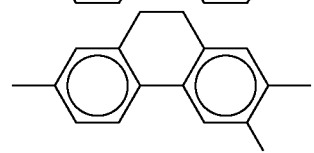

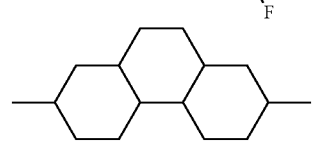

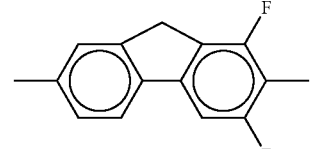

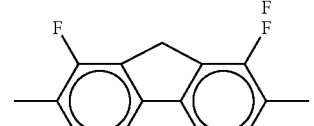

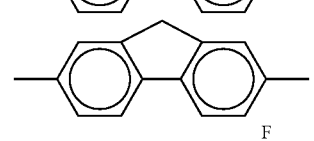

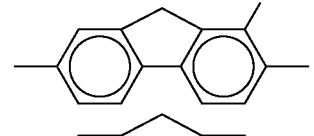

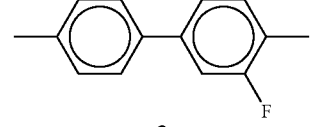

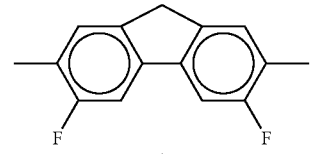

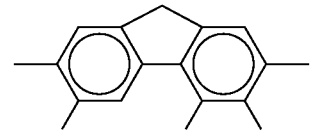

-continued
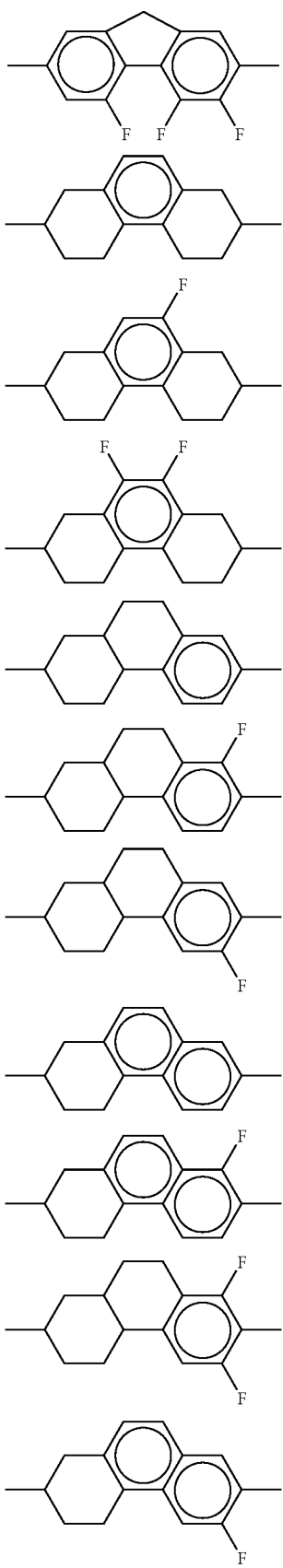
-continued
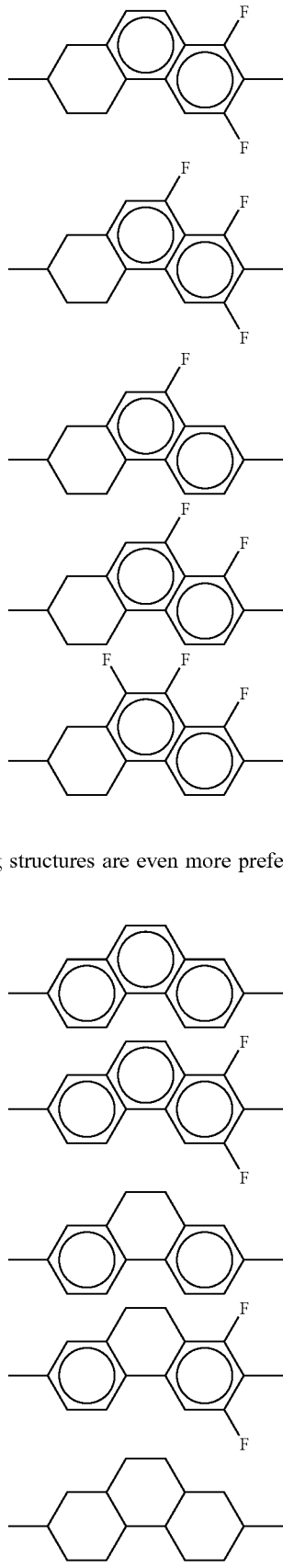
the following structures are even more preferable:
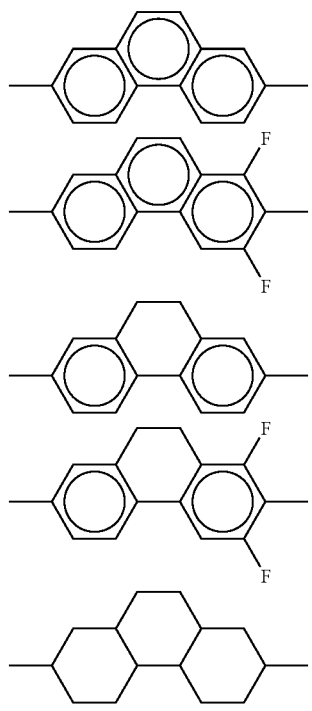

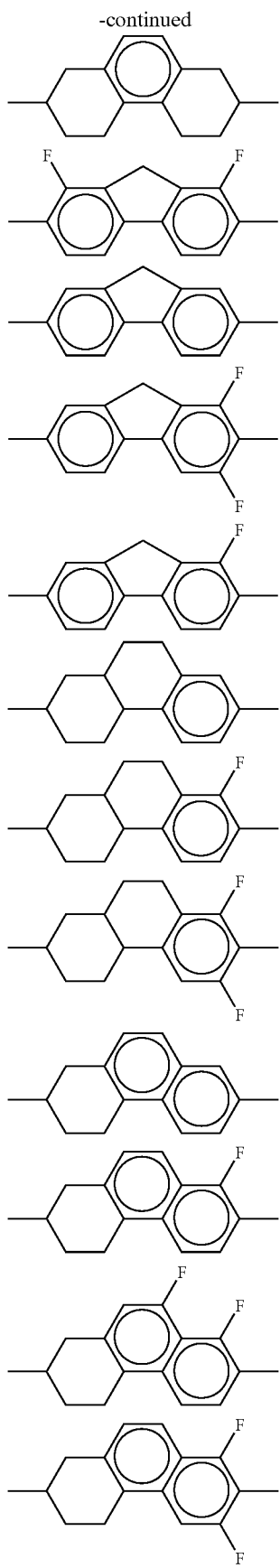

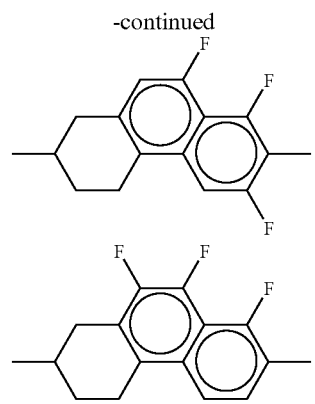

and the following structures are particularly desirable.

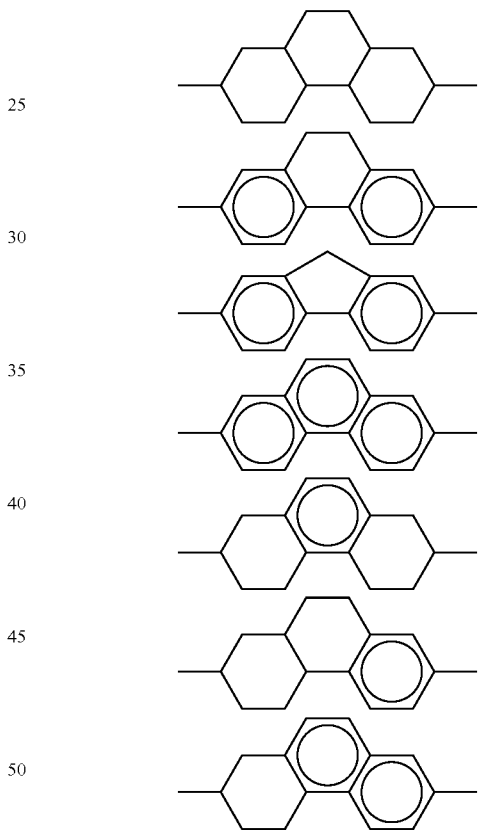

$L^1$ and $L^2$ each represent, independently, —CH₂CH₂—, —C≡C—, —(CH₂)₄—, —CF=CF—, —OCH₂—, —CH₂O—, —OCF₂—, —CF₂O—, —CO₂—, —OCO—, —CH=N—N=CH—, —CH=CH—CH₂—CH₂—, —CH₂—CH₂—CH=CH— or a single bond, although —CH₂CH₂—, —C≡C— or a single bond are preferred, and a single bond is particularly desirable. m and n each represent, independently, 0, 1 or 2, although m+n≦2, and it is preferable that either both m and n represent 0, or that either one of m or n represents 1. Y represents a hydrogen atom, a fluorine atom, a chlorine atom, a trifluoromethoxy group, a difluoromethoxy group, a trifluoromethyl group, a 3,3,3-trifluoroethoxy group, a cyano group, a straight chain alkyl group of 1 to 12 carbon atoms, a straight chain alkenyl group of 2 to 12 carbon atoms, a straight chain alkyloxy group of 1 to 12 carbon atoms, or a straight chain alkenyloxy group of 2 to 12 carbon atoms, although a fluorine atom, a chlorine atom, a trifluoromethoxy group, a difluoromethoxy group, a trifluoromethyl group, a 3,3,3-trifluoroethoxy group, or a cyano group are preferred, a fluorine atom, a trifluoromethoxy group, or a cyano group are even more preferable, and a fluorine atom or a cyano group are particularly desirable. As described above, the compound of the aforementioned general formula (I) incorporates an extremely large number of types of compounds depending on the selection of the group R, the ring A, the ring B, the ring C, $L^1$, $L^2$, m, n and Y, although of these compounds, each of the compounds represented by general formulas (I-1aa) through (I-3 hr) below is particularly preferred.

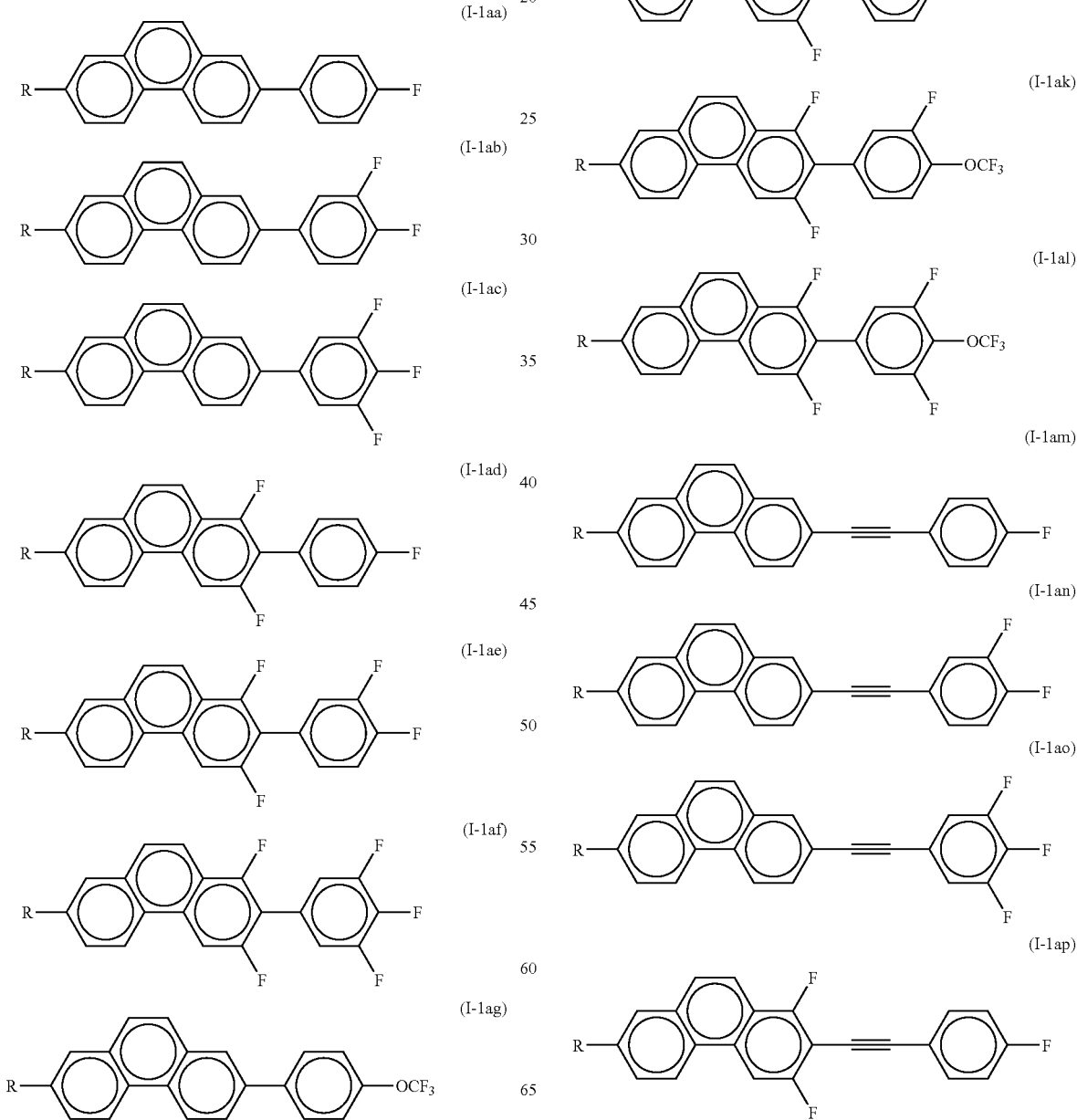

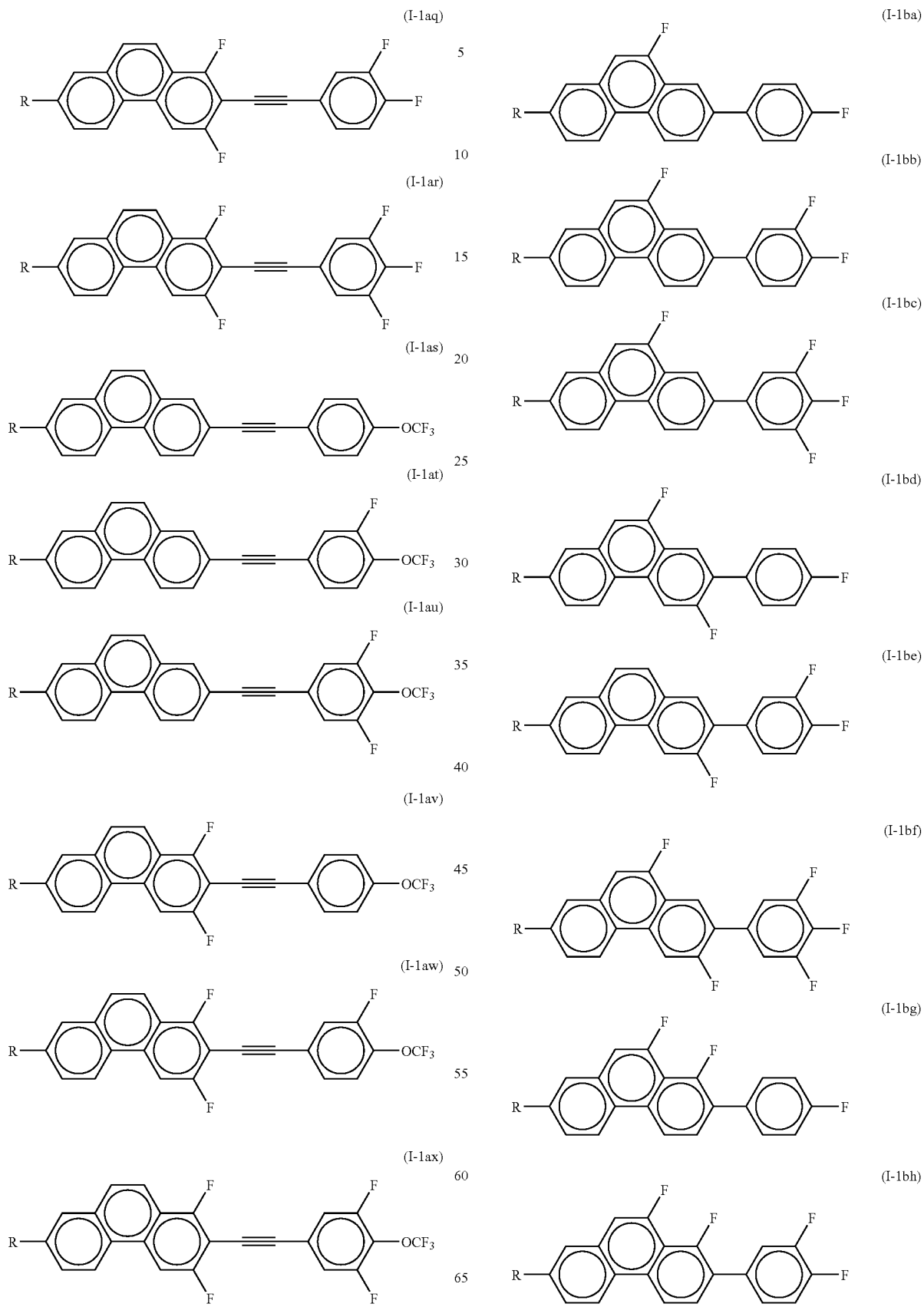

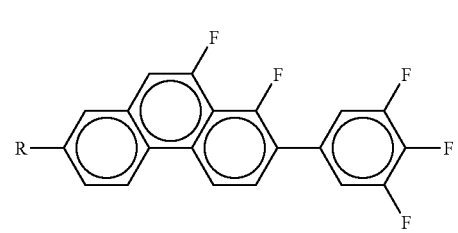 (I-1bi)
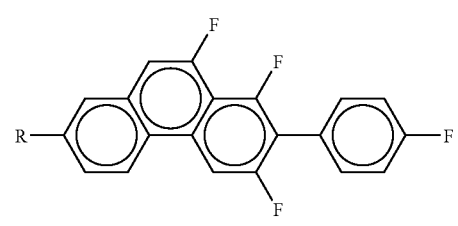 (I-1bj)
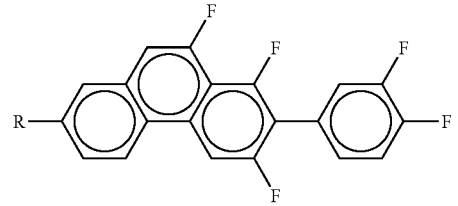 (I-1bk)
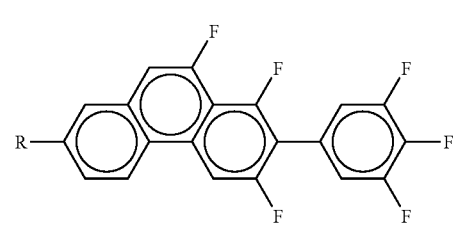 (I-1bl)
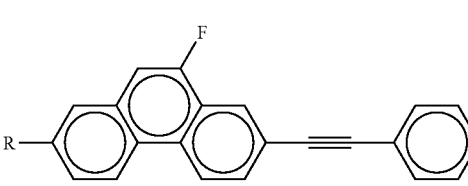 (I-1bm)
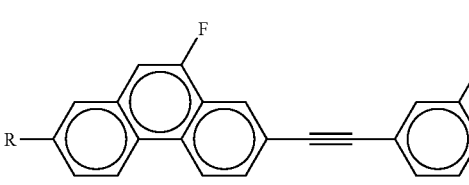 (I-1bn)
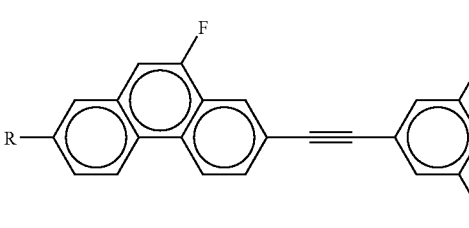 (I-1bo)
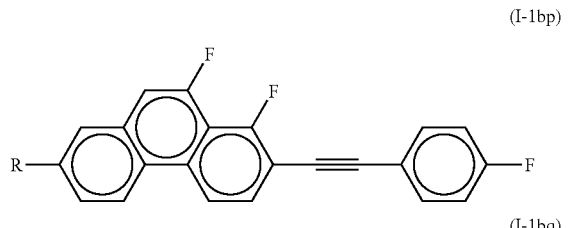 (I-1bp)
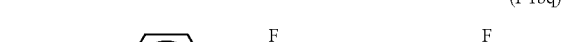 (I-1bq)
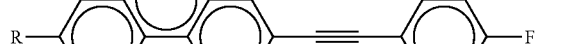 (I-1br)
 (I-1bs)
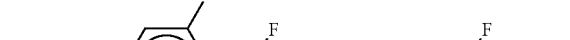 (I-1bt)
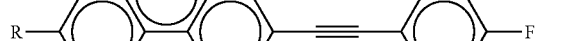 (I-1bu)
 (I-1bv)

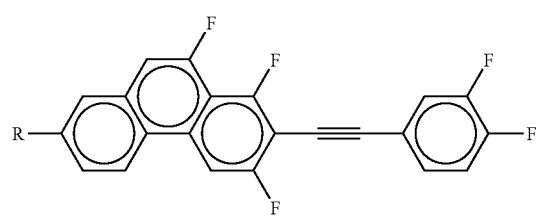
(I-1bw)
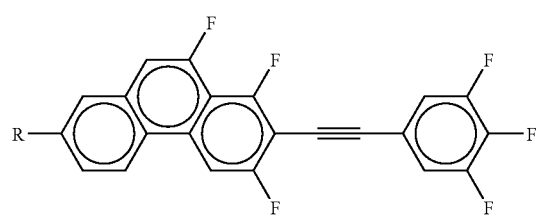
(I-1bx)
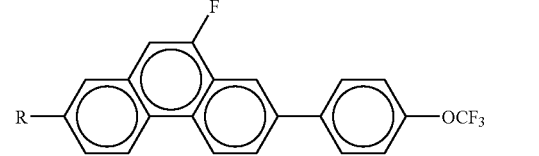
(I-1ca)
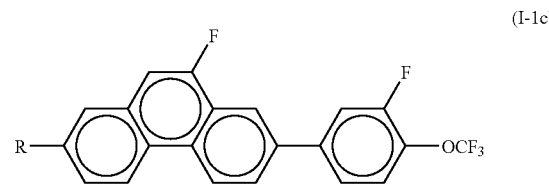
(I-1cb)
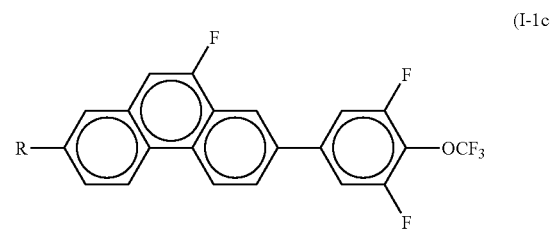
(I-1cc)
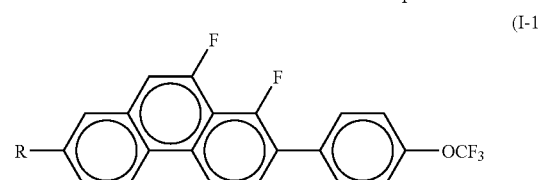
(I-1cd)
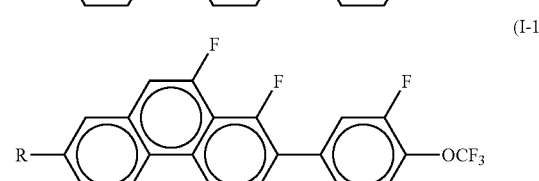
(I-1ce)
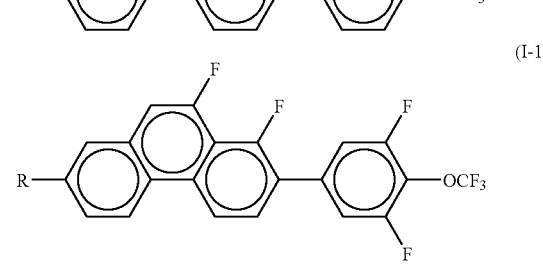
(I-1cf)
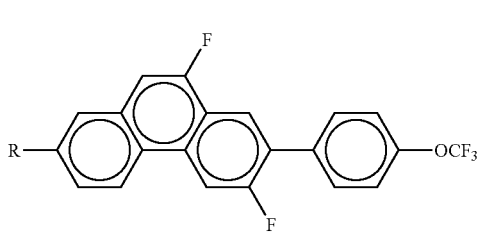
(I-1cg)
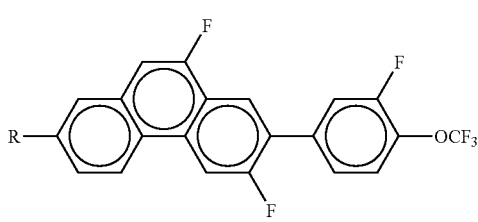
(I-1ch)
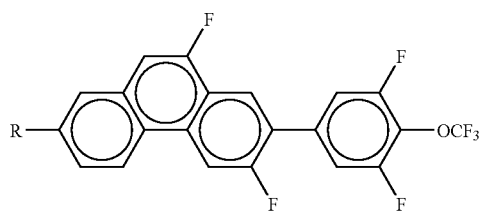
(I-1ci)
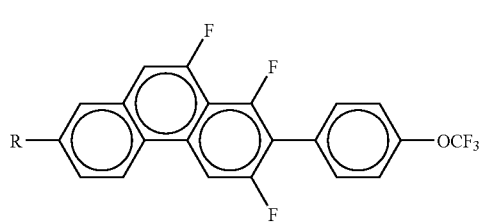
(I-1cj)
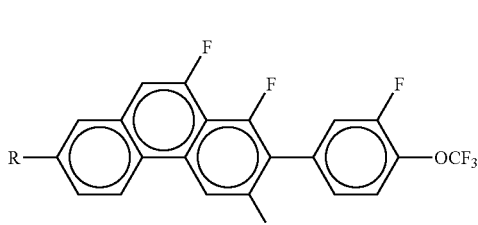
(I-1ck)
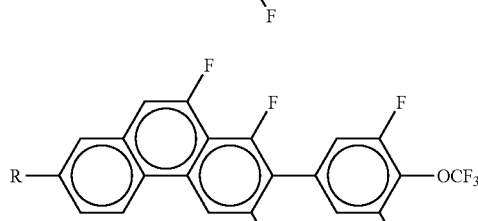
(I-1cl)
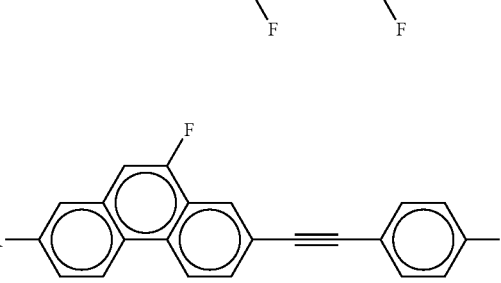
(I-1cm)

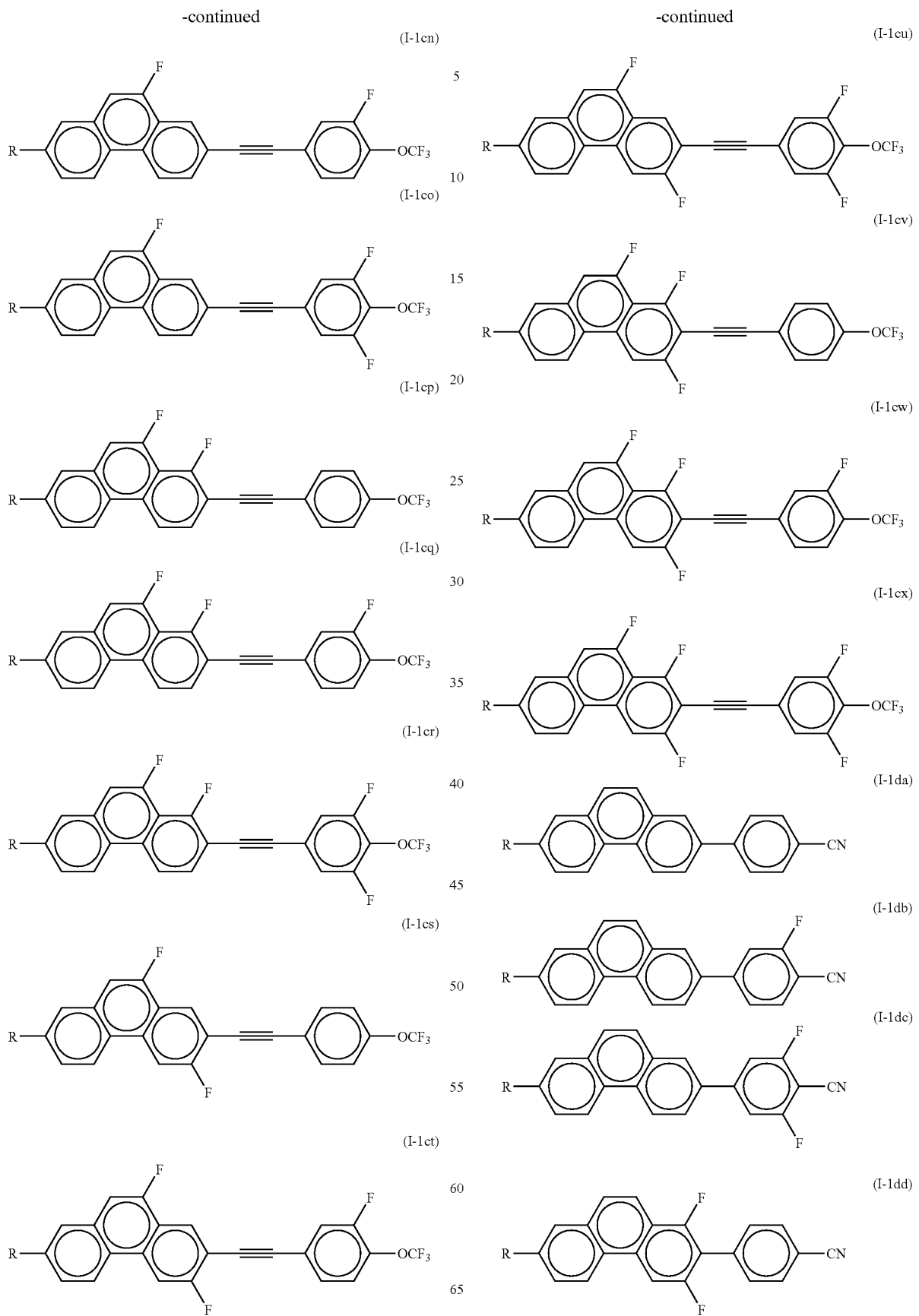

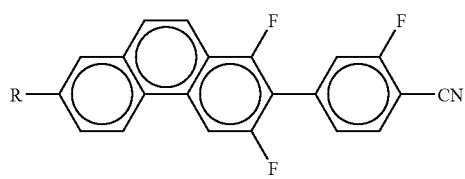 (I-1de)
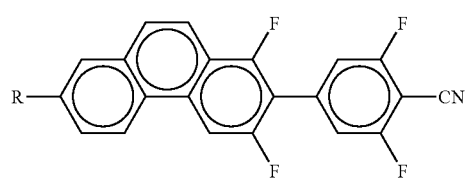 (I-1df)
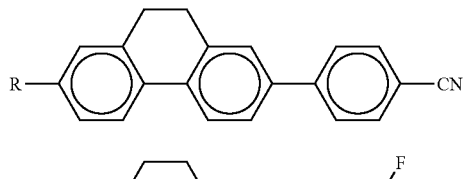 (I-1dg)
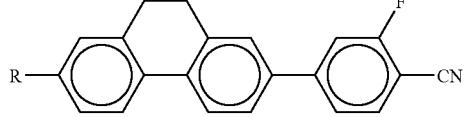 (I-1dh)
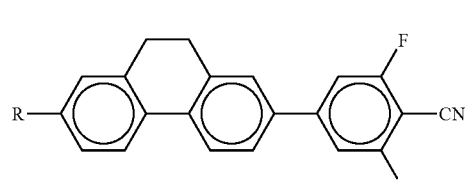 (I-1di)
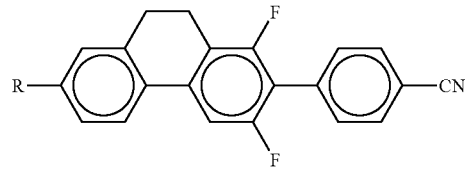 (I-1dj)
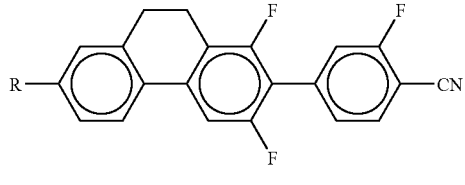 (I-1dk)
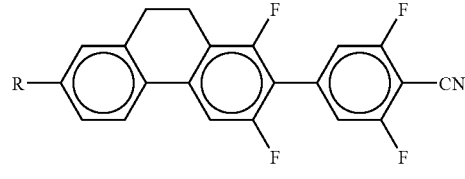 (I-1dl)
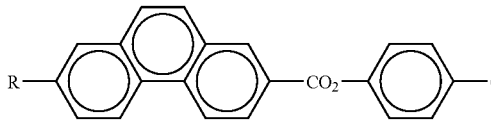 (I-1dm)
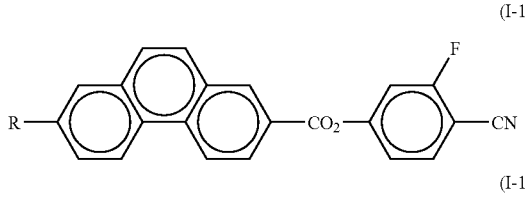 (I-1dn)
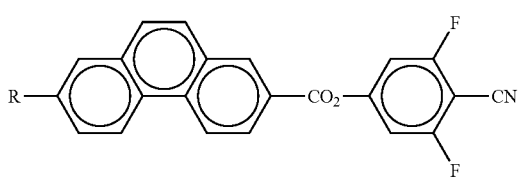 (I-1do)
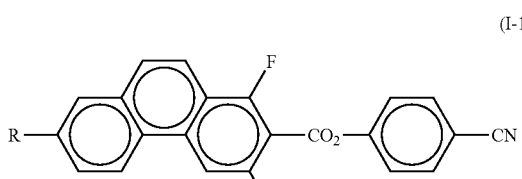 (I-1dp)
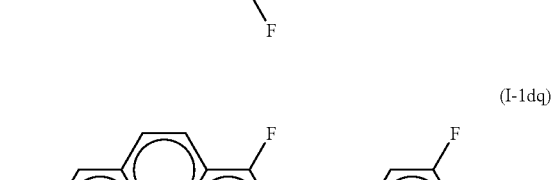 (I-1dq)
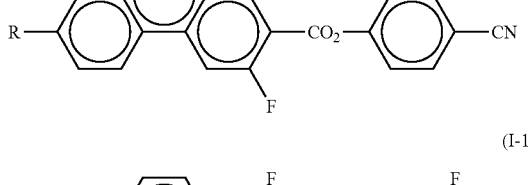 (I-1dr)
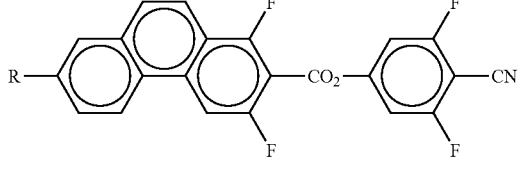 (I-1ds)
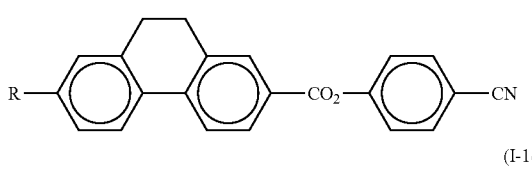 (I-1dt)
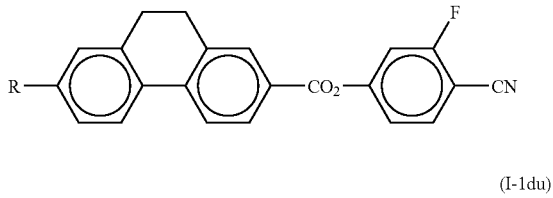 (I-1du)

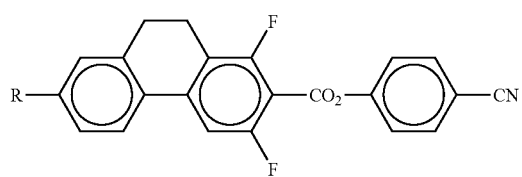
(I-1dv)
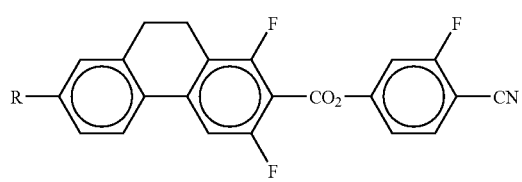
(I-1dw)
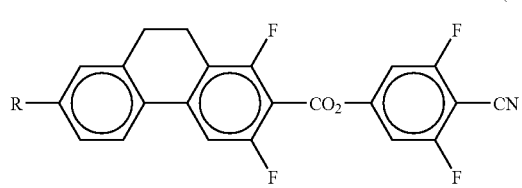
(I-1dx)
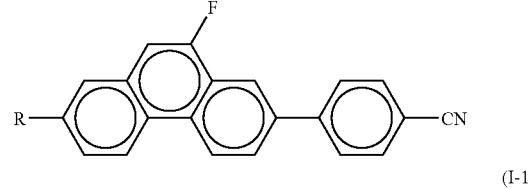
(I-1ea)
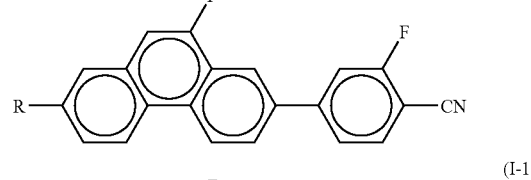
(I-1eb)
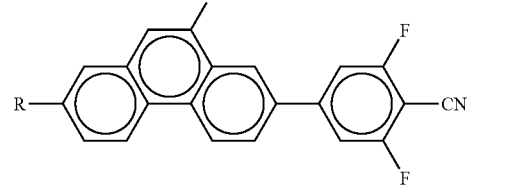
(I-1ec)
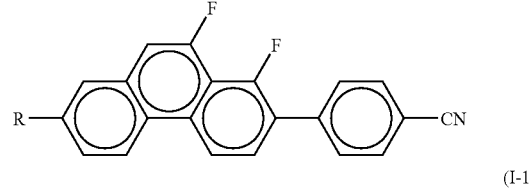
(I-1ed)
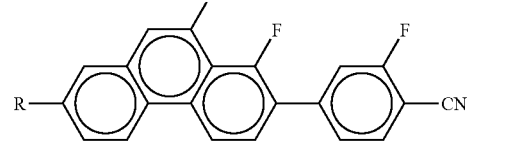
(I-1ee)
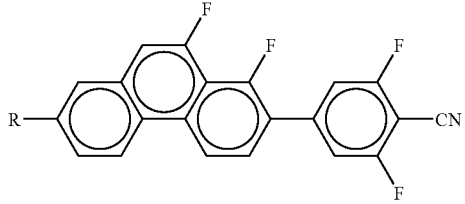
(I-1ef)
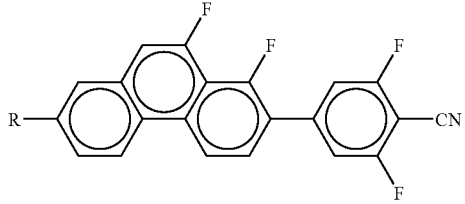
(I-1eg)
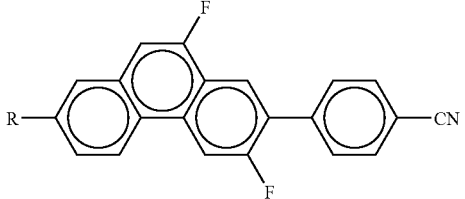
(I-1eh)
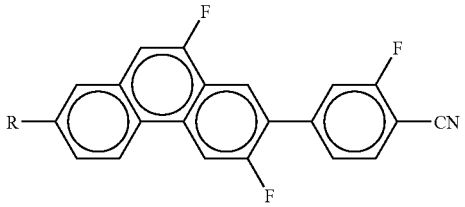
(I-1ei)
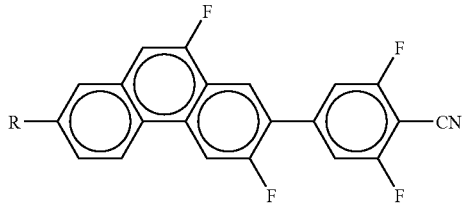
(I-1ej)
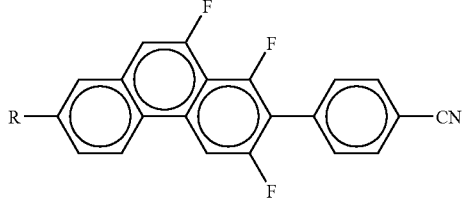
(I-1ek)
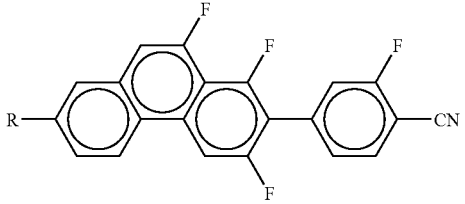
(I-1el)
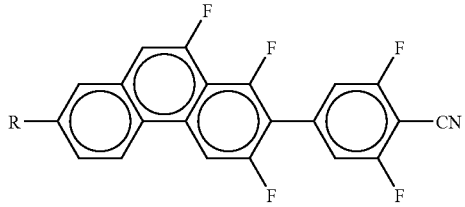

-continued
(I-1em)
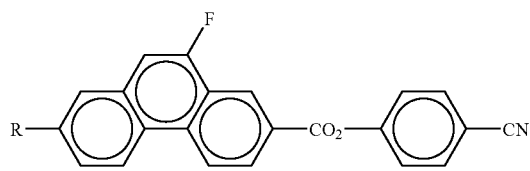
(I-1en)
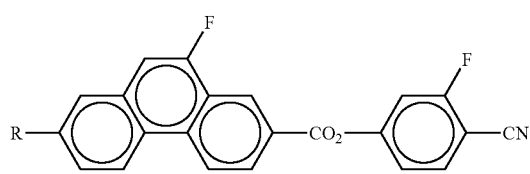
(I-1eo)
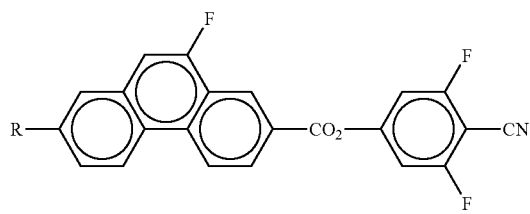
(I-1ep)
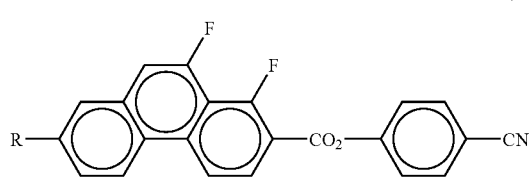
(I-1eq)
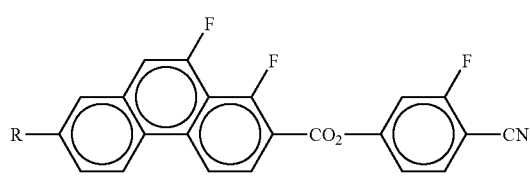
(I-1er)
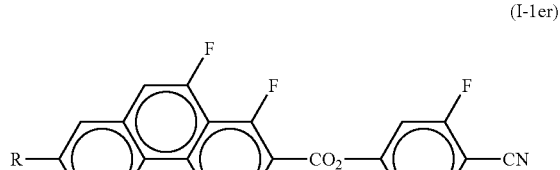
(I-1es)
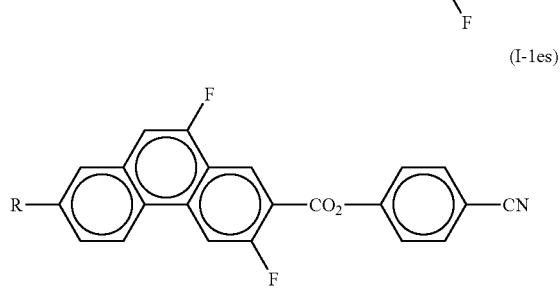
-continued
(I-1et)
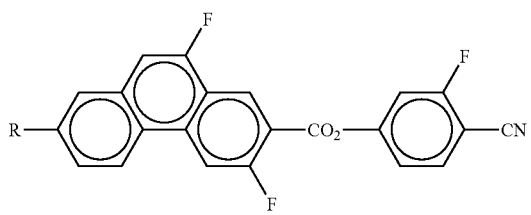
(I-1eu)
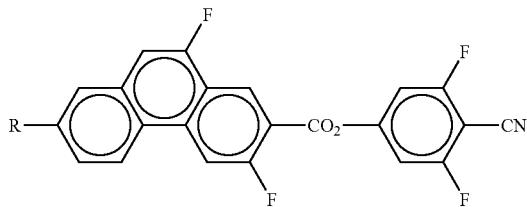
(I-1ev)
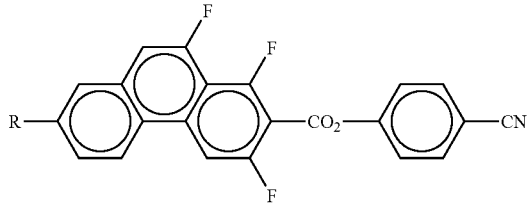
(I-1ew)
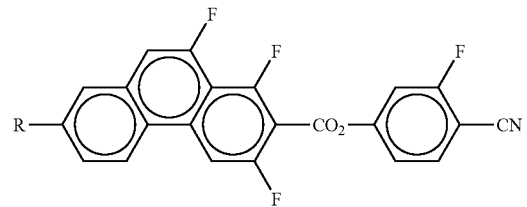
(I-1ex)
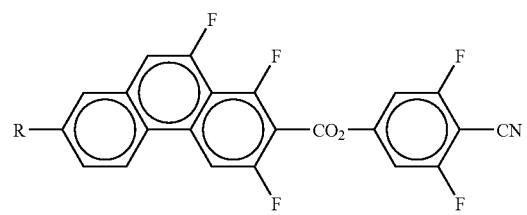
(I-1fa)
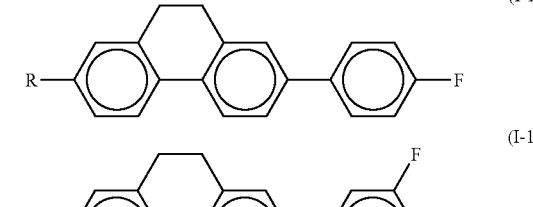
(I-1fb)
(I-1fc)
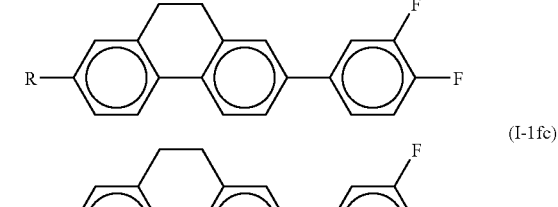

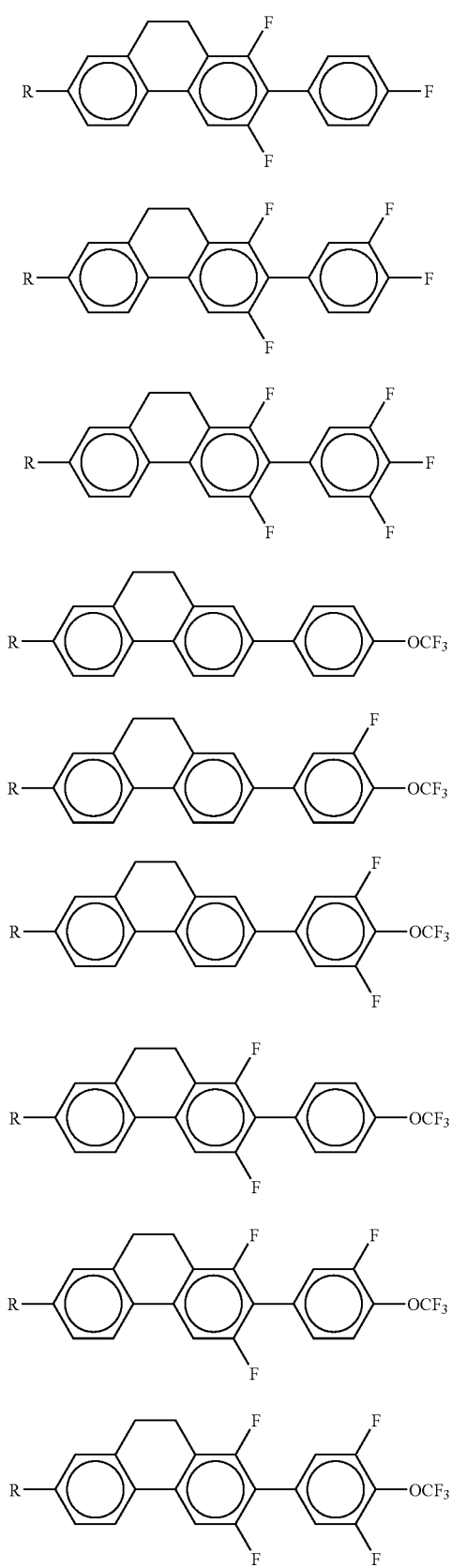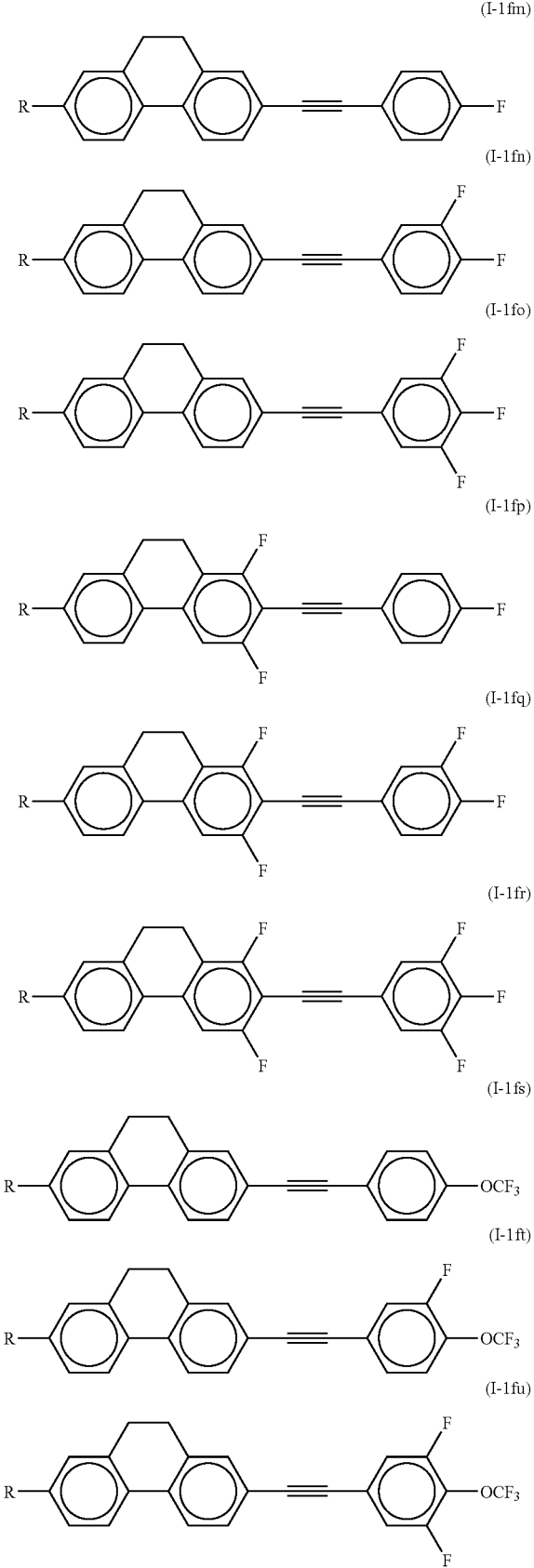

-continued
(I-1fv)
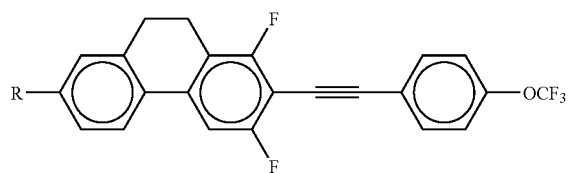
(I-1fw)
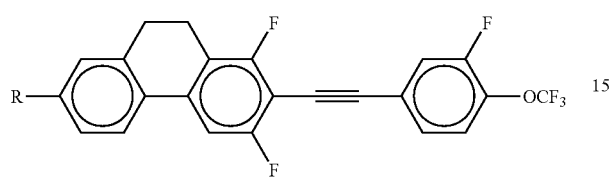
(I-1fx)
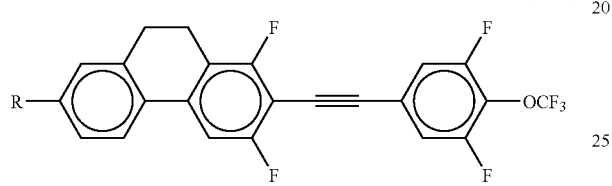
(I-1ga)
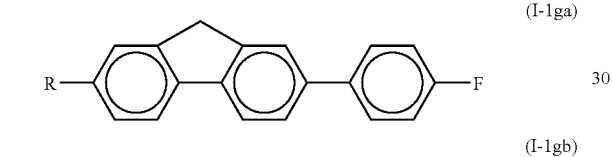
(I-1gb)
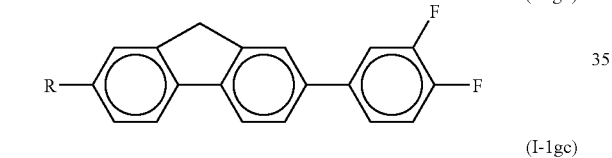
(I-1gc)
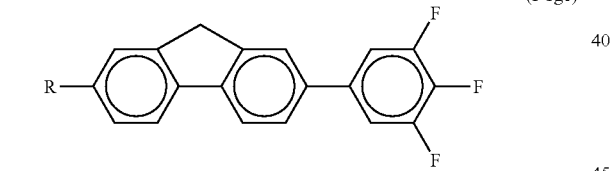
(I-1gd)
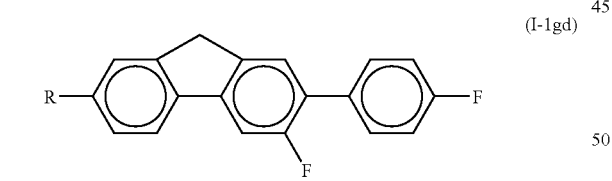
(I-1ge)
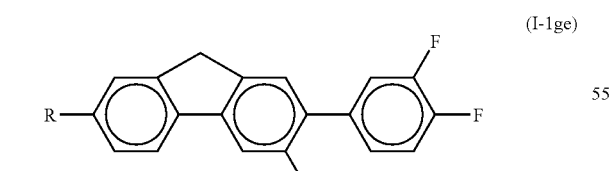
(I-1gf)
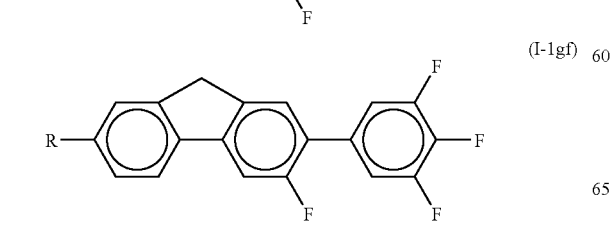
-continued
(I-1gg)
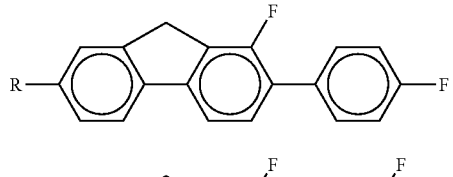
(I-1gh)
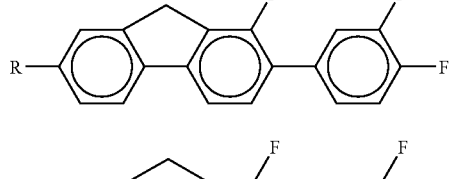
(I-1gi)
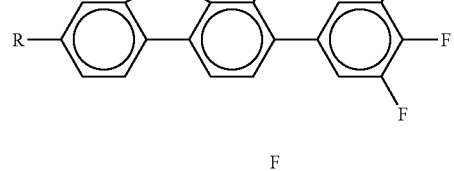
(I-1gj)
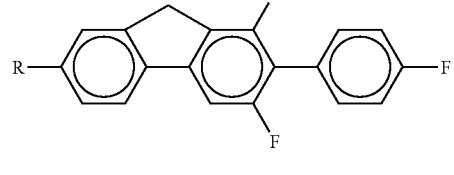
(I-1gk)
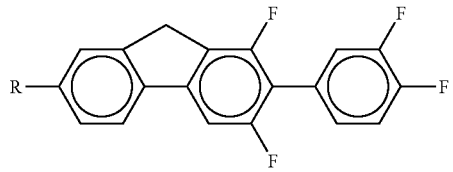
(I-1gl)
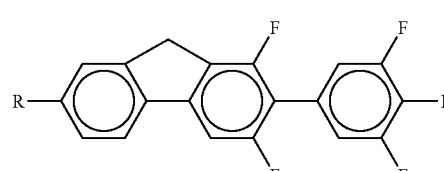
(I-1gm)
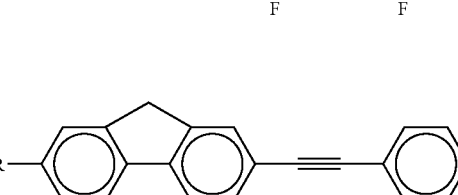
(I-1gn)
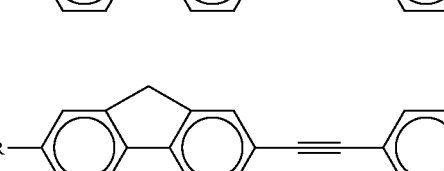
(I-1go)
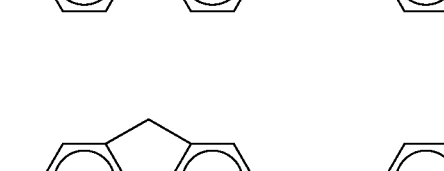
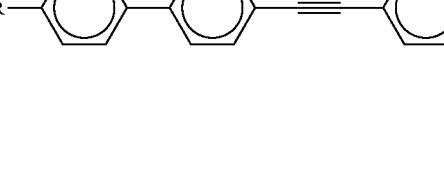

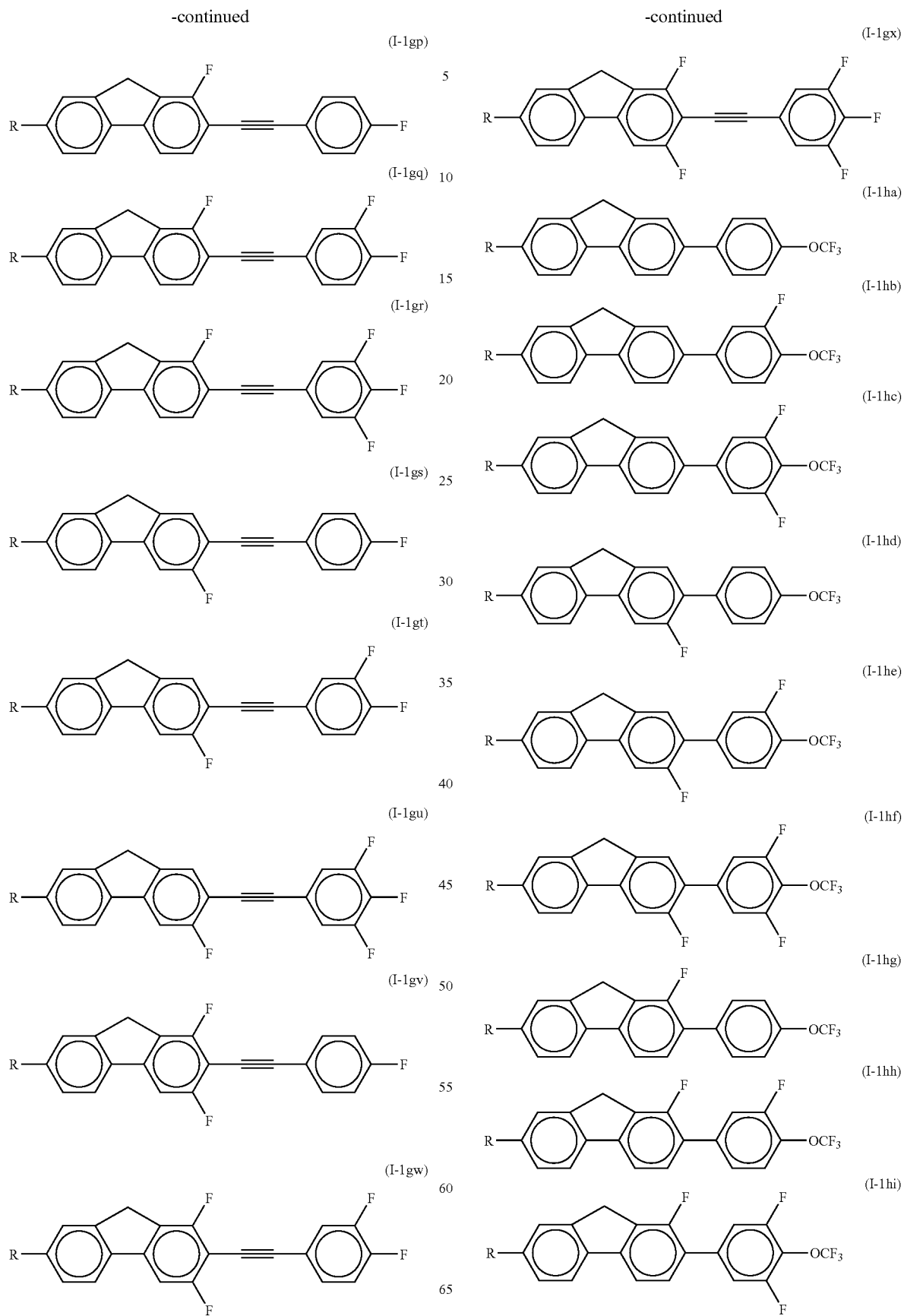

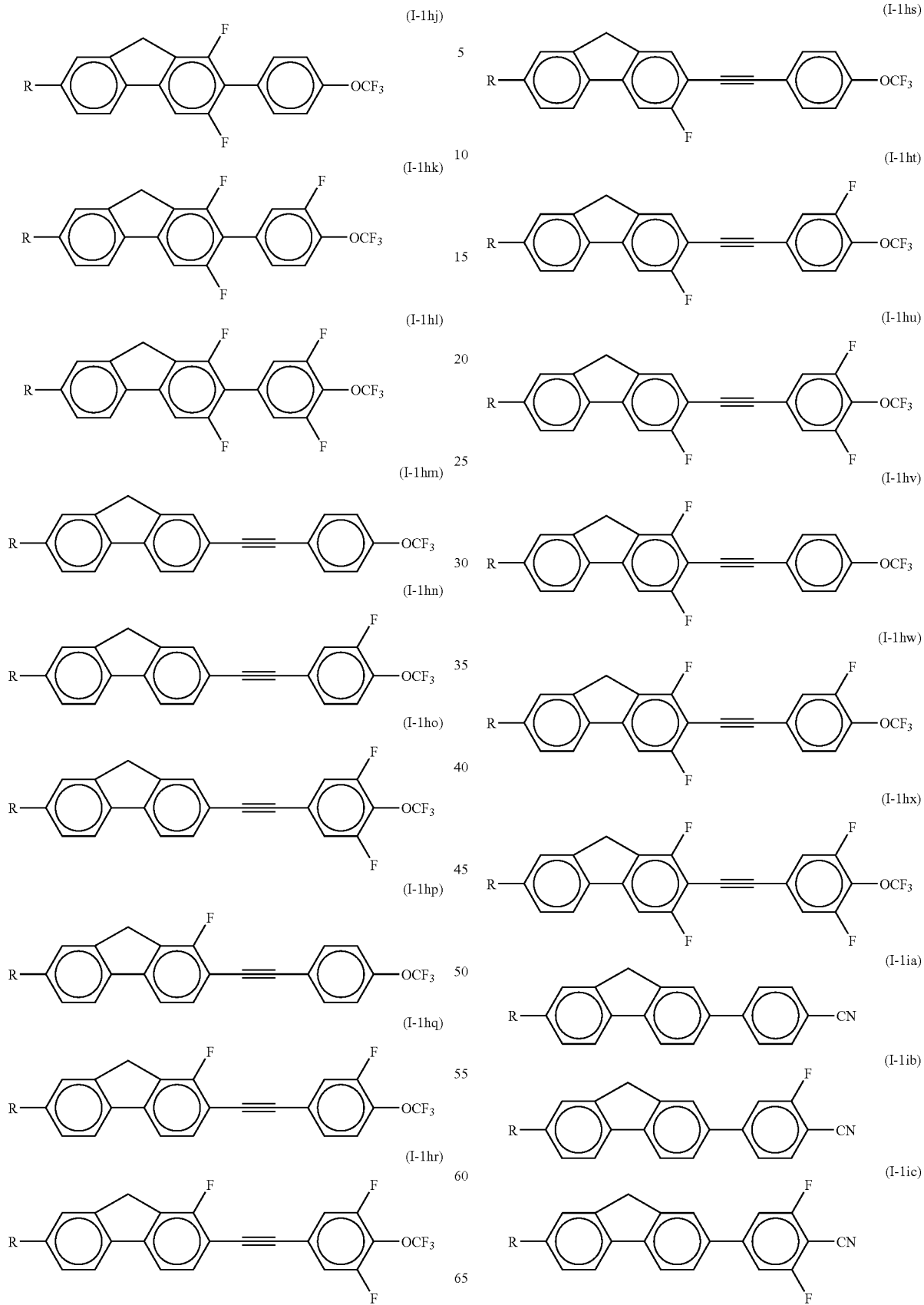

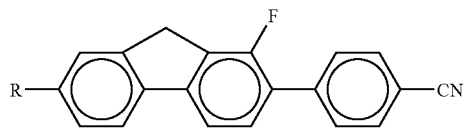 (I-1id)
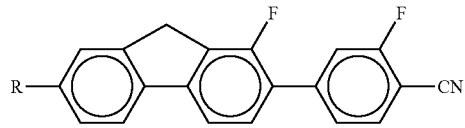 (I-1ie)
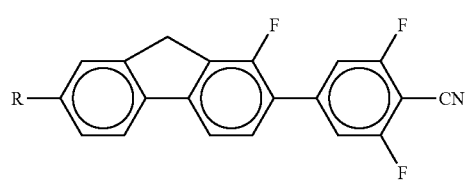 (I-1if)
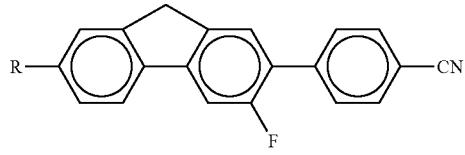 (I-1ig)
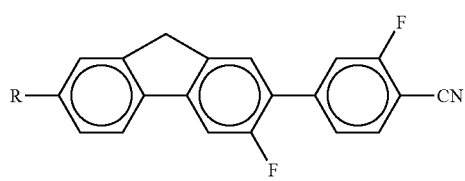 (I-1ih)
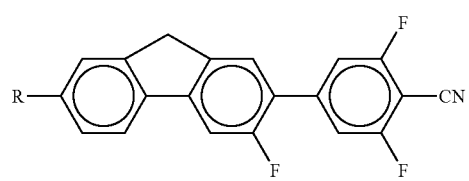 (I-1ii)
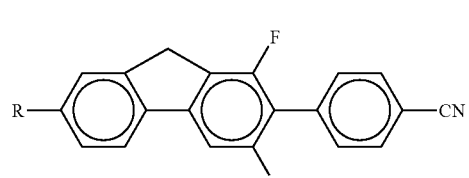 (I-1ij)
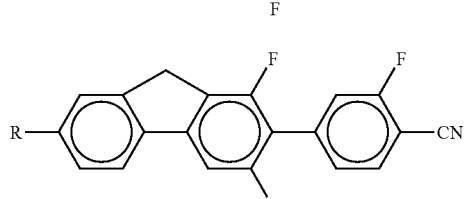 (I-1ik)
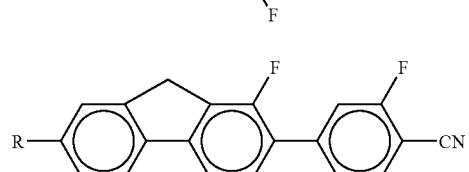 (I-1il)
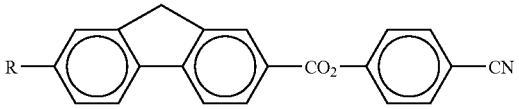 (I-1im)
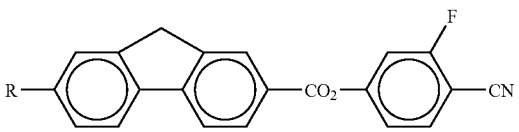 (I-1in)
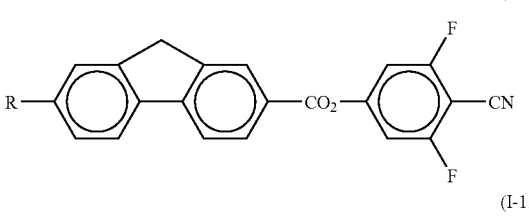 (I-1io)
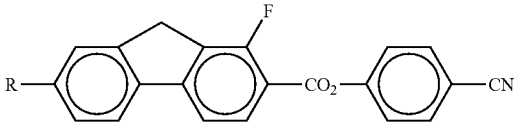 (I-1ip)
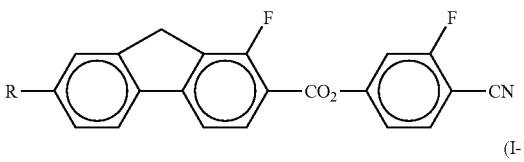 (I-1iq)
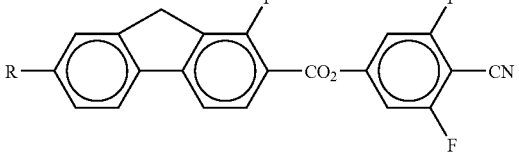 (I-1ir)
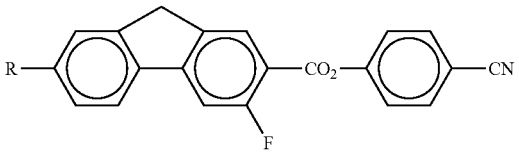 (I-1is)
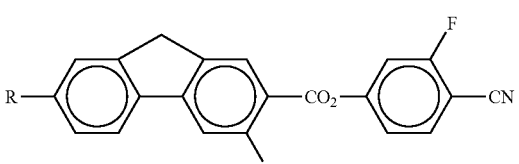 (I-1it)
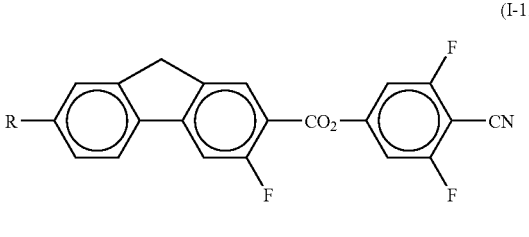 (I-1iu)

-continued
(I-1iv)
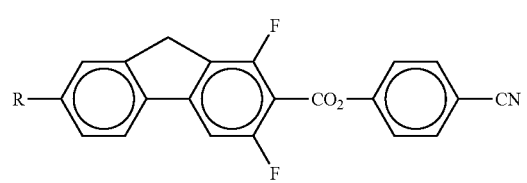
(I-1iw)
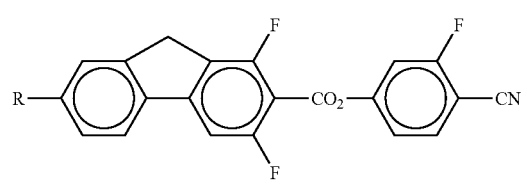
(I-1ix)
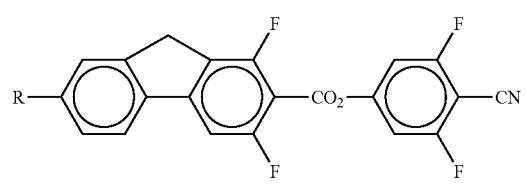
(I-2aa)
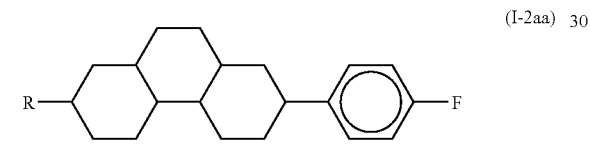
(I-2ab)
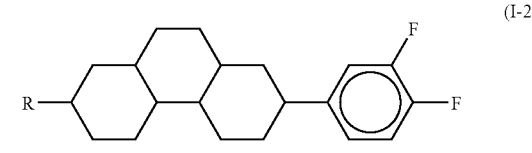
(I-2ac)
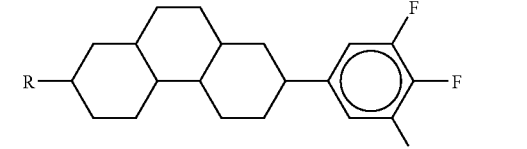
(I-2ad)
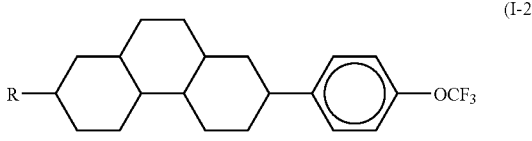
(I-2ae)
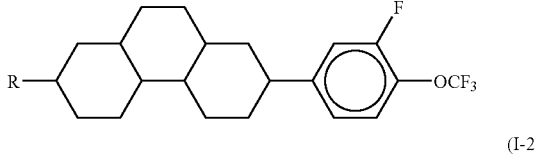
(I-2af)
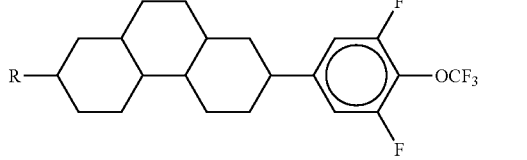
-continued
(I-2ag)
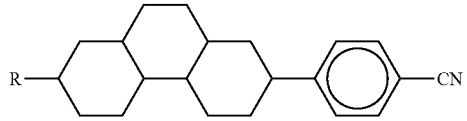
(I-2ah)
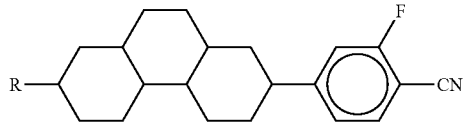
(I-2ai)
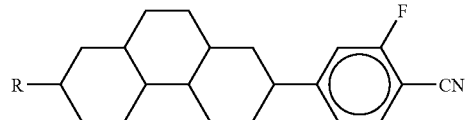
(I-2aj)
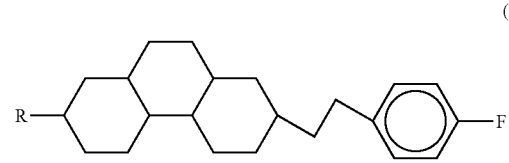
(I-2ak)
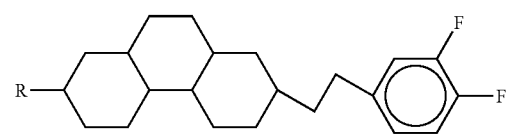
(I-2al)
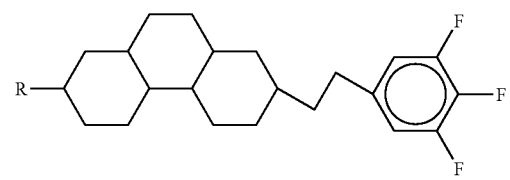
(I-2am)
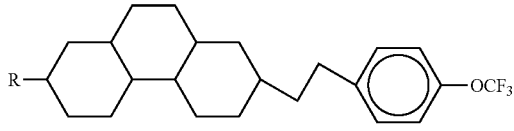
(I-2an)
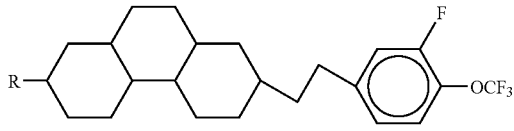
(I-2ao)
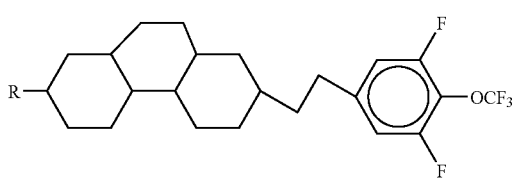

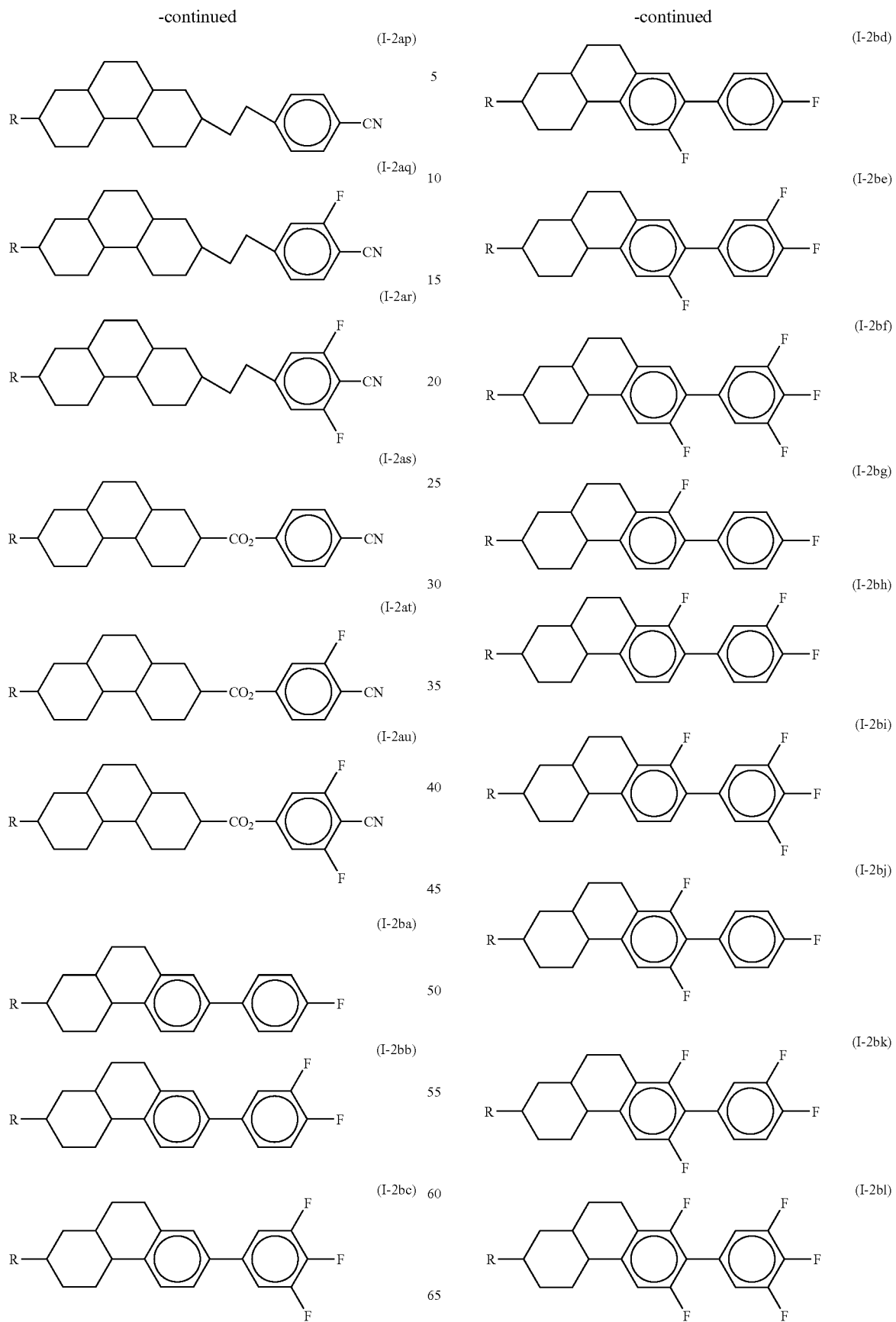

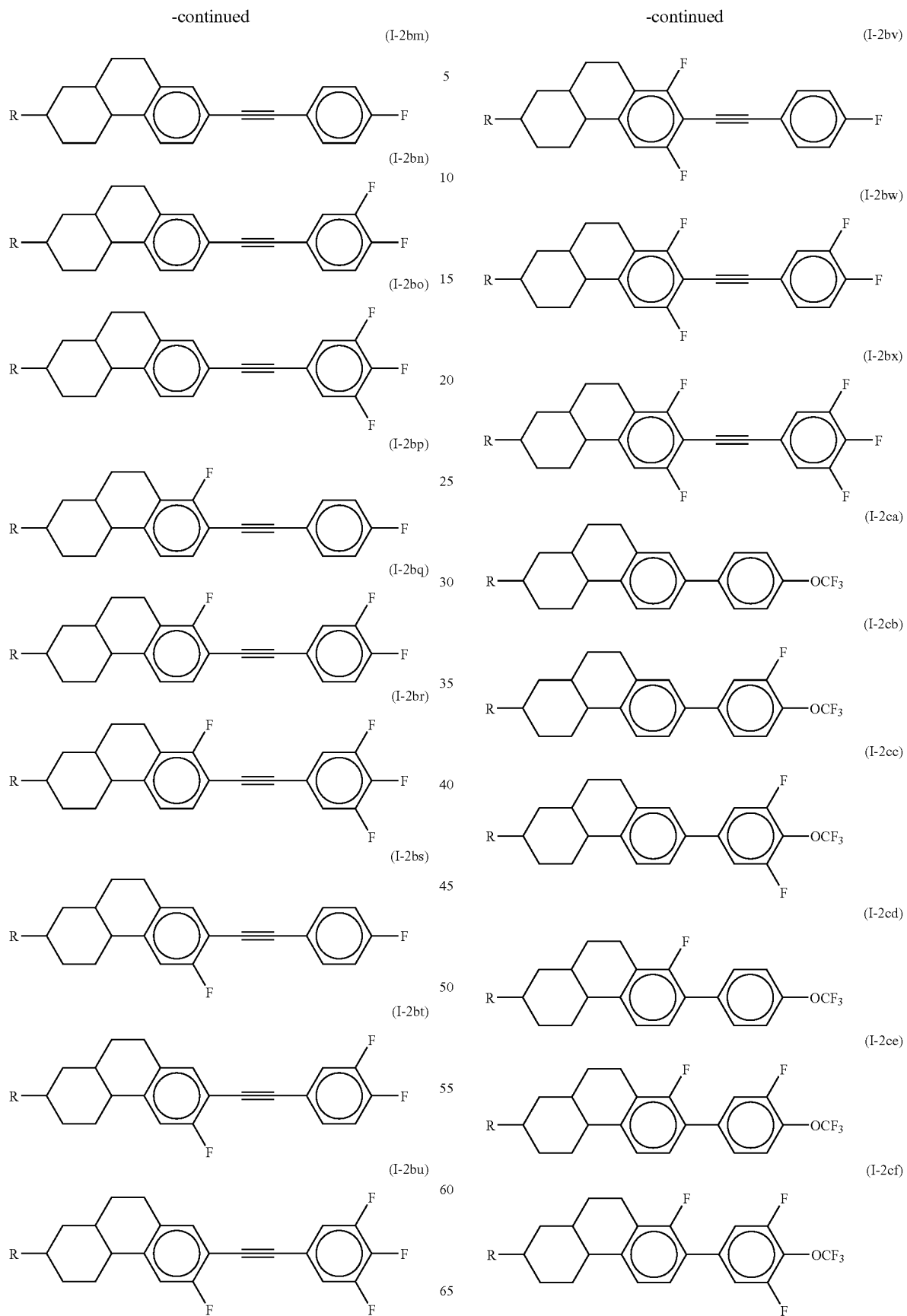

-continued
(I-2cg)
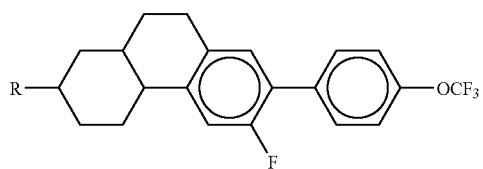
(I-2ch)
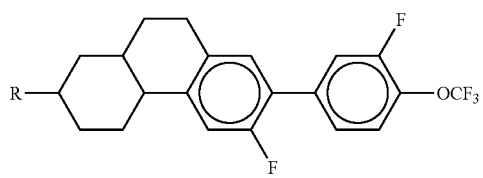
(I-2ci)
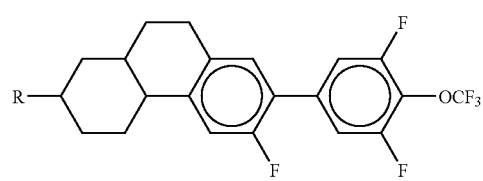
(I-2cj)
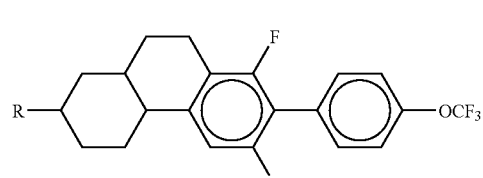
(I-2ck)
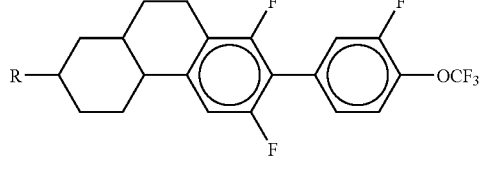
(I-2cl)
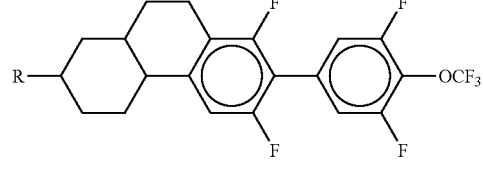
(I-2cm)
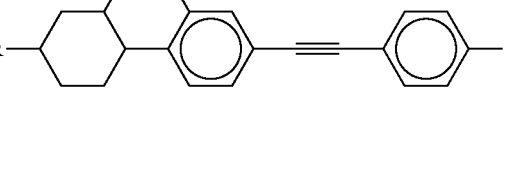
(I-2cn)
-continued
(I-2co)
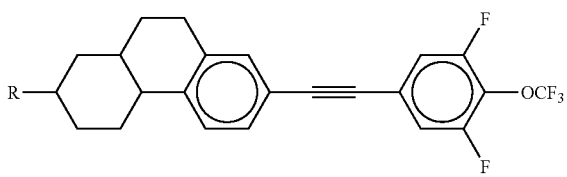
(I-2cp)
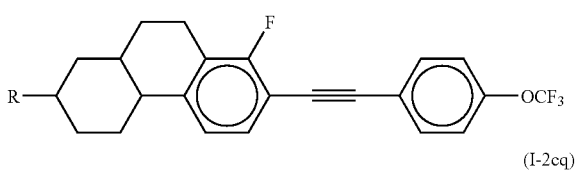
(I-2cq)
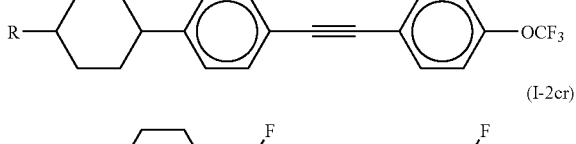
(I-2cr)
(I-2cs)
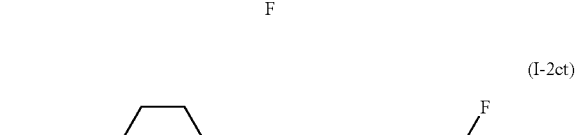
(I-2ct)
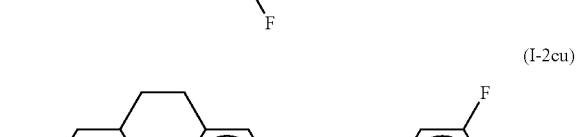
(I-2cu)
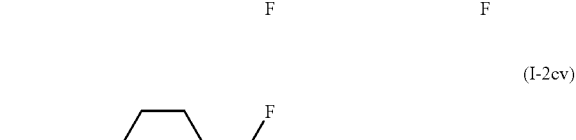
(I-2cv)

-continued
(I-2cw)
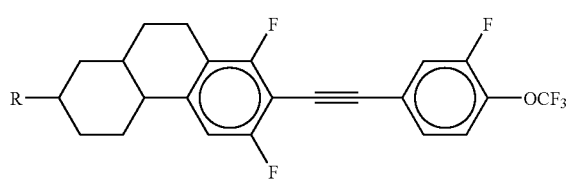
(I-2cx)
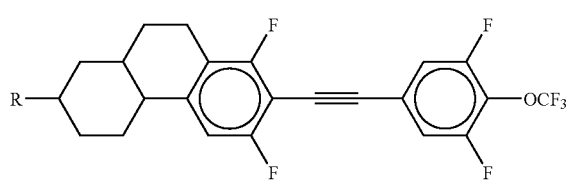
(I-2da)
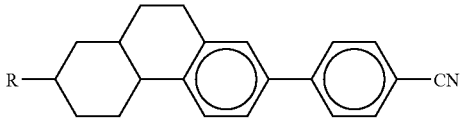
(I-2db)
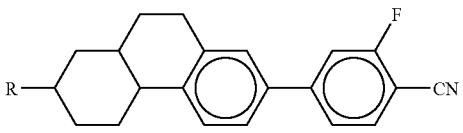
(I-2dc)
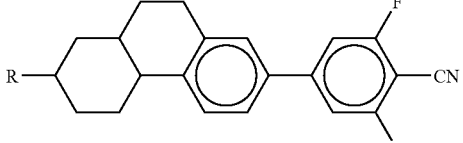
(I-2dd)
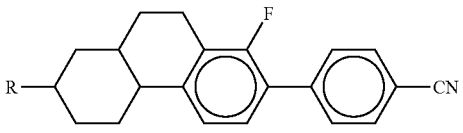
(I-2de)
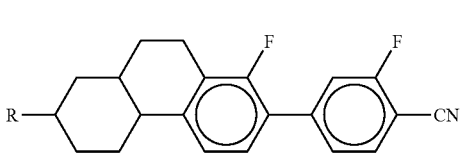
(I-2df)
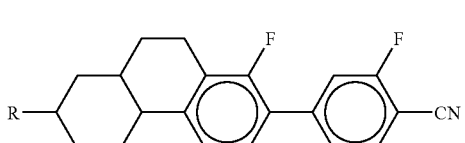
(I-2dg)
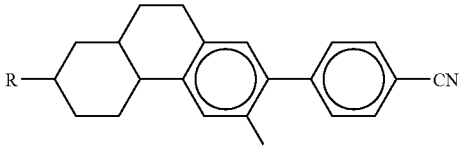
-continued
(I-2dh)
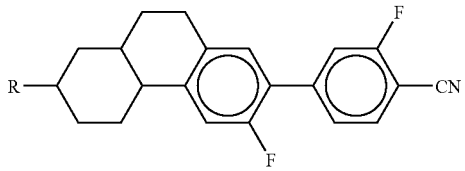
(I-2di)
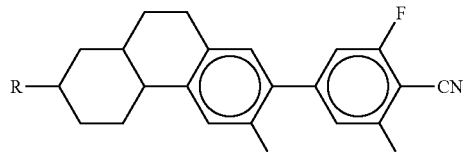
(I-2dj)
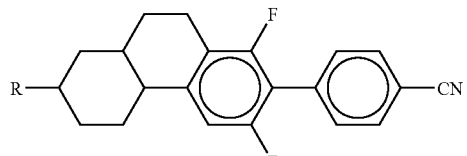
(I-2dk)
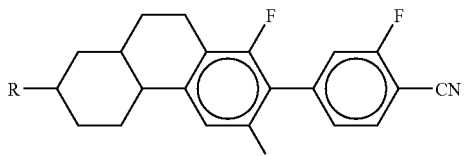
(I-2dl)
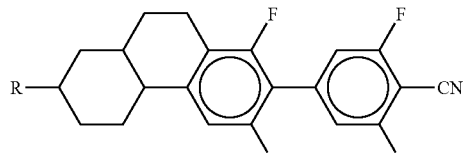
(I-2dm)
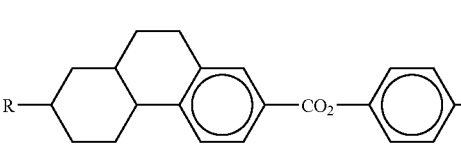
(I-2dn)
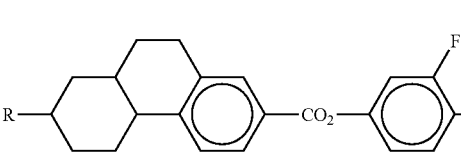
(I-2do)
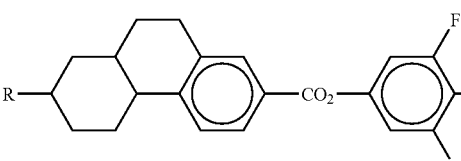
(I-2dp)
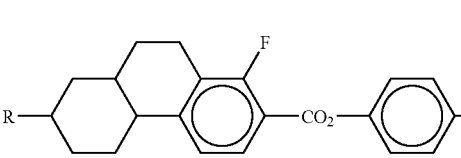

-continued
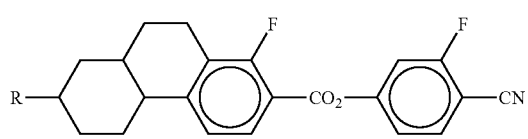
(I-2dq)
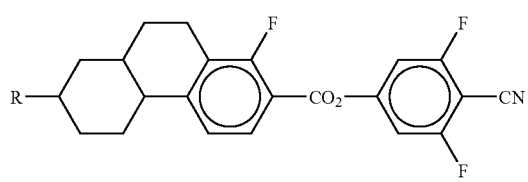
(I-2dr)
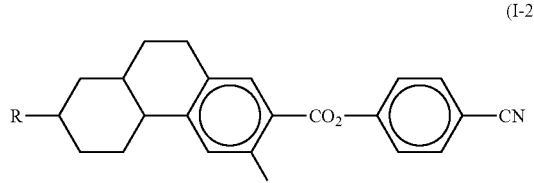
(I-2ds)
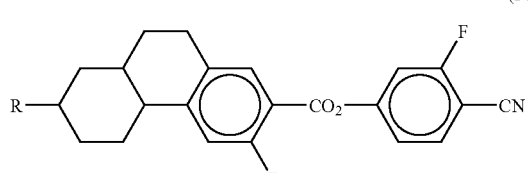
(I-2dt)
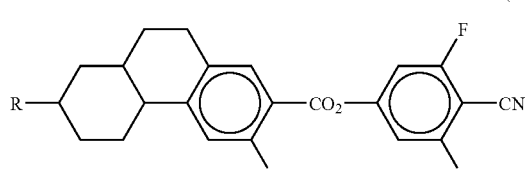
(I-2du)
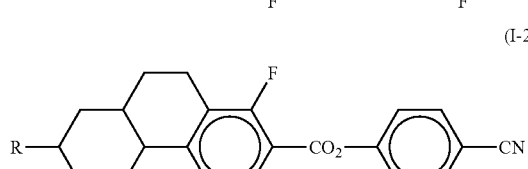
(I-2dv)
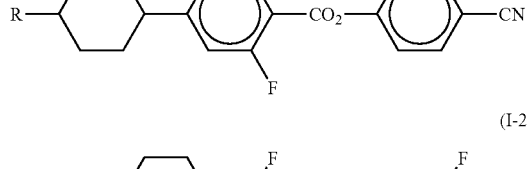
(I-2dw)
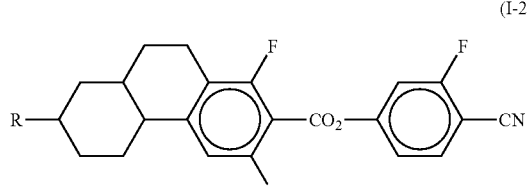
(I-2dx)
-continued
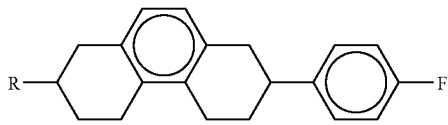
(I-2ea)
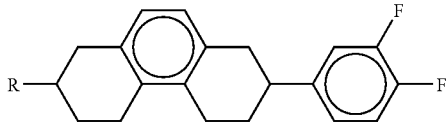
(I-2eb)
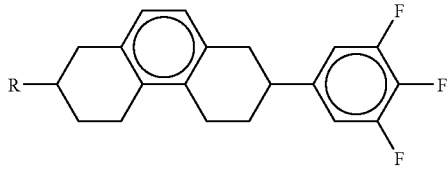
(I-2ec)
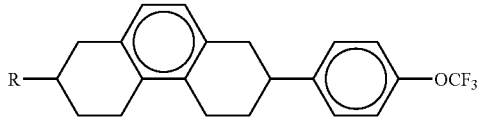
(I-2ed)
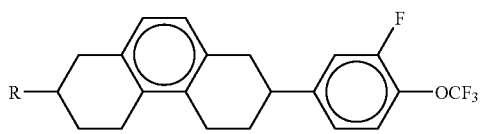
(I-2ee)
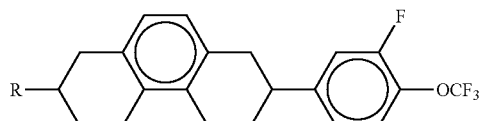
(I-2ef)
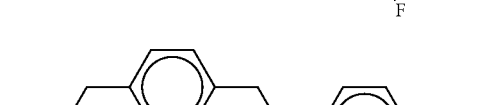
(I-2eg)
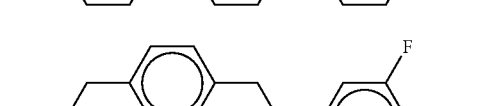
(I-2eh)
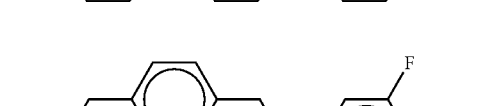
(I-2ei)
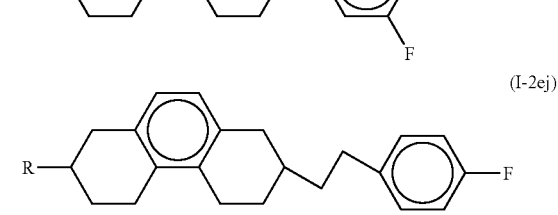
(I-2ej)

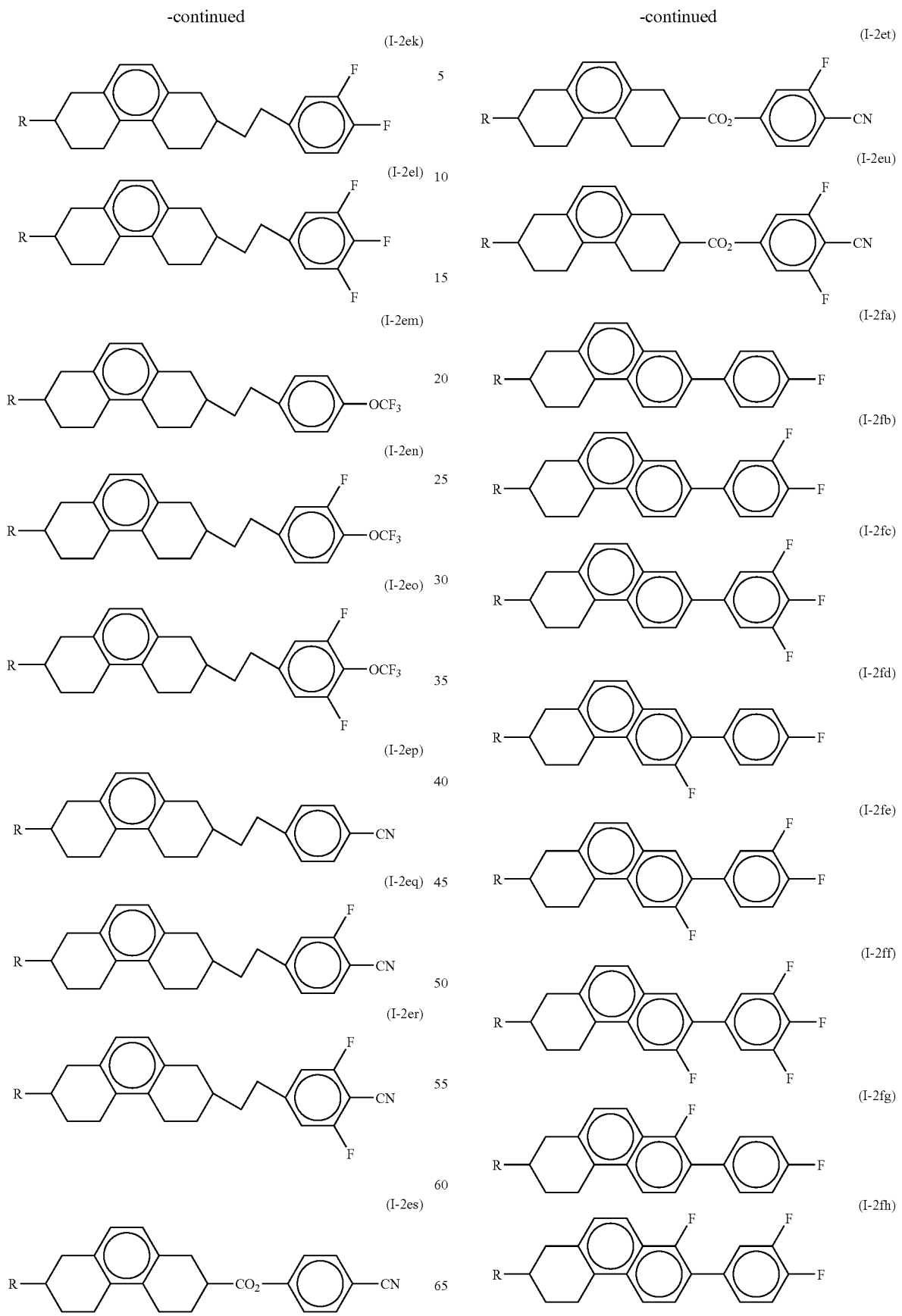

-continued
(I-2fi) 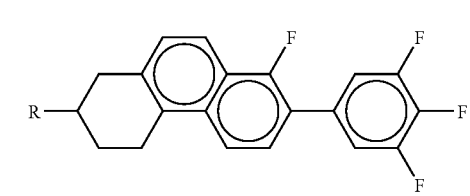
(I-2fj) 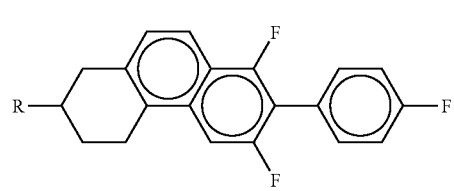
(I-2fk) 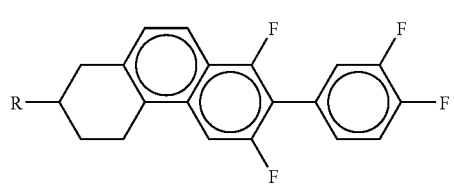
(I-2fl) 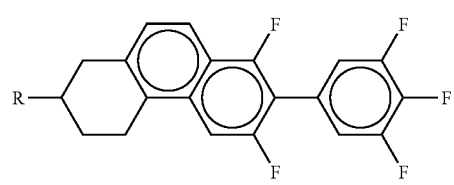
(I-2fm) 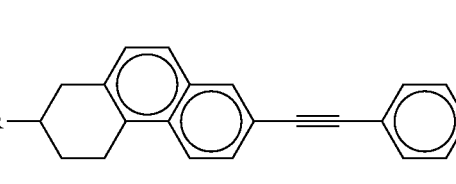
(I-2fn) 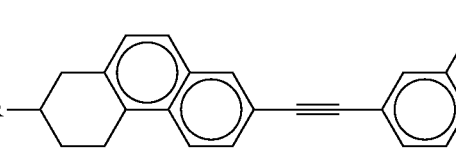
(I-2fo) 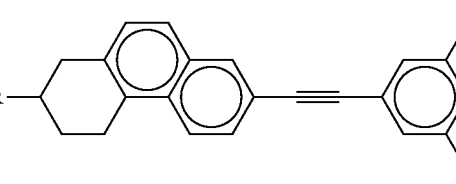
(I-2fp) 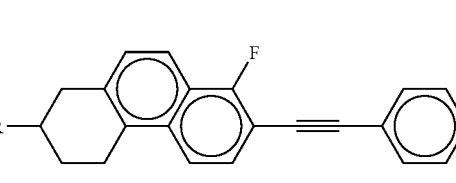
-continued
(I-2fq) 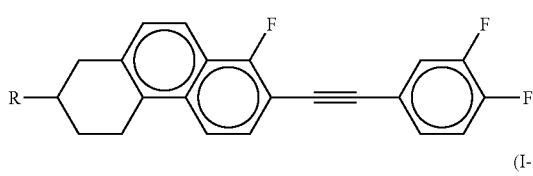
(I-2fr) 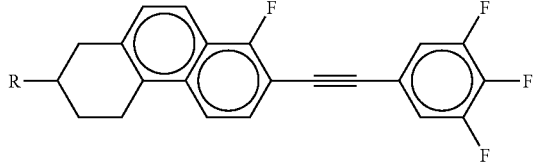
(I-2fs) 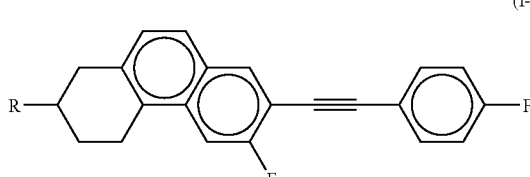
(I-2ft) 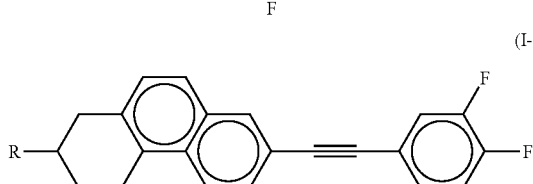
(I-2fu) 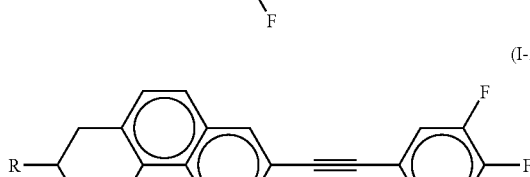
(I-2fv) 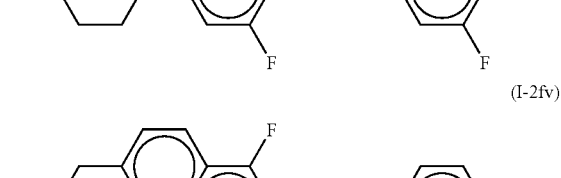
(I-2fw) 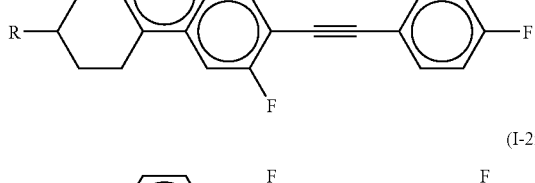
(I-2fx) 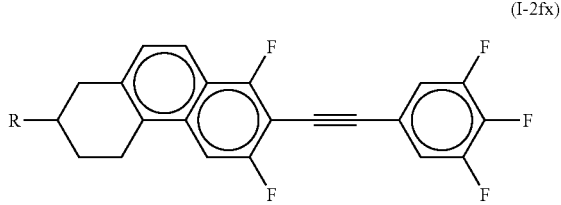

(I-2ga) 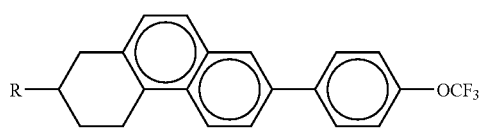
(I-2gb) 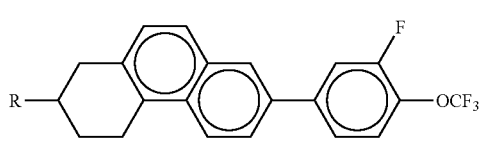
(I-2gc) 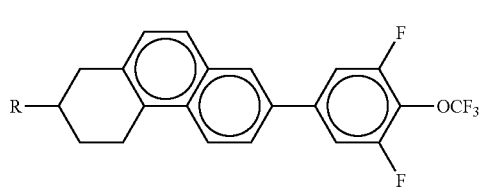
(I-2gd) 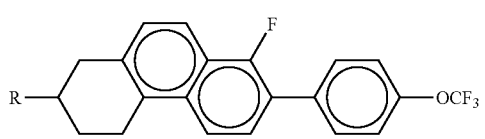
(I-2ge) 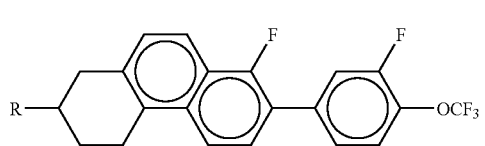
(I-2gf) 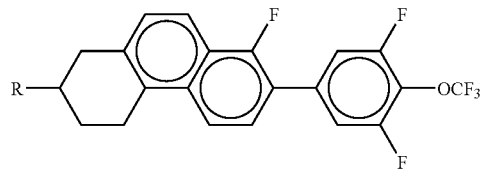
(I-2gg) 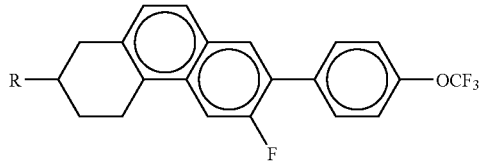
(I-2gh) 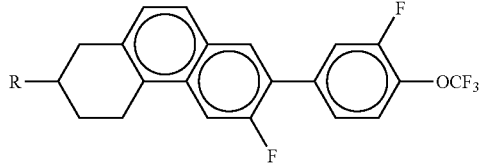
(I-2gi) 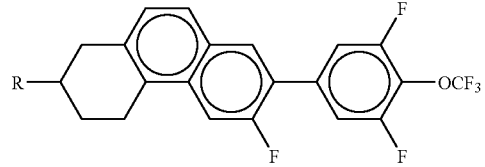
(I-2gj) 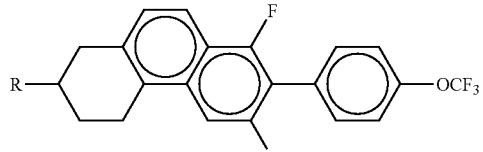
(I-2gk) 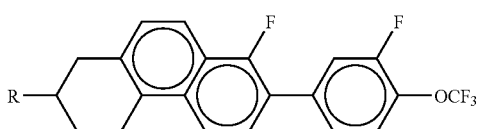
(I-2gl) 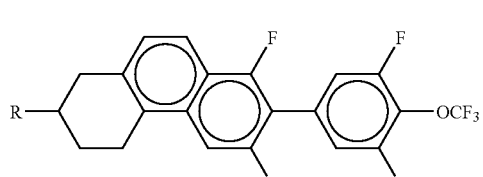
(I-2gm) 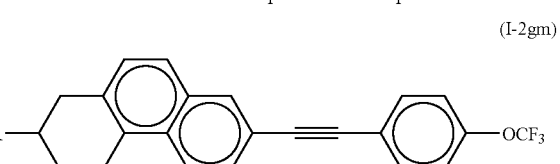
(I-2gn) 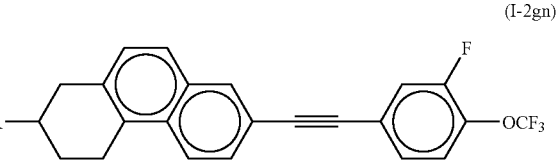
(I-2go) 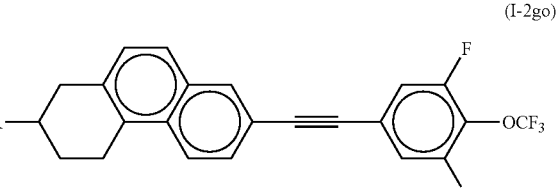
(I-2gp) 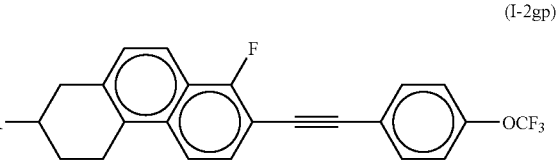
(I-2gq) 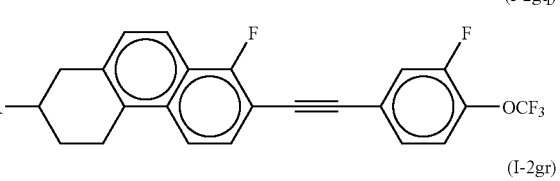
(I-2gr) 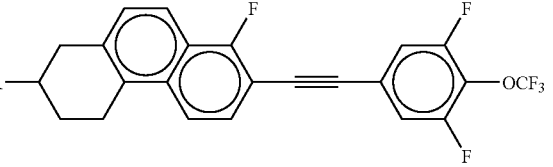

-continued
(I-2gs)
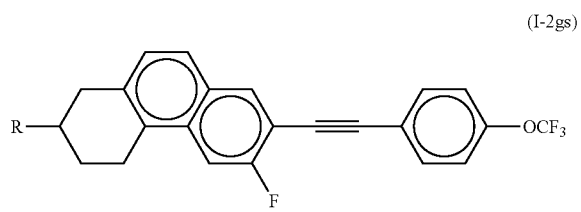
(I-2gt)
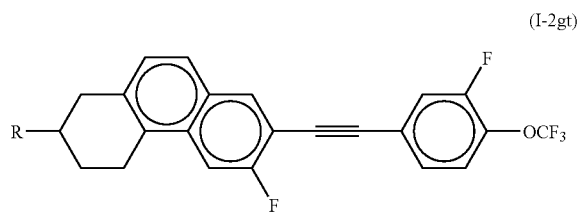
(I-2gu)
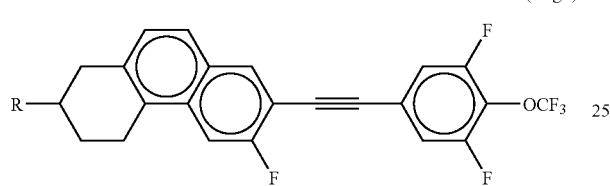
(I-2gv)
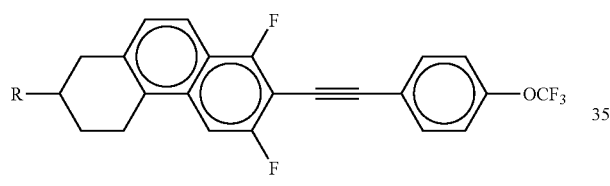
(Igw)
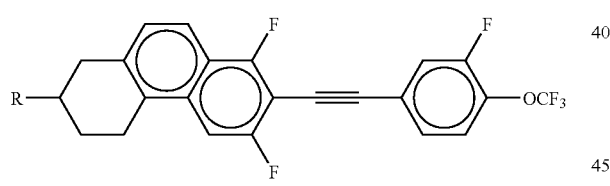
(I-2gx)
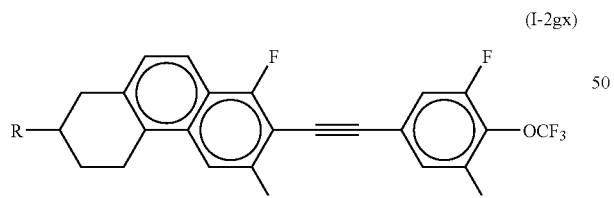
(I-2ha)
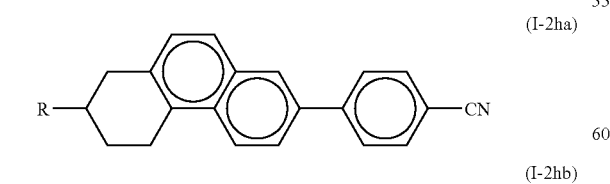
(I-2hb)
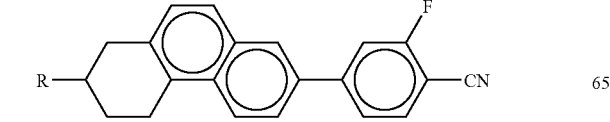
-continued
(I-2hc)
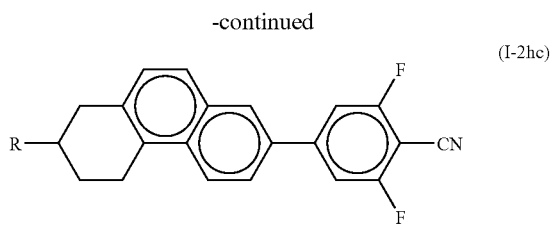
(I-2hd)
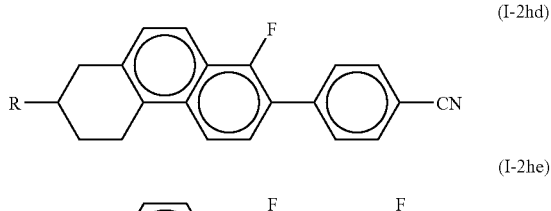
(I-2he)
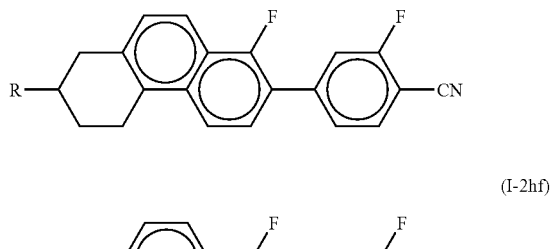
(I-2hf)
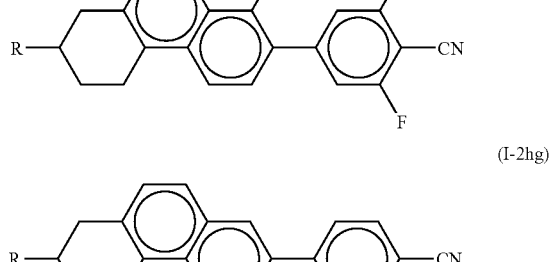
(I-2hg)
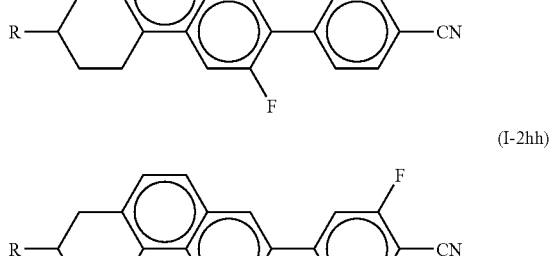
(I-2hh)
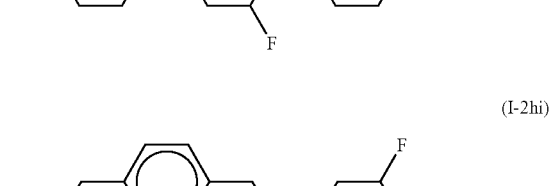
(I-2hi)
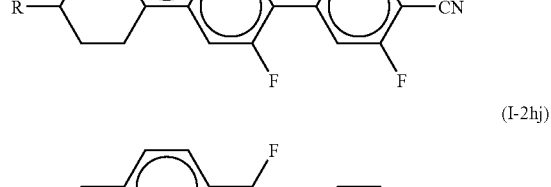
(I-2hj)
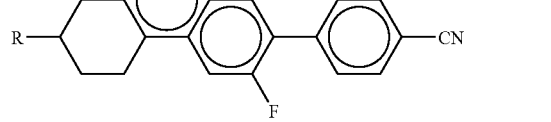

-continued
(I-2hk)
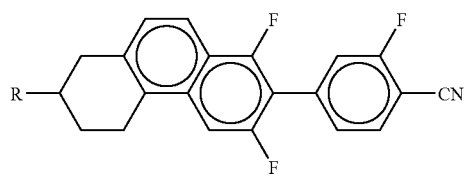
(I-2hl)
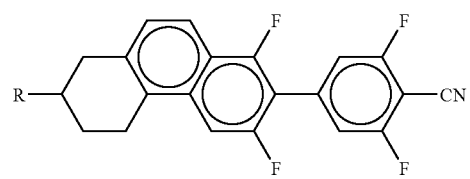
(I-2hm)
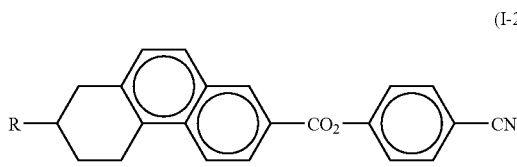
(I-2hn)
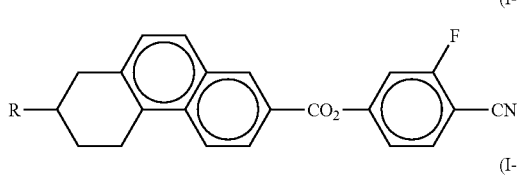
(I-2ho)
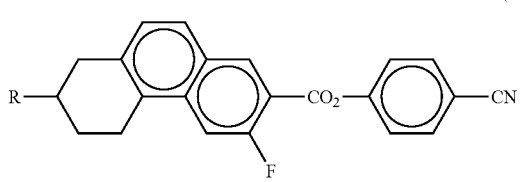
(I-2hp)
(I-2hq)
(I-2hr)
(I-2hs)
-continued
(I-2ht)
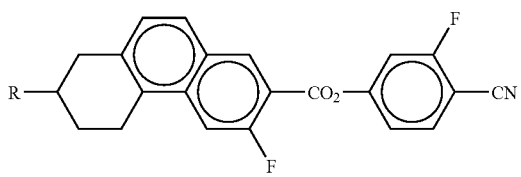
(I-2hu)
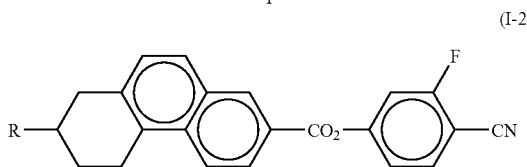
(I-2hv)
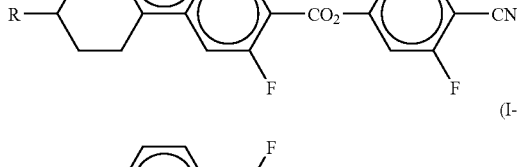
(I-2hw)
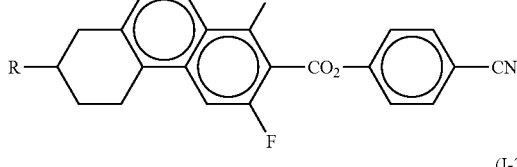
(I-2hx)
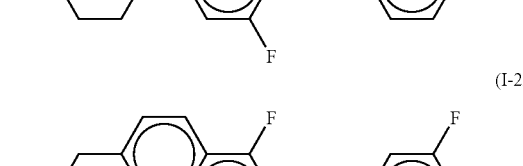
(I-3aa)
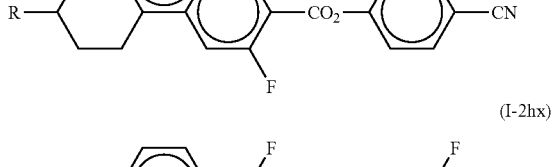
(I-3ab)
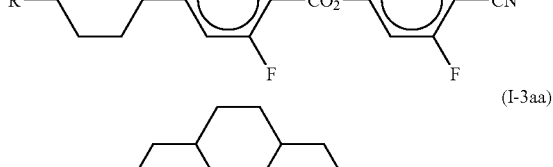
(I-3bc)
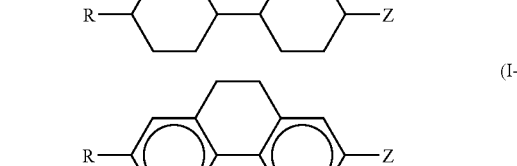
(I-3ad)
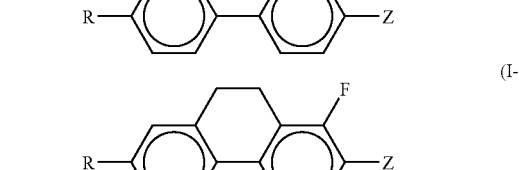

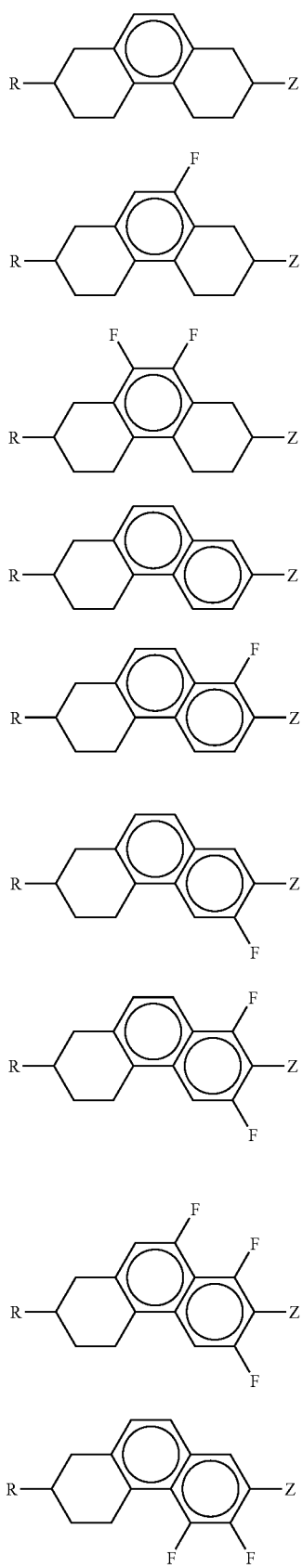
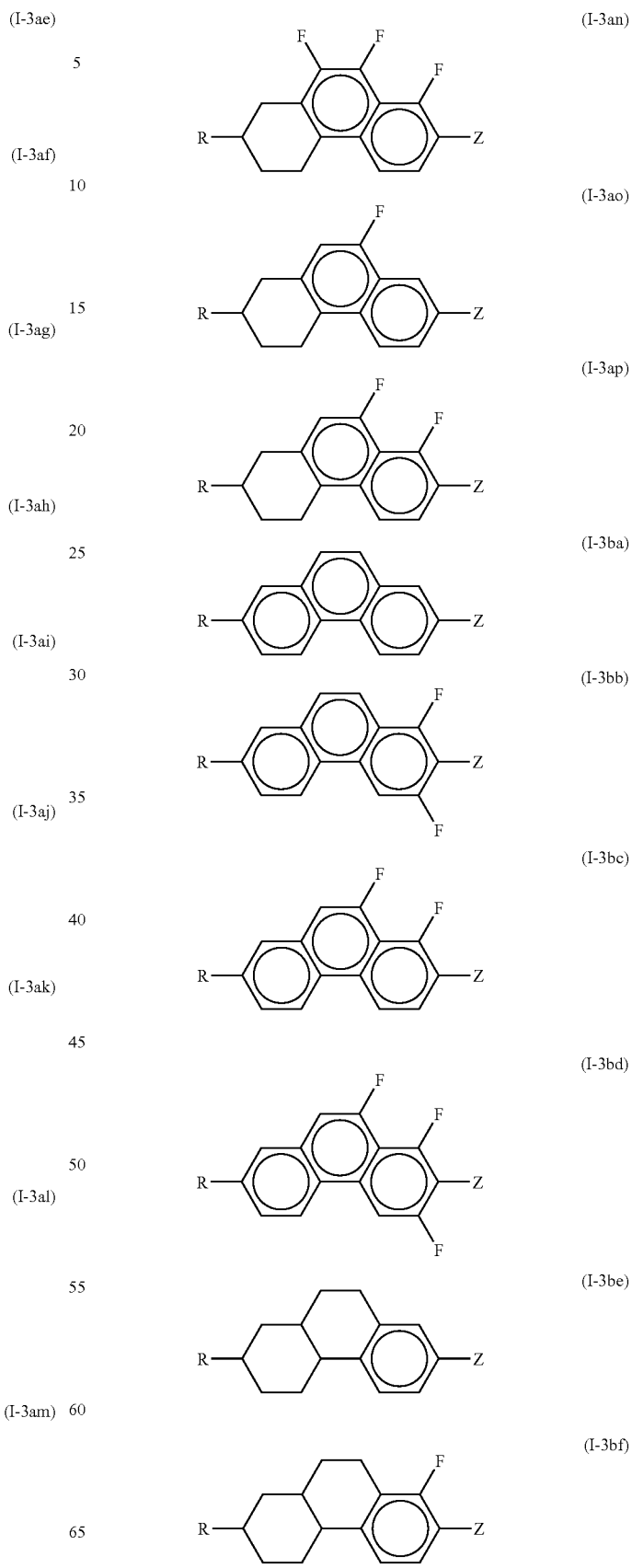

-continued
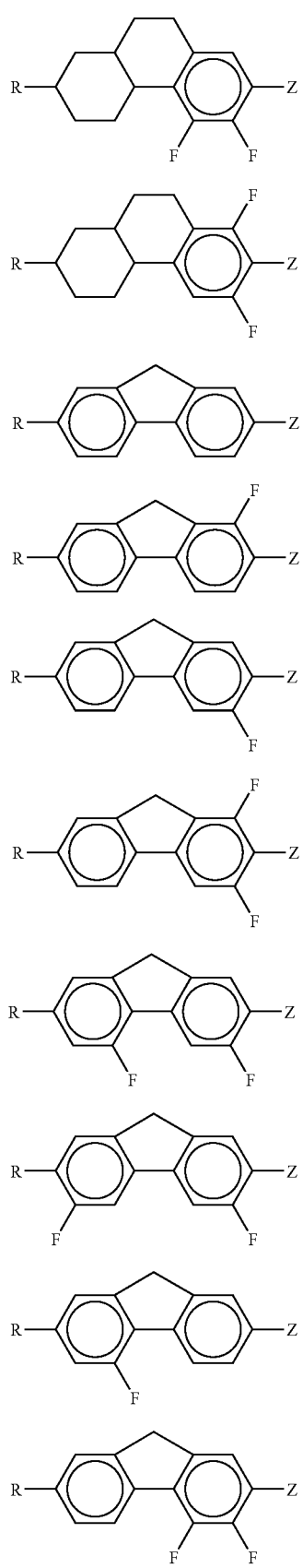
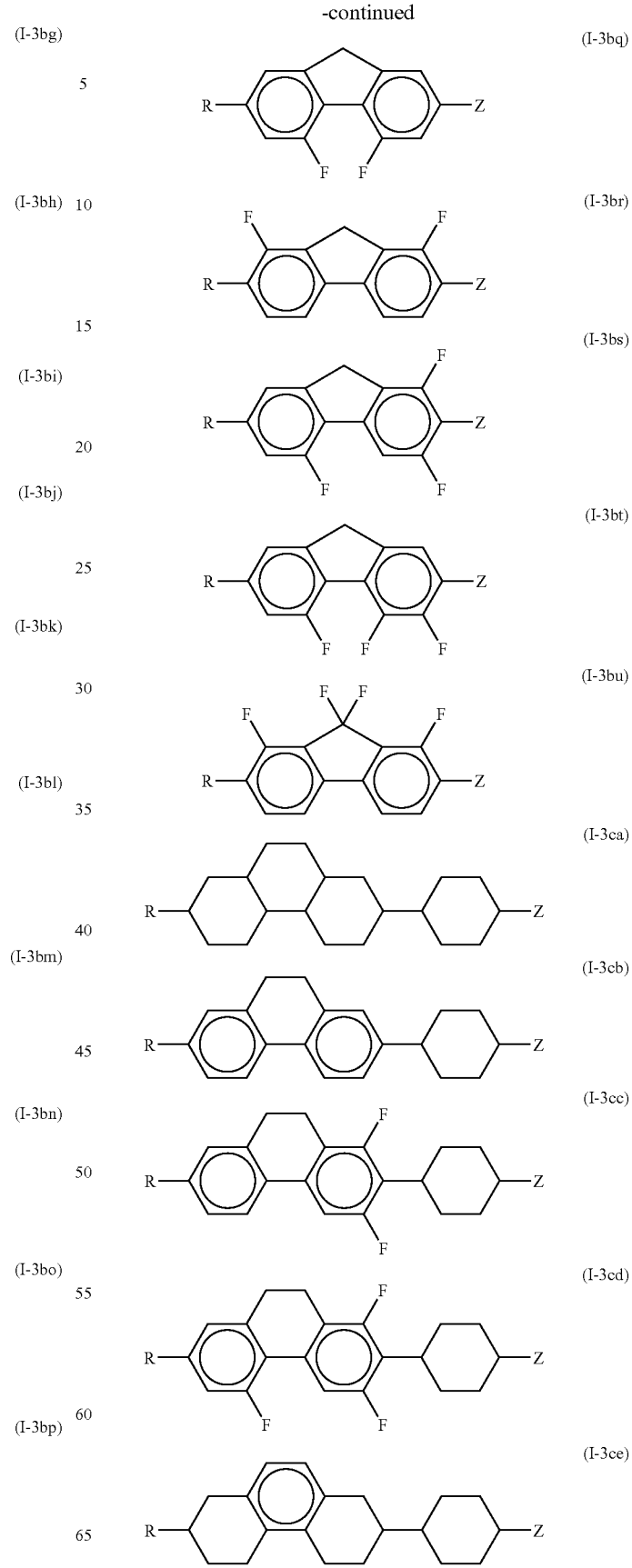

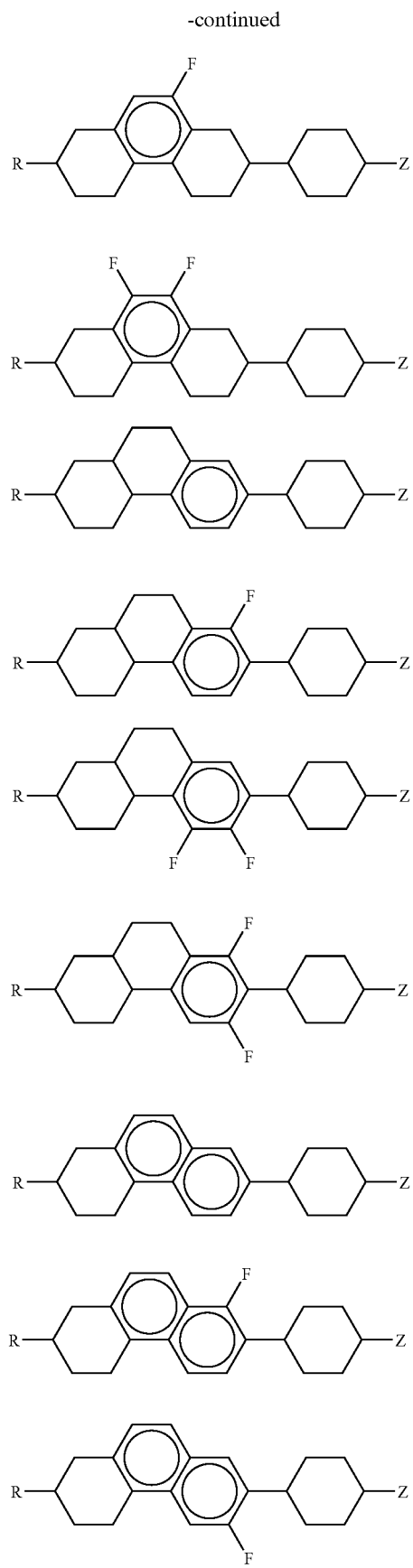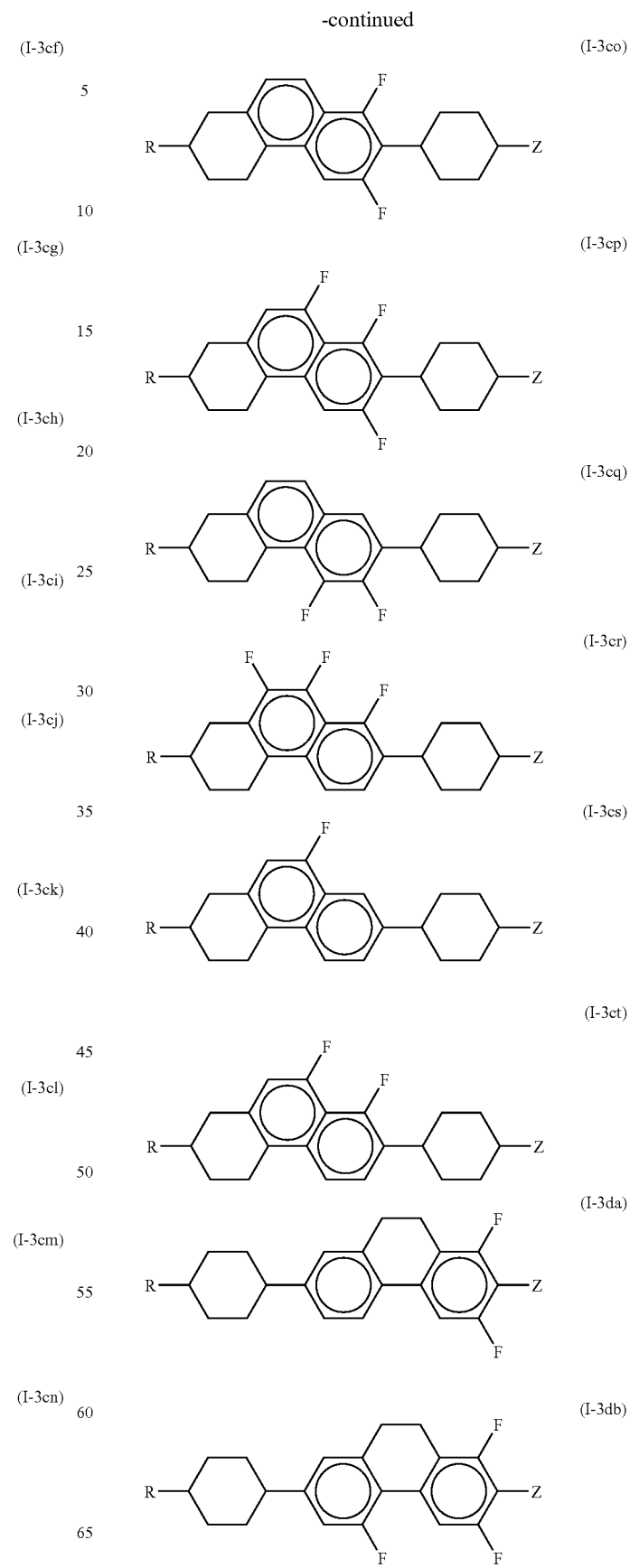

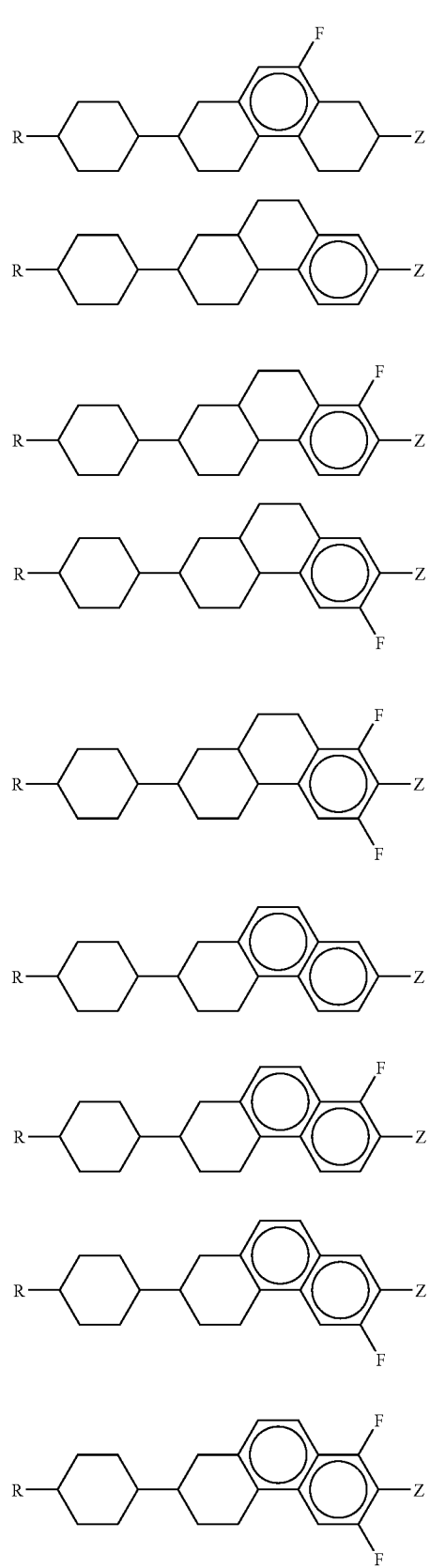
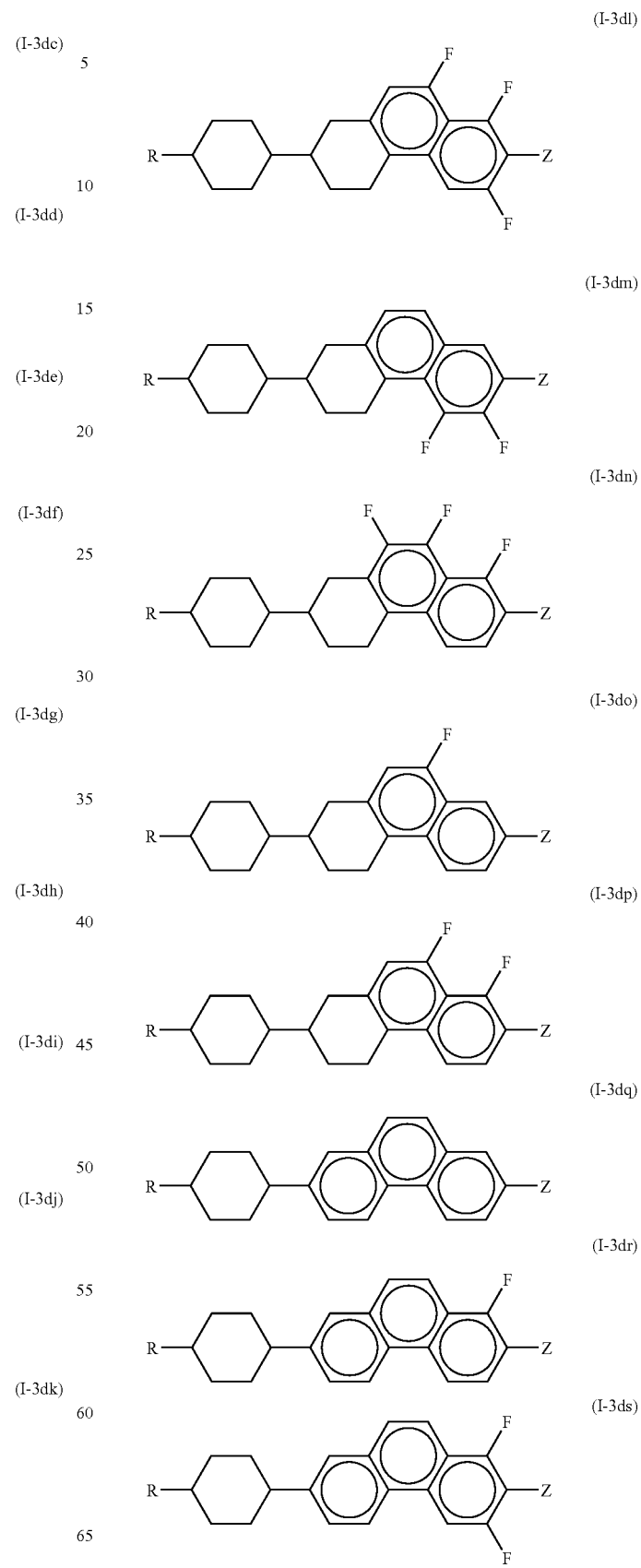

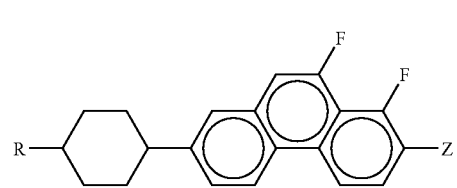
(I-3dt)
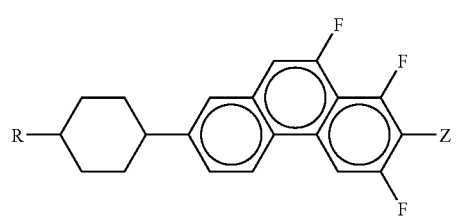
(I-3du)
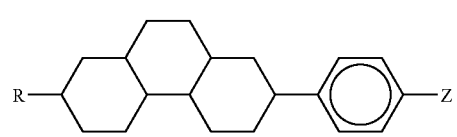
(I-3ea)
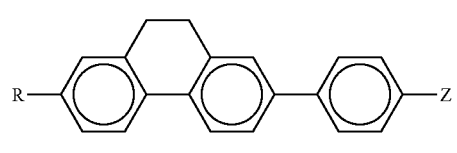
(I-3eb)
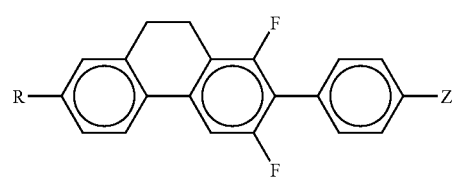
(I-3ec)
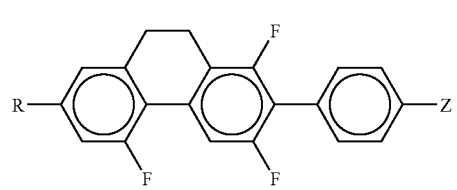
(I-3ed)
(I-3ee)
(I-3ef)
(I-3eg)
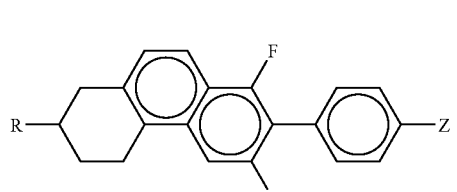
(I-3eh)
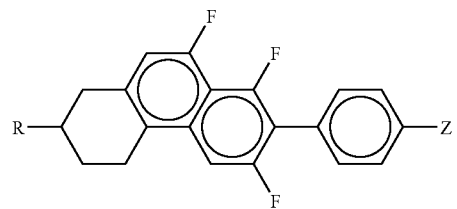
(I-3ei)
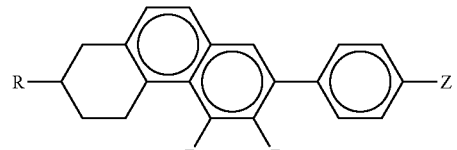
(I-3ej)
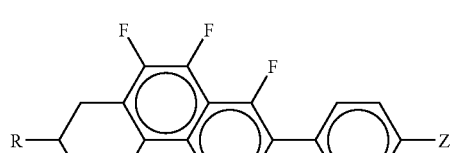
(I-3ek)
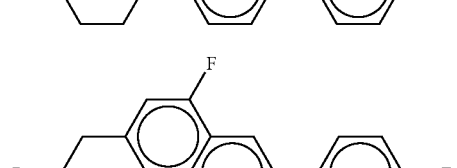
(I-3el)
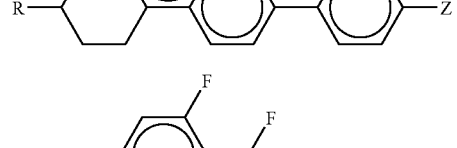
(I-3em)
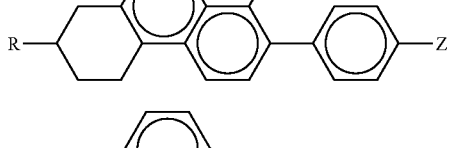
(I-3fa)
(I-3fb)
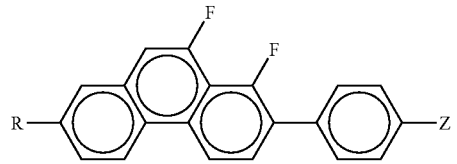
(I-3fb)
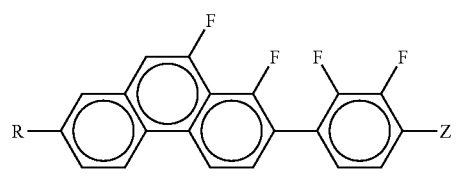
(I-3fc)

-continued
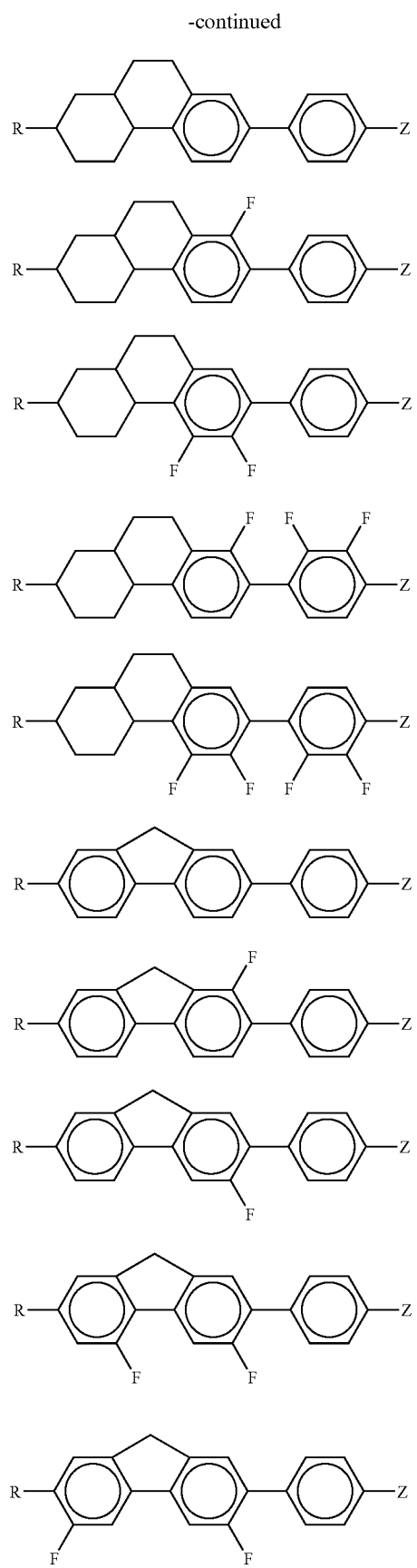
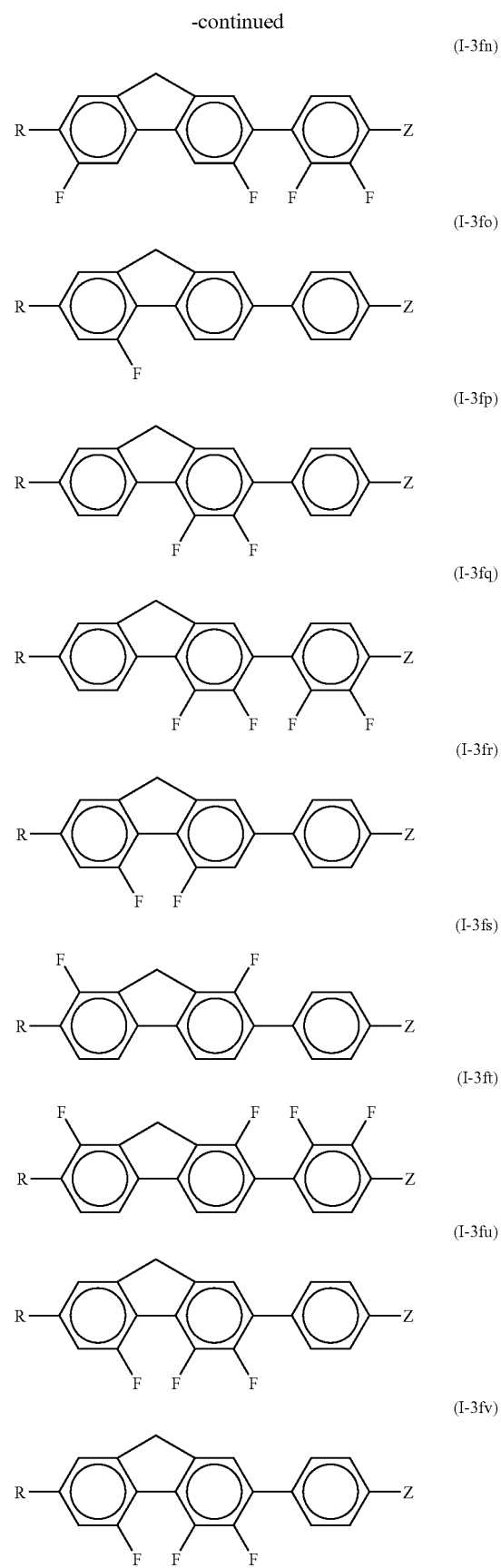

-continued
(I-3fw)
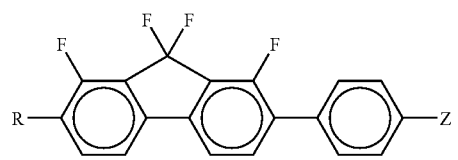
(I-3fx)
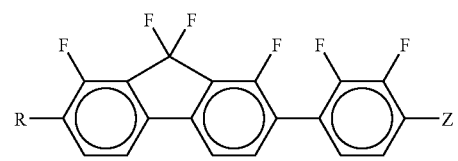
(I-3ga)
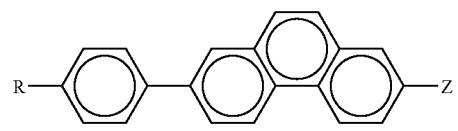
(I-3gb)
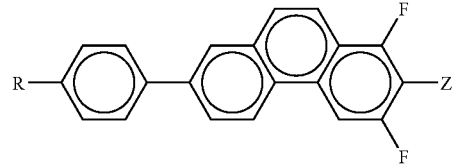
(I-3gc)
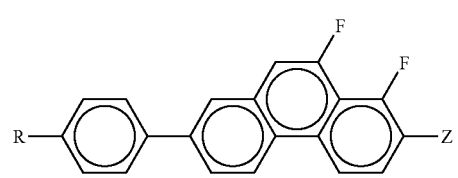
(I-3gd)
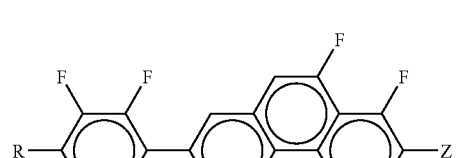
(I-3ge)
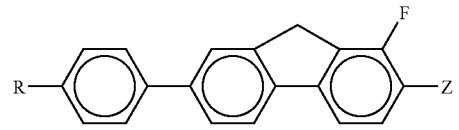
(I-3gf)
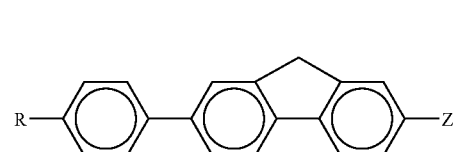
(I-3gg)
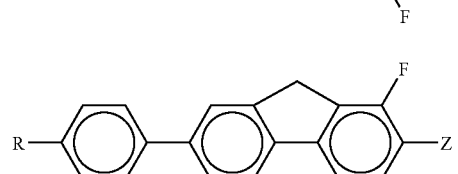
-continued
(I-3gh)
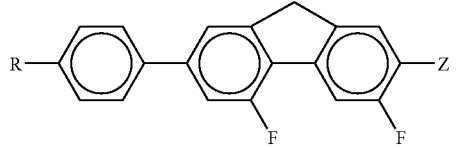
(I-3gi)
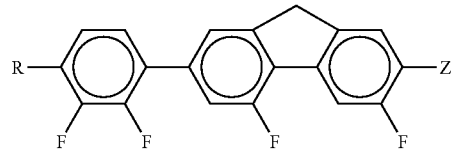
(I-3gj)
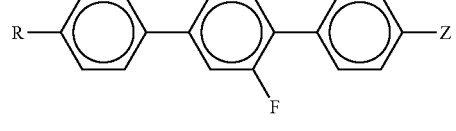
(I-3gk)
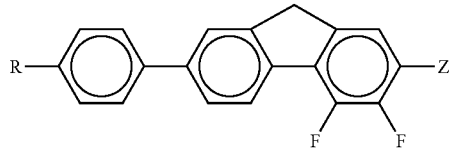
(I-3gl)
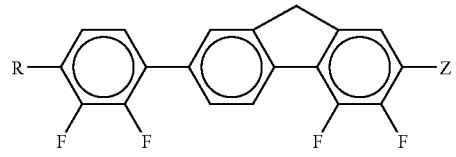
(I-3gm)
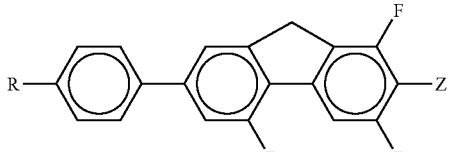
(I-3gn)
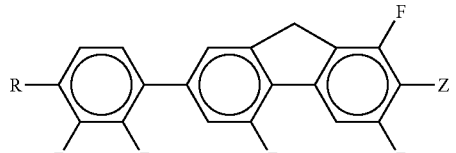
(I-3go)
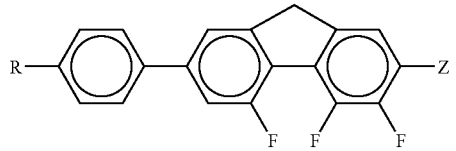
(I-3gp)
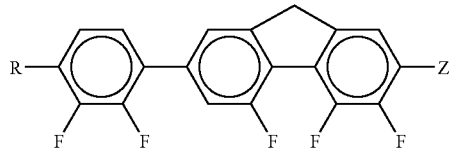

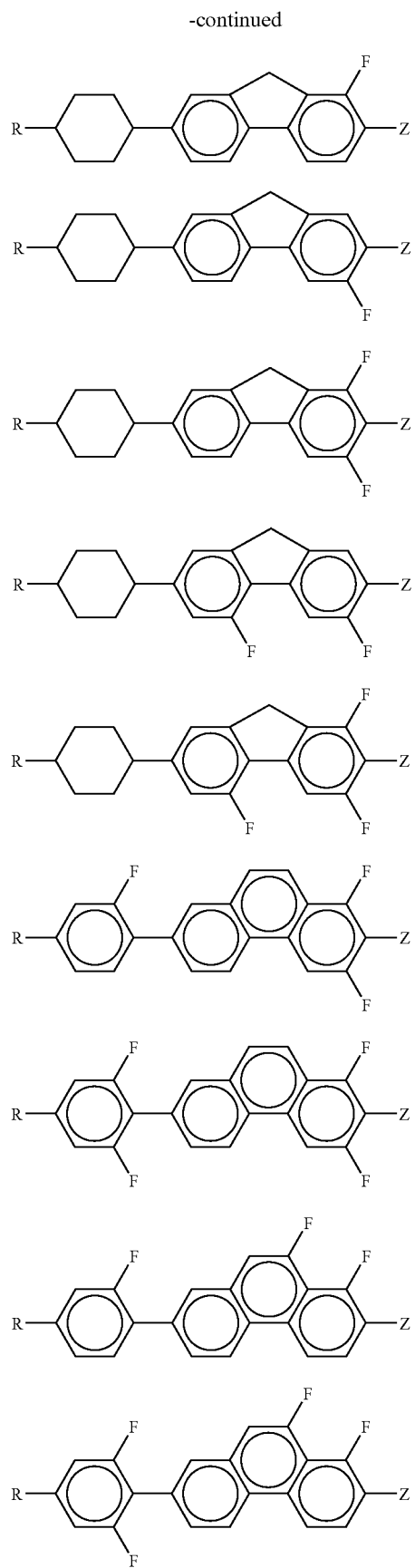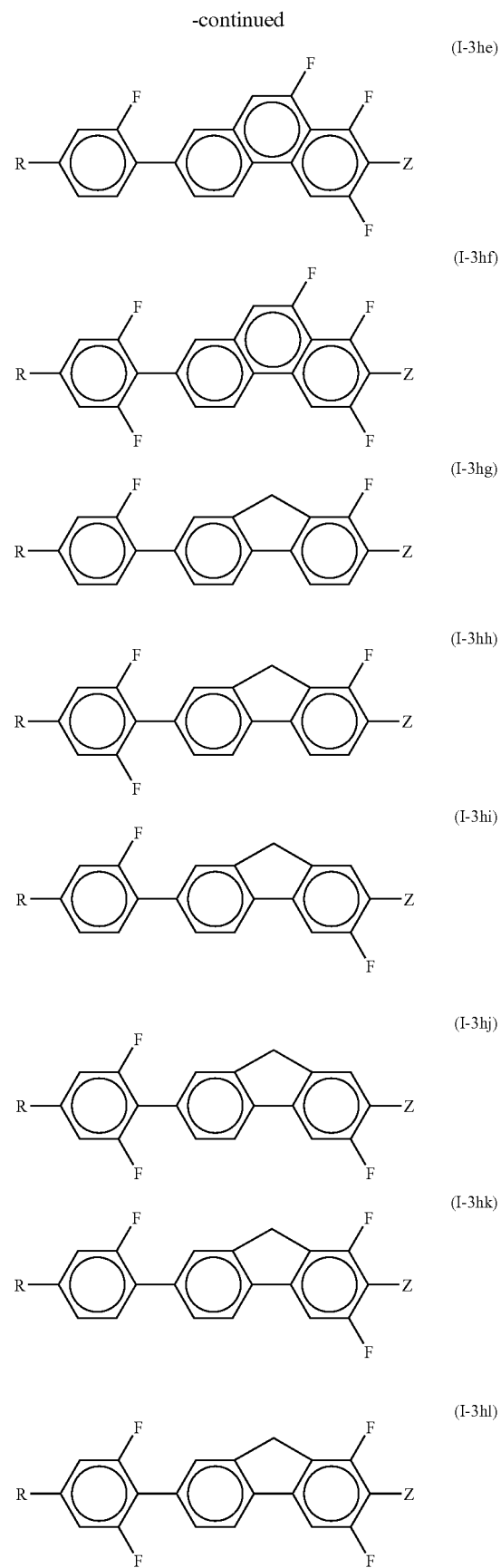

-continued

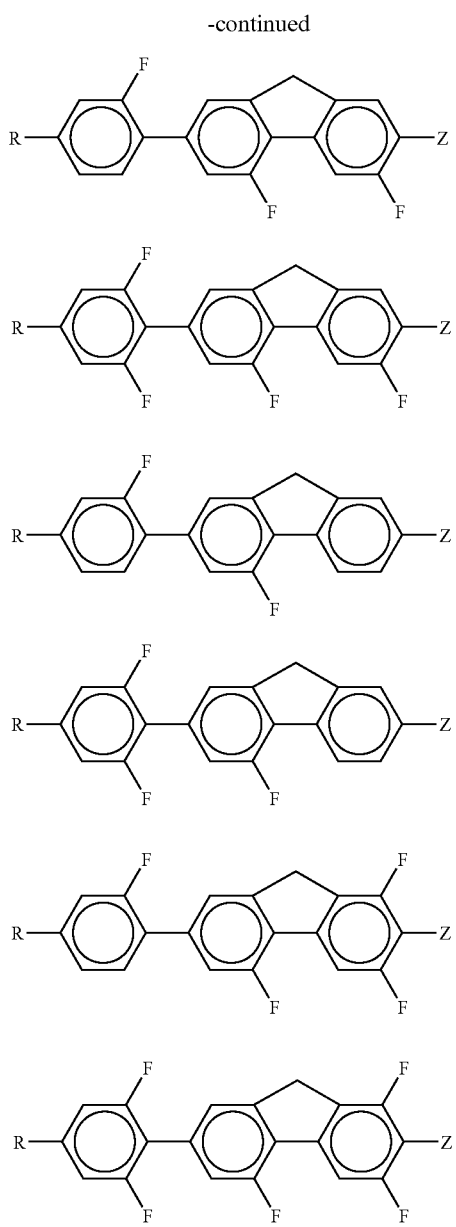

(I-3hm)
(I-3hn)
(I-3ho)
(I-3hp)
(I-3hq)
(I-3hr)

(wherein, R represents a straight chain alkyl group of 1 to 7 carbon atoms, or a straight chain alkenyl group of one of the structures shown below, and Z represents either the same meaning as R, or a fluorine atom.)

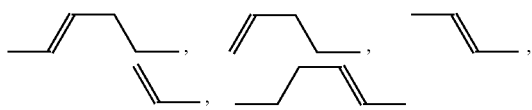

(the structural formulas shown are assumed to link to a ring at the right hand terminal)

A compound of the general formula (I) can be produced in the manner described below.

1. Production of the General Formula (I) in which the Ring B Comprises a 9,10-dihydrophenanthrene Skeleton or a Fluorene Skeleton 1-1. Production of General Formulas from (I-1fa) to (I-1fc), General Formulas from (I-1fg) to (I-1fi), General Formulas from (I-1ga) to (I-1gc), and General Formulas from (I-1ha) to (I-1hc)

By reacting a compound represented by the general formula (II)

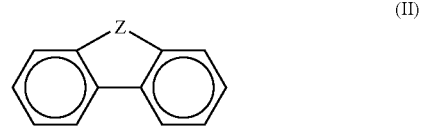
(II)

(wherein, Z represents a —$CH_2CH_2$— or —$CH_2$—) with a carboxylic acid chloride of the general formula (III) in the presence of a Lewis acid such as aluminum chloride,

(III)

(wherein, R represents a hydrogen atom or an alkyl group of 1 to 17 carbon atoms), a compound represented by the general formula (IV) can be produced

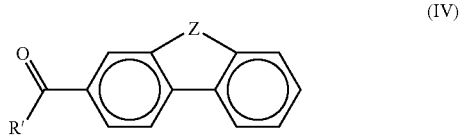
(IV)

(wherein, R represents the same meaning as in (III), and Z represents the same meaning as in (II)), and by reducing the carbonyl group by a Wolff Kishner reduction or the like, a compound represented by the general formula (V) can be obtained

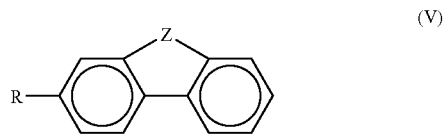
(V)

(wherein, R represents the same meaning as in (III), and Z represents the same meaning as in (II)), and subsequent halogenation yields the general formula (VI)

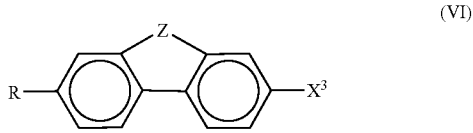
(VI)

(wherein, R represents the same meaning as in (III), Z represents the same meaning as in (II), and $X^3$ represents a bromine atom or an iodine atom). By reacting this compound with a compound of the general formula (VII) in the presence of a transition metal catalyst,

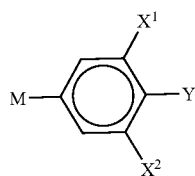

(VII)

(wherein, M represents MgX (where X represents a chlorine atom, a bromine atom or an iodine atom), a metal atom such as Li, B(OH)$_2$, or SiF(CH$_3$)$_2$, X$^1$, X$^2$ and Y represent the same meaning as in the general formula (I), although the case in which Y is a cyano group is excluded), compounds of the general formula (IA-1), including the general formulas from (I-1fa) to (I-1fc), general formulas from (I-1fg) to (I-1fi), general formulas from (I-1ga) to (I-1gc) and general formulas from (I-1ha) to (I-1hc) can be produced.

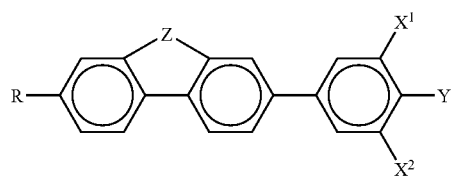

(IA-1)

(wherein, R, Y, X$^1$ and X$^2$ represent the same meaning as in (I), although the case in which Y is a cyano group is excluded, and Z represents the same meaning as in (II))

1-2. Production of General Formulas from (I-1fm) to (I-1fo), General Formulas from (I-1fs) to (I-1fu), General Formulas from (I-1gm) to (I-1go), and General Formulas from (I-1hm) to (I-1ho)

By reacting a compound represented by the general formula (VIII)

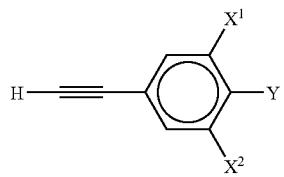

(VIII)

(wherein, Y, X$^1$ and X$^2$ represent the same meaning as in (I)) with a compound of the general formula (VI), in the presence of a transition metal catalyst such as tetrakis(triphenylphosphine)palladium (0), compounds of the general formula (IA-2), including the general formulas from (I-1fm) to (I-1fo), general formulas from (I-1fs) to (I-1fu), general formulas from (I-1gm) to (I-1go), and general formulas from (I-1hm) to (I-1ho) can be produced.

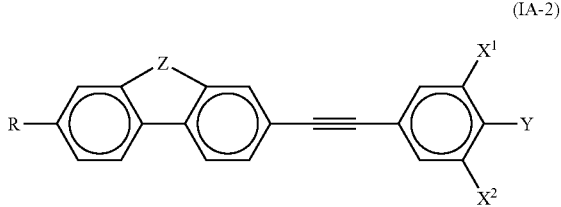

(IA-2)

(wherein, R, Y, X$^1$ and X$^2$ represent the same meaning as in (I), and Z represents the same meaning as in (II))

1-3. Production of General Formulas from (I-1gd) to (I-1gi), and General Formulas from (I-1hd) to (I-1hi)

Reaction of the aforementioned general formula (VI) with an alkoxide such as sodium methoxide or the like yields a compound represented by the general formula (IX)

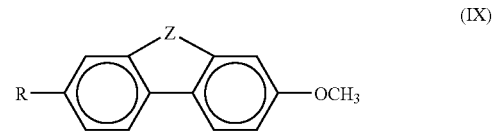

(IX)

(wherein, R represents the same meaning as in (III), and Z represents the same meaning as in (II)), and by subsequently removing the phenol protective group using hydrobromic acid or the like, the general formula (X) is obtained.

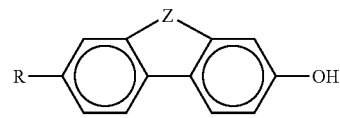

(X)

(wherein, R represents the same meaning as in (III), and Z represents the same meaning as in (II)). Halogenation of the general formula (X) using an electrophilic halogenation reagent yields the general formula (XI).

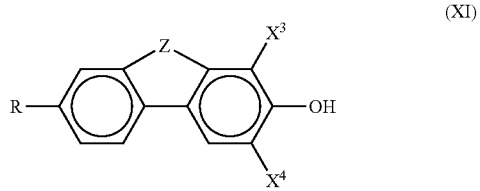

(XI)

(wherein, R represents the same meaning as in (I), Z represents the same meaning as in (II), and X$^3$ and X$^4$ each represent, independently, a hydrogen atom, a fluorine atom or a chlorine atom, although at least one of X$^3$ and X$^4$ represents a hydrogen atom.) Representative examples of the electrophilic halogenation reagent used in this reaction include bromine, chlorine gas, fluorine gas or fluorinated xenon, as well as N-fluoro pyridinium derivatives such as MEC reagent (manufactured by Daikin Industries (Ltd.)) or Accuflor NFPy (manufactured by Allied Signal), and Accuflor NFTh, Accuflor NFSi (manufactured by Allied Signal), or F-TEDA-BF4 (manufactured by Air Products). By reacting the general formula (XI) with trifluoromethanesulfonic anhydride or the like, a compound of the general formula (XII) is obtained

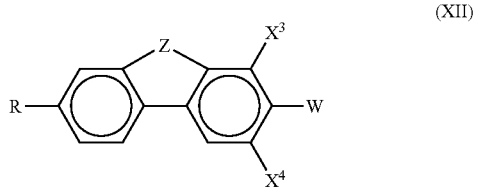

(XII)

(wherein, R represents the same meaning as in (I), Z represents the same meaning as in (II), $X^3$ and $X^4$ represent the same meaning as in (XI), and W represents a leaving group such as a trifluoromethanesulfonyloxy group, a methanesulfonyloxy group, a benzenesulfonyloxy group or a p-toluenesulfonyloxy group), and by subsequent reaction with the general formula (VII) in the presence of a transition metal catalyst such as tetrakis(triphenylphosphine)palladium (0), and separation of the thus obtained isomers by column chromatography, compounds of the general formula (IA-3), including the general formulas from (I-1gd) to (I-1gi), and the general formulas from (I-1hd) to (I-1hi) can be produced.

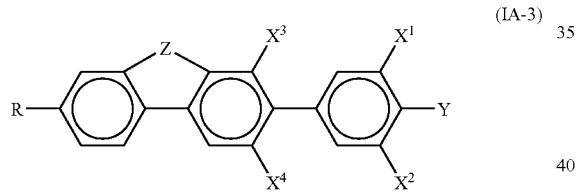

(IA-3)

(wherein, R, Y, $X^1$ and $X^2$ represent the same meaning as in (I), Z represents the same meaning as in (II), and $X^3$ and $X^4$ represent the same meaning as in (XI))

1-4. Production of General Formulas from (I-1gp) to (I-1gu), and General Formulas from (I-1hp) to (I-1hu)

By reacting the aforementioned general formula (VIII) and the general formula (XII) in the presence of a transition metal catalyst such as tetrakis(triphenylphosphine)palladium (0), compounds of the general formula (IA-4), including the general formulas from (I-1gp) to (I-1gu), and the general formulas from (I-1hp) to (I-1hu) can be produced.

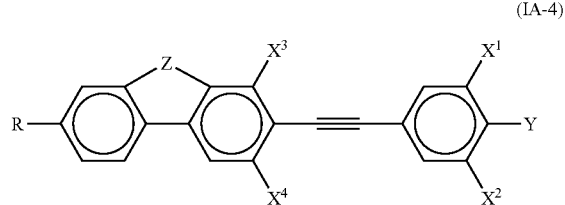

(IA-4)

(wherein, R, Y, $X^1$ and $X^2$ represent the same meaning as in (I), Z represents the same meaning as in (II), and $X^3$ and $X^4$ represent the same meaning as in (XI))

1-5. Production of General Formulas from (I-1fd) to (I-1ff), General Formulas from (I-1fj) to (I-1fl), General Formulas from (I-1gi) to (I-1gl), and General Formulas from (I-1hj) to (I-1hl)

Reaction of a compound represented by the general formula (XIII)

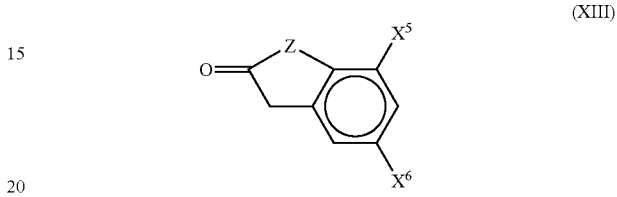

(XIII)

(wherein, Z represents the same meaning as in (II), and $X^5$ and $X^6$ each represent, independently, a fluorine atom or a chlorine atom) with a secondary amine such as pyrrolidine yields an enamine of the general formula (XIX).

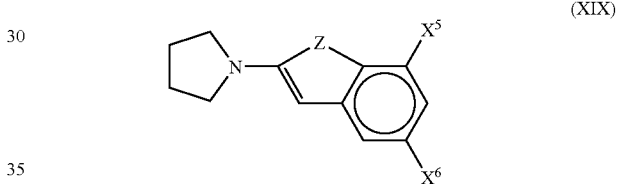

(XIX)

(wherein, Z represents the same meaning as in (II), and $X^5$ and $X^6$ represent the same meaning as in (XIII)). Reaction of this compound with methyl vinyl ketone, followed by a cyclization under acid conditions yields a compound of the general formula (XX),

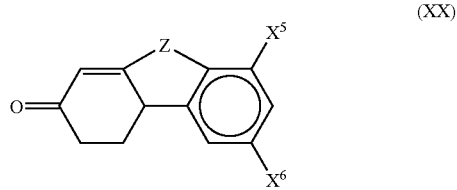

(XX)

(wherein, Z represents the same meaning as in (II), and $X^5$ and $X^6$ represent the same meaning as in (XIII)), and further reaction of this compound with a compound of the general formula (XXI)

RM    (XXI)

(wherein, R represents the same meaning as in (I), and M represents MgX (where X represents a chlorine atom, a bromine atom or an iodine atom), or a metal atom such as Li), and subsequent dehydration in the presence of an acid catalyst yields a compound represented by the general formula (XXII).

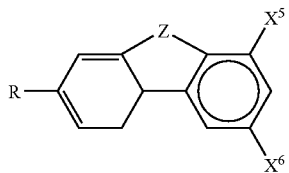

(XXII)

(wherein, R represents the same meaning as in (I), Z represents the same meaning as in (II), and $X^5$ and $X^6$ represent the same meaning as in (XIII)). Oxidation of this compound using an oxidizing agent such as bromine, DDQ (2,3-dichloro-5,6-dicyano-1,4-benzoquinone) or chloranil yields a compound of the general formula (XXIII).

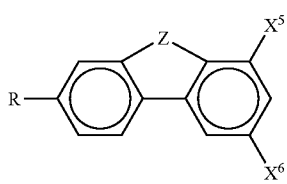

(XXIII)

(wherein, R represents the same meaning as in (I), Z represents the same meaning as in (II), and $X^5$ and $X^6$ represent the same meaning as in (XIII)). Lithiation of this compound with an alkyl lithium such as butyl lithium and subsequent reaction with bromine or iodine yields the general formula (XXIV),

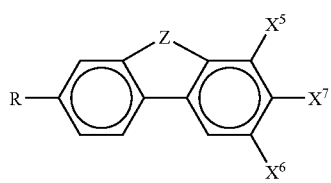

(XXIV)

(wherein, R represents the same meaning as in (I), Z represents the same meaning as in (II), $X^5$ and $X^6$ represent the same meaning as in (XIII), and $X^7$ represents a bromine atom or an iodine atom), and by reacting this compound with a compound of the general formula (VII), compounds of the general formula (IA-5), including the general formulas from (I-1fd) to (I-1ff), the general formulas from (I-1fj) to (I-1fl), the general formulas from (I-1gi) to (I-1gl), and the general formulas from (I-1hj) to (I-1hl) can be produced.

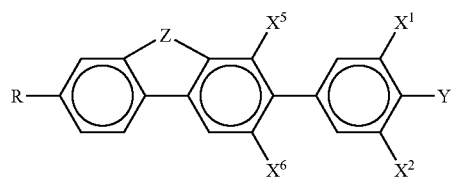

(IA-5)

(wherein, R, $X^1$, $X^2$ and Y represent the same meaning as in (I), Z represents the same meaning as in (II), and $X^5$ and $X^6$ represent the same meaning as in (XIII))

1-6. Production of General Formulas from (I-1fv) to (I-1fx), General Formulas from (I-1fp) to (I-1fr), General Formulas from (I-1gv) to (I-1gx), and General Formulas from (I-1hv) to (I-1hx)

By reacting the aforementioned general formula (VIII) and the general formula (XIV) in the presence of a transition metal catalyst such as tetrakis(triphenylphosphine)palladium (0), compounds of the general formula (IA-6), including the general formulas from (I-1fv) to (I-1fx), the general formulas from (I-1fp) to (I-1fr), the general formulas from (I-1gv) to (I-1gx), and the general formulas from (I-1hv) to (I-1hx) can be produced.

(IA-6)

(wherein, R, Y, $X^1$ and $X^2$ represent the same meaning as in (I), Z represents the same meaning as in (II), and $X^5$ and $X^6$ represent the same meaning as in (XIII))

1-7. Production of General Formulas from (I-1ia) to (I-1ib), and General Formulas from (I-1dg) to (I-1dh)

Reaction of the general formula (VI) with a compound of a general formula (XXV)

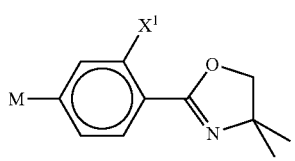

(XXV)

(wherein, $X^1$ represents the same meaning as in (I), and M represents the same meaning as in (XXI)) yields a compound of the general formula (IX)

(XXVI)

(wherein, R and $X^1$ represent the same meaning as in (I), and Z represents the same meaning as in (II)), and by subsequent removal of the cyano group protective group using phosphorus oxychloride or the like, compounds of the general formula (IA-7), including the general formulas from (I-1ia) to (I-1ib), and the general formulas from (I-1dg) to (I-1dh) can be produced.

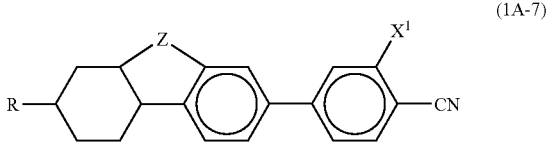
(1A-7)

(wherein, R and $X^1$ represent the same meaning as in (I), and Z represents the same meaning as in (II))

1-8. Production of General Formulas (I-1ic) and (I-1di)

Lithiation with an alkyl lithium such as butyl lithium of a compound of the general formula (IA-1a), which is a compound of the general formula (IA-1), the production of which has been previously described, in which the group Y is a hydrogen atom,

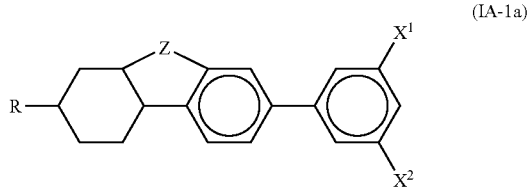
(IA-1a)

(wherein, R, $X^1$ and $X^2$ represent the same meaning as in (I) although those cases in which these groups are hydrogen atoms are excluded, and Z represents the same meaning as in (II)), and subsequent reaction with carbon dioxide gas yields the general formula (XXVII)

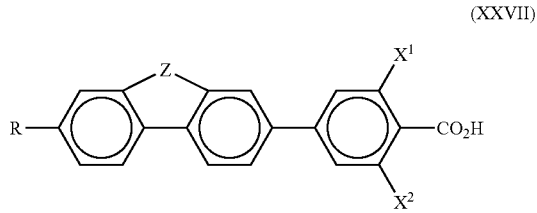
(XXVII)

(wherein, R, $X^1$ and $X^2$ represent the same meaning as in (I) although those cases in which these groups are hydrogen atoms are excluded, and Z represents the same meaning as in (II)), and conversion of this compound to an acid chloride, and subsequent reaction with ammonia yields a compound of the general formula (XXVIII)

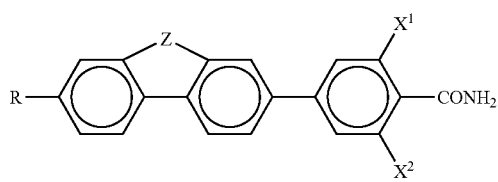
(XXVIII)

(wherein, R, $X^1$ and $X^2$ represent the same meaning as in (I) although those cases in which these groups are hydrogen atoms are excluded, and Z represents the same meaning as in (II)), and by performing a dehydration using phosphorus oxychloride or the like, compounds of the general formula (IA-8), including the general formulas (I-1ic) and (I-1di) can be produced.

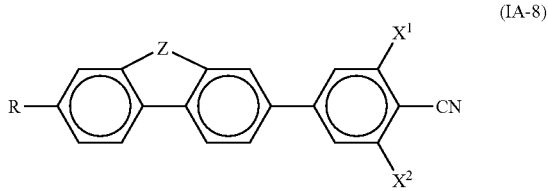
(IA-8)

(wherein, R, $X^1$ and $X^2$ represent the same meaning as in (I), and Z represents the same meaning as in (II))

1-9. Production of General Formulas from (I-1id) to (I-1ie), and General Formulas from (I-1ig) to (I-1ih)

Reaction of the general formula (XII) with the general formula (XXV) in the presence of a transition metal catalyst such as tetrakis(triphenylphosphine)palladium (0), yields the general formula (XXIX).

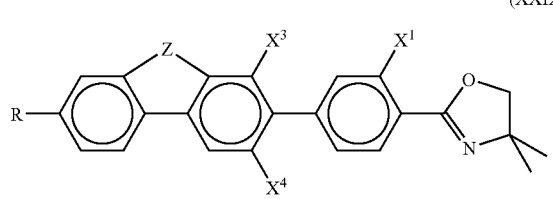
(XXIX)

(wherein, R and $X^1$ represent the same meaning as in (I), $X^3$ and $X^4$ represent the same meaning as in (XI), and Z represents the same meaning as in (II)). By deprotecting the general formula (XXIX) with phosphorus oxychloride or the like, and then separating the thus obtained isomeric mixture by column chromatography, compounds of the general formula (IA-9), including the general formulas from (I-1id) to (I-1ie), and the general formulas from (I-1ig) to (I-1ih) can be produced.

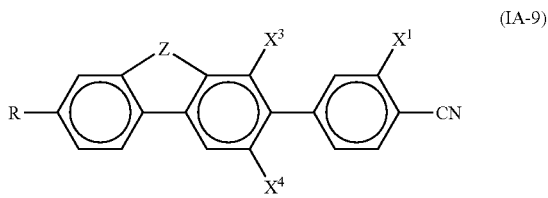
(IA-9)

(wherein, R and $X^1$ represent the same meaning as in (I), $X^3$ and $X^4$ represent the same meaning as in (XI), and Z represents the same meaning as in (II))

1-10. Production of General Formulas (I-1if) and (I-1ii)

Lithiation with an alkyl lithium such as butyl lithium of a compound of the general formula (IA-3a), which is a compound of the general formula (IA-3), for which the production has been previously described, in which the group Y is a hydrogen atom,

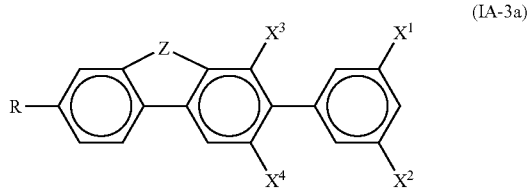

(IA-3a)

(wherein, R, $X^1$ and $X^2$ represent the same meaning as in (I) although those cases in which these groups are hydrogen atoms are excluded, $X^3$ and $X^4$ represent the same meaning as in (XI), and Z represents the same meaning as in (II)), and subsequent reaction with carbon dioxide gas yields the general formula (XXX)

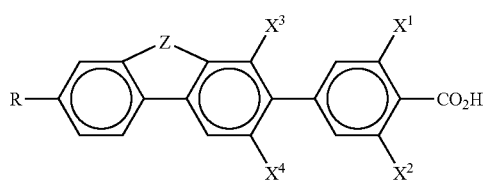

(XXX)

(wherein, R, $X^1$ and $X^2$ represent the same meaning as in (I) although those cases in which these groups are hydrogen atoms are excluded, and $X^3$ and $X^4$ represent the same meaning as in (XI)), and conversion of this compound to an acid chloride, and subsequent reaction with ammonia yields a compound of the general formula (XXXI)

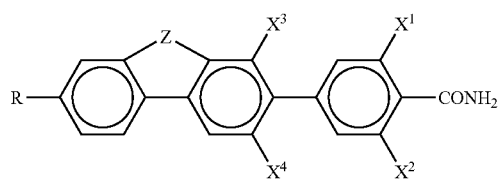

(XXXI)

(wherein, R, $X^1$ and $X^2$ represent the same meaning as in (I) although those cases in which these groups are hydrogen atoms are excluded, $X^3$ and $X^4$ represent the same meaning as in (XI), and Z represents the same meaning as in (II)), and by dehydrating this compound with phosphorus oxychloride or the like, and then separating the thus obtained isomeric mixture by column chromatography, compounds of the general formula (IA-10), including the general formulas (I-1if) and (I-1ii) can be produced.

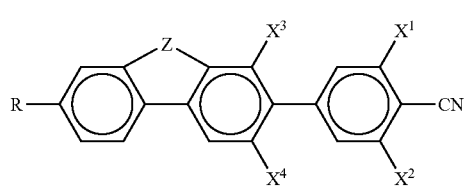

(IA-10)

(wherein, R, $X^1$ and $X^2$ represent the same meaning as in (I) although those cases in which these groups are hydrogen atoms are excluded, $X^3$ and $X^4$ represent the same meaning as in (XI), and Z represents the same meaning as in (II))

1-11. Production of General Formulas from (I-1ij) to (I-1ik), and General Formulas from (I-1dj) to (I-1dk)

Reaction of the general formula (XXIV) with the general formula (XXV) in the presence of a transition metal catalyst such as tetrakis(triphenylphosphine)palladium (0), yields the general formula (XXXII).

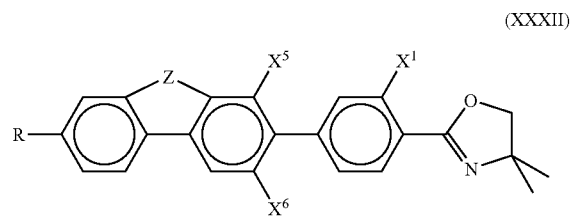

(XXXII)

(wherein, R and $X^1$ represent the same meaning as in (I), Z represents the same meaning as in (II), and $X^5$ and $X^6$ represent the same meaning as in (XIII)). By deprotecting the general formula (XXXII) with phosphorus oxychloride or the like, compounds of the general formula (IA-11), including the general formulas from (I-1ij) to (I-1ik), and the general formulas from (I-1dj) to (I-1dk) can be produced.

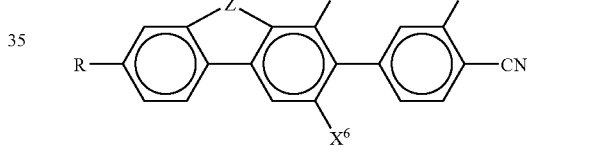

(IA-11)

(wherein, R and $X^1$ represent the same meaning as in (I), Z represents the same meaning as in (II), and $X^5$ and $X^6$ represent the same meaning as in (XIII))

1-12. Production of General Formulas (I-1il) and (I-1dl)

Lithiation with an alkyl lithium such as butyl lithium of a compound of the general formula (IA-5a), which is a compound of the general formula (IA-5), for which the production has been previously described, in which the group Y is a hydrogen atom,

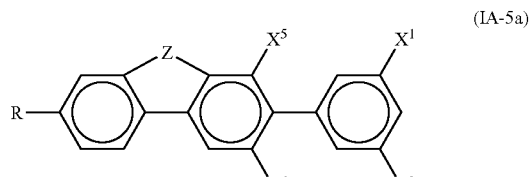

(IA-5a)

(wherein, R, $X^1$ and $X^2$ represent the same meaning as in (I) although those cases in which these groups are hydrogen atoms are excluded, $X^5$ and $X^6$ represent the same meaning as in (XIII), and Z represents the same meaning as in (II)), and subsequent reaction with carbon dioxide gas yields the general formula (LV)

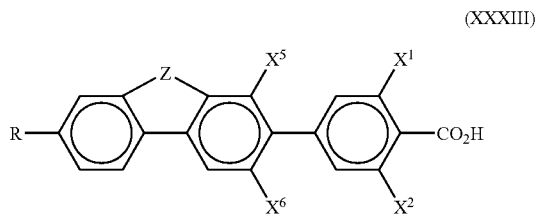

(XXXIII)

(wherein, R, $X^1$ and $X^2$ represent the same meaning as in (I) although those cases in which these groups are hydrogen atoms are excluded, $X^5$ and $X^6$ represent the same meaning as in (XIII), and Z represents the same meaning as in (II)), and conversion of this compound to an acid chloride, and subsequent reaction with ammonia yields a compound of the general formula (XXXIV)

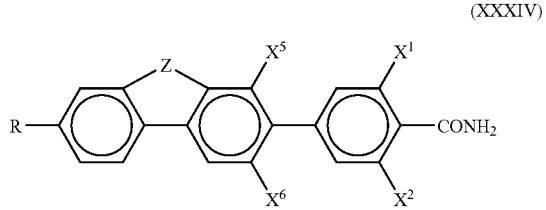

(XXXIV)

(wherein, R, $X^1$ and $X^2$ represent the same meaning as in (I) although those cases in which these groups are hydrogen atoms are excluded, $X^5$ and $X^6$ represent the same meaning as in (XIII), and Z represents the same meaning as in (II)), and by dehydrating this compound with phosphorus oxychloride or the like, compounds of the general formula (IA-12), including the general formulas (I-1il) and (I-1dl) can be produced.

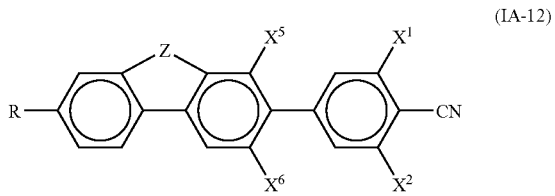

(IA-12)

(wherein, R, $X^1$ and $X^2$ represent the same meaning as in (I) although those cases in which these groups are hydrogen atoms are excluded, $X^5$ and $X^6$ represent the same meaning as in (XIII), and Z represents the same meaning as in (II))

1-13. Production of General Formulas from (I-1im) to (I-1iu), and General Formulas from (I-1ds) to (I-1du)

Reaction of the aforementioned general formula (V) or the general formula (XXIII) with oxalyl dichloride or the like, in the presence of a Lewis acid catalyst such as aluminum chloride yields a compound of the general formula (XXXV),

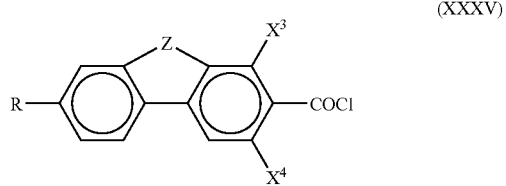

(XXXV)

(wherein, R represents the same meaning as in (I), $X^3$ and $X^4$ represent the same meaning as in (XI), and Z represents the same meaning as in (II)), and by reacting this compound with the general formula (XXXVI)

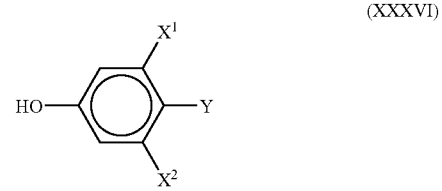

(XXXVI)

(wherein, R, $X^1$ and $X^2$ represent the same meaning as in (I)), and then separating the isomers by column chromatography in those case where isomers exist, compounds of the general formula (IA-13), including the general formulas from (I-1im) to (I-1iu), and the general formulas from (I-1ds) to (I-1du) can be produced.

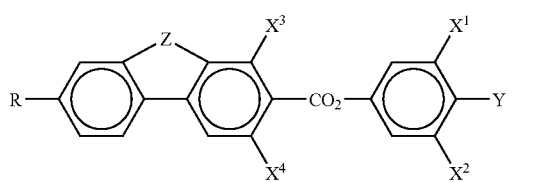

(IA-13)

(wherein, R, $X^1$, $X^2$ and Y represent the same meaning as in (I), $X^3$ and $X^4$ represent the same meaning as in (XI), and Z represents the same meaning as in (II))

1-14. Production of General Formulas from (I-1iv) to (I-1ix), and General Formulas from (I-1dv) to (I-1dx)

Lithiation of the general formula (XXIII) with an alkyl lithium such as butyl lithium, and subsequent reaction with carbon dioxide gas yields a compound of the general formula (XXXVII),

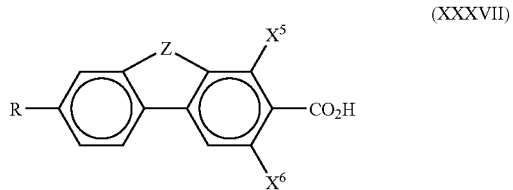

(XXXVII)

(wherein, R represents the same meaning as in (I), $X^5$ and $X^6$ represent the same meaning as in (XIII), and Z represents the same meaning as in (II)), and by converting this compound to an acid chloride and subsequently reacting with the general formula (XXXVI), compounds of the general formula (IA-14), including the general formulas from (I-1iv) to (I-1ix), and the general formulas from (I-1dv) to (I-1dx) can be produced.

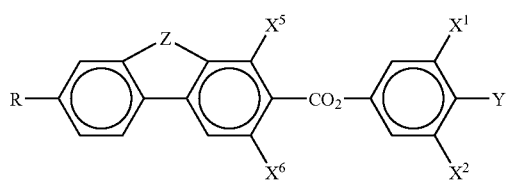
(IA-14)

(wherein, R, Y, $X^1$, $X^2$ represent the same meaning as in (I), $X^5$ and $X^6$ represent the same meaning as in (XIII), and Z represents the same meaning as in (II))

2. Production of the General Formula (I) in which the Ring B Comprises a Phenanthrene Skeleton 2-1. Production of General Formulas from (I-1aa) to (I-1ac), and General Formulas from (I-1ag) to (I-1ai)

Oxidation of a compound of the general formula (VI-1), which is the aforementioned general formula (VI) in which the group Z is —$CH_2CH_2$—,

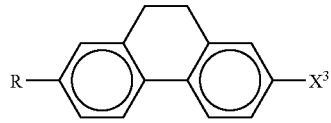
(VI-1)

(wherein, R represents the same meaning as in (III), and $X^3$ represents the same meaning as in (VI)) using an oxidizing agent such as bromine, DDQ (2,3-dichloro-5,6-dicyano-1,4-benzoquinone) or chloranil (tetrachloro-1,2-benzoquinone, tetrachloro-1,4-benzoquinone), yields a compound of the general formula (XXXVIII)

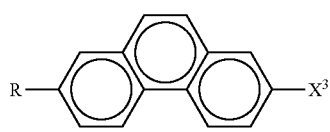
(XXXVIII)

(wherein, R represents the same meaning as in (III), and $X^3$ represents the same meaning as in (VI)), and by subsequently reacting this compound with the general formula (VII) in the presence of a transition metal catalyst, compounds of the general formula (IB-1), including the general formulas from (I-1aa) to (I-1ac), and the general formulas from (I-1ag) to (I-1ai) can be produced.

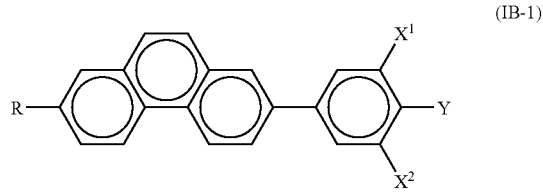
(IB-1)

(wherein, R, Y, $X^1$ and $X^2$ represent the same meaning as in (I), although the case in which Y is a cyano group is excluded). Furthermore, these compounds can also be produced by oxidizing the general formula (IA-1) using an oxidizing agent such as bromine, DDQ (2,3-dichloro-5,6-dicyano-1,4-benzoquinone) or chloranil (tetrachloro-1,2-benzoquinone, tetrachloro-1,4-benzoquinone).

2-2. Production of General Formulas from (I-1am) to (I-1ao), and General Formulas from (I-1as) to (I-1au)

By reacting the general formula (VIII) with the general formula (XXXVIII) in the presence of a transition metal catalyst such as tetrakis(triphenylphosphine)palladium (0), compounds of the general formula (IB-2), including the general formulas from (I-1am) to (I-1ao), and the general formulas from (I-1as) to (I-1au) can be produced.

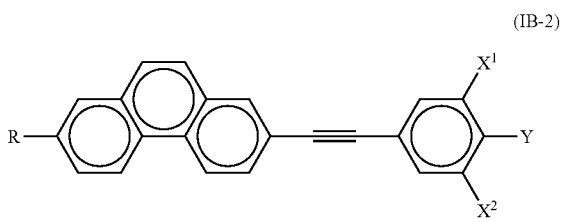
(IB-2)

(wherein, R, Y, $X^1$ and $X^2$ represent the same meaning as in (I))

2-3. Production of General Formula (IB-3)

Oxidation of a compound of the general formula (XI-1), which is the aforementioned general formula (XI) in which the group Z is —$CH_2CH_2$—,

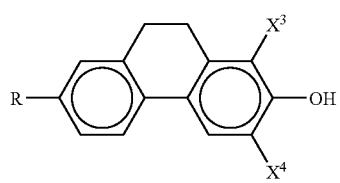
(XI-1)

(wherein, R represents the same meaning as in (III), and $X^3$ and $X^4$ represent the same meaning as in (XI)) using an oxidizing agent such as bromine, DDQ (2,3-dichloro-5,6-dicyano-1,4-benzoquinone) or chloranil (tetrachloro-1,2-benzoquinone, tetrachloro-1,4-benzoquinone), yields a compound of the general formula (XXXIX).

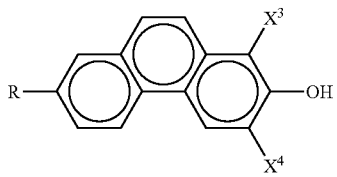

(XXXIX)

(wherein, R represents the same meaning as in (III), and $X^3$ and $X^4$ represent the same meaning as in (XI)). Reaction of the general formula (XXXIX) with trifluoromethanesulfonic anhydride or the like yields the general formula (XL)

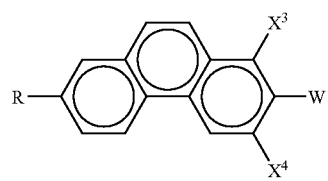

(XL)

(wherein, R represents the same meaning as in (I), $X^3$ and $X^4$ represent the same meaning as in (XI), and W represents the same meaning as in (XII)), and by subsequently reacting this compound with the general formula (VII) in the presence of a transition metal catalyst such as tetrakis(triphenylphosphine)palladium (0), and separating the thus obtained isomers by column chromatography, the general formula (IB-3) can be produced.

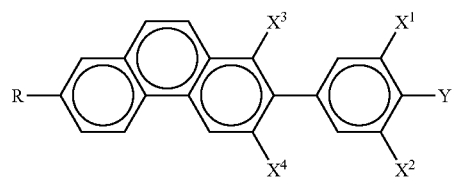

(IB-3)

(wherein, R, Y, $X^1$ and $X^2$ represent the same meaning as in (I), and $X^3$ and $X^4$ represent the same meaning as in (XI))

2-4. Production of General Formula (IB-4)

By reacting the aforementioned general formula (VIII) with the general formula (XL) in the presence of a transition metal catalyst such as tetrakis(triphenylphosphine)palladium (0), a compound of the general formula (IB-4) can be produced.

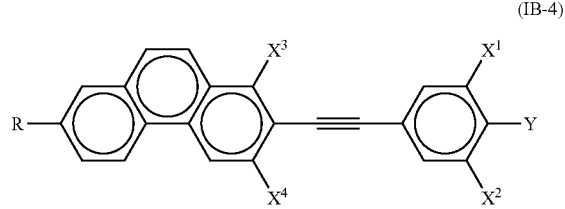

(IB-4)

(wherein, R, Y, $X^1$ and $X^2$ represent the same meaning as in (I), and $X^3$ and $X^4$ represent the same meaning as in (XI))

2-5. Production of General Formulas from (I-1ad) to (I-1af), and General Formulas from (I-1aj) to (I-1al)

Oxidation of a compound of the general formula (XXIII-1), which is the aforementioned general formula (XIII) in which the group Z is —$CH_2CH_2$—,

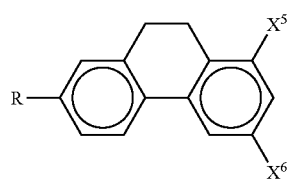

(XXIII-1)

(wherein, R represents the same meaning as in (III), and $X^5$ and $X^6$ represent the same meaning as in (XIII)) using an oxidizing agent such as bromine, DDQ (2,3-dichloro-5,6-dicyano-1,4-benzoquinone) or chloranil (tetrachloro-1,2-benzoquinone, tetrachloro-1,4-benzoquinone), yields a compound of the general formula (XLI).

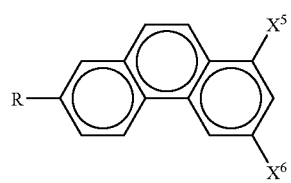

(XLI)

(wherein, R represents the same meaning as in (I), and $X^5$ and $X^6$ represent the same meaning as in (XIII)). Lithiation of this compound using an alkyl lithium such as butyl lithium, and subsequent reaction with bromine or iodine yields the general formula (XLII),

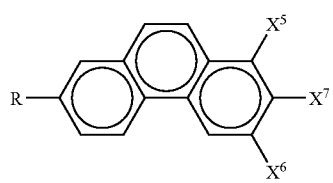

(XLII)

(wherein, R represents the same meaning as in (I), $X^5$ and $X^6$ represent the same meaning as in (XIII), and $X^7$ represents a bromine atom or an iodine atom), and by reacting this compound with the general formula (VII), compounds of the general formula (IB-5), including the general formulas from (I-1ad) to (I-1af), and the general formulas from (I-1aj) to (I-1al) can be produced.

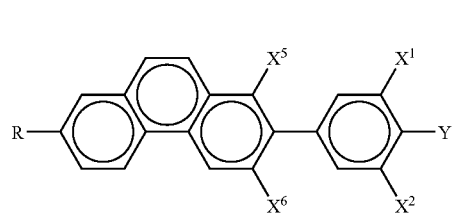

(IB-5)

(wherein, R, $X^1$, $X^2$ and Y represent the same meaning as in (I), and $X^5$ and $X^6$ represent the same meaning as in (XIII))

2-6. Production of General Formulas from (I-1ap) to (I-1ar), and General Formulas from (I-1av) to (I-1ax)

By reacting the aforementioned general formula (VIII) with the general formula (XII) in the presence of a transition metal catalyst such as tetrakis(triphenylphosphine)palladium (0), compounds of the general formula (IB-6), including the general formulas from (I-1ap) to (I-1ar), and the general formulas from (I-1av) to (I-1ax) can be produced.

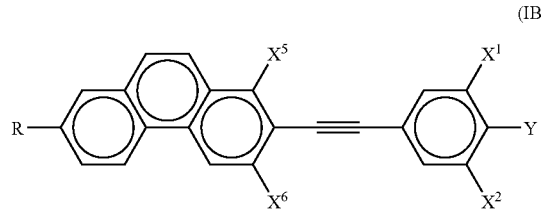

(IB-6)

(wherein, R, Y, $X^1$ and $X^2$ represent the same meaning as in (I), and $X^5$ and $X^6$ represent the same meaning as in (XIII))

2-7. Production of General Formulas from (I-1da) to (I-1db), and General Formulas from (I-1dd) to (I-1de)

Reaction of the general formula (XXV) with a compound of the general formula (XLIII) which can be produced by methods described above,

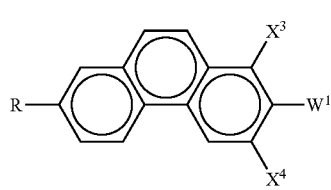

(XLIII)

(wherein, R represents the same meaning as in (I), $W^1$ represents a leaving group such as a bromine atom, an iodine atom, a trifluoromethanesulfonyloxy group, a methanesulfonyloxy group, a benzenesulfonyloxy group or a p-toluenesulfonyloxy group, and $X^3$ and $X^4$ each represent, independently, a hydrogen atom, a fluorine atom or a chlorine atom) yields the general formula (XLIV)

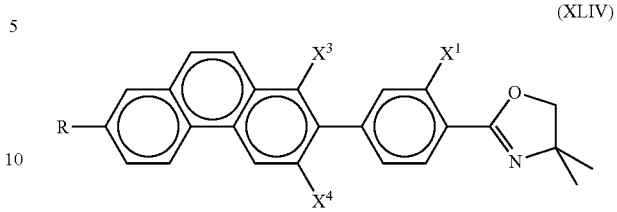

(XLIV)

(wherein, R and $X^1$ represent the same meaning as in (I), and $X^3$ and $X^4$ represent the same meaning as in (XLIII)), and by removing the cyano group protective group using phosphorus oxychloride or the like, compounds of the general formula (IB-7), including the general formulas from (I-1da) to (I-1db), and the general formulas from (I-1dd) to (I-1de) can be produced.

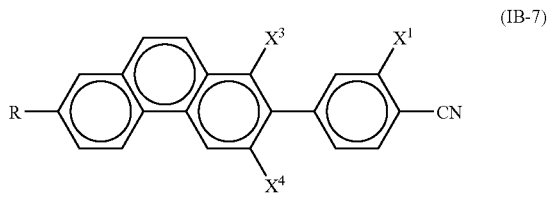

(IB-7)

(wherein, R and $X^1$ represent the same meaning as in (I), and $X^3$ and $X^4$ represent the same meaning as in (XLIII))

2-8. Production of General Formula (I-1dc) and General Formula (I-1df)

Oxidation of a compound of the general formula (IA-3b), which is a compound of the previously described general formula (IA-1), the general formula (IA-3) or the general formula (IA-5) in which the group Y is a hydrogen atom,

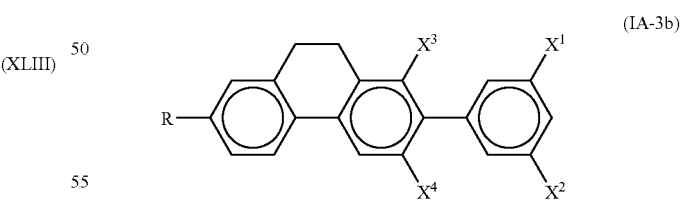

(IA-3b)

(wherein, R, $X^1$ and $X^2$ represent the same meaning as in (I), although the cases in which these groups are hydrogen atoms are excluded, and $X^3$ and $X^4$ represent the same meaning as in (XLIII)) using an oxidizing agent such as bromine, DDQ (2,3-dichloro-5,6-dicyano-1,4-benzoquinone) or chloranil (tetrachloro-1,2-benzoquinone, tetrachloro-1,4-benzoquinone) yields a compound of the general formula (XLV).

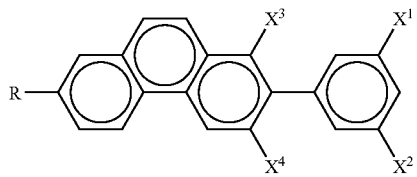

(XLV)

(wherein, R, $X^1$ and $X^2$ represent the same meaning as in (I), although the cases in which these groups are hydrogen atoms are excluded, and $X^3$ and $X^4$ represent the same meaning as in (XLIII)). Lithiation of this compound with an alkyl lithium such as butyl lithium, and subsequent reaction with carbon dioxide gas yields the general formula (XLVI),

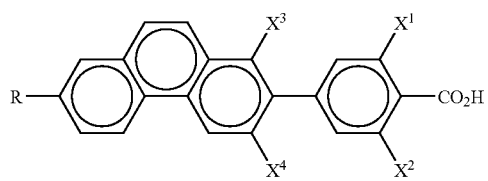

(XLVI)

(wherein, R, $X^1$ and $X^2$ represent the same meaning as in (I), although the cases in which these groups are hydrogen atoms are excluded, and $X^3$ and $X^4$ represent the same meaning as in (XLIII)), and conversion of this compound to an acid chloride and subsequent reaction with ammonia gas yields a compound of the general formula (XLVII),

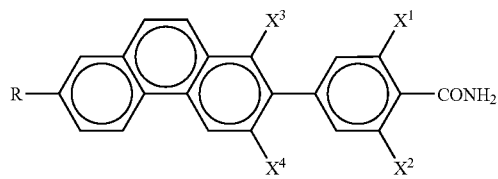

(XLVII)

(wherein, R, $X^1$ and $X^2$ represent the same meaning as in (I), although the cases in which these groups are hydrogen atoms are excluded, and $X^3$ and $X^4$ represent the same meaning as in (XLIII)), and by performing a subsequent dehydration using phosphorus oxychloride or the like, compounds of the general formula (IB-8), including the general formula (I-1dc) and the general formula (I-1df) can be produced.

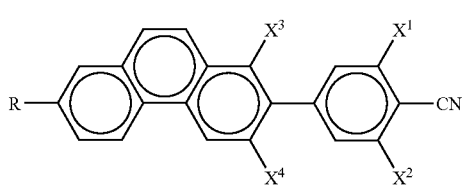

(IB-8)

(wherein, R, $X^1$ and $X^2$ represent the same meaning as in (I), although the cases in which these groups are hydrogen atoms are excluded, and $X^3$ and $X^4$ represent the same meaning as in (XLIII))

2-9. Production of General Formulas from (I-1dm) to (I-1dr)

By converting a compound of the general formula (XLVIII), which can be produced by methods described previously,

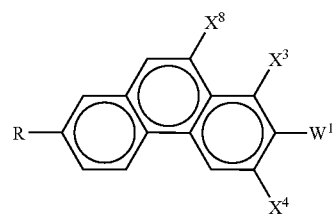

(XLVIII)

(wherein, R represents the same meaning as in (I), and $X^3$ and $X^4$ represent the same meaning as in (XLIII)), to an acid chloride, and subsequently reacting with the general formula (XXXVI), compounds of the general formula (IB-9), including the general formulas from (I-1dm) to (I-1dr) can be produced.

(IB-9)

(wherein, R represents the same meaning as in (I), and $X^3$ and $X^4$ represent the same meaning as in (XLIII))

2-10. Production of General Formulas from (I-1ba) to (I-1bl), and General Formulas from (I-1ca) to (I-1cl)

By reacting a compound of the general formula (XLIX)

(XLIX)

(wherein, R represents the same meaning as in (I), $W^1$ represents a leaving group such as a bromine atom, an iodine atom, a trifluoromethanesulfonyloxy group, a methanesulfonyloxy group, a benzenesulfonyloxy group or a p-toluenesulfonyloxy group, $X^3$ and $X^4$ represent the same meaning as in (XLIII), and $X^8$ represents a fluorine atom or a chlorine atom) with the general formula (VII) in the presence of a transition metal catalyst, compounds of the general formula (IB-10), including the general formulas from (I-1ba) to (I-1bl), and the general formulas from (I-1ca) to (I-1cl) can be produced.

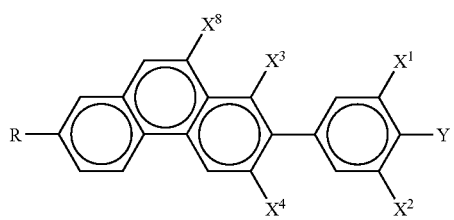

(IB-10)

(wherein, R, Y, $X^1$ and $X^2$ represent the same meaning as in (I), although the case in which Y is a cyano group is excluded, $X^3$ and $X^4$ represent the same meaning as in (XLIII), and $X^8$ represents the same meaning as in (XLIX))

2-11. Production of General Formulas from (I-1bm) to (I-1bx), and General Formulas from (I-1cm) to (I-1cx)

By reacting the general formula (VIII) with the general formula (XLIX) in the presence of a transition metal catalyst such as tetrakis(triphenylphosphine)palladium (0), compounds of the general formula (IB-11), including the general formulas from (I-1bm) to (I-1bx), and the general formulas from (I-1cm) to (I-1cx) can be produced.

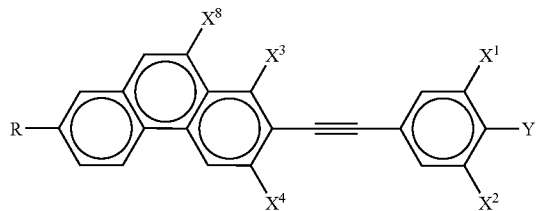

(IB-11)

(wherein, R, Y, $X^1$ and $X^2$ represent the same meaning as in (I), although the case in which Y is a cyano group is excluded, $X^3$ and $X^4$ represent the same meaning as in (XLIII), and $X^8$ represents the same meaning as in (XLIX))

2-12. Production of General Formulas from (I-1ea) to (I-1eb), General Formulas from (I-1ed) to (I-1ee), and General Formulas from (I-1ej) to (I-1ek)

Reaction of the general formula (XXV) with the general formula (XLIX) in the presence of a transition metal catalyst such as tetrakis(triphenylphosphine)palladium (0) yields a compound of the general formula (L),

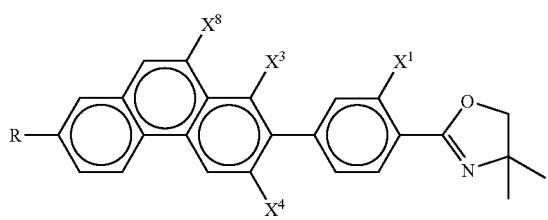

(L)

(wherein, R, $X^1$ and $X^2$ represent the same meaning as in (I), $X^3$ and $X^4$ represent the same meaning as in (XLIII), and $X^8$ represents the same meaning as in (XLIX)), and by removing the cyano group protective group from this compound using phosphorus oxychloride or the like, compounds of the general formula (IB-12), including the general formulas from (I-1ea) to (I-1eb), the general formulas from (I-1ed) to (I-1ee), and the general formulas from (I-1ej) to (I-1ek) can be produced.

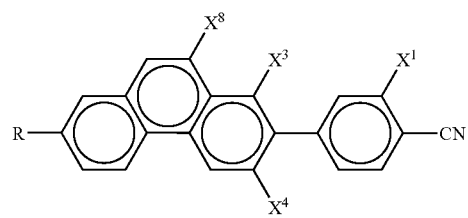

(IB-12)

(wherein, R, $X^1$ and $X^2$ represent the same meaning as in (I), $X^3$ and $X^4$ represent the same meaning as in (XLIII), and $X^8$ represents the same meaning as in (XLIX))

2-13. Production of General Formula (I-1ec), General Formula (I-1ef), General Formula (I-1ei), and General Formula (I-1el)

Lithiation of a compound of the general formula (IB-10a), which is the aforementioned general formula (IB-10) in which the group Y is a hydrogen atom,

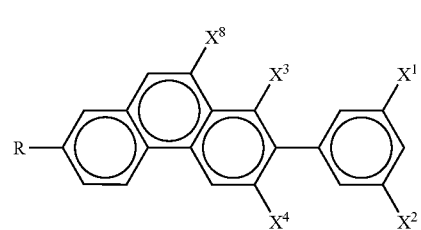

(IB-10a)

(wherein, R, $X^1$ and $X^2$ represent the same meaning as in (I), $X^3$ and $X^4$ represent the same meaning as in (XLIII), and $X^8$ represents the same meaning as in (XLIX)), with an alkyl lithium such as butyl lithium, and subsequent reaction with carbon dioxide gas yields a compound of the general formula (LI),

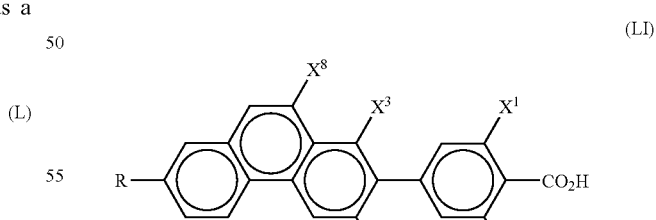

(LI)

(wherein, R, $X^1$ and $X^2$ represent the same meaning as in (I), although the cases in which these groups are hydrogen atoms are excluded, $X^3$ and $X^4$ represent the same meaning as in (XLIII), and $X^8$ represents the same meaning as in (XLIX)), and conversion of this compound to an acid chloride and subsequent reaction with ammonia yields the general formula (LII),

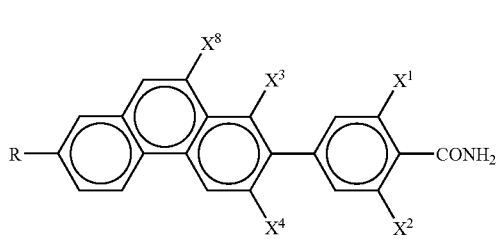

(LII)

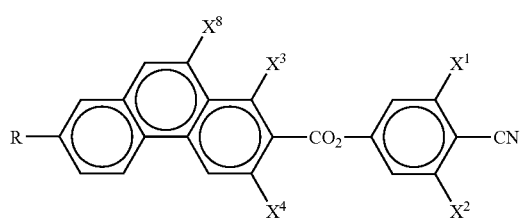

(IB-14)

(wherein, R, $X^1$ and $X^2$ represent the same meaning as in (I), although the cases in which these groups are hydrogen atoms are excluded, $X^3$ and $X^4$ represent the same meaning as in (XLIII), and $X^8$ represents the same meaning as in (XLIX)), and by performing a subsequent dehydration using phosphorus oxychloride or the like, compounds of the general formula (IB-13), including the general formula (I-1ec), the general formula (I-1ef), the general formula (I-1ei), and the general formula (I-1el) can be produced.

(wherein, R represents the same meaning as in (I), $X^3$ and $X^4$ represent the same meaning as in (XLIII), and $X^8$ represents the same meaning as in (XLIX))

3. Production of the General Formula (I) in which the Ring B Comprises a Decahydrophenanthrene Skeleton 3-1. Production of General Formulas from (I-2aa) to (I-2af)

Reaction of a compound represented by the general formula (CII)

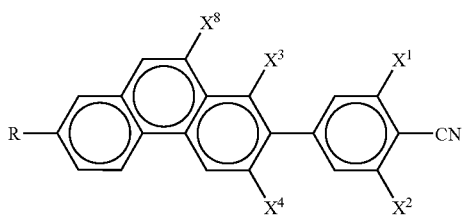

(IB-13)

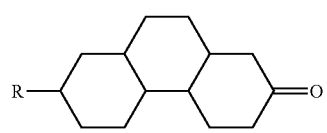

(CII)

(wherein, R, $X^1$ and $X^2$ represent the same meaning as in (I), although the cases in which these groups are hydrogen atoms are excluded, $X^3$ and $X^4$ represent the same meaning as in (XLIII), and $X^8$ represents the same meaning as in (XLIX))

(wherein, R represents the same meaning as in (I), and the cyclohexane rings represent a trans isomer) with the general formula (CIII)

2-14. Production of General Formulas from (I-1em) to (I-1ex)

By converting a compound of the general formula (LIII), which can be produced by methods described above,

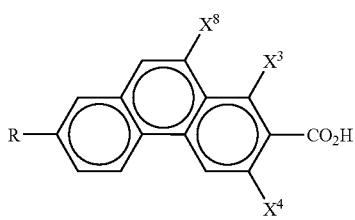

(LIII)

(CIII)

M—⌬—Y with $X^1$, $X^2$ (wherein, $X^1$, $X^2$ and Y represent the same meaning as in (I), although the cases in which these groups are cyano groups are excluded, and M represents MgX (wherein X represents a chlorine atom, a bromine atom or an iodine atom), a metal atom such as Li or the like, B(OH)$_2$, or SiF(CH$_3$)$_2$), and subsequent dehydration in the presence of an acid catalyst yields the general formula (CIVa) and the general formula (CIVb), (wherein, R represents the same meaning as in (I), $X^3$ and $X^4$ represent the same meaning as in (XLIII), and $X^8$ represents the same meaning as in (XLIX)), to an acid chloride, and subsequently reacting with the general formula (XXXVI), compounds of the general formula (IB-14), including the general formulas from (I-1em) to (I-1ex) can be produced.

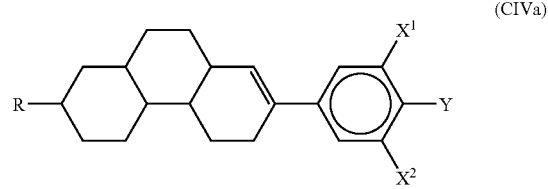

(CIVa)

-continued

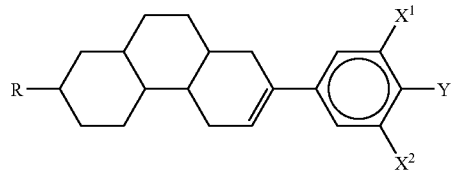
(CIVb)

(wherein, R, $X^1$, $X^2$ and Y represent the same meaning as in (I), and the cyclohexane rings represent a trans isomer), and by performing a catalytic reduction on these compounds using a transition metal catalyst such as palladium-carbon, and subsequently performing an isomerization using a strong base such as potassium t-butoxide, compounds of the general formula (Ia-1), including the aforementioned general formulas from (I-2aa) to (I-2af) can be produced.

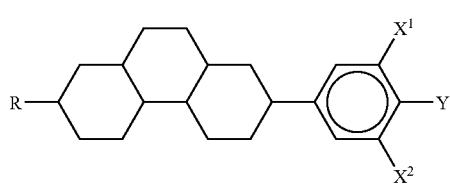
(Ia-1)

(wherein, R, $X^1$, $X^2$ and Y represent the same meaning as in (I), and the cyclohexane rings represent a trans isomer)

3-2. Production of General Formulas from (I-2aj) to (I-2ao)

Reaction of the general formula (CII) with a compound represented by the formula (CV),

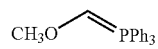
(CV)

followed by hydrolysis in the presence of an acid catalyst, and subsequent isomerization using a base, yields a compound of the general formula (CVIa),

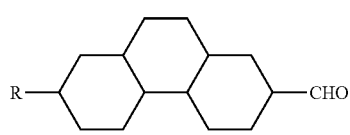
(CVIa)

(wherein, R represents the same meaning as in (I), and the cyclohexane rings represent a trans isomer), and further reaction of this compound with the formula (CV) and subsequent hydrolysis in the presence of an acid catalyst yields a compound of the general formula (CVIb),

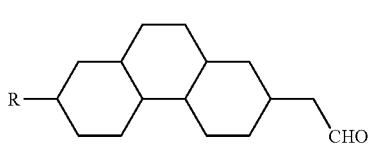
(CVIb)

(wherein, R represents the same meaning as in (I), and the cyclohexane rings represent a trans isomer), and reaction of this compound with the general formula (III), followed by dehydration in the presence of an acid catalyst yields the general formula (CVII),

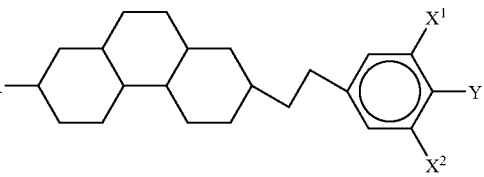
(CVII)

(wherein, R, $X^1$, $X^2$ and Y represent the same meaning as in (I), and the cyclohexane rings represent a trans isomer), and by performing a catalytic reduction on this compound using a transition metal catalyst such as palladium-carbon, compounds of the general formula (Ia-2), including the aforementioned general formulas from (I-2aj) to (I-2ao) can be produced.

(Ia-2)

(wherein, R, $X^1$, $X^2$ and Y represent the same meaning as in (I), and the cyclohexane rings represent a trans isomer)

3-3. Production of General Formulas from (I-2ag) to (I-2ai), and General Formulas from (I-2ap) to (I-2ar)

Reaction of the general formula (II) with a compound of the general formula (CVIII)

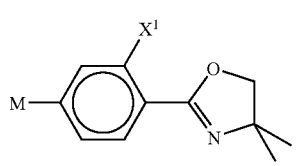
(CVIII)

(wherein, $X^1$ represents the same meaning as in (I), and M represents the same meaning as in (III)) yields a compound of the general formula (CIX),

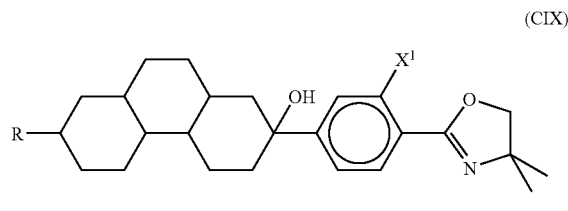
(CIX)

(wherein, R and X¹ represent the same meaning as in (I), and the cyclohexane rings represent a trans isomer), and dehydration of this compound using phosphorus oxychloride or the like yields the general formula (CX),

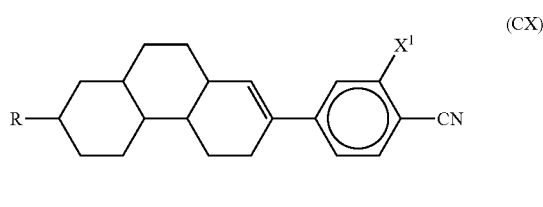
(CX)

(wherein, R and X¹ represent the same meaning as in (I), and the cyclohexane rings represent a trans isomer), and by reducing this compound in the presence of a catalyst such as Raney nickel or palladium-carbon, compounds of the general formula (Ia-3), including the general formulas from (I-2ag) to (I-2ai) can be produced.

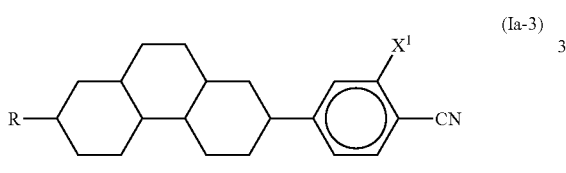
(Ia-3)

(wherein, R and X¹ represent the same meaning as in (I), and the cyclohexane rings represent a trans isomer). Furthermore, by using the general formula (CVIIb) instead of the general formula (CII), then in a similar manner, compounds of the general formula (Ia-4), including the general formulas from (I-2ap) to (I-2ar) can be produced.

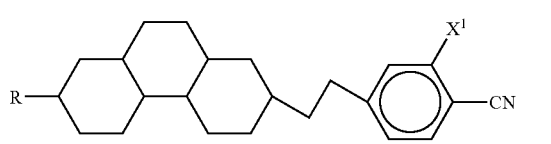
(Ia-4)

(wherein, R and X¹ represent the same meaning as in (I), and the cyclohexane rings represent a trans isomer)

3-4. Production of the General Formula (I-2ai), and General Formula (I-2ar)

Lithiation with an alkyl lithium such as butyl lithium of a compound of the general formula (Ia-1a), which is a compound of the general formula (Ia-1), for which the production has been previously described, in which the group Y is a hydrogen atom,

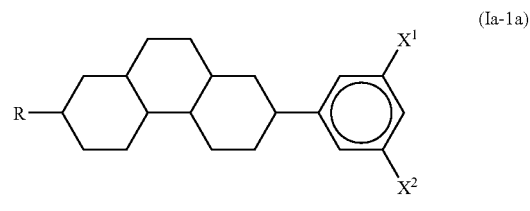
(Ia-1a)

(wherein, R, X¹ and X² represent the same meaning as in (I) although those cases in which these groups are hydrogen atoms are excluded, and the cyclohexane rings represent a trans isomer), and subsequent reaction with carbon dioxide gas yields the general formula (CXI),

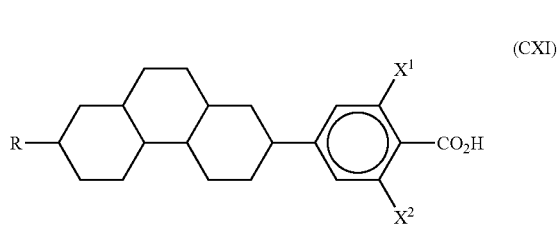
(CXI)

(wherein, R, X¹ and X² represent the same meaning as in (I) although those cases in which these groups are hydrogen atoms are excluded, and the cyclohexane rings represent a trans isomer), and conversion of this compound to an acid chloride, and subsequent reaction with ammonia yields a compound of the general formula (CXII),

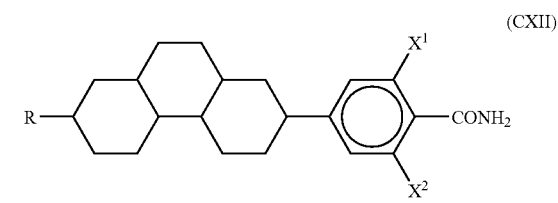
(CXII)

(wherein, R, X¹ and X² represent the same meaning as in (I) although those cases in which these groups are hydrogen atoms are excluded, and the cyclohexane rings represent a trans isomer), and by dehydrating this compound using phosphorus oxychloride or the like, compounds of the general formula (Ia-5), including the general formula (I-2ai) can be produced.

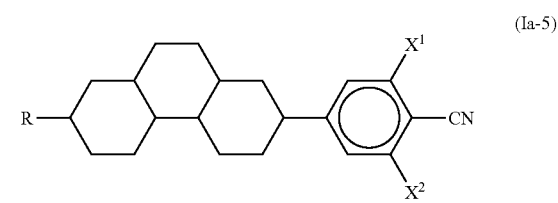
(Ia-5)

(wherein, R, X¹ and X² represent the same meaning as in (I), and the cyclohexane rings represent a trans isomer). Furthermore, by using the general formula (Ia-1b) instead of the general formula (Ia-1a),

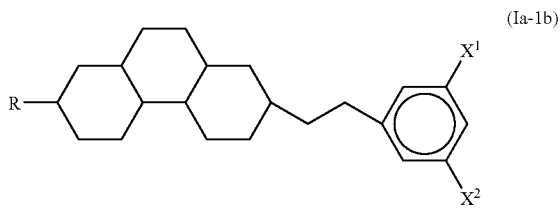
(Ia-1b)

(wherein, R, $X^1$ and $X^2$ represent the same meaning as in (I) although those cases in which these groups are hydrogen atoms are excluded, and the cyclohexane rings represent a trans isomer), then in a similar manner, compounds of the general formula (Ia-6), including the general formula (I-2ar) can be produced.

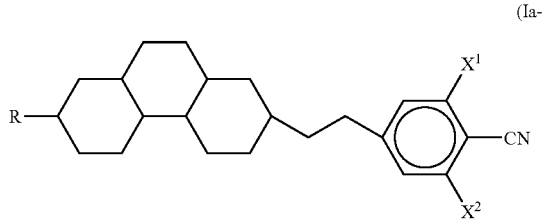
(Ia-6)

(wherein, R, $X^1$ and $X^2$ represent the same meaning as in (I), and the cyclohexane rings represent a trans isomer)

3-5. Production of General Formulas from (I-2 as) to (I-2au)

Reaction of the general formula (CVIa), for which the production has been previously described, with an oxidizing agent such as silver oxide or the like yields a compound of the general formula (CXIII),

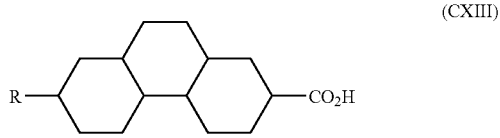
(CXIII)

(wherein, R represents the same meaning as in (I), and the cyclohexane rings represent a trans isomer), and by converting this compound to an acid chloride, and subsequently reacting with a compound of the general formula (CXIV)

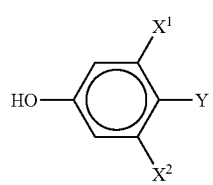
(CXIV)

(wherein, $X^1$, $X^2$ and Y represent the same meaning as in (I)), compounds of the general formula (Ia-7), including the general formulas from (I-2 as) to (I-2au) can be produced.

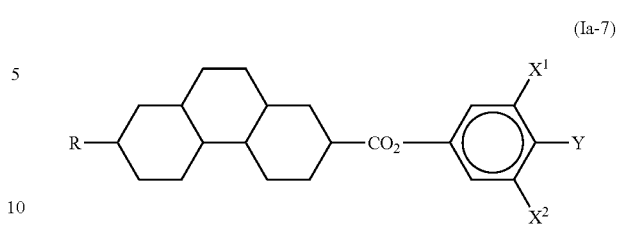
(Ia-7)

(wherein, R, Y, $X^1$ and $X^2$ represent the same meaning as in (I), and the cyclohexane rings represent a trans isomer)

3-6. Production of General Formulas from (I-2aa) to (I-2ai)

Reaction of a compound represented by the formula (CXV)

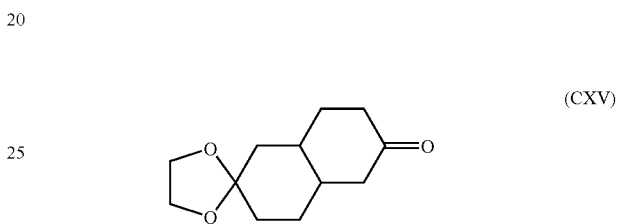
(CXV)

with a secondary amine such as pyrrolidine yields an enamine, and reaction of this enamine with methyl vinyl ketone, followed by a cyclization under acid conditions, and a subsequent reduction using metallic lithium or the like yields the general formula (CXVI),

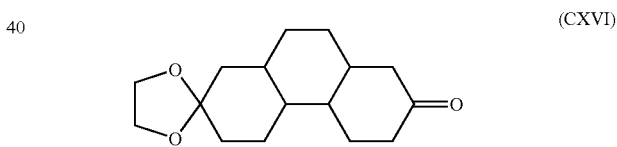
(CXVI)

(wherein, the cyclohexane rings represent a trans isomer), and reaction of this compound with the general formula (III), followed by dehydration in the presence of an acid catalyst, a subsequent reduction in the presence of a metal catalyst such as palladium-carbon, and then an isomerization under basic conditions yields the general formula (CXVII).

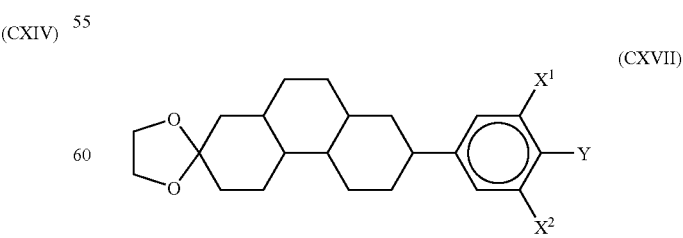
(CXVII)

(wherein, Y, $X^1$ and $X^2$ represent the same meaning as in (I), and the cyclohexane rings represent a trans isomer).

Hydrolysis of this compound under acid conditions removes the carbonyl group protective group, yielding a compound represented by the general formula (CXVIII).

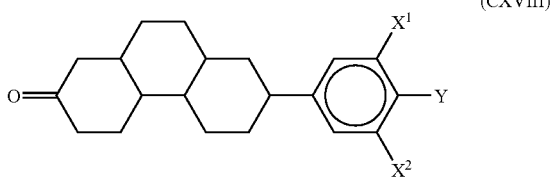

(CXVIII)

(wherein, Y, $X^1$ and $X^2$ represent the same meaning as in (I), and the cyclohexane rings represent a trans isomer). Reaction of this compound with the formula (CV), followed by hydrolysis under acid conditions, and then an isomerization under basic conditions yields a compound represented by the general formula (CXIX).

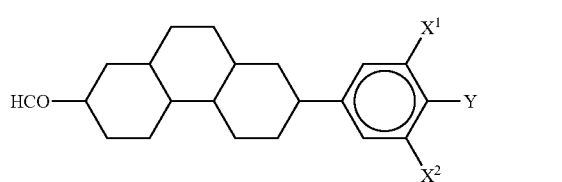

(CXIX)

(wherein, Y, $X^1$ and $X^2$ represent the same meaning as in (I), and the cyclohexane rings represent a trans isomer). By repeating a desired number of repetitions of the reaction of this compound with the formula (CV) and the subsequent hydrolysis process, and subsequently reacting with the general formula (CXX),

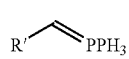

(CXX)

(wherein, R' represents an alkyl group or alkoxyl group of 1 to 15 carbon atoms), compounds of the general formula (Ia-8) with any desired alkenyl group, including the general formulas from (I-2aa) to (I-2ai) can be produced.

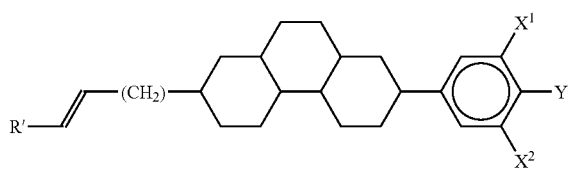

(Ia-8)

(wherein, R' represents the same meaning as in (CXX), Y, $X^1$ and $X^2$ represent the same meaning as in (I), and the cyclohexane rings represent a trans isomer)

4. Production of the General Formula (I) in which the Ring B Comprises a 1,2,3,4,4a,9,10,10a-octahydrophenanthrene Skeleton 4-1. Production of General Formulas from (I-2ba) to (I-2bc), and General Formulas from (I-2ca) to (I-2cc)

Demethoxylation of a compound represented by the general formula (CXXX)

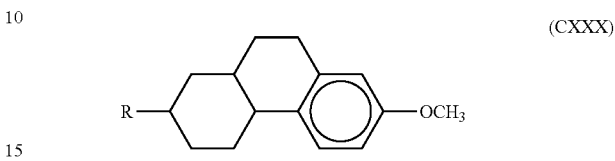

(CXXX)

(wherein, R represents the same meaning as in (I), and the cyclohexane rings represent a trans isomer) using hydrobromic acid or the like yields a compound represented by the general formula (CXXXI).

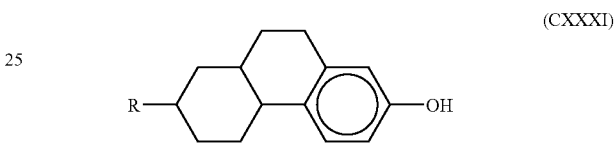

(CXXXI)

(wherein, R represents the same meaning as in (I), and the cyclohexane rings represent a trans isomer). Reaction of this compound with trifluoromethanesulfonic anhydride yields the general formula (CXXXII)

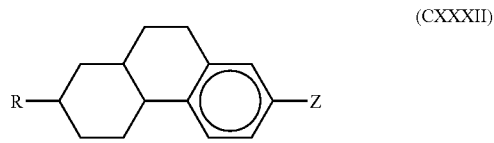

(CXXXII)

(wherein, R represents the same meaning as in (I), Z represents a leaving group such as a trifluoromethanesulfonyloxy group, a methanesulfonyloxy group, a benzenesulfonyloxy group or a p-toluenesulfonyloxy group, and the cyclohexane rings represent a trans isomer), and by reacting this compound with the general formula (CIII) in the presence of a transition metal catalyst such as tetrakis(triphenylphosphine)palladium (0), compounds of the general formula (Ib-1), including the general formulas from (I-2ba) to (I-2bc), and the general formulas from (I-2ca) to (I-2cc) can be produced.

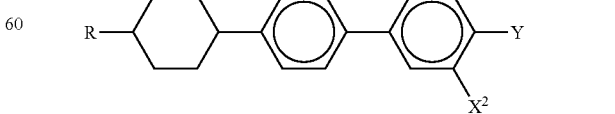

(Ib-1)

(wherein, R, Y, $X^1$ and $X^2$ represent the same meaning as in (I), and the cyclohexane rings represent a trans isomer)

4-2. Production 2 of General Formulas from (I-2ba) to (I-2bc), and General Formulas from (I-2ca) to (I-2cc)

Reaction of a compound of the general formula (CXXXIII)

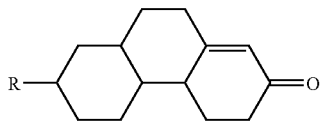
(CXXXIII)

(wherein, R represents the same meaning as in (I), and the cyclohexane rings represent a trans isomer) with the general formula (CIII) and subsequent dehydration yields a compound of the general formula (CXXXIV),

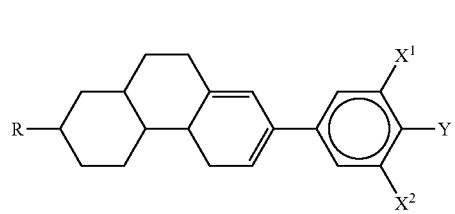
(CXXXIV)

(wherein, R, Y, $X^1$ and $X^2$ represent the same meaning as in (I), although the case in which Y is a cyano group is excluded, and the cyclohexane rings represent a trans isomer), and by oxidizing this compound with an oxidizing agent such as bromine, DDQ (2,3-dichloro-5,6-dicyano-1,4-benzoquinone) or chloranil (tetrachloro-1,2-benzoquinone, tetrachloro-1,4-benzoquinone), compounds of the general formula (Ib-1), including the general formulas from (I-2ba) to (I-2bc), and the general formulas from (I-2ca) to (I-2cc) can be produced.

4-3. Production of General Formulas from (I-2bm) to (I-2bo), and General Formulas from (I-2cm) to (I-2co)

By reacting a compound of the general formula (CXXXV)

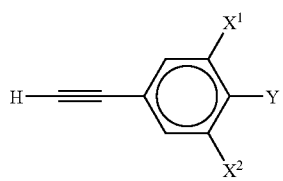
(CXXXV)

(wherein, Y, $X^1$ and $X^2$ represent the same meaning as in (I)) with the general formula (CXXXII) in the presence of a transition metal catalyst such as tetrakis(triphenylphosphine)palladium (0), compounds of the general formula (Ib-2), including the general formulas from (I-2bm) to (I-2bo), and the general formulas from (I-2cm) to (I-2co) can be produced.

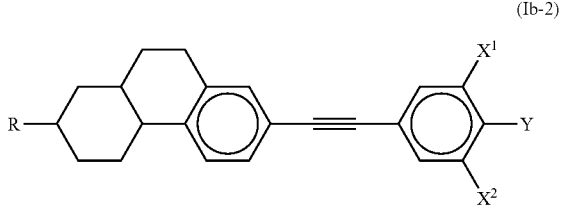
(Ib-2)

(wherein, R, Y, $X^1$ and $X^2$ represent the same meaning as in (I), and the cyclohexane rings represent a trans isomer)

4-4. Production of General Formulas from (I-2bd) to (I-2bi), and General Formulas from (I-2cd) to (I-2ci)

Halogenation of the general formula (CXVI) using an electrophilic halogenation reagent, in the same manner as 1–3, yields a compound of the general formula (CXXXVI).

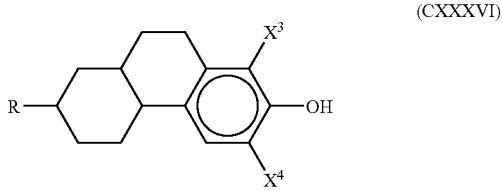
(CXXXVI)

(wherein, R represents the same meaning as in (I), $X^3$ and $X^4$ each represent, independently, a hydrogen atom, a fluorine atom or a chlorine atom, although at least one of $X^3$ and $X^4$ represents a hydrogen atom, and the cyclohexane rings represent a trans isomer). Reaction of this compound with trifluoromethanesulfonic anhydride or the like yields a compound of the general formula (CXXXVII), (CXXXVII)

(wherein, R represents the same meaning as in (I), $X^3$ and $X^4$ represent the same meaning as in (CXXXVI), Z represents a leaving group such as a trifluoromethanesulfonyloxy group, a methanesulfonyloxy group, a benzenesulfonyloxy group or a p-toluenesulfonyloxy group, and the cyclohexane rings represent a trans isomer), and by reacting this compound with the general formula (CIII) in the presence of a transition metal catalyst such as tetrakis(triphenylphosphine)palladium (0) and then separating the thus obtained isomers by column chromatography, compounds of the general formula (Ib-3), including the general formulas from (I-2bd) to (I-2bi), and the general formulas from (I-2cd) to (I-2ci) can be produced.

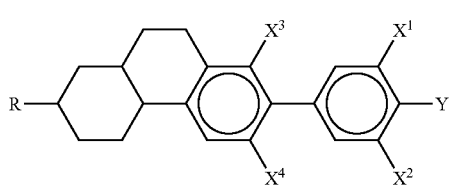 (Ib-3)

(wherein, R, Y, X¹ and X² represent the same meaning as in (I), X³ and X⁴ represent the same meaning as in (CXXXVI), and the cyclohexane rings represent a trans isomer)

4-5. Production of General Formulas from (I-2bp) to (I-2bu), and General Formulas from (I-2cp) to (I-2cu)

By reacting the general formula (CXXXVII) with the general formula (CXXXV) in the presence of a transition metal catalyst such as tetrakis(triphenylphosphine)palladium (0) and then separating the thus obtained isomers by column chromatography, compounds of the general formula (Ib-4), including the general formulas from (I-2bp) to (I-2bu), and the general formulas from (I-2cp) to (I-2cu) can be produced.

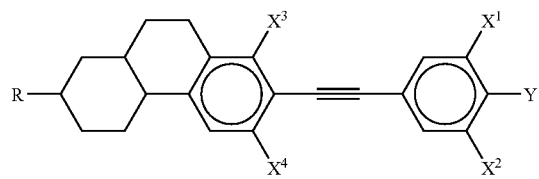 (Ib-4)

(wherein, R, Y, X¹ and X² represent the same meaning as in (I), X³ and X⁴ represent the same meaning as in (CXXXVI), and the cyclohexane rings represent a trans isomer)

4-6. Production of General Formulas from (I-2bj) to (I-2bl), and General Formulas from (I-2cj) to (I-2cl)

Reaction of a compound represented by the formula (CXXXVIII)

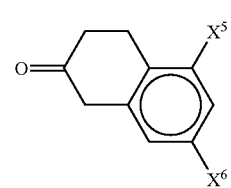 (CXXXVIII)

(wherein, $X^5$ and $X^6$ each represent, independently, a fluorine atom or a chlorine atom) with a secondary amine such as pyrrolidine yields an enamine of the general formula (CXXXIX).

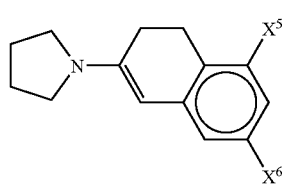 (CXXXIX)

(wherein, $X^5$ and $X^6$ represent the same meaning as in (CXXXVIII)). Reaction of this enamine with methyl vinyl ketone, followed by a cyclization under acid conditions yields the general formula (CXL),

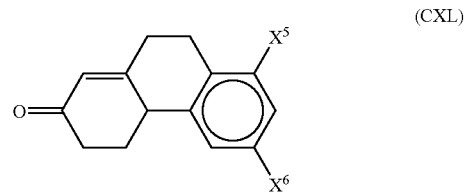 (CXL)

(wherein, $X^5$ and $X^6$ represent the same meaning as in (CXXXVIII)), and reduction of this compound using metallic lithium or the like yields the general formula (CXLI),

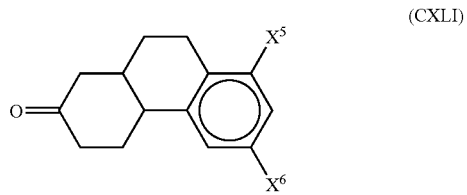 (CXLI)

(wherein, $X^5$ and $X^6$ represent the same meaning as in (CXXXVIII)), and subsequent reaction with the general formula (CV), hydrolysis under acid conditions, and then isomerization under basic conditions yields a compound represented by the general formula (CXLII).

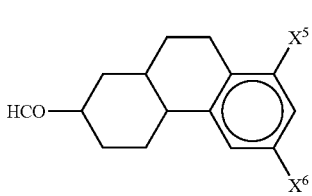 (CXLII)

(wherein, $X^5$ and $X^6$ represent the same meaning as in (CXXXVIII), and the cyclohexane rings represent a trans isomer). Reaction of this compound with the general formula (CXX) yields the general formula (CXLIII).

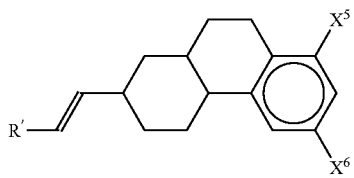
(CXLIII)

(wherein, R' represents the same meaning as in (CXX), $X^5$ and $X^6$ represent the same meaning as in (CXXXVIII), and the cyclohexane rings represent a trans isomer). At this point, instead of the reaction with the general formula (CXX), by repeating the process of reaction with the formula (CV) and subsequent hydrolysis, prior to the reaction with the general formula (CXX), any desired alkenyl group can also be produced. Catalytic reduction of the general formula (CXLIII) using a transition metal catalyst such as palladium-carbon yields a compound of the general formula (CXLIV).

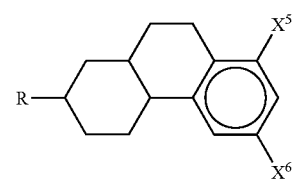
(CXLIV)

(wherein, R represents the same meaning as in (I), $X^5$ and $X^6$ represent the same meaning as in (CXXXVIII), and the cyclohexane rings represent a trans isomer). Lithiation of this compound with an alkyl lithium such as butyl lithium, followed by reaction with bromine or iodine yields the general formula (CXLV),

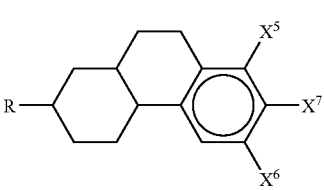
(CXLV)

(wherein, R represents the same meaning as in (I), $X^5$ and $X^6$ represent the same meaning as in (CXXXVIII), $X^7$ represents a bromine atom or an iodine atom, and the cyclohexane rings represent a trans isomer), and by reacting this compound with the general formula (CIII), compounds of the general formula (Ib-5), including the general formulas from (I-2bj) to (I-2bl), and the general formulas from (I-2cj) to (I-2cl) can be produced.

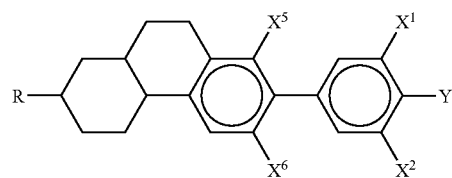
(Ib-5)

(wherein, R, $X^1$, $X^2$ and Y represent the same meaning as in (I), $X^5$ and $X^6$ represent the same meaning as in (CXXXVIII), and the cyclohexane rings represent a trans isomer)

4-7. Production of General Formula (I-2da) and General Formula (I-2db)

Reaction of the general formula (CXXXII) with the general formula (CVIII) yields a compound of the general formula (CXLVI),

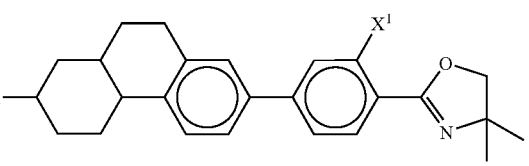
(CXLVI)

(wherein, R and $X^1$ represent the same meaning as in (I), and the cyclohexane rings represent a trans isomer), and by removing the protective group using phosphorus oxychloride or the like, compounds of the general formula (Id-1), including the general formula (I-2da) and the general formula (I-2db) can be produced.

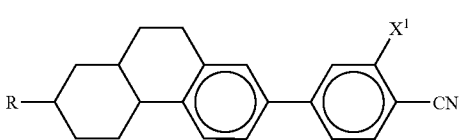
(Id-1)

(wherein, R and $X^1$ represent the same meaning as in (I), and the cyclohexane rings represent a trans isomer)

Reaction of the general formula (CXXXIII) with the general formula (CVIII) yields a compound of the general formula (CXLVII),

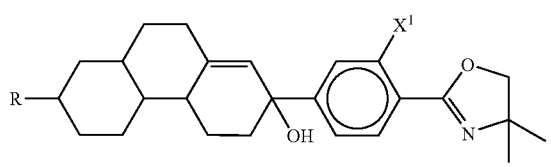
(CXLVII)

(wherein, R and X¹ represent the same meaning as in (I), and the cyclohexane rings represent a trans isomer), and reaction of this compound with phosphorus oxychloride or the like removes the protective group and performs a dehydration, yielding a compound of the general formula (CXLVIII).

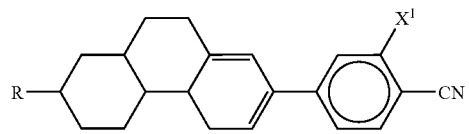

(CXLVIII)

(wherein, R and X¹ represent the same meaning as in (I), and the cyclohexane rings represent a trans isomer). By oxidizing this compound using an oxidizing agent such as bromine, DDQ (2,3-dichloro-5,6-dicyano-1,4-benzoquinone) or chloranil (tetrachloro-1,2-benzoquinone, tetrachloro-1,4-benzoquinone), compounds of the general formula (Id-1), including the general formula (I-2da) and the general formula (I-2db) can be produced:

4-8. Production of General Formula (I-2dc)

Lithiation with an alkyl lithium such as butyl lithium of a compound of the general formula (Id-1a), which is a compound of the general formula (Id-1), the production of which has been previously described, in which the group Y is a hydrogen atom,

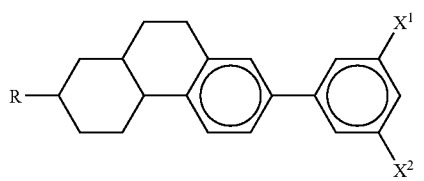

(Id-1a)

(wherein, R, X¹ and X² represent the same meaning as in (I) although those cases in which these groups are hydrogen atoms are excluded, and the cyclohexane rings represent a trans isomer), and subsequent reaction with carbon dioxide gas yields the general formula (CXLIX),

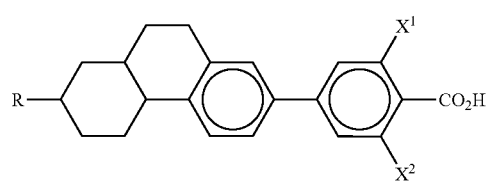

(CXLIX)

(wherein, R, X¹ and X² represent the same meaning as in (I) although those cases in which these groups are hydrogen atoms are excluded, and the cyclohexane rings represent a trans isomer), and conversion of this compound to an acid chloride, and subsequent reaction with ammonia yields a compound of the general formula (CL),

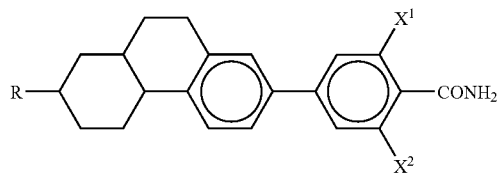

(CL)

(wherein, R, X¹ and X² represent the same meaning as in (I) although those cases in which these groups are hydrogen atoms are excluded, and the cyclohexane rings represent a trans isomer), and by performing a dehydration using phosphorus oxychloride or the like, compounds of the general formula (Id-2), including the general formula (I-2dc) can be produced.

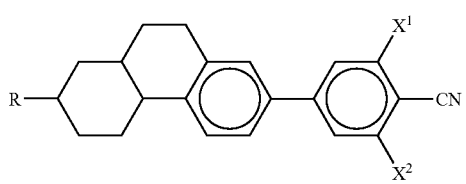

(Id-2)

(wherein, R, X¹ and X² represent the same meaning as in (I), and the cyclohexane rings represent a trans isomer)

4-9. Production of General Formulas from (I-2dd) to (I-2de), and General Formulas from (I-2dg) to (I-2dh)

Reaction of the general formula (CXXXVI) with the general formula (CVIII) in the presence of a transition metal catalyst such as tetrakis(triphenylphosphine)palladium (0) yields a compound of the general formula (CLI).

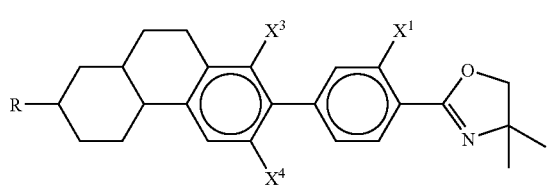

(CLI)

(wherein, R and X¹ represent the same meaning as in (I), X³ and X⁴ represent the same meaning as in (CXXXVI), and the cyclohexane rings represent a trans isomer). By deprotecting the general formula (CLI) using phosphorus oxychloride or the like, and separating the thus produced mixture of isomers by column chromatography, compounds of the general formula (Id-3), including the general formulas from (I-2dd) to (I-2de), and the general formulas from (I-2dg) to (I-2dh) can be produced.

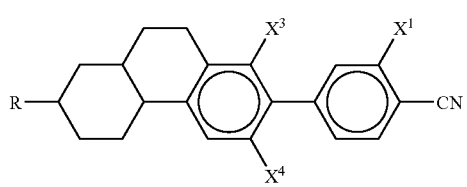
(Id-3)

(wherein, R, $X^1$ and $X^2$ represent the same meaning as in (I), $X^3$ and $X^4$ represent the same meaning as in (CXXXVI), and the cyclohexane rings represent a trans isomer)

4-10. Production of General Formula (I-2df) and General Formula (I-2di)

Lithiation with an alkyl lithium such as butyl lithium of a compound of the general formula (Ib-3a), which is a compound of the general formula (Ib-3), the production of which has been previously described, in which the group Y is a hydrogen atom,

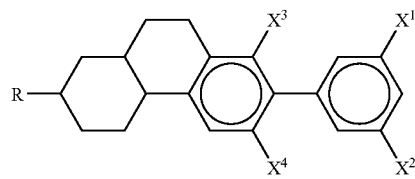
(Ib-3a)

(wherein, R, $X^1$ and $X^2$ represent the same meaning as in (I) although those cases in which these groups are hydrogen atoms are excluded, $X^3$ and $X^4$ represent the same meaning as in (CXXXVI), and the cyclohexane rings represent a trans isomer), and subsequent reaction with carbon dioxide gas yields the general formula (CLII).

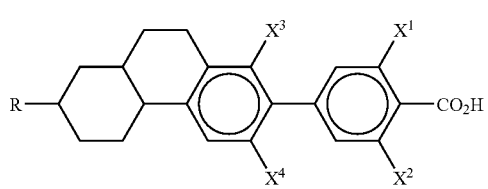
(CLII)

(wherein, R, $X^1$ and $X^2$ represent the same meaning as in (I) although those cases in which these groups are hydrogen atoms are excluded, $X^3$ and $X^4$ represent the same meaning as in (XXXVI), and the cyclohexane rings represent a trans isomer), and conversion of this compound to an acid chloride, and subsequent reaction with ammonia yields a compound of the general formula (CLIII)

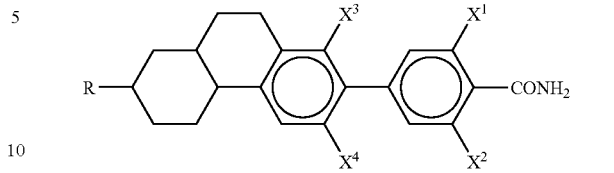
(CLIII)

(wherein, R, $X^1$ and $X^2$ represent the same meaning as in (I) although those cases in which these groups are hydrogen atoms are excluded, $X^3$ and $X^4$ represent the same meaning as in (CXXXVI), and the cyclohexane rings represent a trans isomer), and by performing a dehydration using phosphorus oxychloride or the like, compounds of the general formula (Id-4), including the general formula (I-2df) and the general formula (I-2di) can be produced.

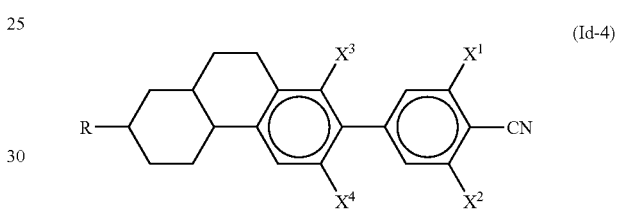
(Id-4)

(wherein, R, $X^1$ and $X^2$ represent the same meaning as in (I) although those cases in which these groups are hydrogen atoms are excluded, $X^3$ and $X^4$ represent the same meaning as in (CXXXVI), and the cyclohexane rings represent a trans isomer)

4-11. Production of General Formula (I-2dj) and General Formula (I-2dk)

Reaction of the general formula (CXLV) with the general formula (CVIII) in the presence of a transition metal catalyst such as tetrakis(triphenylphosphine)palladium (0) yields a compound of the general formula (CLIV).

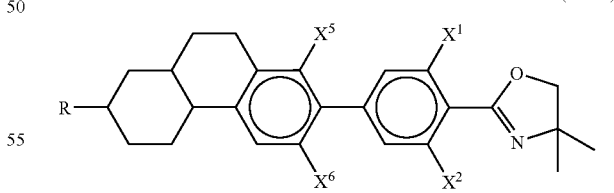
(CLIV)

(wherein, R, $X^1$ and $X^2$ represent the same meaning as in (I), $X^5$ and $X^6$ represent the same meaning as in (CXXXIX), and the cyclohexane rings represent a trans isomer). By deprotecting the general formula (CLIV) using phosphorus oxychloride or the like, compounds of the general formula (Id-5), including the general formula (I-2dj) and the general formula (I-2dk) can be produced.

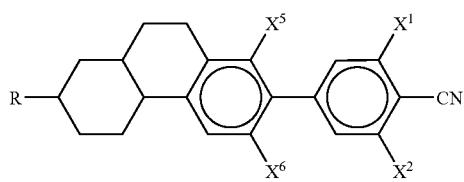

(Id-5)

(wherein, R, $X^1$ and $X^2$ represent the same meaning as in (I), $X^5$ and $X^6$ represent the same meaning as in (CXXXIX), and the cyclohexane rings represent a trans isomer)

4-12. Production of General Formula (I-2dl)

Lithiation with an alkyl lithium such as butyl lithium of a compound of the general formula (Ib-3b), which is a compound of the general formula (Ib-3), the production of which has been previously described, in which the group Y is a hydrogen atom,

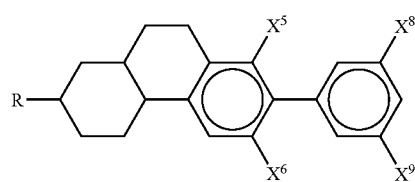

(Ib-3b)

(wherein, R represents the same meaning as in (I), $X^5$ and $X^6$ represent the same meaning as in (CXXXIX), $X^8$ and $X^9$ each represent, independently, a fluorine atom or a chlorine atom, and the cyclohexane rings represent a trans isomer), and subsequent reaction with carbon dioxide gas yields the general formula (CLV)

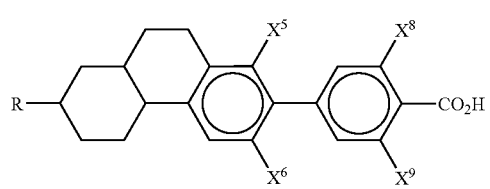

(CLV)

(wherein, R represents the same meaning as in (I), $X^5$ and $X^6$ represent the same meaning as in (CXXXIX), $X^8$ and $X^9$ each represent, independently, a fluorine atom or a chlorine atom, and the cyclohexane rings represent a trans isomer), and conversion of this compound to an acid chloride, and subsequent reaction with ammonia yields a compound of the general formula (CLVI)

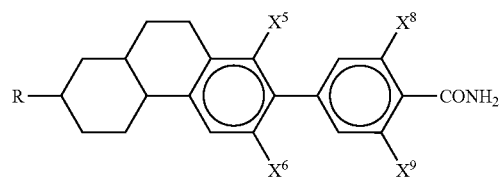

(CLVI)

(wherein, R represents the same meaning as in (I), $X^5$ and $X^6$ represent the same meaning as in (CXXXIX), $X^8$ and $X^9$ each represent, independently, a fluorine atom or a chlorine atom, and the cyclohexane rings represent a trans isomer), and by performing a dehydration using phosphorus oxychloride or the like, compounds of the general formula (Id-6), including the general formula (I-2dl) can be produced.

(Id-6)

(wherein, R represents the same meaning as in (I), $X^5$ and $X^6$ represent the same meaning as in (CXXXIX), $X^8$ and $X^9$ each represent, independently, a fluorine atom or a chlorine atom, and the cyclohexane rings represent a trans isomer)

4-13. Production of General Formulas from (I-2dm) to (I-2do), and General Formulas from (I-2dp) to (I-2du)

Reaction of a compound represented by the general formula (CLV)

(CLV)

(wherein, $X^3$ and $X^4$ represent the same meaning as in (CXXXVI)) with a secondary amine such as pyrrolidine yields an enamine of the general formula (CLVI).

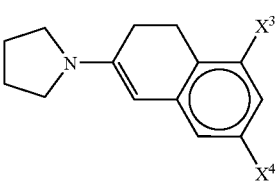

(CLVI)

(wherein, $X^3$ and $X^4$ represent the same meaning as in (CXXXVI)). Reaction of this enamine with methyl vinyl ketone, followed by a cyclization under acid conditions yields the general formula (CLVII), (CLVII)
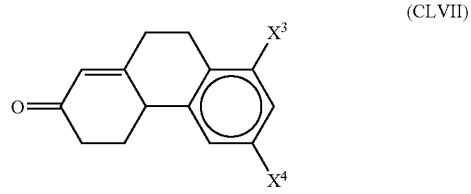

(wherein, $X^3$ and $X^4$ represent the same meaning as in (CXXXVI)), and reduction of this compound using metallic lithium or the like yields the general formula (CLVIII), (CLVIII)
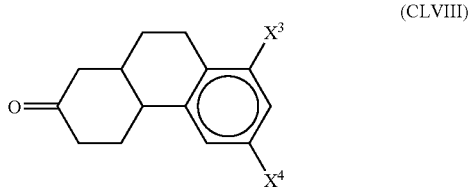

(wherein, $X^3$ and $X^4$ represent the same meaning as in (CXXXVI)), and subsequent reaction with the general formula (CV), hydrolysis under acid conditions, and then isomerization under basic conditions yields a compound represented by the general formula (CLIX).

(CLIX)
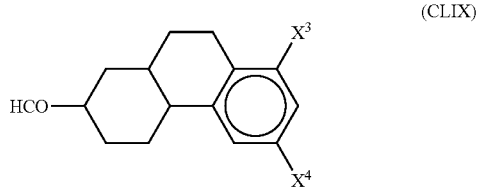

(wherein, $X^3$ and $X^4$ represent the same meaning as in (CXXXVI), and the cyclohexane rings represent a trans isomer). Reaction of this compound with the general formula (CXX) yields the general formula (CLX).

(CLX)
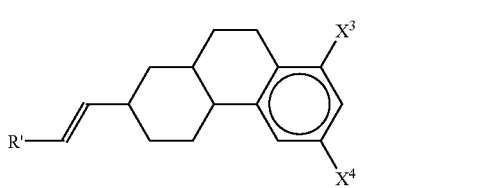

(wherein, R' represents the same meaning as in (CXX), $X^3$ and $X^4$ represent the same meaning as in (CXXXVI), and the cyclohexane rings represent a trans isomer). At this point, instead of the reaction with the general formula (CXX), by repeating the process of reaction with the formula (CV) and subsequent hydrolysis, prior to the reaction with the general formula (CXX), any desired alkenyl group can also be produced. Catalytic reduction of the general formula (CLX) using a transition metal catalyst such as palladium-carbon yields a compound of the general formula (CLXI).

(CLXI)
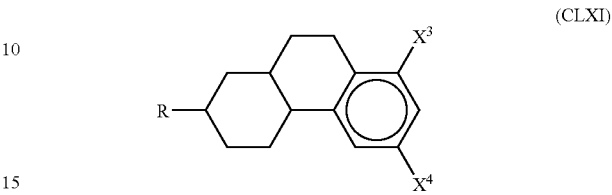

(wherein, R represents the same meaning as in (I), $X^3$ and $X^4$ represent the same meaning as in (CXXXVI), and the cyclohexane rings represent a trans isomer). Reaction of this compound with oxalyl dichloride or the like, in the presence of a Lewis acid catalyst such as aluminum chloride yields a compound of the general formula (CLXII), (CLXII)
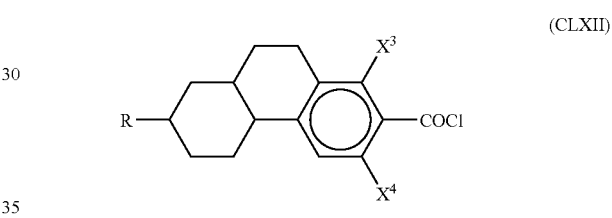

(wherein, R represents the same meaning as in (I), and $X^3$ and $X^4$ represent the same meaning as in (CXXXVI)), and by reacting this compound with the general formula (CIII), and then separating the isomers by column chromatography in those cases where isomers exist, compounds of the general formula (Id-7), including the general formulas from (I-2dm) to (I-2do), and the general formulas from (I-2dp) to (I-2du) can be produced.

(Id-7)
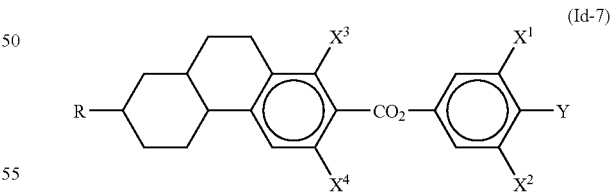

(wherein, R, $X^1$, $X^2$ and Y represent the same meaning as in (I), $X^3$ and $X^4$ represent the same meaning as in (CXXXVI), and the cyclohexane rings represent a trans isomer)

4-14. Production of General Formulas from (I-2dv) to (I-2dx)

Lithiation of the general formula (XLIV) with an alkyl lithium such as butyl lithium, and subsequent reaction with carbon dioxide gas yields the general formula (CLXIII)

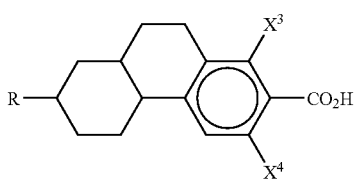
(CLXIII)

(wherein, R represents the same meaning as in (I), $X^5$ and $X^6$ represent the same meaning as in (CXXXIX), and the cyclohexane rings represent a trans isomer), and by converting this compound to an acid chloride, and subsequently reacting with the general formula (CXIV), compounds of the general formula (Id-8), including the general formulas from (I-2dv) to (I-2dx) can be produced.

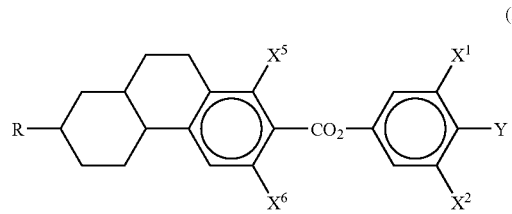
(Id-8)

(wherein, R, Y, $X^1$ and $X^2$ represent the same meaning as in (I), $X^5$ and $X^6$ represent the same meaning as in (CXXXIX), and the cyclohexane rings represent a trans isomer)

5. Production of the General Formula (I) in which the Ring B Comprises a 1,2,3,4-tetrahydrophenanthrene Skeleton Reaction of a compound represented by the formula (CLXIV)

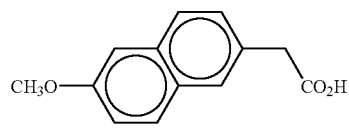
(CLXIV)

with a halogenation reagent such as thionyl chloride yields the formula (CLXV).

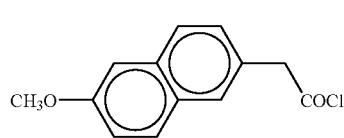
(CLXV)

Reaction of this compound with ethylene gas in the presence of a Lewis acid such as aluminum chloride yields the formula (CLXVI),

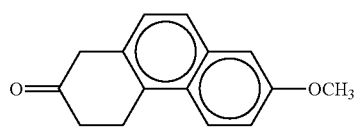
(CLXVI)

and further reaction with a compound of the general formula (CLXVII)

RM (CLXVII)

(wherein, R represents the same meaning as in (I), M represents MgX (where X represents a chlorine atom, a bromine atom or an iodine atom), a metal atom such as Li, $B(OH)_2$, or $SiF(CH_3)_2$), followed by dehydration in the presence of an acid catalyst yields a compound of the general formula (CLXVIII),

(CLXVIII)

(wherein, R represents the same meaning as in (I)), and by reducing the double bond in this compound using a transition metal catalyst such as palladium-carbon, and then performing an isomerization using a strong base such as potassium-t-butoxide, a compound of the general formula (CLXIX) is produced.

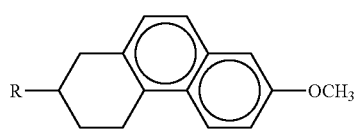
(CLXIX)

(wherein, R represents the same meaning as in (I), and the cyclohexane ring represents a trans isomer)

Furthermore, reaction of the formula (CLXV) with the formula (CV), followed by hydrolysis under acid conditions, and a subsequent isomerization under basic conditions yields a compound represented by the general formula (CLXX).

(CLXX)

CHO—⬡—⬡—OCH₃

(wherein, the cyclohexane ring represents a trans isomer). Reaction of this compound with the general formula (CXX) yields the general formula (CLXXI).

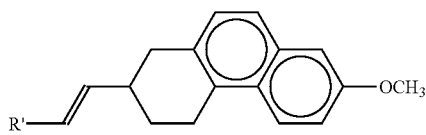

(wherein, R' represents the same meaning as in (CXX), and the cyclohexane ring represents a trans isomer). At this point, instead of the reaction with the general formula (CXX), by repeating the process of reaction with the formula (CV) and subsequent hydrolysis, prior to the reaction with the general formula (CXX), any desired alkenyl group can be produced. Deprotection of the phenol group of the general formula (CLXIX) or the general formula (CLXXI) using hydrobromic acid or the like yields the general formula (CLXXII).

(CLXXIII)

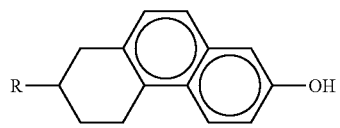

(wherein, R represents the same meaning as in (I), and the cyclohexane ring represents a trans isomer). Reaction of this compound with the same halogenation reagent used in the production of the general formula (CXXXVI) enables the production of a compound of the general formula (CLXXIII).

(CLXXIII)

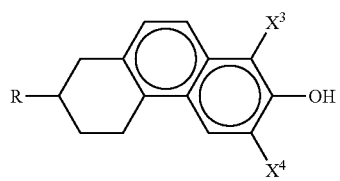

(wherein, R, $X^3$ and $X^4$ represent the same meaning as in (I), and the cyclohexane ring represents a trans isomer). By using the produced general formula (CLXXII) instead of the general formula (CXXXI) in the aforementioned production methods for compounds of the general formula (I) comprising a 1,2,3,4,4a,9,10,10a-octahydrophenanthrene skeleton, corresponding compounds with a 1,2,3,4-tetrahydrophenanthrene skeleton can be produced. Similarly, by using the general formula (CLXXIII) instead of the general formula (CXXXVI), corresponding compounds can be produced.

6. Production of the General Formula (I) in which the Ring B Comprises a 1,2,3,4,5,6,7,8-octahydrophenanthrene Skeleton Reaction of a compound represented by the formula (CLXXIV)

(CLXXIV)

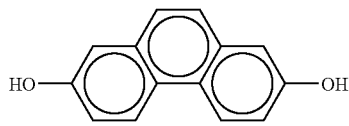

with hydrogen in the presence of a metal catalyst such as palladium, ruthenium, or platinum causing a partial reduction of the aromatic rings, yields the formula (CLXXV).

(CLXXV)

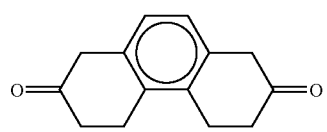

Protection of one of the carbonyl groups of this compound using a diol yields a compound of the formula (CLXXVI), (CLXXVI)

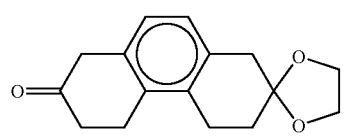

and reaction of this compound with the general formula (CLXVII) and subsequent dehydration in the presence of an acid catalyst yields the general formula (CLXXVII).

(CLXXVII)

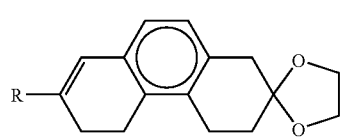

(wherein, R represents the same meaning as in (I)). Reduction of the double bond within this compound with hydrogen, in the presence of a metal catalyst yields a compound of the general formula (CLXXVIII);

(CLXXVIII)

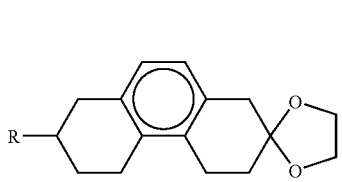

(wherein, R represents the same meaning as in (I)). Deprotection of this compound in the presence of an acid catalyst produces the general formula (CLXXIX).

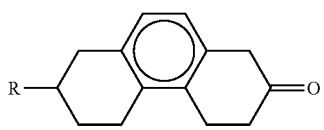

(CLXXIX)

(wherein, R represents the same meaning as in (I)). By using the thus obtained general formula (CLXXIX) instead of the general formula (CII) in the aforementioned production methods for compounds of the general formula (I) comprising a tetradecahydrophenanthrene skeleton, corresponding compounds with a 1,2,3,4,5,6,7,8-octahydrophenanthrene skeleton can be produced.

7. Production 1 of Other Compounds of the General Formula (I)

7-1. Production of General Formulas from (I-3ab) to (I-3ad), General Formulas from (I-3ba) to (I-3bd), and General Formulas from (I-3bi) to (I-3bu)

These compounds can be produced in the manner described below.

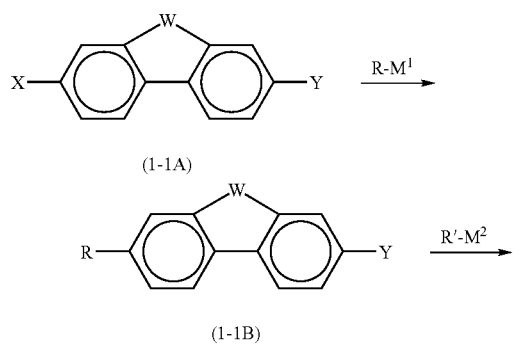

(1-1A)

(1-1B)

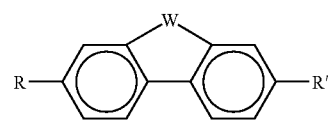

(1-1C)

(wherein, W represents —$CH_2CH_2$—, —CH=CH—, or —$CH_2$—, X and Y each represent, independently, a leaving group such as chlorine, bromine, iodine, a p-toluene sulfonyl group, a methane sulfonyl group, or a trifluoromethanesulfonyl group, R and R' represent an alkyl group or an alkenyl group, and $M^1$ and $M^2$ represent a metal ion such as MgCl, MgBr, MgI, Li or $B(OH)_2$). In other words, reaction of a compound represented by the general formula (1-1A) comprising a suitable leaving group, with an organometallic compound represented by the general formula R—$M^1$, in the presence of a transition metal catalyst such as a palladium complex or a nickel complex, yields a compound represented by the general formula (1-1B), and by further reacting this compound with an organometallic compound represented by the general formula R'—$M^2$, compounds represented by the general formula (1-1C), including the general formula (I-3ab), the general formula (I-3ba), and the general formula (I-3bi) can be produced.

The compound (1-1A) can be prepared easily by known methods. An example is presented below for the case in which Y is either bromine or iodine.

Furthermore, in the cases of compounds in which W represents —$CH_2CH_2$— or —CH=CH—, production can also be carried out using the type of method shown below.

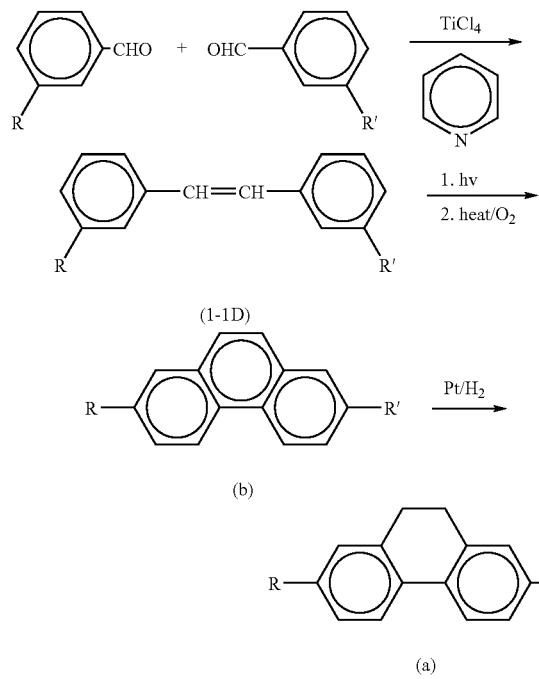

(1-1D)

(b)

(a)

(wherein, R and R' represent the same meaning as described above)

In other words, cross-coupling of 2 different benzaldehyde derivatives using a titanium tetrachloride-pyridine complex yields a stilbene derivative represented by the general formula (1-1D). Photoisomerization of this compound followed by an oxidative thermal cyclization produces a compound represented by the general formula (b). By then hydrogenating this compound in the presence of a transition metal catalyst such as Pd—C, Rh—C, Pt—C or Pd(OH)$_2$, a compound represented by the general formula (a) can be produced.

7-2. Production of General Formulas from (I-3ah) to (I-3ap), and General Formulas from (I-3be) to (I-3bh)

These compounds can be produced in the manner described below.

In the case of compounds represented by the general formulas (f) or (g), these compounds can be produced by partial hydrogenation of the compound represented by the general formula (b) produced in 7-1, in the presence of a transition metal catalyst such as Pd—C, Rh—C, Pt—C or Pd(OH)$_2$.

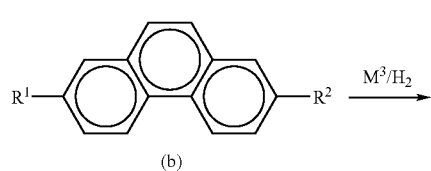

(b)

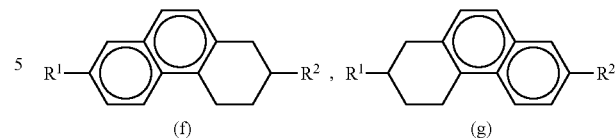

(f) , (g)

(hereafter, $R^1$ represents the same as R and $R^2$ the same as R', and $M^3$ represents a transition metal such as Pd—C, Rh—C, Pt—C or Pd(OH)$_2$)

Furthermore, in the case of compounds represented by the general formulas (d) or (e), these compounds can be produced in the manner described below.

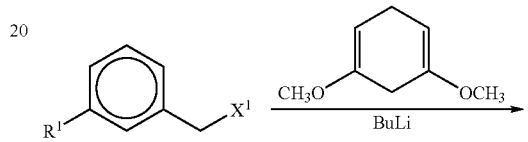

(1-2A)

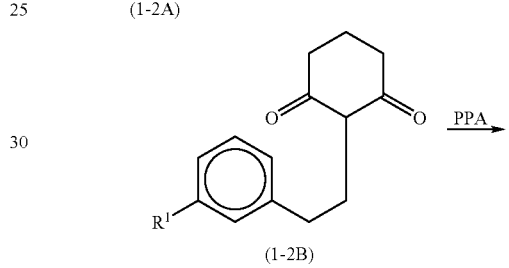

(1-2B)

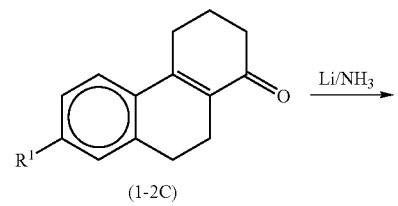

(1-2C)

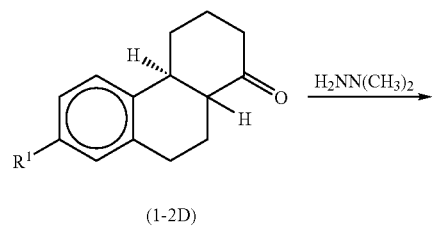

(1-2D)

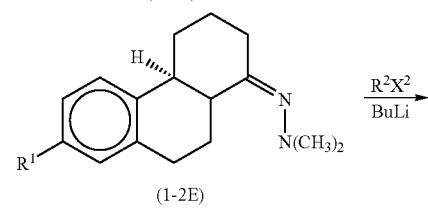

(1-2E)

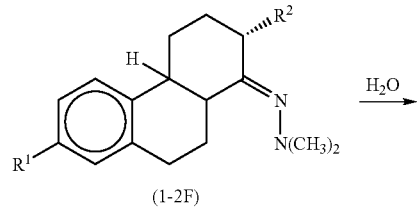

(1-2F)

-continued

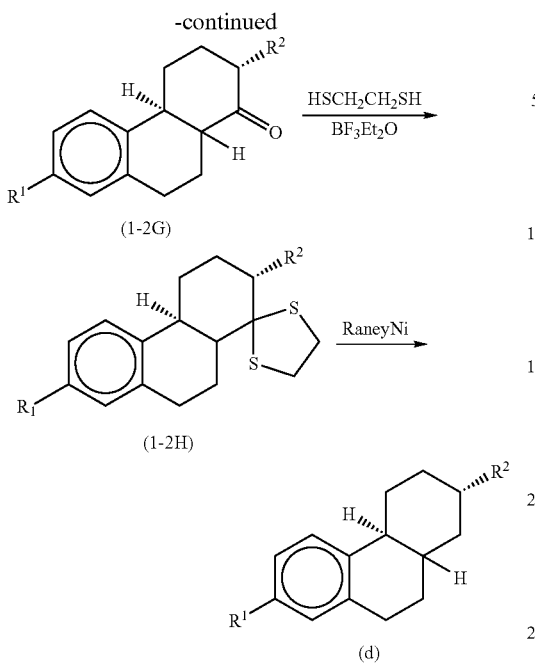

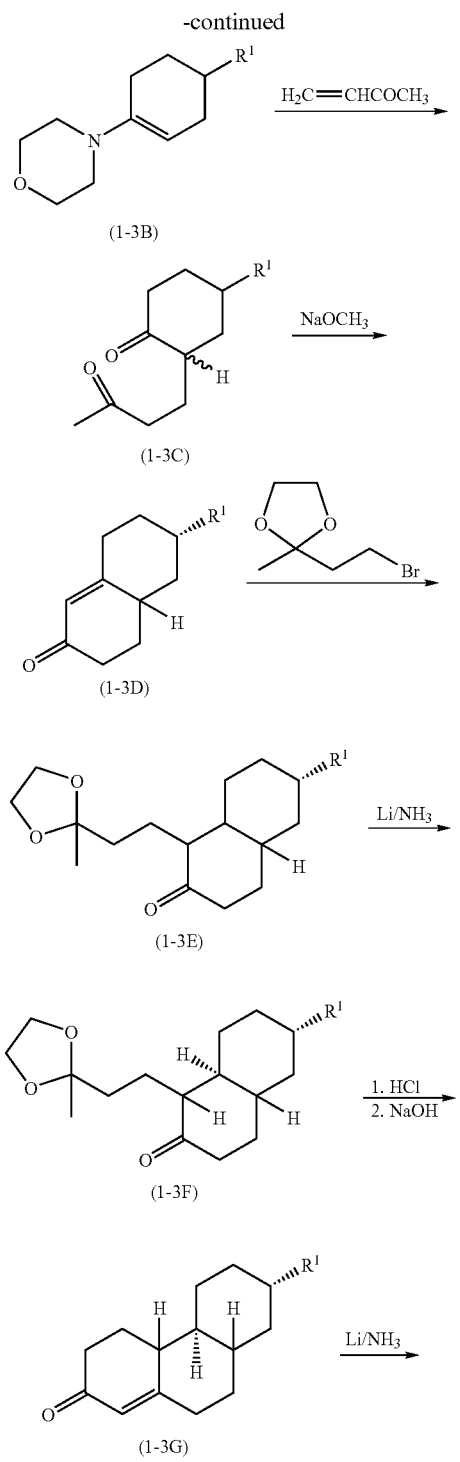

(wherein, $R^1$, $R^2$ are as described above. $X^1$ and $X_2$ represent chlorine, bromine or iodine.)

In other words, reaction of the benzyl halide derivative represented by the general formula (1-2A) with the anion of 1,5-dimethoxycyclohexa-1,4-diene yields the 1,3-cyclohexadione derivative represented by the general formula (1-2B), and subsequent cyclodehydration using phosphoric acid or sulfuric acid yields the enone represented by the general formula (1-2C). Following conversion of this compound to a saturated ketone by a Birch reduction, an imine derivative anion represented by the by general formula (1-2E) is prepared by reaction with hydrazine. An $R^2$ group is then introduced by reaction with an alkyl or allyl halide. By converting the carbonyl group produced by hydrolysis to a dithiane derivative, for example, and then performing a reduction with Raney nickel, compounds of the general formula (d), including the general formula (I-3ah) and the general formula (I-3be) can be produced.

7-3. Production of General Formula (I-3aa), and General Formulas from (I-3ae) to (I-3ag)

In the case of compounds represented by the general formula (h), production can be carried out in the manner described below.

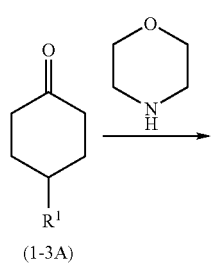

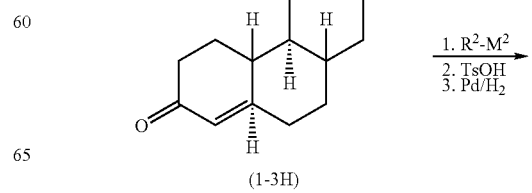

-continued

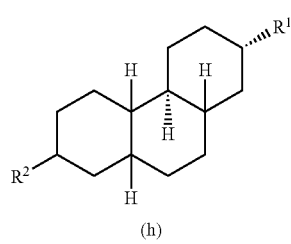

(h)

(wherein, $R^1$, $R^2$ and $M^2$ are as described above)

In other words, conversion of the cyclohexanone derivative represented by the general formula (1-3A) to an enamine, and subsequent reaction with 3-buten-2-one yields the diketone (1-3C). Cyclization of this compound through a Robinson cyclization, and a subsequent reaction with 2-(2-bromoethyl)-2-methyl-1,3-dioxolane, followed by a Birch reduction, an aldol condensation, and a second Birch reduction, yields the phenanthrene derivative represented by the general formula (1-3H). Next, an $R^2$ group is introduced by reaction with an organometallic reagent $R^2$—$M^2$, and a dehydration is carried out in the presence of an acid catalyst such as p-toluenesulfonic acid, and by then performing a dehydrogenation in the presence of a transition metal catalyst such as Pd—C, Rh—C, Pt—C or Pd(OH)$_2$, compounds of the general formula (h), including the general formula (1-3aa), can be produced.

In the case of compounds represented by the general formula (i), production can be carried out in the manner described below.

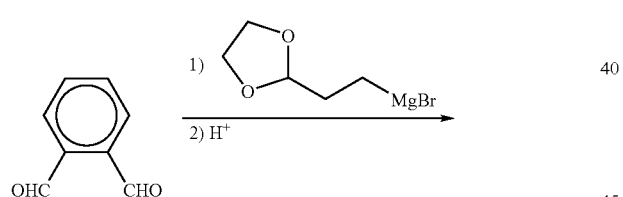

-continued

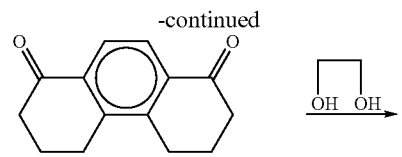
(1-3L)

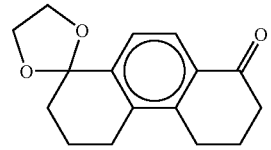
(1-3M)

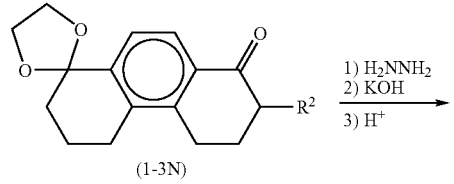
(1-3N)

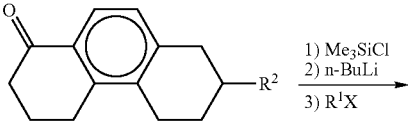
(1-3O)

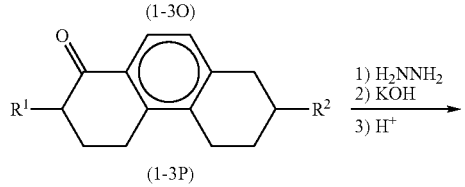
(1-3P)

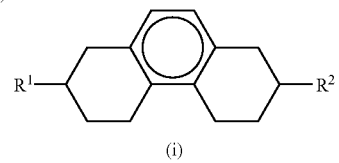
(i)

(wherein, $R^1$, $R^2$ and X are as described above)

In other words, reaction of phthalaldehyde with 3,3-ethylenedioxypropylmagnesium bromide increases the number of carbon atoms by six, forming an hydroxyaldehyde derivative (1-3I). Oxidation of this compound with an oxidizing agent such as potassium permanganate yields the ketocarboxylic acid (1-3J), and reduction of the carbonyl groups by zinc amalgam or the like yields the carboxylic acid (1-3K). Cyclodehydration using polyphosphoric acid (PPA) or sulfuric acid or the like produces the octahydrophenanthrene dione derivative represented by the general formula (1-3L). Next, following protection of one of the carbonyl groups, a substitutent group $R^2$ is introduced via a silyl enol ether for example. By then removing the protective group, and using a similar reaction to introduce a substitutent group $R^1$ to the opposite side of the molecule, compounds of the general formula (i), including the general formula (I-3ae), can be produced.

7-4. Production of General Formulas from (I-3ca) to (I-3ct), General Formulas from (I-3da) to (I-3dp), General Formulas from (I-3ea) to (I-3em), General Formulas from (I-3fa) to (I-3fx), General Formulas from (I-3ga) to (I-3gp), and General Formulas from (I-3ha) to (I-3 hr) (in the Cases in which at least one of n and m is 1, and $L^1$ and $L^2$ are Single Bonds)

In general, these compounds can be produced by using compounds represented by the general formulas shown below instead of using the organometallic reagents $R—M^1$ or $R'—M^2$ or the halogenated compounds $R^1—X^1$ or $R^2—X^2$ described above,

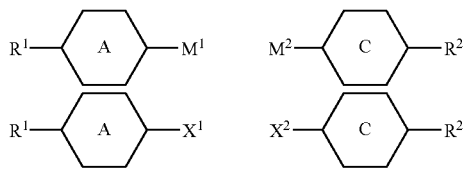

(wherein, the ring A and the ring C represent the same meaning as in (I), and $R^1$, $R^2$, $M^1$, $M^2$, $X^1$ and $X^2$ are as described above), or alternatively by preparing the corresponding ketones or aldehydes in advance. For example, as shown in the equations below, by reacting 1,4-cyclohexanedione monoacetal with an organometallic reagent incorporating a ring A, subsequently performing a dehydration in the presence of an acid catalyst such as p-toluenesulfonic acid, and then conducting a reduction and an elimination of the protective group by hydrogenation in the presence of a transition metal catalyst such as Pd—C, Rh—C, Pt—C or Pd(OH)$_2$, a cyclohexanone derivative (2-A) can be produced.

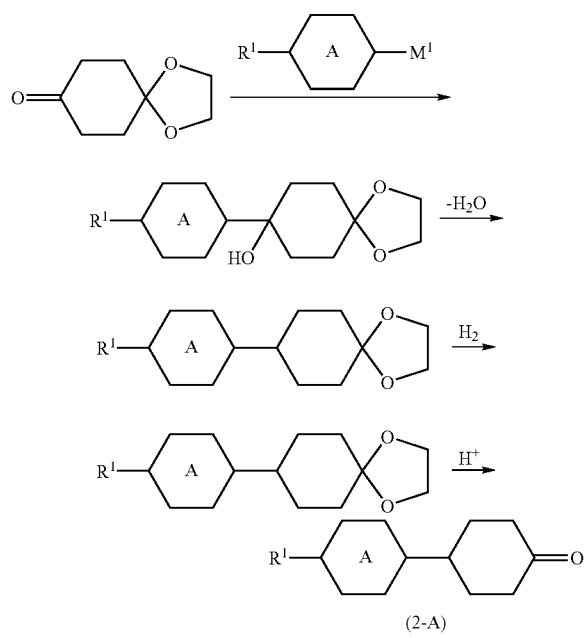

(wherein, the ring A, $R^1$ and $M^1$ are as described above)

By applying this compound to the production method for the compound represented by the general formula (h), a tetradecahydrophenanthrenone (2-B) can be produced.

Moreover, subsequent reaction with an organometallic reagent incorporating a ring C yields an alcohol (2-C). By dehydrating this compound in the presence of an acid catalyst such as p-toluenesulfonic acid, and then performing a hydrogenation in the presence of a transition metal catalyst such as Pd—C, Rh—C, Pt—C or Pd(OH)$_2$, a compound (2-D) of the general formula (I) can be produced.

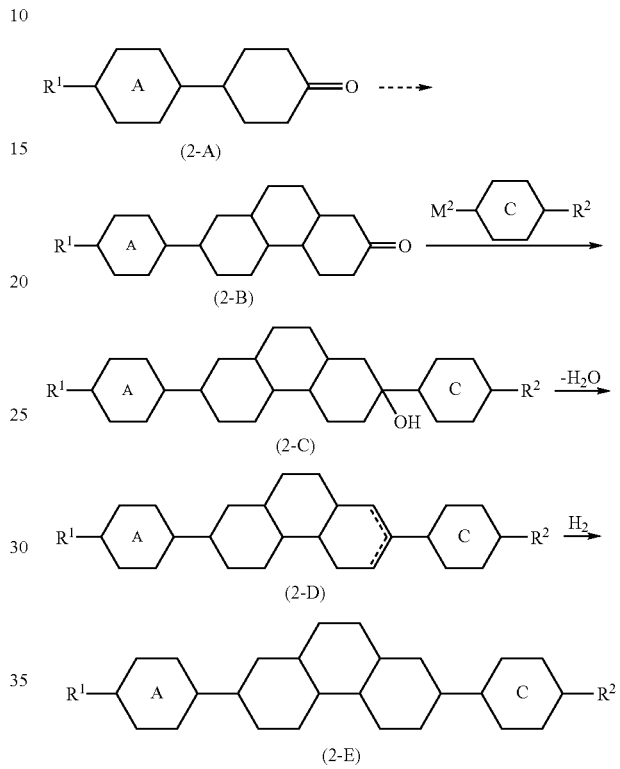

(wherein, the ring A, the ring C, $R^1$, $R^2$ and $M^2$ are as described above)

7-5. Production of General Formula (3-C) (in the Case in which at least one of n and m is 1, and $L^1$ and $L^2$ are Single Bonds or CH$_2$CH$_2$, although at least one is a CH$_2$CH$_2$ Group)

In general, these compounds can be produced by using the reagents shown below instead of using the organometallic reagents $R—M^1$ or $R'—M^2$ described in (1) above.

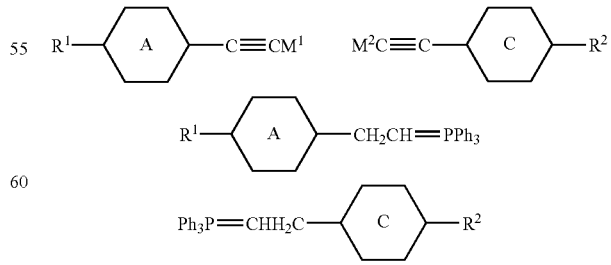

(wherein, the ring A, the ring C, $R^1$, $R^2$, $M^1$ and $M^2$ are as described above).

The equations below show an example of a production method which utilizes the same intermediate (2-B) used in the production of the aforementioned compound (2-E).

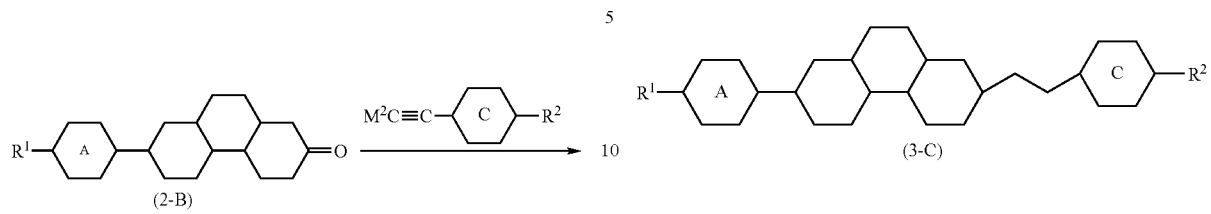

(2-B)

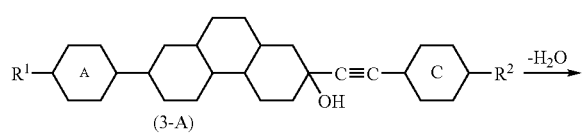

(3-A)

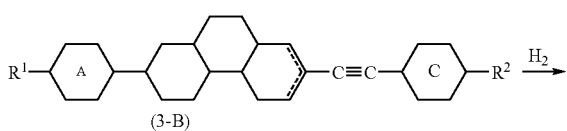

(3-B)

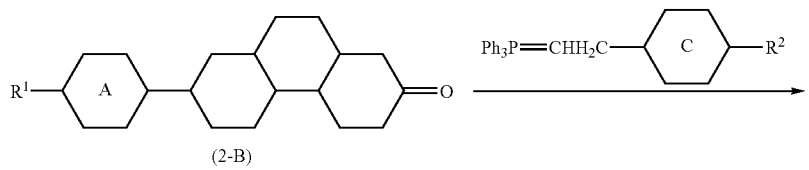

(3-C)

wherein, the ring A, the ring C, $R^1$, $R^2$, and $M^2$ are as described above).

In other words, reaction of the tetradecahydrophenanthrenone (2-B) with an organometallic reagent (acetylide) incorporating a ring C yields an alcohol (3-A). By dehydrating this compound in the presence of an acid catalyst such as p-toluenesulfonic acid, and then performing a hydrogenation in the presence of a metal catalyst such as Pd—C, Rh—C, Pt—C or Pd(OH)$_2$, a compound (3-C) of the general formula (I) can be produced. In a similar manner,

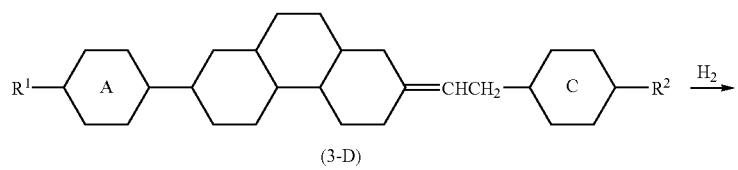

(2-B)

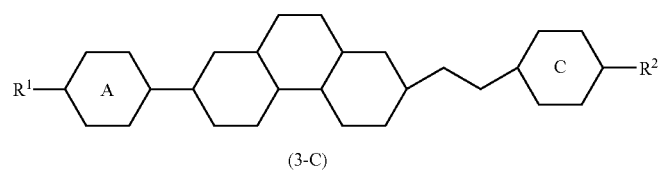

(3-D)

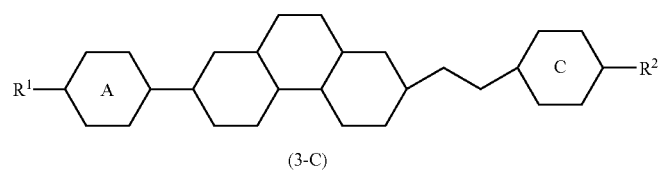

(3-C)

(wherein, the ring A, the ring C, $R^1$ and $R^2$ are as described above)

reaction of the tetradecahydrophenanthrenone (2-B) with a Wittig reagent incorporating a ring C yields an olefin (3-D). By performing a subsequent hydrogenation in the presence of a metal catalyst such as Pd—C, Rh—C, Pt—C or Pd(OH)$_2$, a compound (3-C) of the general formula (I) can be produced.

In addition, production of the compound (3-C) can also be achieved in the manner shown below.

pound with a Wittig reagent incorporating a ring C yields an olefin (3-F). By performing a subsequent hydrogenation in the presence of a metal catalyst such as Pd—C, Rh—C, Pt—C or Pd(OH)$_2$, a compound (3-C) represented by the general formula (I) can be produced.

8. Production of other Compounds of the General Formula (I)

8-1. Production of General Formulas from (I-3dd) to (I-3dg), and General Formulas from (I-3be) to (I-3bh) (in the Case in

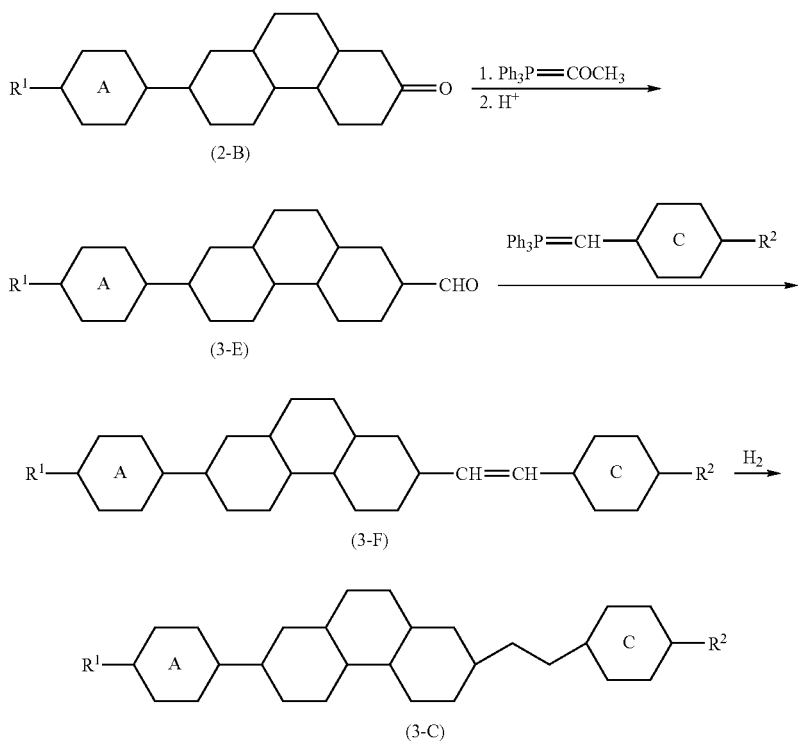

(wherein, the ring A, the ring C, $R^1$ and $R^2$ are as described above).

In other words, reaction of the tetradecahydrophenanthrenone (2-B) with methoxymethyl ylide and subsequent hydrolysis yields an aldehyde (3-E). Reaction of this comwhich Z Represents a Polar Group such as a Halogen or a Cyano Group)

These compounds can be produced in the manner described below.

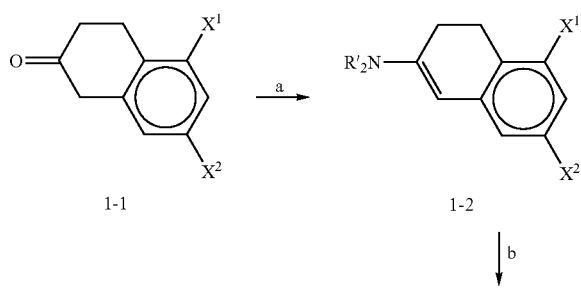

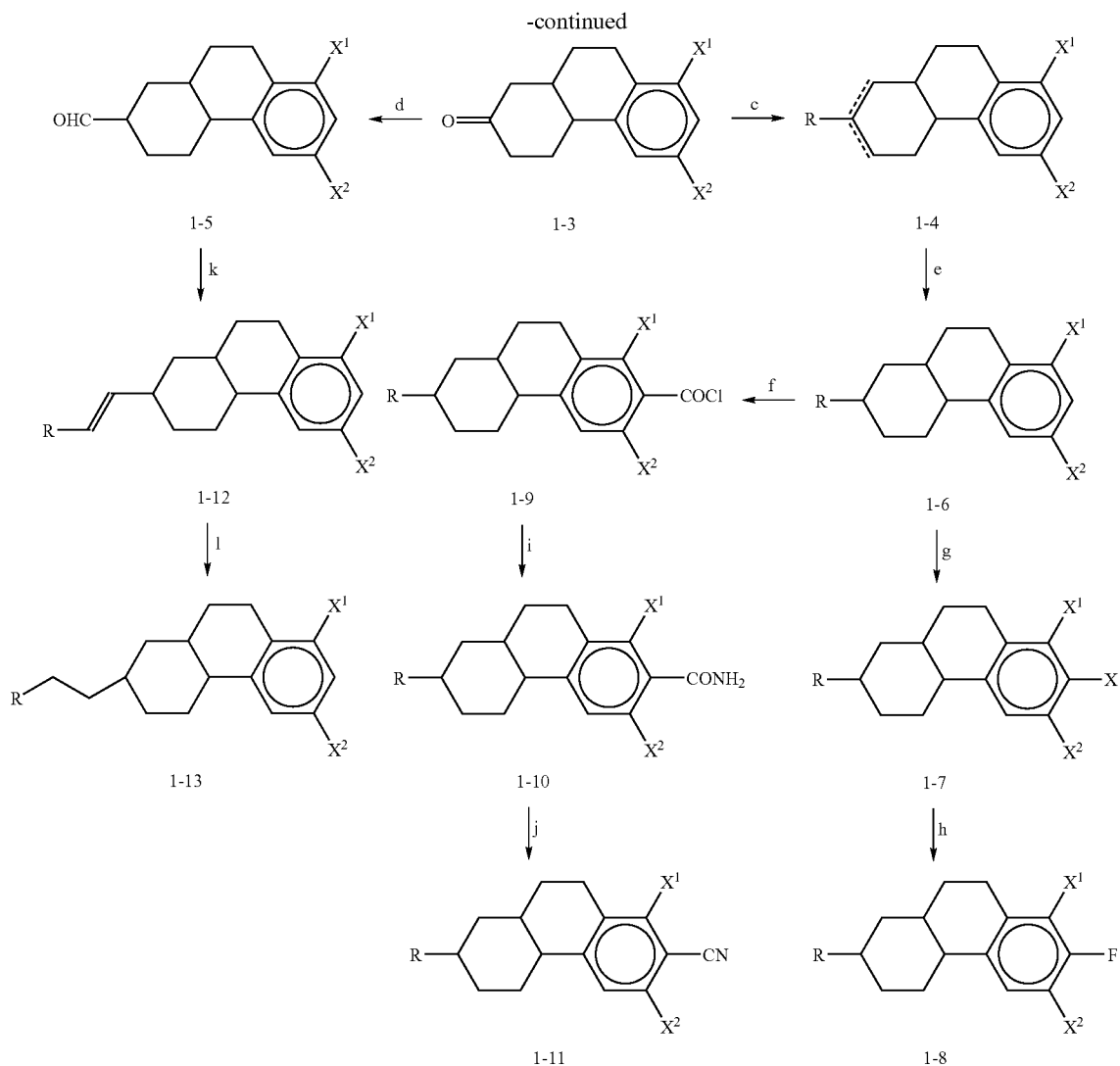

(wherein, R, $X^1$ and $X^2$ represent the same meaning as in (I), R' represents an alkyl group, and X represents iodine or bromine)

An enamine (1-2) is first prepared by reaction of a ketone (1-1) with a secondary amine such as morpholine or pyrrolidine (a). Reaction of this enamine (1-2) with methyl vinyl ketone, followed by a cyclization under acid conditions yields an enone derivative, which upon a Birch reduction produces an octahydrophenanthrone (1-3) (b). Reaction of the compound (1-3) with an organometallic reagent (R—M) (wherein, M represents a metal containing group such as MgCl, MgBr, MgI, Li or $B(OH)_2$), and subsequent dehydration of the thus obtained alcohol with an acid catalyst such as p-toluenesulfonic acid yields an olefin derivative (1-4) (c). Hydrogenation of this compound in the presence of a metal catalyst such as Pd—C, Rh—C, Pt—C or Pd(OH)$_2$ yields an octahydrophenanthrene derivative (1-6) (e). Following subsequent conversion to a halogenated compound (1-7) using metallic lithium and either iodine or bromine (g), subsequent reaction with a compound such as potassium fluoride produces a fluorine derivative (1-8) (h). Alternatively, the compound (1-8) can be derived directly from the compound (1-6) in a single step by using metallic lithium and a fluorination agent such as MEC-31. Furthermore, reaction of the phenanthrenone (1-3) with a Wittig reagent ($CH_3OCH=PPh_3$) and subsequent hydrolysis yields an aldehyde (1-5) (d). Reaction of this aldehyde with a Wittig reagent ($RCH=PPh_3$) yields an olefin (1-12) (k). Hydrogenation of this compound in the presence of an acid catalyst such as Pd—C enables production of the compound (3-C) in which L is an ethylene chain. (l). Furthermore, reaction of the compound (1-6) with oxalyl dichloride or the like, in the presence of a Lewis acid catalyst such as aluminum chloride yields an acid chloride (1-9) (f), which on subsequent reaction with ammonia yields an amide (1-10) (i), and by then performing a dehydration using sulfuric acid or phosphorus oxychloride, a cyano derivative (1-11) can be produced (j).

8-2. Production of General Formulas from (I-3ah) to (I-3ap), and General Formulas from (I-3dh) to (I-3dp) (in the Case in which Z Represents a Polar Group such as a Halogen or a Cyano Group)

These compounds can be produced in the manner described below.

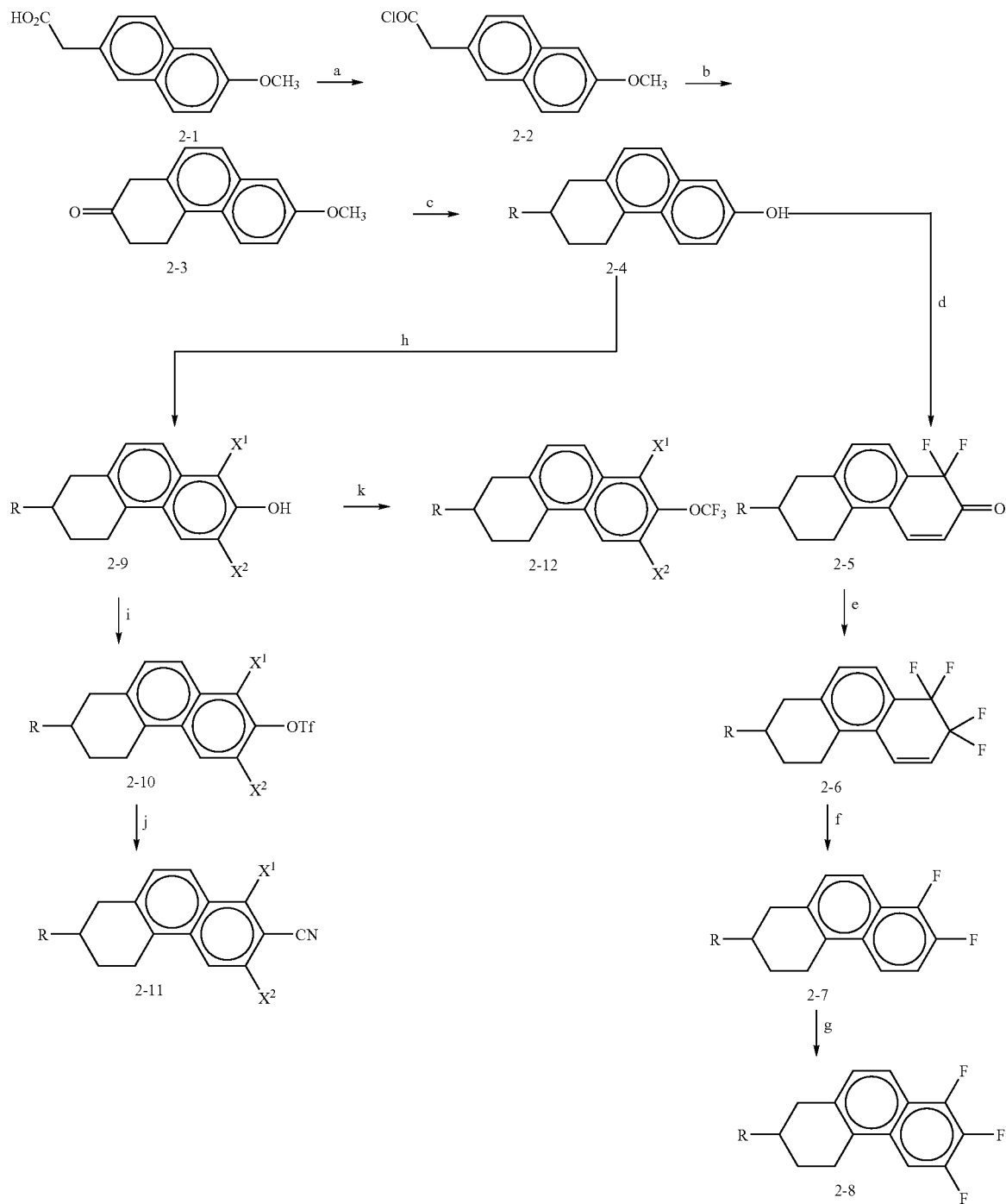

(wherein, R, $X^1$ and $X^2$ represent the same meaning as in (I))

Conversion of a naphthylacetic acid derivative (2-1) to an acid chloride (2-2) using thionyl chloride or the like (a), and subsequent reaction with ethylene gas in the presence of a Lewis acid catalyst such as aluminum chloride produces a tetrahydrophenanthrene (2-3) (b). Next, in the same manner as described above in section (8-1), reaction with an organometallic reagent (R—M) (wherein M represents a metal containing group such as MgCl, MgBr, MgI, Li or B(OH)$_2$), and subsequent dehydration and hydrogenation, followed by elimination of the protective group with hydrobromic acid or the like yields a compound (2-4) (c). Reaction of this compound with a fluorination agent (such as F—TEDA—BF$_4$) produces a compound (2-5) (d). Further reaction with a fluorination agent (such as DAST) yields a tetrafluoro compound (2-6) (e). Reduction of this compound in the presence of a tertiary amine such as triethylamine using a Pd—C catalyst enables a difluorotetrahydrophenanthrene derivative (2-7) to be produced (f).

Moreover, treatment of the compound (2-7) with n-butyl lithium and subsequent reaction with a fluorination agent (such as NFSi) enables the production of a trifluorotetrahydrophenanthrene derivative (2-8) (g). Furthermore, reaction of the compound (2-4) with a fluorination agent (such as MEC-31) yields a compound (2-9) (wherein one of $X^1$ and $X^2$ is a hydrogen atom) (h). Conversion of this compound to a triflate (2-10) by reaction with trifluoromethanesulfonic anhydride (i), and subsequent reaction with cuprous cyanide using a palladium complex as a catalyst enables a cyano derivative (2-11) to be produced (j). Furthermore, conversion of the compound (2-9) to a sodium salt using sodium hydride or the like, and subsequent reaction with S-ethyl chlorodithiocarbonate produces a dithiocarbonate ester. Fluorination of this ester using a hydrogen fluoride-melamine complex or the like enables the production of a trifluoromethoxy derivative (2-12) (k).

8-3. Production of General Formulas from (I-3ab) to (I-3ad), and General Formulas from (I-3da) to (I-3db) (in the Case in which Z Represents a Polar Group such as a Halogen or a Cyano Group)

These compounds can be produced in the manner described below.

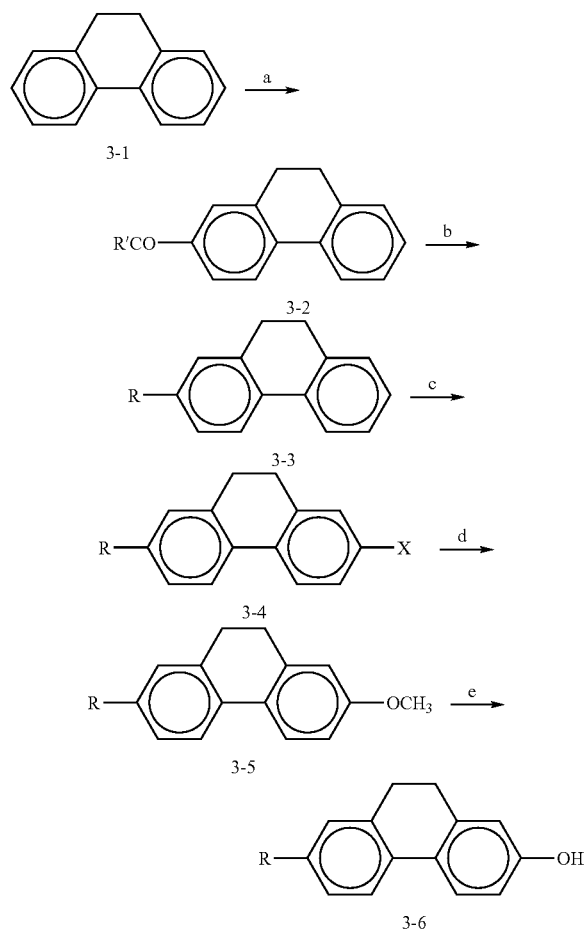

(wherein, R, $X^1$ and $X^2$ represent the same meaning as in (I), R' represents an alkyl group which may be substituted, and X represents a chlorine atom, a bromine atom or an iodine atom).

Acylation of 9,10-dihydrophenanthrene in the presence of aluminum chloride or the like (3-2) (a), and subsequent reduction of the carbonyl group using zinc amalgam or the like produces a monoalkyl compound (3-3) (b). Halogenation of this compound using a metal or a metal salt as a catalyst yields a compound (3-4) (c). Reaction of this compound with sodium methoxide in the presence of a catalyst such as cuprous iodide produces a methoxy derivative (3-5) (d). Subsequent hydrolysis using hydrochloric acid or hydrobromic acid or the like produces a compound (3-6). By employing the same production methods described above in section (8-2), this compound can be converted to a variety of derivatives represented by the general formula (I).

8-4. Production of General Formulas from (I-3ba) to (I-3bd), General Formulas from (I-3dq) to (I-3du) and General Formulas from (I-3ga) to (I-3gd) (in the Case in which Z Represents a Polar Group such as a Halogen or a Cyano Group)

These compounds can be produced in the manner described below.

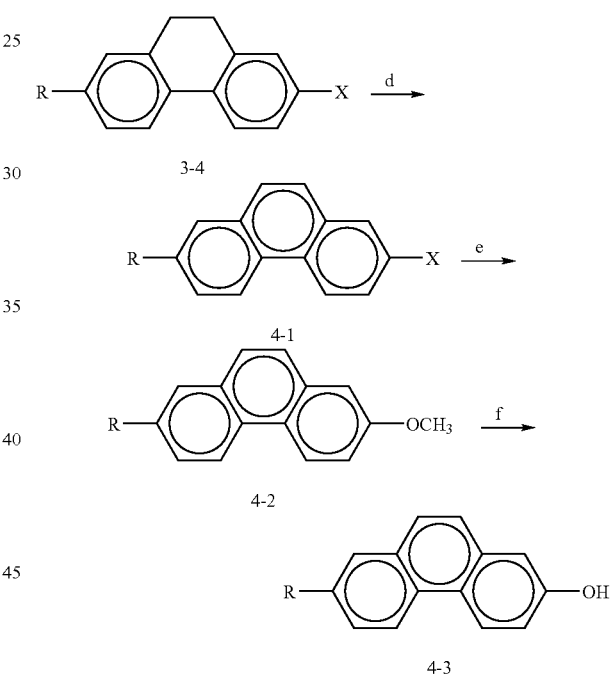

Dibromination of the 9,10-dihydrophenanthrene derivative (3-4) described above in section (8-3) with N-bromosuccinimide in the presence of a peroxide, and subsequent dehalogenation using zinc or sodium iodide enables the production of a compound (4-1) (d). This compound can be easily converted to a hydroxy derivative (4-3) using the method described above in section (8-3) (e–f). In addition, by employing the same production methods described above in section (8-2), the compound (4-3) can be converted to a variety of derivatives represented by the general formula (I).

8-5. Production of General Formulas from (I-3bi) to (I-3bu), and General Formulas from (I-3ge) to (I-3gu) (in the Case in which Z Represents a Polar Group such as a Halogen or a Cyano Group)

In the case of compounds with a fluorene skeleton (IIe), production can be achieved in the manner described below.

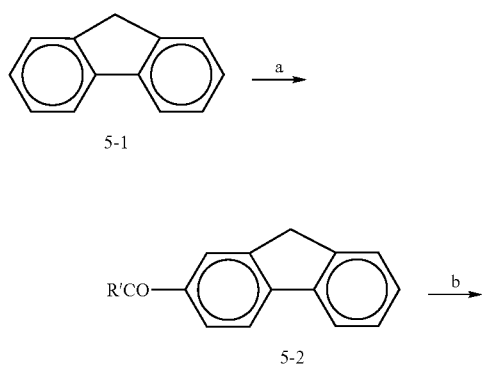

5-1

5-2

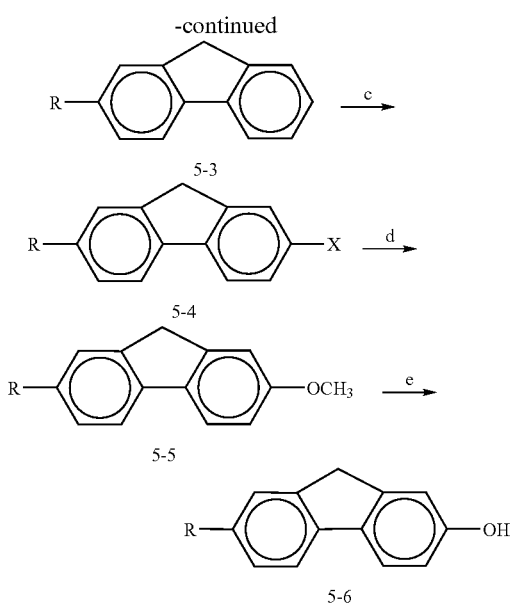

5-3

5-4

5-5

5-6

Using fluorene (5-1) as a starting material and using the methods described above in section (8-3), a hydroxy derivative (5-6) can be produced easily (a–e). In addition, by employing the same production methods described above in section (8-2), the compound (5-6) can be converted to a variety of derivatives represented by the general formula (I).

The descriptions above represent only sample methods of producing the compounds of the present invention, and compounds of the present specification can also be produced by other methods. As a representative example of preferred nematic liquid crystal compounds which can be used in a mixture with a compound represented by the general formula (I), then in a composition provided by the present invention, although at least one type of compound represented by the general formula (I) is included as a first component, it is preferable that at least one type of compound from the second through fourth components described below is also included.

Namely, the second component is a so-called fluorine system (halogen system) p-type liquid crystal compound, and comprises a compound represented by the general formulas (A1) to (A3) shown below.

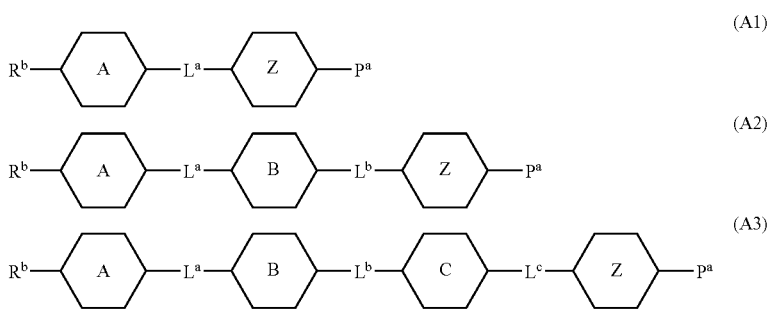

wherein $R^b$ represents an alkyl group of 1 to 12 carbon atoms, which may be either a straight chain or contain methyl or ethyl branches, may contain a 3 to 6 membered ring structure, may have any particular —CH$_2$— structure within the group replaced by a —O—, —CH=CH—, —CH=CF—, —CF=CH—, —CF=CF— or —C≡C—, and may have any particular hydrogen atom within the group substituted with a fluorine atom or a trifluoromethoxy group, although straight chain alkyl groups of 2 to 7 carbon atoms, straight chain 1-alkenyl groups of 2 to 7 carbon atoms, straight chain 3-alkenyl groups of 4 to 7 carbon atoms, and alkyl groups of 1 to 5 carbon atoms in which the terminal is substituted with an alkoxyl group of 1 to 3 carbon atoms are preferred. Furthermore, in those cases in which branching leads to an asymmetric carbon atom, either optically active compounds or racemic mixtures may be used.

The ring A, the ring B and the ring C each represent, independently, a trans-1,4-cyclohexylene group, a trans-decahydronaphthalene-trans-2,6-diyl group, a 1,4-phenylene group which may be substituted with one or more fluorine atoms, a naphthalene-2,6-diyl group which may be substituted with one or more fluorine atoms, a tetrahydronaphthalene-2,6-diyl group which may be substituted with one or more fluorine atoms, a 1,4-cyclohexenylene group which may be substituted with a fluorine atom, a 1,3-dioxane-trans-2,5-diyl group, a pyrimidine-2,5-diyl group or a pyridine-2,5-diyl group, although a trans-1,4-cyclohexylene group, a trans-decahydronaphthalene-trans-2,6-diyl group, a naphthalene-2,6-diyl group which may be substituted with a fluorine atom or a 1,4-phenylene group which may be substituted with one or two fluorine atoms are preferred. Particularly in those cases in which the ring B is a trans-1,4-cyclohexylene group or a trans-decahydronaphthalene-trans-2,6-diyl group, it is preferable that the ring A is a trans-1,4-cyclohexylene group, and in those cases in which the ring C is a trans-1,4-cyclohexylene group or a trans-decahydronaphthalene-trans-2,6-diyl group, it is preferable that the ring B and the ring A are trans-1,4-cyclohexylene groups. Furthermore in (A3), it is preferable that the ring A is a trans-1,4-cyclohexylene group.

$L^a$, $L^b$ and $L^c$ are linkage groups, and each represent, independently, a single bond, an ethylene group (—CH$_2$CH$_2$—), a 1,2-propylene group (—CH(CH$_3$)CH$_2$— and —CH$_2$CH(CH$_3$)—), a 1,4-butylene group, —COO—, —OCO—, —OCF$_2$—, —CF$_2$O—, —CH=CH—, —CH=CF—, —CF=CH—, —CF=CF—, —C≡C— or —CH=NN=CH—, although a single bond, an ethylene group, a 1,4-butylene group, —COO—, —OCF$_2$—, —CF$_2$O—, —CF=CF— or —C≡C— are preferred, and a single bond or an ethylene group are particularly desirable. Furthermore it is preferable that at least one of these linkage groups in (A2), and at least two of the linkage groups in (A3) are single bonds.

The ring Z is an aromatic ring, and can be represented by the general formulas (La) to (Lc) shown below.

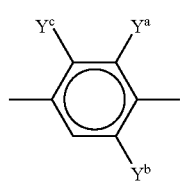
(La)

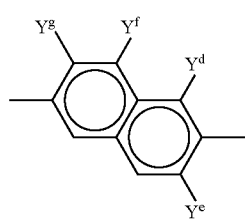
(Lb)

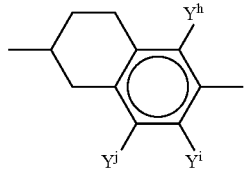
(Lc)

wherein, $Y^a$ to $Y^i$ each represent, independently, a hydrogen atom or a fluorine atom, although in (La) it is preferable that at least one of $Y^a$ and $Y^b$ is a fluorine atom, and in (Lb) it is preferable that at least one of $Y^d$ to $Y^f$ is a fluorine atom, with the structure in which $Y^d$ is a fluorine atom being particularly desirable.

The terminal group $P^a$ represents a fluorine atom, a chlorine atom, a trifluoromethoxy group, a difluoromethoxy group, or an alkoxyl group, alkyl group, alkenyl group or alkenyloxy group of 2 or 3 carbon atoms substituted with a trifluoromethyl group or a difluoromethyl group or 2 or more fluorine atoms, although a fluorine atom, a trifluoromethoxy group or a difluoromethoxy group are preferred, and a fluorine atom is particularly desirable.

Furthermore, compounds of the general formula (I) of the present invention are not included in (A2).

The third component is a so-called cyano system p-type liquid crystal compound, and comprises a compound represented by the general formulas (B1) to (B3) shown below.

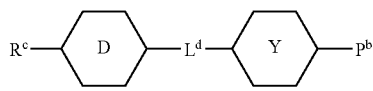
(B1)

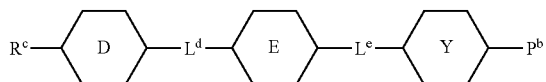
(B2)

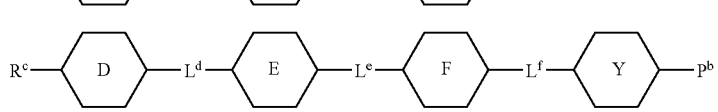
(B3)

wherein $R^c$ represents an alkyl group of 1 to 12 carbon atoms, which may be either a straight chain or contain methyl or ethyl branches, may contain a 3 to 6 membered ring structure, may have any particular —CH$_2$— structure within the group replaced by a —O—, —CH=CH—, —CH=CF—, —CF=CH—, —CF=CF— or —C≡C—, and may have any particular hydrogen atom within the group replaced with a fluorine atom or a trifluoromethoxy group, although straight chain alkyl groups of 2 to 7 carbon atoms, straight chain 1-alkenyl groups of 2 to 7 carbon atoms, straight chain 3-alkenyl groups of 4 to 7 carbon atoms, and alkyl groups of 1 to 5 carbon atoms in which the terminal is substituted with an alkoxyl group of 1 to 3 carbon atoms are preferred. Furthermore, in those cases in which branching leads to an asymmetric carbon atom, either optically active compounds or racemic mixtures may be used.

The ring D, the ring E and the ring F each represent, independently, a trans-1,4-cyclohexylene group, a transdecahydronaphthalene-trans-2,6-diyl group, a 1,4-phenylene group which may be substituted with one or more fluorine atoms, a naphthalene-2,6-diyl group which may be substituted with one or more fluorine atoms, a tetrahydronaphthalene-2,6-diyl group which may be substituted with one or more fluorine atoms, a 1,4-cyclohexenylene group which may be substituted with a fluorine atom, a 1,3-dioxane-trans-2,5-diyl group, a pyrimidine-2,5-diyl group or a pyridine-2,5-diyl group, although a trans-1,4-cyclohexylene group, a trans-decahydronaphthalene-trans-2,6-diyl group, a naphthalene-2,6-diyl group which may be substituted with a fluorine atom or a 1,4-phenylene group which may be substituted with one or two fluorine atoms are preferred. Particularly in those cases in which the ring E is a trans-1,4-cyclohexylene group or a trans-decahydronaphthalene-trans-2,6-diyl group, it is preferable that the ring D is a trans-1,4-cyclohexylene group, and in those cases in which the ring F is a trans-1,4-cyclohexylene group or a trans-decahydronaphthalene-trans-2,6-diyl group, it is preferable that the ring D and the ring E are trans-1,4-cyclohexylene groups. Furthermore in (B3), it is preferable that the ring D is a trans-1,4-cyclohexylene group.

$L^d$, $L^e$ and $L^f$ are linkage groups, and each represent, independently, a single bond, an ethylene group (—CH$_2$CH$_2$—), a 1,2-propylene group (—CH(CH$_3$)CH$_2$— and —CH$_2$CH(CH$_3$)—), a 1,4-butylene group, —COO—, —OCO—, —OCF$_2$—, —CF$_2$O—, —CH═CH—, —CH═CF—, —CF═CH—, —CF═CF—, —C≡C—, —OCH$_2$—, —CH$_2$O— or —CH═NN═CH—, although a single bond, an ethylene group, —COO—, —OCF$_2$—, —CF$_2$O—, —CF═CF— or —C≡C— are preferred, and a single bond, an ethylene group or a —COO— are particularly desirable. Furthermore it is preferable that at least one of these linkage groups in (B2), and at least two of the linkage groups in (B3) are single bonds.

The ring Y is an aromatic ring, and can be represented by the general formulas (Ld) to (Lf) shown below.

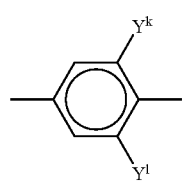
(Ld)

-continued

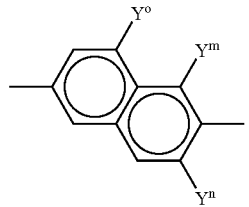
(Le)

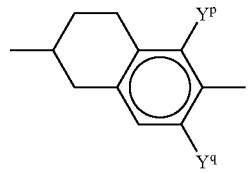
(Lf)

wherein, $Y_k$ to $Y_g$ each represent independently a hydrogen atom or a fluorine atom, although in (Le) it is preferable that $Y^m$ and $Y^o$ are hydrogen atoms.

The terminal group $P^b$ represents a cyano group (—CN), a cyanato group (—OCN) or a —C≡CCN group, although a cyano group is preferred.

Furthermore, compounds of the general formula (I) of the present invention are not included in (B2).

The fourth component is a non-polar liquid crystal compound in which the dielectric anisotropy is a value close to zero, and comprises a compound represented by the general formulas (C1) to (C3) shown below.

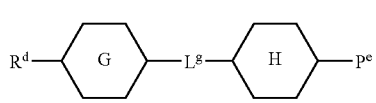
(C1)

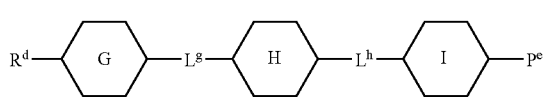
(C2)

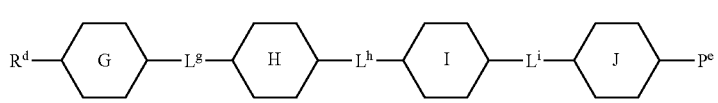
(C3)

wherein $R^d$ and $P^e$ each represent, independently, an alkyl group of 1 to 12 carbon atoms, which may be either a straight chain or contain methyl or ethyl branches, may contain a 3 to 6 membered ring structure, may have any particular —CH$_2$— structure within the group replaced by a —O—, —CH═CH—, —CH═CF—, —CF═CH—, —CF═CF— or —C≡C—, and may have any particular hydrogen atom within the group substituted with a fluorine atom or a trifluoromethoxy group, although straight chain alkyl groups of 1 to 7 carbon atoms, straight chain 1-alkenyl groups of 2 to 7 carbon atoms, straight chain 3-alkenyl groups of 4 to 7 carbon atoms, straight chain alkoxyl groups of 1 to 3 carbon atoms and straight chain alkyl groups of 1 to 5 carbon atoms in which the terminal is substituted with an alkoxyl group of 1 to 3 carbon atoms are preferred, and moreover, compounds in which at least one of $R^d$ and $P^e$ represent a straight chain alkyl group of 1 to 7 carbon atoms, a straight chain 1-alkenyl group of 2 to 7 carbon atoms, or a straight chain 3-alkenyl group of 4 to 7 carbon atoms are particularly desirable.

The ring G, the ring H, the ring I and the ring J each represent, independently, a trans-1,4-cyclohexylene group, a trans-decahydronaphthalene-trans-2,6-diyl group, a 1,4-phenylene group which may be substituted with one or two fluorine atoms or methyl groups, a naphthalene-2,6-diyl group which may be substituted with one or more fluorine atoms, a tetrahydronaphthalene-2,6-diyl group which may be substituted with one or two fluorine atoms, a 1,4-cyclohexenylene group which may be substituted with one or two fluorine atoms, a 1,3-dioxane-trans-2,5-diyl group, a pyrimidine-2,5-diyl group or a pyridine-2,5-diyl group, although in each compound it is preferable that there be no more than one trans-decahydronaphthalene-trans-2,6-diyl group, naphthalene-2,6-diyl group which may be substituted with one or more fluorine atoms, tetrahydronaphthalene-2,6-diyl group which may be substituted with one or two fluorine atoms, 1,4-cyclohexenylene group which may be substituted with a fluorine atom, 1,3-dioxane-trans-2,5-diyl group, pyrimidine-2,5-diyl group or pyridine-2,5-diyl group, and that the other rings in such cases should preferably be a trans-1,4-cyclohexylene group or a 1,4-phenylene group which may be substituted with one or two fluorine atoms or methyl groups.

$L^g$, $L^h$ and $L^i$ are linkage groups, and each represent, independently, a single bond, an ethylene group (—CH$_2$CH$_2$—), a 1,2-propylene group (—CH(CH$_3$)CH$_2$— and —CH$_2$CH(CH$_3$)—), a 1,4-butylene group, —COO—, —OCO—, —OCF$_2$—, —CF$_2$O—, —CH═CH—, —CH═CF—, —CF═CH—, —CF═CF—, —C≡C—, or —CH═NN═CH—, although a single bond, an ethylene group, a 1,4-butylene group, —COO—, —OCO—, —OCF$_2$—, —CF$_2$O—, —CF═CF—, —C≡C—, or —CH═NN═CH— are preferred, and it is also preferable that at least one of these linkage groups in (C2), and at least two of the linkage groups in (C3) are single bonds.

Preferred forms for (C1) can be represented by the general formulas (C1a) to (C1h) shown below.

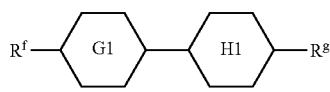
(C1a)

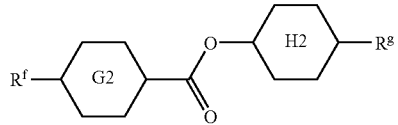
(C1b)

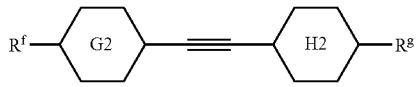
(C1c)

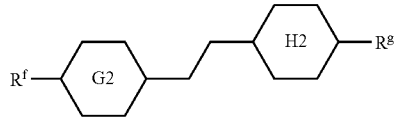
(C1d)

-continued

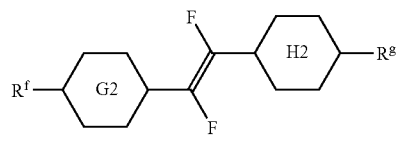
(C1e)

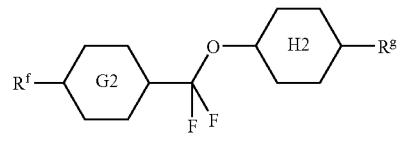
(C1f)

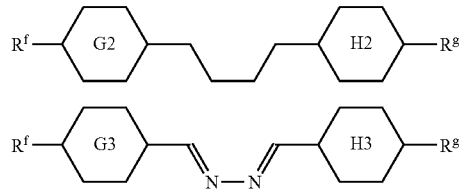
(C1g)

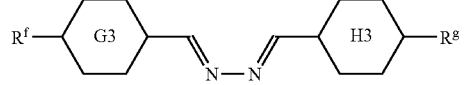
(C1h)

In each of the formulas above, $R^f$ and $R^g$ each represent, independently, a straight chain alkyl group of 1 to 7 carbon atoms, a straight chain 1-alkenyl group of 2 to 7 carbon atoms, a straight chain 3-alkenyl group of 4 to 7 carbon atoms, a straight chain alkoxyl group of 1 to 3 carbon atoms or a straight chain alkyl groups of 1 to 5 carbon atoms in which the terminal is substituted with an alkoxyl group of 1 to 3 carbon atoms, although at least one of $R^f$ and $R^g$ represents a straight chain alkyl group of 1 to 7 carbon atoms, a straight chain 1-alkenyl group of 2 to 7 carbon atoms, or a straight chain 3-alkenyl group of 4 to 7 carbon atoms. In those cases in which the rings G1 to G3 are aromatic, the corresponding $R^f$ excludes 1-alkenyl groups and alkoxyl groups, and in those cases in which the rings H1 to H3 are aromatic, the corresponding $R^g$ excludes 1-alkenyl groups and alkoxyl groups.

The ring G1 and the ring H1 each represent, independently, a trans-1,4-cyclohexylene group, a trans-decahydronaphthalene-trans-2,6-diyl group, a 1,4-phenylene group which may be substituted with one or two fluorine atoms or methyl groups, a naphthalene-2,6-diyl group which may be substituted with one or more fluorine atoms, a tetrahydronaphthalene-2,6-diyl group which may be substituted with one or two fluorine atoms, a 1,4-cyclohexenylene group which may be substituted with one or two fluorine atoms, a 1,3-dioxane-trans-2,5-diyl group, a pyrimidine-2,5-diyl group or a pyridine-2,5-diyl group, although in each compound it is preferable that there be no more than one trans-decahydronaphthalene-trans-2,6-diyl group, naphthalene-2,6-diyl group which may be substituted with one or more fluorine atoms, tetrahydronaphthalene-2,6-diyl group which may be substituted with one or two fluorine atoms, 1,4-cyclohexenylene group which may be substituted with a fluorine atom, 1,3-dioxane-trans-2,5-diyl group, pyrimidine-2,5-diyl group or pyridine-2,5-diyl group, and that the other ring in such cases should preferably be a trans-1,4-cyclohexylene group or a 1,4-phenylene group which may be substituted with one or two fluorine atoms or methyl groups. The ring G2 and the ring H2 each represent, independently, a trans-1,4-cyclohexylene group, a trans-decahydronaphthalene-trans-2,6-diyl group, a 1,4-phenylene group which may be substituted with one or two fluorine atoms or methyl groups, a naphthalene-2,6-diyl group which may be substituted with one or more fluorine atoms, or a tetrahydronaphthalene-2,6-diyl group which may be substituted with one or two fluorine atoms, although in each compound it is preferable that there be no more than one trans-decahydronaphthalene-trans-2,6-diyl group, naphthalene-2,6-diyl group which may be substituted with one or more fluorine atoms, or tetrahydronaphthalene-2,6-diyl group which may be substituted with one or two fluorine atoms, and that the other ring in such cases should preferably be a trans-1,4-cyclohexylene group or a 1,4-phenylene group which may be substituted with one or two fluorine atoms or methyl groups. The ring G3 and the ring H3 each represent, independently, a 1,4-phenylene group which may be substituted with one or two fluorine atoms or methyl groups, a naphthalene-2,6-diyl group which may be substituted with one or more fluorine atoms, or a tetrahydronaphthalene-2,6-diyl group which may be substituted with one or two fluorine atoms, although in each compound it is preferable that there be no more than one naphthalene-2,6-diyl group which may be substituted with one or more fluorine atoms or one tetrahydronaphthalene-2,6-diyl group which may be substituted with one or two fluorine atoms.

Preferred forms for (C2) can be represented by the general formula (C2a) to (C2m) shown below.

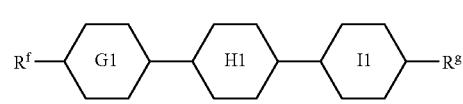
(C2a)

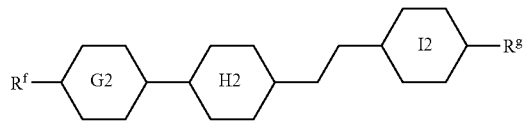
(C2b)

(C2c)

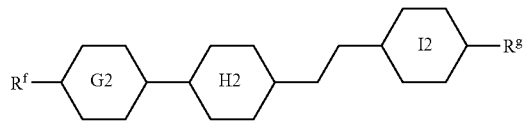
(C2d)

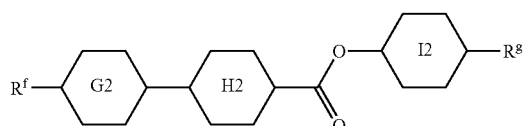
(C2e)

(C2f)

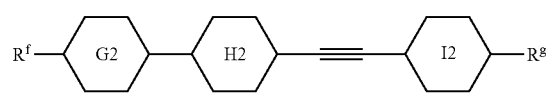

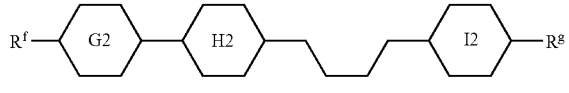

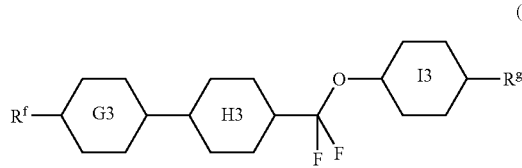

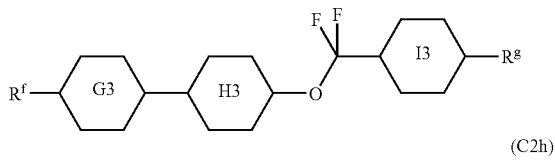
(C2g)

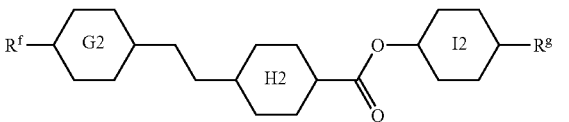
(C2h)

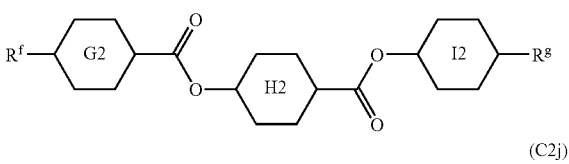
(C2i)

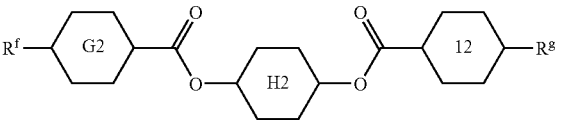
(C2j)

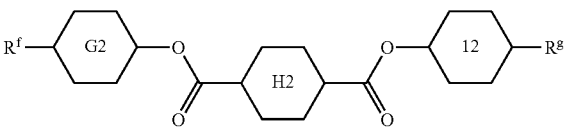
(C2k)

(C2l)

(C2m)

In each of the formulas above, the ring G1, ring G2, ring G3, ring H1, ring H2 and the ring H3 each represent the same meaning as that described above, and the ring I1 represents the same meaning as the ring G1, the ring I2 the same as the ring G2, and the ring I3 the same as the ring G3. Furthermore, in each of the compounds listed above, it is preferable that there be no more than one trans-decahydronaphthalene-trans-2,6-diyl group, naphthalene-2,6-diyl group which may be substituted with one or more fluorine atoms, tetrahydronaphthalene-2,6-diyl group which may be substituted with one or two fluorine atoms, 1,4-cyclohexenylene group which may be substituted with a fluorine atom, 1,3-dioxane-trans-2,5-diyl group, pyrimidine-2,5-diyl group or pyridine-2,5-diyl group, and that the other rings in such cases should preferably be a trans-1,4-cyclohexylene group or a 1,4-phenylene group which may be substituted with one or two fluorine atoms or methyl groups.

Preferred forms for (C3) can be represented by the general formulas (C3a) to (C3f) shown below.

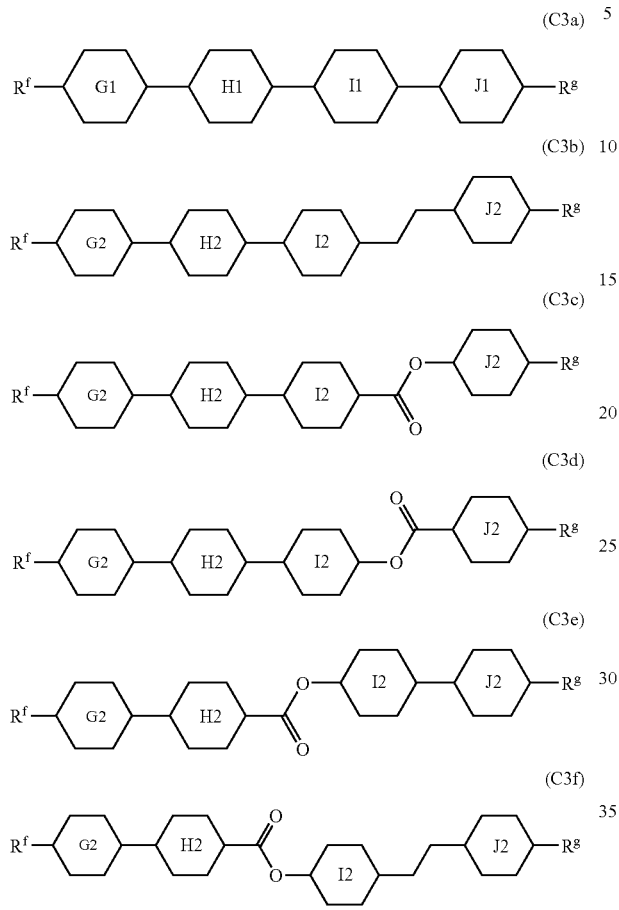

In each of the formulas above, the ring G1, ring G2, ring H1, ring H2, ring I1 and the ring I2 each represent the same meaning as that described above, and the ring J1 represents the same meaning as the ring G1, and the ring J2 the same as the ring G2. Furthermore, in each of the compounds listed above, it is preferable that there be no more than one trans-decahydronaphthalene-trans-2,6-diyl group, naphthalene-2,6-diyl group which may be substituted with one or more fluorine atoms, tetrahydronaphthalene-2,6-diyl group which may be substituted with one or two fluorine atoms, 1,4-cyclohexenylene group which may be substituted with a fluorine atom, 1,3-dioxane-trans-2,5-diyl group, pyrimidine-2,5-diyl group or pyridine-2,5-diyl group, and that the other rings in such cases should preferably be a trans-1,4-cyclohexylene group or a 1,4-phenylene group which may be substituted with one or two fluorine atoms or methyl groups.

EXAMPLES

As follows is a more detailed description of the present invention based on a series of examples, although the present invention is in no way limited to the examples presented.

Example 1

Synthesis of 2-propyl-7-(3,4,5-trifluorophenyl)-9,10-dihydrophenanthrene

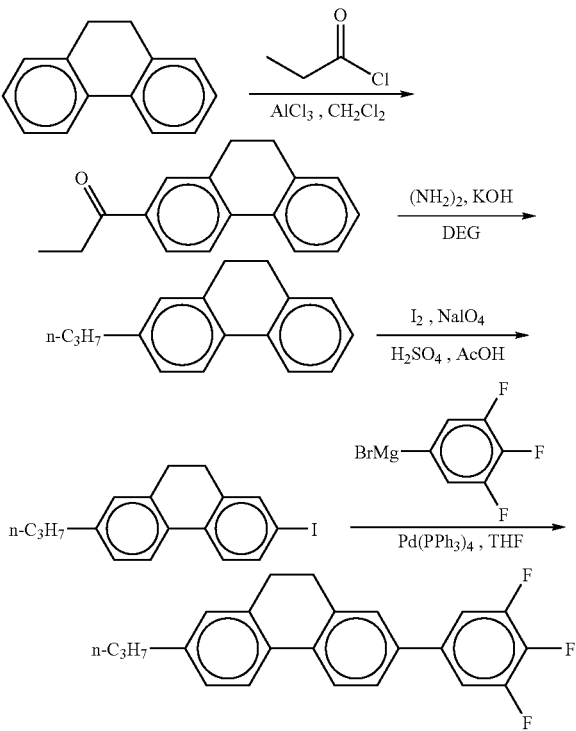

A suspension of 360 g of aluminum chloride in 1 L of methylene chloride was cooled to 0° C., and a solution of 250 g of propanoic chloride in 800 mL of methylene chloride was then added dropwise to the suspension. Following completion of the addition, the mixture was stirred at the same temperature for 30 minutes, and a solution of 443 g of 9,10-dihydrophenanthrene in 800 mL of methylene chloride was then added dropwise. The reaction mixture was stirred for a further one hour, and the reaction then halted by pouring the reaction mixture into ice water. The organic layer was separated, the aqueous layer was extracted with methylene chloride, and the extract was combined with the organic layer. The organic layer was then washed with water, a saturated aqueous solution of sodium bicarbonate, and a saturated aqueous solution of sodium chloride, and was then dried over anhydrous sodium sulfate. The solvent was removed by evaporation and the product subsequently purified by column chromatography to yield 504 g of 1-(9,10-dihydrophenanthrene-2-yl)propan-1-one. 497 g of this 1-(9,10-dihydrophenanthrene-2-yl)propan-1-one was then suspended in 3 L of diethylene glycol, 421 g of hydrazine hydrate was added, and the suspension was stirred, with heating, for one hour at 100° C. The temperature was then raised to 120° C., and following removal of any unreacted hydrazine by evaporation, the temperature was once again lowered. 13.9 g of potassium hydroxide was then added, and with sufficient care taken over foaming, the mixture was heated at 160° C., with stirring, for two hours. The reaction mixture was then returned to room temperature, toluene and water were added, and the organic layer was separated. The organic layer was then washed with a saturated aqueous solution of sodium bicarbonate, water, and a saturated aqueous solution of sodium chloride, and was then dried over anhydrous sodium sulfate. The solvent was removed by evaporation and the product subsequently purified by column chromatography (hexane) to yield 361 g of 2-propyl-9,10-dihydrophenanthrene. To a solution of 330 g of this 2-propyl-9,10-dihydrophenanthrene in 300 mL of 1,2-dichloroethane was added 2.4 L of acetic acid, 12 mL of sulfuric acid, 600 mL of water, 226 g of iodine and 165 g of periodic acid hydrate, and the resulting mixture was stirred for 3 hours with the internal temperature at 50° C. Following cooling, an aqueous solution of sodium hydrogen sulfite was added, and following decomposition of any residual iodine, methylene chloride was added and the organic layer was separated. The organic layer was washed with a saturated aqueous solution of sodium bicarbonate, water, and a saturated aqueous solution of sodium chloride, and was then dried over anhydrous sodium sulfate. The solvent was removed by evaporation and the product subsequently purified by column chromatography (hexane) to yield 245 g of 2-iodo-7-propyl-9,10-dihydrophenanthrene. To a solution of 100 g of this 2-iodo-7-propyl-9,10-dihydrophenanthrene in 300 mL of THF was added 3.3 g of tetrakis(triphenylphosphine)palladium (0) and the mixture was stirred at room temperature. This mixture was then reacted with a Grignard reagent prepared from 79 g of 3,4,5-trifluorobromobenzene and 9.1 g of magnesium. Following stirring for 2 hours at room temperature, the mixture was allowed to cool to room temperature, water was added, the product was extracted into toluene, and the organic layer was washed sequentially with water and a saturated aqueous solution of sodium chloride before being dried over anhydrous sodium sulfate. The crude product obtained by removal of the solvent by evaporation was purified by silica gel column chromatography (hexane) and then recrystallized 3 times from ethanol to yield 45 g of white crystals of 2-propyl-7-(3,4,5-trifluorophenyl)-9,10-dihydrophenanthrene. Measurement of the phase transition temperature revealed a transition from the crystalline phase to an isotropic liquid phase at 68° C. under rising temperature conditions.

NMR: δ=0.99 (t, J=7 Hz, 3H), δ=1.65 (m, 2H), δ=2.52 (t, J=7 Hz, 2H), δ=2.88 (s, 4H), δ=6.9 to 7.6 (m, 8H),

MS: m/e=352 (M+)

The compounds listed below can be produced in a similar manner.

2-propyl-7-(4-fluorophenyl)-9,10-dihydrophenanthrene,
2-propyl-7-(3,4-difluorophenyl)-9,10-dihydrophenanthrene C 114 (N 82.0) I,
2-propyl-7-(3,5-difluorophenyl)-9,10-dihydrophenanthrene,
2-propyl-7-(4-trifluoromethoxyphenyl)-9,10-dihydrophenanthrene,
2-propyl-7-(3-fluoro-4-trifluoromethoxyphenyl)-9,10-dihydrophenanthrene,
2-propyl-7-(3,5-difluoro-4-trifluoromethoxyphenyl)-9,10-dihydrophenanthrene,
2-propyl-7-(4-difluoromethoxyphenyl)-9,10-dihydrophenanthrene,
2-propyl-7-(4-trifluoromethylphenyl)-9,10-dihydrophenanthrene,
2-propyl-7-(3-fluoro-4-trifluoromethylphenyl)-9,10-dihydrophenanthrene,
2-propyl-7-(3,5-difluoro-4-trifluoromethylphenyl)-9,10-dihydrophenanthrene,
2-propyl-7-(4-chlorophenyl)-9,10-dihydrophenanthrene,
2-propyl-7-(3-fluoro-4-chlorophenyl)-9,10-dihydrophenanthrene,
2-propyl-7-(3,5-difluoro-4-chlorophenyl)-9,10-dihydrophenanthrene,
2-propyl-7-(4-fluorophenyl)fluorene,
2-propyl-7-(3,4-difluorophenyl)fluorene,
2-propyl-7-(3,5-difluorophenyl)fluorene,
2-propyl-7-(3,4,5-trifluorophenyl)fluorene C 136 I,
2-propyl-7-(4-trifluoromethoxyphenyl)fluorene,
2-propyl-7-(3-fluoro-4-trifluoromethoxyphenyl)fluorene,
2-propyl-7-(3,5-difluoro-4-trifluoromethoxyphenyl)fluorene,
2-propyl-7-(4-difluoromethoxyphenyl)fluorene,
2-propyl-7-(4-trifluoromethylphenyl)fluorene,
2-propyl-7-(3-fluoro-4-trifluoromethylphenyl)fluorene,
2-propyl-7-(3,5-difluoro-4-trifluoromethylphenyl)fluorene,
2-propyl-7-(4-chlorophenyl)fluorene,
2-propyl-7-(3-fluoro-4-chlorophenyl)fluorene, and
2-propyl-7-(3,5-difluoro-4-chlorophenyl)fluorene.

Example 2

Synthesis of 2-propyl-7-(3,4-difluorophenylethynyl)fluorene

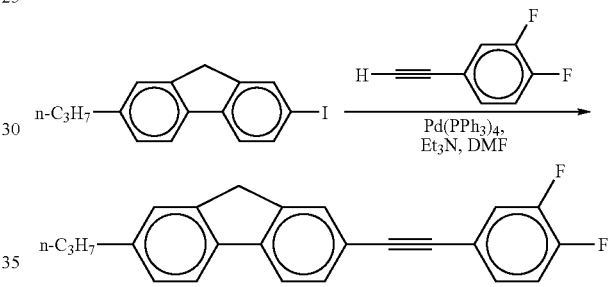

2-iodo-7-propyl-fluorene in dimethylformamide and triethylamine was reacted with 4-ethynyl-1,2-difluorobenzene in the presence of tetrakis(triphenylphosphine)palladium (0), and the product was purified by silica gel column chromatography (hexane) and then recrystallized from ethanol to yield 2-propyl-7-(3,4-difluorophenylethynyl)fluorene.

The compounds listed below can be produced in a similar manner.

2-propyl-7-(4-fluorophenylethynyl)fluorene,
2-propyl-7-(3,4-difluorophenylethynyl)fluorene,
2-propyl-7-(3,5-difluorophenylethynyl)fluorene,
2-propyl-7-(4-trifluoromethoxyphenylethynyl)fluorene,
2-propyl-7-(3-fluoro-4-trifluoromethoxyphenylethynyl) fluorene,
2-propyl-7-(3,5-difluoro-4-trifluoromethoxyphenylethynyl) fluorene,
2-propyl-7-(3,4,5-trifluorophenylethynyl)fluorene,
2-propyl-7-(4-difluoromethoxyphenylethynyl)fluorene,
2-propyl-7-(4-trifluoromethylphenylethynyl)fluorene,
2-propyl-7-(3-fluoro-4-trifluoromethylphenylethynyl)fluorene,
2-propyl-7-(3,5-difluoro-4-trifluoromethylphenylethynyl) fluorene,
2-propyl-7-(4-chlorophenylethynyl)fluorene,
2-propyl-7-(3-fluoro-4-chlorophenylethynyl)fluorene,
2-propyl-7-(3,5-difluoro-4-chlorophenylethynyl)fluorene,
2-propyl-7-(4-fluorophenylethynyl)-9,10-dihydrophenanthrene,
2-propyl-7-(3,4-difluorophenylethynyl)-9,10-dihydrophenanthrene, 2-propyl-7-(3,5-difluorophenylethynyl)-9,10-dihydrophenanthrene, 2-propyl-7-(3,4,5-trifluorophenylethynyl)-9,10-dihydrophenanthrene, 2-propyl-7-(4-trifluoromethoxyphenylethynyl)-9,10-dihydrophenanthrene, 2-propyl-7-(3-fluoro-4-trifluoromethoxyphenylethynyl)-9,10-dihydrophenanthrene, 2-propyl-7-(3,5-difluoro-4-trifluoromethoxyphenylethynyl)-9,10-dihydrophenanthrene, 2-propyl-7-(4-difluoromethoxyphenylethynyl)-9,10-dihydrophenanthrene, 2-propyl-7-(4-trifluoromethylphenylethynyl)-9,10-dihydrophenanthrene, 2-propyl-7-(3-fluoro-4-trifluoromethylphenylethynyl)-9,10-dihydrophenanthrene, 2-propyl-7-(3,5-difluoro-4-trifluoromethylphenylethynyl)-9,10-dihydrophenanthrene, 2-propyl-7-(4-chlorophenylethynyl)-9,10-dihydrophenanthrene, 2-propyl-7-(3-fluoro-4-chlorophenylethynyl)-9,10-dihydrophenanthrene, and 2-propyl-7-(3,5-difluoro-4-chlorophenylethynyl)-9,10-dihydrophenanthrene.

Example 3

Synthesis of 8-fluoro-2-propyl-7-(3,4,5-trifluorophenyl)-9,10-dihydrophenanthrene and 6-fluoro-2-propyl-7-(3,4,5-trifluorophenyl)-9,10-dihydrophenanthrene

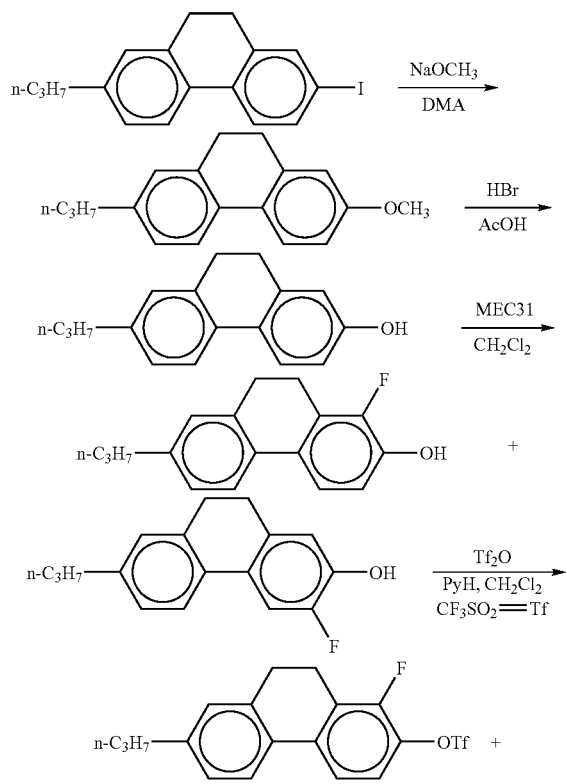

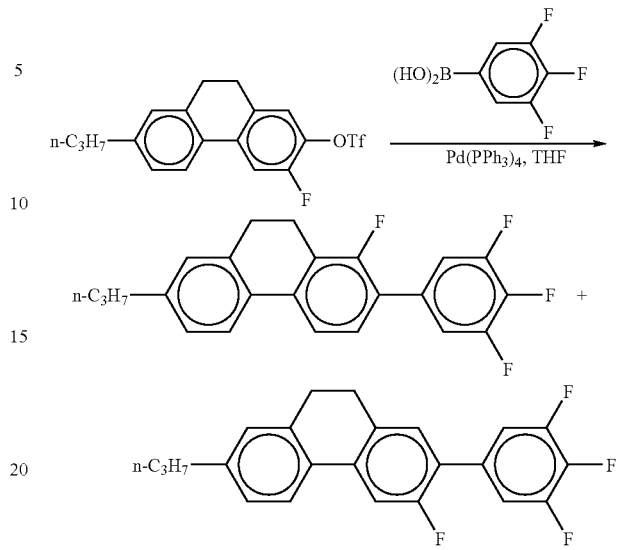

Following conversion of the 2-iodo-7-propyl-9,10-dihydrophenanthrene obtained in Example 1 into a phenol derivative using standard methods, the thus obtained 7-propyl-9,10-dihydrophenanthren-2-ol was dissolved in methylene chloride, and N,N'-difluoro-2,2'-bipyridinium bistetrafluoroborate (MEC-31) was added gradually, and following completion of the addition the mixture was stirred for 5 hours at room temperature. Water and a 10% aqueous solution of sodium hydroxide were then added, any residual fluorination agent was decomposed, and following the addition of sufficient dilute hydrochloric acid to return the reaction mixture to an acidic state, the organic layer was separated. The aqueous layer was extracted with dichloromethane and this extract was combined with the organic layer, which was subsequently washed with water and then a saturated aqueous solution of sodium chloride before being dried over anhydrous sodium sulfate. The crude product obtained by removal of the solvent by evaporation was separated and purified by silica gel column chromatography (hexane and toluene) to yield both 1-fluoro-7-propyl-9,10-dihydrophenanthren-2-ol and 3-fluoro-7-propyl-9,10-dihydrophenanthren-2-ol.

The thus obtained 1-fluoro-7-propyl-9,10-dihydrophenanthren-2-ol was dissolved in methylene chloride, a suspension was formed by adding trifluoromethanesulfonic anhydride, and the suspension was then cooled to 5° C. With the mixture being stirred vigorously, pyridine was then added dropwise and the mixture stirred for a further one hour. Water was added, the reaction halted, and the organic layer was separated. The aqueous layer was extracted with dichloromethane and this extract was combined with the organic layer, which was subsequently washed with dilute hydrochloric acid, a saturated aqueous solution of sodium bicarbonate, water, and then a saturated aqueous solution of sodium chloride before being dried over anhydrous sodium sulfate. The solvent was removed by evaporation, and the product purified by silica gel column chromatography (hexane) to yield 1-fluoro-7-propyl-9,10-dihydrophenanthren-2-yl trifluoromethanesulfonate. This compound was combined with 3,4,5-trifluorophenylboric acid (which was produced by a reaction between a Grignard reagent prepared from 3,4,5-trifluorobromobenzene and magnesium, and trimethylborate, followed by hydrolysis with dilute hydrochloric acid), tetrakis(triphenylphosphine)palladium (0) and potassium phosphate in a dimethylformamide solvent and was then stirred for 10 hours at 80° C. The reaction mixture was then cooled to room temperature, water was added, the mixture was extracted with toluene, and the resulting organic layer was washed sequentially with water and a saturated aqueous solution of sodium chloride, and then dried over anhydrous sodium sulfate. The crude product obtained by removal of the solvent by evaporation was purified by silica gel column chromatography (hexane) and then recrystallized 3 times from ethanol to yield 8-fluoro-2-propyl-7-(3,4,5-trifluorophenyl)-9,10-dihydrophenanthrene. The separated 3-fluoro-7-propyl-9,10-dihydrophenanthren-2-ol was also reacted in the same manner and yielded 6-fluoro-2-propyl-7-(3,4,5-trifluorophenyl)-9,10-dihydrophenanthrene.

The compounds listed below can be produced in a similar manner.

8-fluoro-2-propyl-7-(4-fluorophenyl)-9,10-dihydrophenanthrene,
8-fluoro-2-propyl-7-(3,4-difluorophenyl)-9,10-dihydrophenanthrene,
8-fluoro-2-propyl-7-(3,5-difluorophenyl)-9,10-dihydrophenanthrene,
8-fluoro-2-propyl-7-(4-trifluoromethoxyphenyl)-9,10-dihydrophenanthrene,
8-fluoro-2-propyl-7-(3-fluoro-4-trifluoromethoxyphenyl)-9,10-dihydrophenanthrene,
8-fluoro-2-propyl-7-(3,5-difluoro-4-trifluoromethoxyphenyl)-9,10-dihydrophenanthrene,
8-fluoro-2-propyl-7-(4-difluoromethoxyphenyl)-9,10-dihydrophenanthrene,
8-fluoro-2-propyl-7-(4-trifluoromethylphenyl)-9,10-dihydrophenanthrene,
8-fluoro-2-propyl-7-(3-fluoro-4-trifluoromethylphenyl)-9,10-dihydrophenanthrene,
8-fluoro-2-propyl-7-(3,5-difluoro-4-trifluoromethylphenyl)-9,10-dihydrophenanthrene,
8-fluoro-2-propyl-7-(4-chlorophenyl)-9,10-dihydrophenanthrene,
8-fluoro-2-propyl-7-(3-fluoro-4-chlorophenyl)-9,10-dihydrophenanthrene,
8-fluoro-2-propyl-7-(3,5-difluoro-4-chlorophenyl)-9,10-dihydrophenanthrene,
6-fluoro-2-propyl-7-(4-fluorophenyl)-9,10-dihydrophenanthrene,
6-fluoro-2-propyl-7-(3,4-difluorophenyl)-9,10-dihydrophenanthrene,
6-fluoro-2-propyl-7-(3,5-difluorophenyl)-9,10-dihydrophenanthrene,
6-fluoro-2-propyl-7-(4-trifluoromethoxyphenyl)-9,10-dihydrophenanthrene,
6-fluoro-2-propyl-7-(3-fluoro-4-trifluoromethoxyphenyl)-9,10-dihydrophenanthrene,
6-fluoro-2-propyl-7-(3,5-difluoro-4-trifluoromethoxyphenyl)-9,10-dihydrophenanthrene,
6-fluoro-2-propyl-7-(4-difluoromethoxyphenyl)-9,10-dihydrophenanthrene,
6-fluoro-2-propyl-7-(4-trifluoromethylphenyl)-9,10-dihydrophenanthrene,
6-fluoro-2-propyl-7-(3-fluoro-4-trifluoromethylphenyl)-9,10-dihydrophenanthrene,
6-fluoro-2-propyl-7-(3,5-difluoro-4-trifluoromethylphenyl)-9,10-dihydrophenanthrene,
6-fluoro-2-propyl-7-(4-chlorophenyl)-9,10-dihydrophenanthrene,
6-fluoro-2-propyl-7-(3-fluoro-4-chlorophenyl)-9,10-dihydrophenanthrene,
6-fluoro-2-propyl-7-(3,5-difluoro-4-chlorophenyl)-9,10-dihydrophenanthrene,
8-fluoro-2-propyl-7-(4-fluorophenyl)fluorene,
8-fluoro-2-propyl-7-(3,4-difluorophenyl)fluorene,
8-fluoro-2-propyl-7-(3,5-difluorophenyl)fluorene,
8-fluoro-2-propyl-7-(4-trifluoromethoxyphenyl)fluorene,
8-fluoro-2-propyl-7-(3-fluoro-4-trifluoromethoxyphenyl)fluorene,
8-fluoro-2-propyl-7-(3,5-difluoro-4-trifluoromethoxyphenyl)fluorene,
8-fluoro-2-propyl-7-(3,4,5-trifluorophenyl)fluorene,
8-fluoro-2-propyl-7-(4-difluoromethoxyphenyl)fluorene,
8-fluoro-2-propyl-7-(4-trifluoromethylphenyl)fluorene,
8-fluoro-2-propyl-7-(3-fluoro-4-trifluoromethylphenyl)fluorene,
8-fluoro-2-propyl-7-(3,5-difluoro-4-trifluoromethylphenyl)fluorene,
8-fluoro-2-propyl-7-(4-chlorophenyl)fluorene,
8-fluoro-2-propyl-7-(3-fluoro-4-chlorophenyl)fluorene,
8-fluoro-2-propyl-7-(3,5-difluoro-4-chlorophenyl)fluorene,
6-fluoro-2-propyl-7-(4-fluorophenyl)fluorene,
6-fluoro-2-propyl-7-(3,4-difluorophenyl)fluorene,
6-fluoro-2-propyl-7-(3,5-difluorophenyl)fluorene,
6-fluoro-2-propyl-7-(4-trifluoromethoxyphenyl)fluorene,
6-fluoro-2-propyl-7-(3-fluoro-4-trifluoromethoxyphenyl)fluorene,
6-fluoro-2-propyl-7-(3,5-difluoro-4-trifluoromethoxyphenyl)fluorene,
6-fluoro-2-propyl-7-(4-difluoromethoxyphenyl)fluorene,
6-fluoro-2-propyl-7-(4-trifluoromethylphenyl)fluorene,
6-fluoro-2-propyl-7-(3-fluoro-4-trifluoromethylphenyl)fluorene,
6-fluoro-2-propyl-7-(3,5-difluoro-4-trifluoromethylphenyl)fluorene,
6-fluoro-2-propyl-7-(4-chlorophenyl)fluorene,
6-fluoro-2-propyl-7-(3-fluoro-4-chlorophenyl)fluorene, and
6-fluoro-2-propyl-7-(3,5-difluoro-4-chlorophenyl)fluorene.

Example 4

Synthesis of 6,8-difluoro-2-propyl-7-(3,4,5-trifluorophenyl)-9,10-dihydrophenanthrene

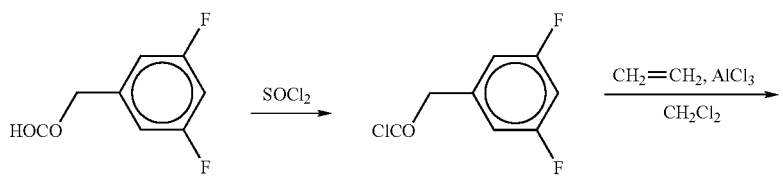

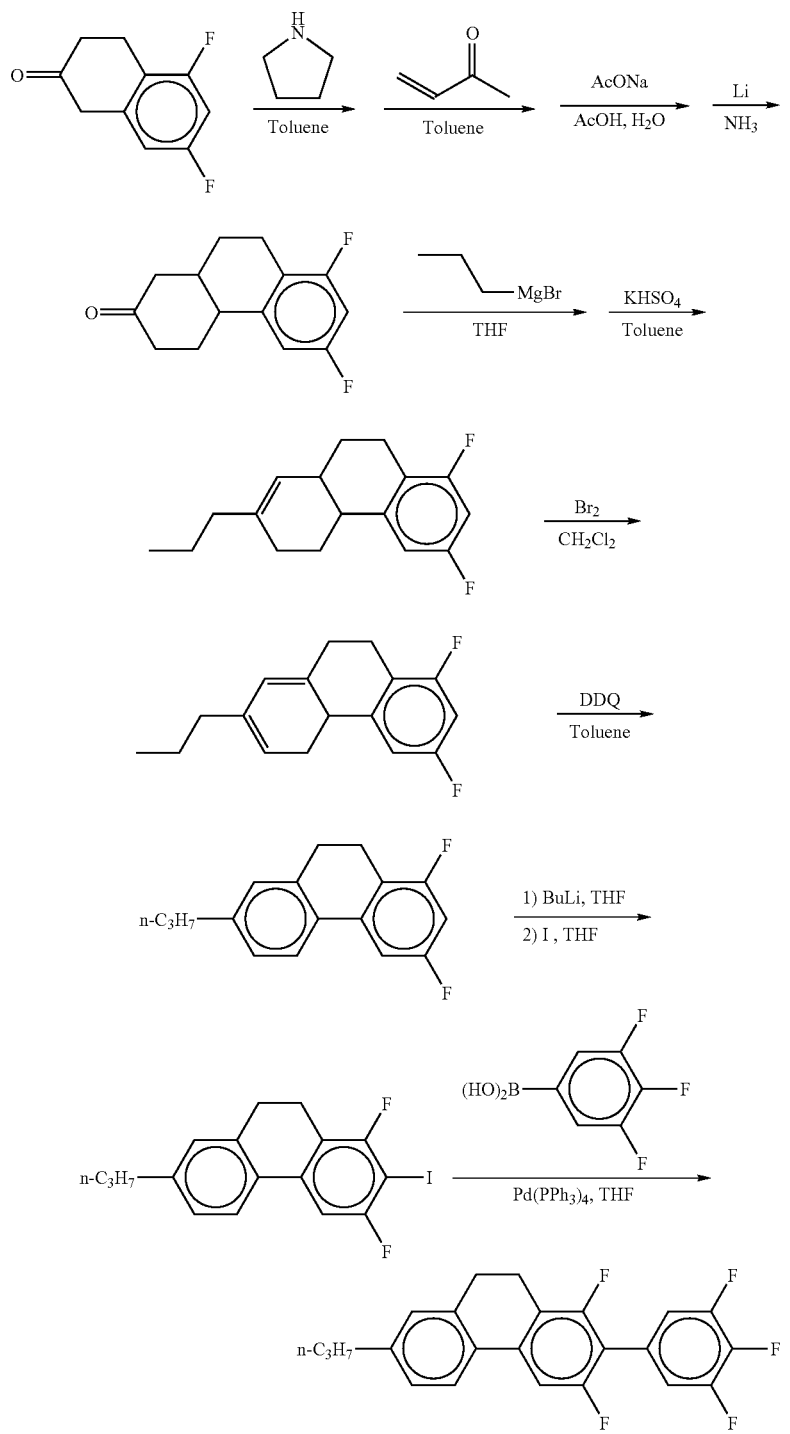

Following conversion of (3,5-difluorophenyl)-acetic acid to an acid chloride with thionyl chloride, subsequent reaction with ethylene gas at −10° C. using methylene chloride as the solvent and in the presence of aluminum chloride yielded 5,7-difluoro-3,4-dihydro-1H-naphthalen-2-one. A solution of pyrrolidine in toluene was then added and the mixture was heated for 3 hours, and any azeotropically distilled water was removed. Excess pyrrolidine was then removed by azeotropic distillation with toluene, to yield 1-(5,7-difluoro-1,4-dihydronaphthalen-2-yl)pyrrolidine.

The crude product was cooled, as is, to room temperature, more toluene was added, the mixture was cooled in a water bath, and methyl vinyl ketone was added dropwise over a period of 1 hour at a temperature of 25° C. or lower.

Following completion of the addition, the mixture was immediately heated and refluxed under heat for 20 hours. The solution was then cooled to room temperature, a buffer solution of pH 5 prepared from sodium acetate, acetic acid and water was added, and the reflux was continued for a further 4 hours. After the solution had been cooled to room temperature, the organic layer was separated and washed with water and a saturated aqueous solution of sodium chloride. The organic layer was then dried over anhydrous sodium sulfate, and the solvent removed by evaporation to yield 6,8-difluoro-trans-4,4a,9,10-tetrahydro-3H-phenanthren-2-one.

At a temperature below −40° C., lithium was added gradually, in small portions, to liquid ammonia and dissolved. With the internal temperature maintained at a temperature from −30 to −40° C., a THF solution of 6,8-difluoro-trans-4,4a,9,10-tetrahydro-3H-phenanthren-2-one and t-butanol was then added dropwise. Following completion of the addition, stirring was continued for a further 30 minutes. Small quantities of solid ammonium chloride were added and following oxidation of the lithium, the temperature was raised to room temperature, and the ammonia removed by evaporation. Water was then added, the mixture was extracted with toluene, and the organic layer was washed with a saturated aqueous solution of sodium chloride, and then dried over anhydrous magnesium sulfate. The solvent was then removed by evaporation, and vacuum distillation used to obtain 6,8-difluoro-trans-3,4,4a,9,10,10a-hexahydro-1H-phenanthren-2-one. This compound was reacted with propyl magnesium bromide, and 10% hydrochloric acid was then added to halt the reaction. Ethyl acetate was then added, the organic layer was separated, and the aqueous layer was extracted with ethyl acetate, with the extract being combined with the organic layer. The organic layer was then washed with water, a saturated aqueous solution of sodium bicarbonate, and then a saturated aqueous solution of sodium chloride before being dried over anhydrous sodium sulfate. The solvent was removed by evaporation, toluene and p-toluenesulfonic acid monohydrate were added, and the mixture was heated, with stirring, at 110° C. with any evaporated water being separated and removed. When the water evaporation had ceased, the temperature was returned to room temperature, water was added, and the organic layer was separated. The organic layer was washed with a saturated aqueous solution of sodium bicarbonate, water, and then a saturated aqueous solution of sodium chloride before being dried over anhydrous sodium sulfate. The solvent was removed by evaporation and the whole crude product was then dissolved in toluene, DDQ (2,3-dichloro-5,6-dicyano-1,4-benzoquinone) was added, and the mixture was heated at 100° C., with stirring, for a period of 5 hours. The solvent was then removed by evaporation, and the product purified by silica gel chromatography to yield 1,3-difluoro-7-propyl-9,10-dihydrophenanthrene. This compound was lithiated in an n-butyl lithium-hexane solution, and was then reacted with iodine to produce 2-iodo-1,3-difluoro-7-propyl-9,10-dihydrophenanthrene.

2-iodo-1,3-difluoro-7-propyl-9,10-dihydrophenanthrene was combined with 3,4,5-trifluorophenylboric acid (which was produced by a reaction between a Grignard reagent prepared from 3,4,5-trifluorobromobenzene and magnesium, and trimethylborate, followed by hydrolysis with dilute hydrochloric acid), tetrakis(triphenylphosphine)palladium (0) and potassium phosphate in a dimethylformamide solvent and was then stirred for 10 hours at 80° C. The reaction mixture was then cooled to room temperature, water was added, the mixture was extracted with toluene, and the resulting organic layer was washed sequentially with water and a saturated aqueous solution of sodium chloride, and then dried over anhydrous sodium sulfate. The crude product obtained by removal of the solvent by evaporation was purified by silica gel column chromatography (hexane) and then recrystallized 3 times from ethanol to yield 6,8-difluoro-2-propyl-7-(3,4,5-trifluorophenyl)-9,10-dihydrophenanthrene.

The compounds listed below can be produced in a similar manner.

6,8-difluoro-2-propyl-7-(4-fluorophenyl)-9,10-dihydrophenanthrene,
6,8-difluoro-2-propyl-7-(3,4-difluorophenyl)-9,10-dihydrophenanthrene,
6,8-difluoro-2-propyl-7-(3,5-difluorophenyl)-9,10-dihydrophenanthrene,
6,8-difluoro-2-propyl-7-(4-trifluoromethoxyphenyl)-9,10-dihydrophenanthrene,
6,8-difluoro-2-propyl-7-(3-fluoro-4-trifluoromethoxyphenyl)-9,10-dihydrophenanthrene,
6,8-difluoro-2-propyl-7-(3,5-difluoro-4-trifluoromethoxyphenyl)-9,10-dihydrophenanthrene,
6,8-difluoro-2-propyl-7-(4-difluoromethoxyphenyl)-9,10-dihydrophenanthrene,
6,8-difluoro-2-propyl-7-(4-trifluoromethylphenyl)-9,10-dihydrophenanthrene,
6,8-difluoro-2-propyl-7-(3-fluoro-4-trifluoromethylphenyl)-9,10-dihydrophenanthrene,
6,8-difluoro-2-propyl-7-(3,5-difluoro-4-trifluoromethylphenyl)-9,10-dihydrophenanthrene,
6,8-difluoro-2-propyl-7-(4-chlorophenyl)-9,10-dihydrophenanthrene,
6,8-difluoro-2-propyl-7-(3-fluoro-4-chlorophenyl)-9,10-dihydrophenanthrene,
6,8-difluoro-2-propyl-7-(3,5-difluoro-4-chlorophenyl)-9,10-dihydrophenanthrene,
6,8-difluoro-2-propyl-7-(4-fluorophenyl)fluorene,
6,8-difluoro-2-propyl-7-(3,4-difluorophenyl)fluorene,
6,8-difluoro-2-propyl-7-(3,5-difluorophenyl)fluorene,
6,8-difluoro-2-propyl-7-(3,4,5-trifluorophenyl)fluorene,
6,8-difluoro-2-propyl-7-(4-trifluoromethoxyphenyl)fluorene,
6,8-difluoro-2-propyl-7-(3-fluoro-4-trifluoromethoxyphenyl)fluorene,
6,8-difluoro-2-propyl-7-(3,5-difluoro-4-trifluoromethoxyphenyl)fluorene,
6,8-difluoro-2-propyl-7-(4-difluoromethoxyphenyl)fluorene,
6,8-difluoro-2-propyl-7-(4-trifluoromethylphenyl)fluorene,
6,8-difluoro-2-propyl-7-(3-fluoro-4-trifluoromethylphenyl)fluorene,
6,8-difluoro-2-propyl-7-(3,5-difluoro-4-trifluoromethylphenyl)fluorene,
6,8-difluoro-2-propyl-7-(4-chlorophenyl)fluorene,
6,8-difluoro-2-propyl-7-(3-fluoro-4-chlorophenyl)fluorene, and
6,8-difluoro-2-propyl-7-(3,5-difluoro-4-chlorophenyl)fluorene.

Example 5

Synthesis of 2-fluoro-4-(7-propyl-9,10-dihydrophenanthren-2-yl)benzonitrile

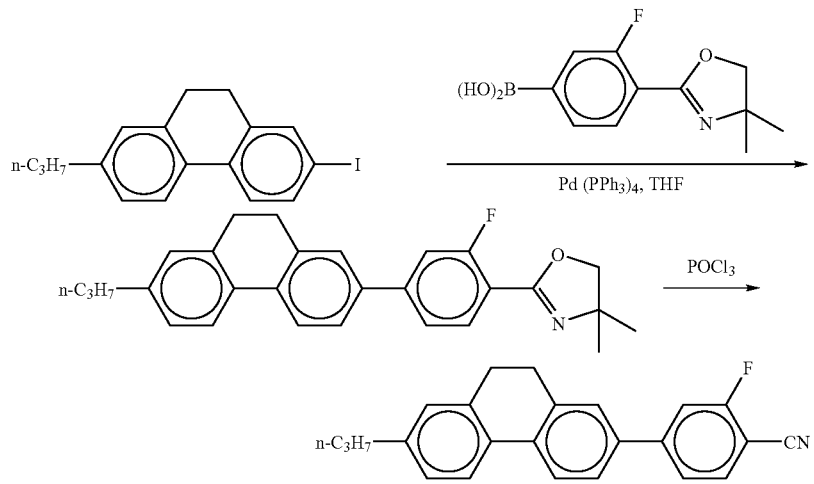

2-iodo-7-propyl-9,10-dihydrophenanthrene produced in Example 1 was reacted with 4-(4,4-dimethyl-4,5-dihydrooxazol-2-yl)-2-fluorophenylboric acid in the presence of tetrakis(triphenylphosphine)palladium (0), and subsequently reacted with phosphorus oxychloride to remove the cyano group protective group, and yielded 2-fluoro-4-(7-propyl-9,10-dihydrophenanthren-2-yl)benzonitrile.

The compounds listed below can be produced in a similar manner.

4-(7-propyl-9,10-dihydrophenanthrene-2-yl)benzonitrile,
2-fluoro-4-(7-ethyl-9,10-dihydrophenanthrene-2-yl)benzonitrile,
4-(7-ethyl-9,10-dihydrophenanthrene-2-yl)benzonitrile,
2-fluoro-4-(7-butyl-9,10-dihydrophenanthrene-2-yl)benzonitrile,
4-(7-butyl-9,10-dihydrophenanthrene-2-yl)benzonitrile,
2-fluoro-4-(7-pentyl-9,10-dihydrophenanthrene-2-yl)benzonitrile,
4-(7-pentyl-9,10-dihydrophenanthrene-2-yl)benzonitrile,
2-fluoro-4-(7-hexyl-9,10-dihydrophenanthrene-2-yl)benzonitrile,
4-(7-hexyl-9,10-dihydrophenanthrene-2-yl)benzonitrile,
2-fluoro-4-(7-heptyl-9,10-dihydrophenanthrene-2-yl)benzonitrile,
4-(7-heptyl-9,10-dihydrophenanthrene-2-yl)benzonitrile,
2-fluoro-4-(8-fluoro-7-propyl-9,10-dihydrophenanthrene-2-yl)benzonitrile,
4-(8-fluoro-7-propyl-9,10-dihydrophenanthrene-2-yl)benzonitrile,
2-fluoro-4-(8-fluoro-7-ethyl-9,10-dihydrophenanthrene-2-yl)benzonitrile,
4-(8-fluoro-7-ethyl-9,10-dihydrophenanthrene-2-yl)benzonitrile,
2-fluoro-4-(8-fluoro-7-butyl-9,10-dihydrophenanthrene-2-yl)benzonitrile,
4-(8-fluoro-7-butyl-9,10-dihydrophenanthrene-2-yl)benzonitrile,
2-fluoro-4-(8-fluoro-7-pentyl-9,10-dihydrophenanthrene-2-yl)benzonitrile,
4-(8-fluoro-7-pentyl-9,10-dihydrophenanthrene-2-yl)benzonitrile,
2-fluoro-4-(8-fluoro-7-hexyl-9,10-dihydrophenanthrene-2-yl)benzonitrile,
4-(8-fluoro-7-hexyl-9,10-dihydrophenanthrene-2-yl)benzonitrile,
2-fluoro-4-(8-fluoro-7-heptyl-9,10-dihydrophenanthrene-2-yl)benzonitrile,
4-(8-fluoro-7-heptyl-9,10-dihydrophenanthrene-2-yl)benzonitrile,
2-fluoro-4-(6-fluoro-7-propyl-9,10-dihydrophenanthrene-2-yl)benzonitrile,
4-(6-fluoro-7-propyl-9,10-dihydrophenanthrene-2-yl)benzonitrile,
2-fluoro-4-(6-fluoro-7-ethyl-9,10-dihydrophenanthrene-2-yl)benzonitrile,
4-(6-fluoro-7-ethyl-9,10-dihydrophenanthrene-2-yl)benzonitrile,
2-fluoro-4-(6-fluoro-7-butyl-9,10-dihydrophenanthrene-2-yl)benzonitrile,
4-(6-fluoro-7-butyl-9,10-dihydrophenanthrene-2-yl)benzonitrile,
2-fluoro-4-(6-fluoro-7-pentyl-9,10-dihydrophenanthrene-2-yl)benzonitrile,
4-(6-fluoro-7-pentyl-9,10-dihydrophenanthrene-2-yl)benzonitrile,
2-fluoro-4-(6-fluoro-7-hexyl-9,10-dihydrophenanthrene-2-yl)benzonitrile,
4-(6-fluoro-7-hexyl-9,10-dihydrophenanthrene-2-yl)benzonitrile,
2-fluoro-4-(6-fluoro-7-heptyl-9,10-dihydrophenanthrene-2-yl)benzonitrile,
4-(6-fluoro-7-heptyl-9,10-dihydrophenanthrene-2-yl)benzonitrile,
4-(6,8-difluoro-7-propyl-9,10-dihydrophenanthrene-2-yl)benzonitrile,
2-fluoro-4-(6,8-difluoro-7-propyl-9,10-dihydrophenanthrene-2-yl)benzonitrile, 2-fluoro-4-(6,8-difluoro-7-ethyl-9,10-dihydrophenanthrene-2-yl)benzonitrile,
4-(6,8-difluoro-7-ethyl-9,10-dihydrophenanthrene-2-yl)benzonitrile,
2-fluoro-4-(6,8-difluoro-7-butyl-9,10-dihydrophenanthrene-2-yl)benzonitrile,
4-(6,8-difluoro-7-butyl-9,10-dihydrophenanthrene-2-yl)benzonitrile,
2-fluoro-4-(6,8-difluoro-7-pentyl-9,10-dihydrophenanthrene-2-yl)benzonitrile,
4-(6,8-difluoro-7-pentyl-9,10-dihydrophenanthrene-2-yl)benzonitrile,
2-fluoro-4-(6,8-difluoro-7-hexyl-9,10-dihydrophenanthrene-2-yl)benzonitrile,
4-(6,8-difluoro-7-hexyl-9,10-dihydrophenanthrene-2-yl)benzonitrile,
2-fluoro-4-(6,8-difluoro-7-heptyl-9,10-dihydrophenanthrene-2-yl)benzonitrile,
4-(6,8-difluoro-7-heptyl-9,10-dihydrophenanthrene-2-yl)benzonitrile,
2-fluoro-4-(7-propylfluorene-2-yl)benzonitrile,
4-(7-propylfluorene-2-yl)benzonitrile,
2-fluoro-4-(7-ethylfluorene-2-yl)benzonitrile,
4-(7-ethylfluorene-2-yl)benzonitrile,
2-fluoro-4-(7-butylfluorene-2-yl)benzonitrile,
4-(7-butylfluorene-2-yl)benzonitrile,
2-fluoro-4-(7-pentylfluorene-2-yl)benzonitrile,
4-(7-pentylfluorene-2-yl)benzonitrile,
2-fluoro-4-(7-hexylfluorene-2-yl)benzonitrile,
4-(7-hexylfluorene-2-yl)benzonitrile,
2-fluoro-4-(7-heptylfluorene-2-yl)benzonitrile,
4-(7-heptylfluorene-2-yl)benzonitrile,
2-fluoro-4-(8-fluoro-7-propylfluorene-2-yl)benzonitrile,
4-(8-fluoro-7-propylfluorene-2-yl)benzonitrile,
2-fluoro-4-(8-fluoro-7-ethylfluorene-2-yl)benzonitrile,
4-(8-fluoro-7-ethylfluorene-2-yl)benzonitrile,
2-fluoro-4-(8-fluoro-7-butylfluorene-2-yl)benzonitrile,
4-(8-fluoro-7-butylfluorene-2-yl)benzonitrile,
2-fluoro-4-(8-fluoro-7-pentylfluorene-2-yl)benzonitrile,
4-(8-fluoro-7-pentylfluorene-2-yl)benzonitrile,
2-fluoro-4-(8-fluoro-7-hexylfluorene-2-yl)benzonitrile,
4-(8-fluoro-7-hexylfluorene-2-yl)benzonitrile,
2-fluoro-4-(8-fluoro-7-heptylfluorene-2-yl)benzonitrile,
4-(8-fluoro-7-heptylfluorene-2-yl)benzonitrile,
2-fluoro-4-(6-fluoro-7-heptylfluorene-2-yl)benzonitrile,
4-(6-fluoro-7-heptylfluorene-2-yl)benzonitrile,
2-fluoro-4-(6-fluoro-7-ethylfluorene-2-yl)benzonitrile,
4-(6-fluoro-7-ethylfluorene-2-yl)benzonitrile,
2-fluoro-4-(6-fluoro-7-butylfluorene-2-yl)benzonitrile,
4-(6-fluoro-7-butylfluorene-2-yl)benzonitrile,
2-fluoro-4-(6-fluoro-7-pentylfluorene-2-yl)benzonitrile,
4-(6-fluoro-7-pentylfluorene-2-yl)benzonitrile,
2-fluoro-4-(6-fluoro-7-pentylfluorene-2-yl)benzonitrile,
4-(6-fluoro-7-hexylfluorene-2-yl)benzonitrile,
2-fluoro-4-(6-fluoro-7-heptylfluorene-2-yl)benzonitrile,
4-(6-fluoro-7-heptylfluorene-2-yl)benzonitrile,
4-(6,8-difluoro-7-propylfluorene-2-yl)benzonitrile,
2-fluoro-4-(6,8-difluoro-7-propylfluorene-2-yl)benzonitrile,
2-fluoro-4-(6,8-difluoro-7-ethylfluorene-2-yl)benzonitrile,
4-(6,8-difluoro-7-ethylfluorene-2-yl)benzonitrile,
2-fluoro-4-(6,8-difluoro-7-butylfluorene-2-yl)benzonitrile,
4-(6,8-difluoro-7-butylfluorene-2-yl)benzonitrile,
2-fluoro-4-(6,8-difluoro-7-pentylfluorene-2-yl)benzonitrile,
4-(6,8-difluoro-7-pentylfluorene-2-yl)benzonitrile,
2-fluoro-4-(6,8-difluoro-7-hexylfluorene-2-yl)benzonitrile,
4-(6,8-difluoro-7-hexylfluorene-2-yl)benzonitrile,
2-fluoro-4-(6,8-difluoro-7-heptylfluorene-2-yl)benzonitrile, and
4-(6,8-difluoro-7-heptylfluorene-2-yl)benzonitrile.

Example 6

Synthesis of 2-fluoro-4-(1-fluoro-7-propyl-9,10-dihydrophenanthren-2-yl) benzonitrile and 2-fluoro-4-(3-fluoro-7-propyl-9,10-dihydrophenanthren-2-yl) benzonitrile

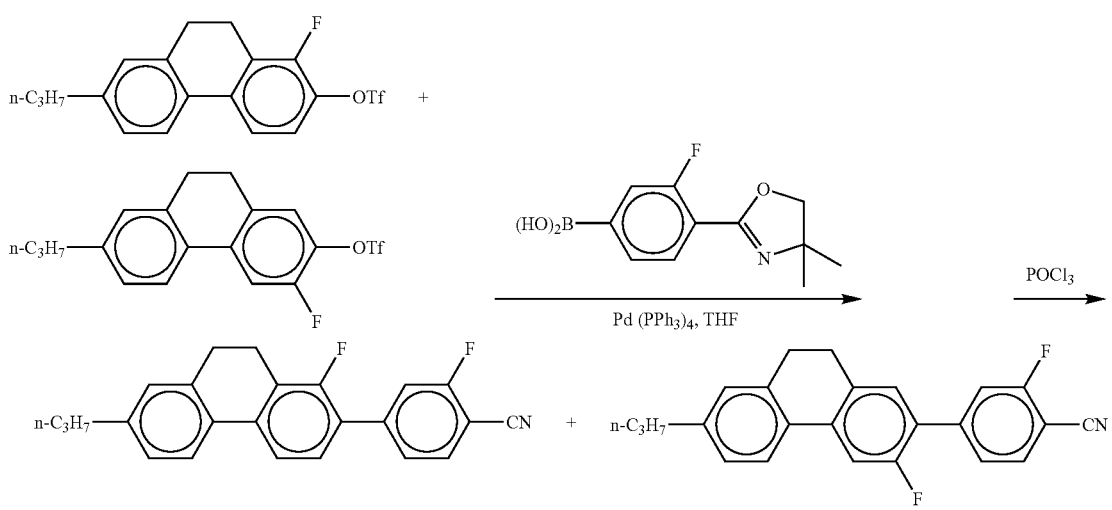

1-fluoro-7-propyl-9,10-dihydrophenanthren-2-yl trifluoromethanesulfonate was reacted with 4-(4,4-dimethyl-4,5-dihydrooxazol-2-yl)-2-fluorophenylboric acid in the presence of tetrakis(triphenylphosphine)palladium, and subsequently reacted with phosphorus oxychloride to remove the cyano group protective group, and yielded 2-fluoro-4-(1-fluoro-trans-7-propyl-9,10-dihydrophenanthren-2-yl) benzonitrile.

The compounds listed below can be produced in a similar manner.

2-fluoro-4-(1-fluoro-trans-7-ethyl-9,10-dihydrophenanthrene-trans-2-yl)benzonitrile,
4-(1-fluoro-trans-7-ethyl-9,10-dihydrophenanthrene-trans-2-yl)benzonitrile,
2-fluoro-4-(1-fluoro-trans-7-ethyl-9,10-dihydrophenanthrene-trans-2-yl)benzonitrile,
4-(1-fluoro-trans-7-ethyl-9,10-dihydrophenanthrene-trans-2-yl)benzonitrile,
2-fluoro-4-(1-fluoro-trans-7-ethyl-9,10-dihydrophenanthrene-trans-2-yl)benzonitrile,
4-(1-fluoro-trans-7-ethyl-9,10-dihydrophenanthrene-trans-2-yl)benzonitrile,
2-fluoro-4-(1-fluoro-trans-7-ethyl-9,10-dihydrophenanthrene-trans-2-yl)benzonitrile,
4-(1-fluoro-trans-7-ethyl-9,10-dihydrophenanthrene-trans-2-yl)benzonitrile,
2-fluoro-4-(1-fluoro-trans-7-ethyl-9,10-dihydrophenanthrene-trans-2-yl)benzonitrile,
4-(1-fluoro-trans-7-ethyl-9,10-dihydrophenanthrene-trans-2-yl)benzonitrile,
2-fluoro-4-(1-fluoro-trans-7-ethyl-9,10-dihydrophenanthrene-trans-2-yl)benzonitrile,
4-(1-fluoro-trans-7-ethyl-9,10-dihydrophenanthrene-trans-2-yl)benzonitrile,
2-fluoro-4-(3-fluoro-trans-7-ethyl-9,10-dihydrophenanthrene-trans-2-yl)benzonitrile,
4-(3-fluoro-trans-7-ethyl-9,10-dihydrophenanthrene-trans-2-yl)benzonitrile,
2-fluoro-4-(3-fluoro-trans-7-ethyl-9,10-dihydrophenanthrene-trans-2-yl)benzonitrile,
4-(3-fluoro-trans-7-ethyl-9,10-dihydrophenanthrene-trans-2-yl)benzonitrile,
2-fluoro-4-(3-fluoro-trans-7-ethyl-9,10-dihydrophenanthrene-trans-2-yl)benzonitrile,
4-(3-fluoro-trans-7-ethyl-9,10-dihydrophenanthrene-trans-2-yl)benzonitrile,
2-fluoro-4-(3-fluoro-trans-7-ethyl-9,10-dihydrophenanthrene-trans-2-yl)benzonitrile,
4-(3-fluoro-trans-7-ethyl-9,10-dihydrophenanthrene-trans-2-yl)benzonitrile,
2-fluoro-4-(3-fluoro-trans-7-ethyl-9,10-dihydrophenanthrene-trans-2-yl)benzonitrile,
4-(3-fluoro-trans-7-ethyl-9,10-dihydrophenanthrene-trans-2-yl)benzonitrile,
2-fluoro-4-(3-fluoro-trans-7-ethyl-9,10-dihydrophenanthrene-trans-2-yl)benzonitrile,
4-(3-fluoro-trans-7-ethyl-9,10-dihydrophenanthrene-trans-2-yl)benzonitrile,
2-fluoro-4-(3-fluoro-trans-7-ethyl-9,10-dihydrophenanthrene-trans-2-yl)benzonitrile,
4-(3-fluoro-trans-7-ethyl-9,10-dihydrophenanthrene-trans-2-yl)benzonitrile,
2-fluoro-4-(1-fluoro-trans-7-propylfluorene-trans-2-yl)benzonitrile,
4-(1-fluoro-trans-7-propylfluorene-trans-2-yl)benzonitrile,
2-fluoro-4-(1-fluoro-trans-7-ethylfluorene-trans-2-yl)benzonitrile,
4-(1-fluoro-trans-7-ethylfluorene-trans-2-yl)benzonitrile,
2-fluoro-4-(1-fluoro-trans-7-butylfluorene-trans-2-yl)benzonitrile,
4-(1-fluoro-trans-7-butylfluorene-trans-2-yl)benzonitrile,
2-fluoro-4-(1-fluoro-trans-7-pentylfluorene-trans-2-yl)benzonitrile,
4-(1-fluoro-trans-7-pentylfluorene-trans-2-yl)benzonitrile,
2-fluoro-4-(1-fluoro-trans-7-hexylfluorene-trans-2-yl)benzonitrile,
4-(1-fluoro-trans-7-hexylfluorene-trans-2-yl)benzonitrile,
2-fluoro-4-(1-fluoro-trans-7-heptylfluorene-trans-2-yl)benzonitrile,
4-(1-fluoro-trans-7-heptylfluorene-trans-2-yl)benzonitrile,
2-fluoro-4-(3-fluoro-trans-7-propylfluorene-trans-2-yl)benzonitrile,
4-(3-fluoro-trans-7-propylfluorene-trans-2-yl)benzonitrile,
2-fluoro-4-(3-fluoro-trans-7-ethylfluorene-trans-2-yl)benzonitrile,
4-(3-fluoro-trans-7-ethylfluorene-trans-2-yl)benzonitrile,
2-fluoro-4-(3-fluoro-trans-7-butylfluorene-trans-2-yl)benzonitrile,
4-(3-fluoro-trans-7-butylfluorene-trans-2-yl)benzonitrile,
2-fluoro-4-(3-fluoro-trans-7-pentylfluorene-trans-2-yl)benzonitrile,
4-(3-fluoro-trans-7-pentylfluorene-trans-2-yl)benzonitrile,
2-fluoro-4-(3-fluoro-trans-7-hexylfluorene-trans-2-yl)benzonitrile,
4-(3-fluoro-trans-7-hexylfluorene-trans-2-yl)benzonitrile,
2-fluoro-4-(3-fluoro-trans-7-heptylfluorene-trans-2-yl)benzonitrile, and
4-(3-fluoro-trans-7-heptylfluorene-trans-2-yl)benzonitrile.

Example 7

Synthesis of 2,6-difluoro-4-(1-fluoro-trans-7-propyl-9,10-dihydrophenanthren-trans-2-yl)benzonitrile

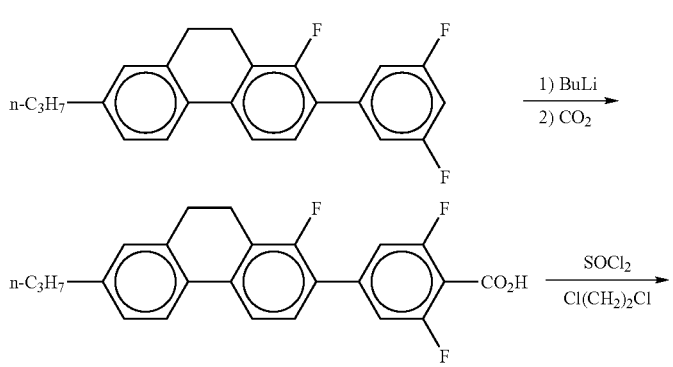

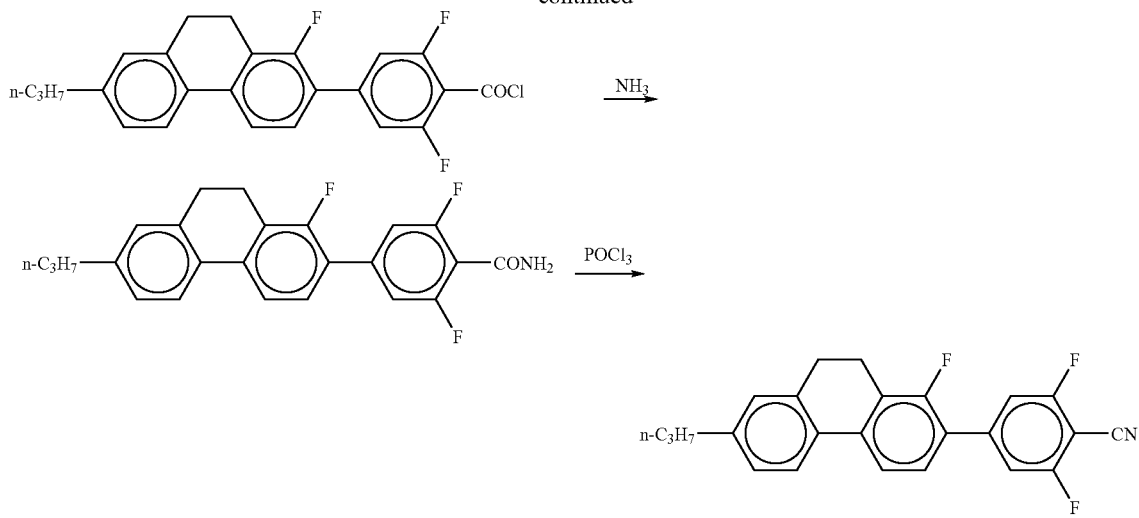

1-fluoro-trans-7-propyl-2-(3,5-difluorophenyl)-9,10-dihydrophenanthrene produced using the same method as Example 3 was lithiated with a butyl lithium-hexane solution, and subsequently reacted with carbon dioxide gas to yield 2,6-difluoro-4-(1-fluoro-trans-7-propyl-9,10-dihydrophenanthren-trans-2-yl)benzoic acid. This compound was converted to an acid chloride with thionyl chloride, and then reacted with ammonia to yield 2,6-difluoro-4-(1-fluoro-trans-7-propyl-9,10-dihydrophenanthren-trans-2-yl)benzamide. Subsequent reaction with phosphorus oxychloride producing a dehydration yielded 2,6-difluoro-4-(1-fluoro-trans-7-propyl-9,10-dihydrophenanthren-trans-2-yl) benzonitrile.

The compounds listed below can be produced in a similar manner.

2,6-difluoro-4-(trans-7-ethyl-9,10-dihydrophenanthrene-trans-2-yl)benzonitrile,
2,6-difluoro-4-(trans-7-ethyl-9,10-dihydrophenanthrene-trans-2-yl)benzonitrile,
2,6-difluoro-4-(trans-7-ethyl-9,10-dihydrophenanthrene-trans-2-yl)benzonitrile,
2,6-difluoro-4-(trans-7-ethyl-9,10-dihydrophenanthrene-trans-2-yl)benzonitrile,
2,6-difluoro-4-(trans-7-ethyl-9,10-dihydrophenanthrene-trans-2-yl)benzonitrile,
2,6-difluoro-4-(trans-7-ethyl-9,10-dihydrophenanthrene-trans-2-yl)benzonitrile,
2,6-difluoro-4-(1,3-difluoro-trans-7-ethyl-9,10-dihydrophenanthrene-trans-2-yl)benzonitrile,
2-fluoro-4-(1,3-difluoro-trans-7-ethyl-9,10-dihydrophenanthrene-trans-2-yl)benzonitrile,
4-(1,3-difluoro-trans-7-ethyl-9,10-dihydrophenanthrene-trans-2-yl)benzonitrile,
2,6-difluoro-4-(1,3-difluoro-trans-7-ethyl-9,10-dihydrophenanthrene-trans-2-yl)benzonitrile,
2-fluoro-4-(1,3-difluoro-trans-7-ethyl-9,10-dihydrophenanthrene-trans-2-yl)benzonitrile,
4-(1,3-difluoro-trans-7-ethyl-9,10-dihydrophenanthrene-trans-2-yl)benzonitrile,
2,6-difluoro-4-(1,3-difluoro-trans-7-ethyl-9,10-dihydrophenanthrene-trans-2-yl)benzonitrile,
2-fluoro-4-(1,3-difluoro-trans-7-ethyl-9,10-dihydrophenanthrene-trans-2-yl)benzonitrile,
4-(1,3-difluoro-trans-7-ethyl-9,10-dihydrophenanthrene-trans-2-yl)benzonitrile,
2,6-difluoro-4-(1,3-difluoro-trans-7-ethyl-9,10-dihydrophenanthrene-trans-2-yl)benzonitrile,
2-fluoro-4-(1,3-difluoro-trans-7-ethyl-9,10-dihydrophenanthrene-trans-2-yl)benzonitrile,
4-(1,3-difluoro-trans-7-ethyl-9,10-dihydrophenanthrene-trans-2-yl)benzonitrile,
2,6-difluoro-4-(1,3-difluoro-trans-7-ethyl-9,10-dihydrophenanthrene-trans-2-yl)benzonitrile,
2-fluoro-4-(1,3-difluoro-trans-7-ethyl-9,10-dihydrophenanthrene-trans-2-yl)benzonitrile,
4-(1,3-difluoro-trans-7-ethyl-9,10-dihydrophenanthrene-trans-2-yl)benzonitrile,
2,6-difluoro-4-(1-fluoro-trans-7-ethyl-9,10-dihydrophenanthrene-trans-2-yl)benzonitrile,
2,6-difluoro-4-(1-fluoro-trans-7-ethyl-9,10-dihydrophenanthrene-trans-2-yl)benzonitrile,
2,6-difluoro-4-(1-fluoro-trans-7-ethyl-9,10-dihydrophenanthrene-trans-2-yl)benzonitrile,
2,6-difluoro-4-(1-fluoro-trans-7-ethyl-9,10-dihydrophenanthrene-trans-2-yl)benzonitrile,
2,6-difluoro-4-(1-fluoro-trans-7-ethyl-9,10-dihydrophenanthrene-trans-2-yl)benzonitrile,
2,6-difluoro-4-(3-fluoro-trans-7-ethyl-9,10-dihydrophenanthrene-trans-2-yl)benzonitrile,
2,6-difluoro-4-(3-fluoro-trans-7-ethyl-9,10-dihydrophenanthrene-trans-2-yl)benzonitrile,
2,6-difluoro-4-(3-fluoro-trans-7-ethyl-9,10-dihydrophenanthrene-trans-2-yl)benzonitrile,
2,6-difluoro-4-(3-fluoro-trans-7-ethyl-9,10-dihydrophenanthrene-trans-2-yl)benzonitrile,
2,6-difluoro-4-(3-fluoro-trans-7-ethyl-9,10-dihydrophenanthrene-trans-2-yl)benzonitrile,
2,6-difluoro-4-(3-fluoro-trans-7-ethyl-9,10-dihydrophenanthrene-trans-2-yl)benzonitrile, 2,6-difluoro-4-(trans-7-ethylfluorene-trans-2-yl)benzonitrile,
2,6-difluoro-4-(trans-7-propylfluorene-trans-2-yl)benzonitrile,
2,6-difluoro-4-(trans-7-butylfluorene-trans-2-yl)benzonitrile,
2,6-difluoro-4-(trans-7-pentylfluorene-trans-2-yl)benzonitrile,
2,6-difluoro-4-(trans-7-hexylfluorene-trans-2-yl)benzonitrile,
2,6-difluoro-4-(trans-7-heptylfluorene-trans-2-yl)benzonitrile,
2,6-difluoro-4-(1,3-difluoro-trans-7-propylfluorene-trans-2-yl)benzonitrile,
2-fluoro-4-(1,3-difluoro-trans-7-propylfluorene-trans-2-yl)benzonitrile,
4-(1,3-difluoro-trans-7-propylfluorene-trans-2-yl)benzonitrile,
2,6-difluoro-4-(1,3-difluoro-trans-7-ethylfluorene-trans-2-yl)benzonitrile,
2-fluoro-4-(1,3-difluoro-trans-7-ethylfluorene-trans-2-yl)benzonitrile,
4-(1,3-difluoro-trans-7-ethylfluorene-trans-2-yl)benzonitrile,
2,6-difluoro-4-(1,3-difluoro-trans-7-butylfluorene-trans-2-yl)benzonitrile,
2-fluoro-4-(1,3-difluoro-trans-7-butylfluorene-trans-2-yl)benzonitrile,
4-(1,3-difluoro-trans-7-butylfluorene-trans-2-yl)benzonitrile,
2,6-difluoro-4-(1,3-difluoro-trans-7-pentylfluorene-trans-2-yl)benzonitrile,
2-fluoro-4-(1,3-difluoro-trans-7-pentylfluorene-trans-2-yl)benzonitrile,
4-(1,3-difluoro-trans-7-pentylfluorene-trans-2-yl)benzonitrile,
2,6-difluoro-4-(1,3-difluoro-trans-7-hexylfluorene-trans-2-yl)benzonitrile,
2-fluoro-4-(1,3-difluoro-trans-7-hexylfluorene-trans-2-yl)benzonitrile,
4-(1,3-difluoro-trans-7-hexylfluorene-trans-2-yl)benzonitrile,
2,6-difluoro-4-(1,3-difluoro-trans-7-heptylfluorene-trans-2-yl)benzonitrile,
2-fluoro-4-(1,3-difluoro-trans-7-heptylfluorene-trans-2-yl)benzonitrile,
4-(1,3-difluoro-trans-7-heptylfluorene-trans-2-yl)benzonitrile,
2,6-difluoro-4-(1-fluoro-trans-7-ethylfluorene-trans-2-yl)benzonitrile,
2,6-difluoro-4-(1-fluoro-trans-7-propylfluorene-trans-2-yl)benzonitrile,
2,6-difluoro-4-(1-fluoro-trans-7-butylfluorene-trans-2-yl)benzonitrile,
2,6-difluoro-4-(1-fluoro-trans-7-pentylfluorene-trans-2-yl)benzonitrile,
2,6-difluoro-4-(1-fluoro-trans-7-hexylfluorene-trans-2-yl)benzonitrile,
2,6-difluoro-4-(1-fluoro-trans-7-heptylfluorene-trans-2-yl)benzonitrile,
2,6-difluoro-4-(3-fluoro-trans-7-propylfluorene-trans-2-yl)benzonitrile,
2,6-difluoro-4-(3-fluoro-trans-7-ethylfluorene-trans-2-yl)benzonitrile,
2,6-difluoro-4-(3-fluoro-trans-7-butylfluorene-trans-2-yl)benzonitrile,
2,6-difluoro-4-(3-fluoro-trans-7-pentylfluorene-trans-2-yl)benzonitrile,
2,6-difluoro-4-(3-fluoro-trans-7-hexylfluorene-trans-2-yl)benzonitrile, and
2,6-difluoro-4-(3-fluoro-trans-7-heptylfluorene-trans-2-yl)benzonitrile.

Example 8

Synthesis of 4-cyano-3-fluorophenyl trans-7-propyl-9,10-dihydrophenanthrene-2-carboxylate

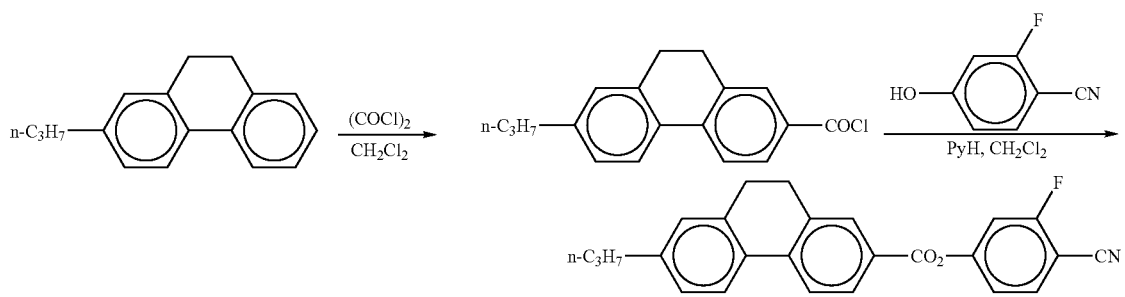

7-propyl-9,10-dihydrophenanthrene produced in Example 1 was reacted with oxalyl dichloride, and subsequently reacted with 2-fluoro-4-hydroxybenzonitrile to yield 4-cyano-3-fluorophenyl trans-7-propyl-9,10-dihydrophenanthrene-2-carboxylate.

The compounds listed below can be produced in a similar manner.

4-cyanophenyl 7-propyl-9,10-dihydrophenanthrene-2-carboxylate,
4-cyano-3,5-difluorophenyl 7-propyl-9,10-dihydrophenanthrene-2-carboxylate,
4-cyanophenyl 1-fluoro-7-propyl-9,10-dihydrophenanthrene-2-carboxylate,
4-cyano-3-fluorophenyl 1-fluoro-7-propyl-9,10-dihydrophenanthrene-2-carboxylate,
4-cyano-3,5-difluorophenyl 1-fluoro-7-propyl-9,10-dihydrophenanthrene-2-carboxylate,
4-cyanophenyl 1-fluoro-7-propylfluorene-2-carboxylate,
4-cyano-3-fluorophenyl 1-fluoro-7-propylfluorene-2-carboxylate,
4-cyano-3,5-difluorophenyl 1-fluoro-7-propylfluorene-2-carboxylate, 4-cyanophenyl 1,3-difluoro-7-propyl-9,10-dihydrophenanthrene-2-carboxylate,
4-cyano-3-fluorophenyl 1,3-difluoro-7-propyl-9,10-dihydrophenanthrene-2-carboxylate,
4-cyano-3,5-difluorophenyl 1,3-difluoro-7-propyl-9,10-dihydrophenanthrene-2-carboxylate,
4-cyanophenyl 1,3-difluoro-7-propylfluorene-2-carboxylate, and
4-cyano-3-fluorophenyl 1,3-difluoro-7-propylfluorene-2-carboxylate.

Example 9

Synthesis of 2-propyl-7-(3,4,5-trifluorophenyl)phenanthrene then recrystallized 3 times from ethanol to yield white crystals of 2-propyl-7-(3,4,5-trifluorophenyl)phenanthrene.

The compounds listed below can be produced in a similar manner.
2-propyl-7-(4-fluorophenyl)phenanthrene,
2-propyl-7-(3,4-difluorophenyl)phenanthrene,
2-propyl-7-(3,5-difluorophenyl)phenanthrene,
2-propyl-7-(3,4,5-trifluorophenyl)phenanthrene,
2-propyl-7-(4-trifluoromethoxyphenyl)phenanthrene,
2-propyl-7-(3-fluoro-4-trifluoromethoxyphenyl)phenanthrene,
2-propyl-7-(3,5-difluoro-4-trifluoromethoxyphenyl)phenanthrene,
2-propyl-7-(4-difluoromethoxyphenyl)phenanthrene,
2-propyl-7-(4-trifluoromethylphenyl)phenanthrene,

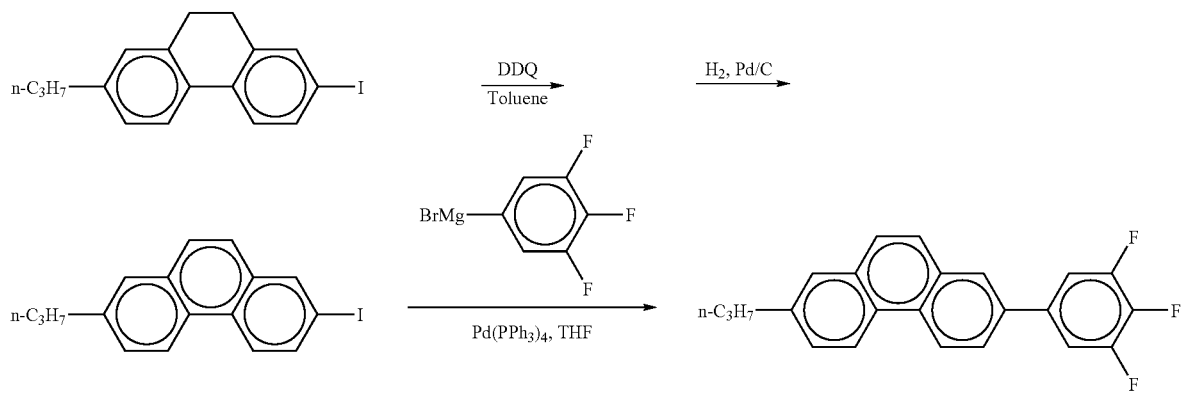

2-iodo-7-propyl-phenanthrene was dissolved in toluene, DDQ was added, and the mixture was heated at 100° C., with stirring, for a period of 5 hours. The solvent was removed by evaporation and the product purified by silica gel chromatography to yield 2-iodo-7-propylphenanthrene. This compound was then reacted with a Grignard reagent prepared from 3,4,5-trifluorobromobenzene and magnesium. Following stirring for 2 hours at room temperature, the mixture was allowed to cool to room temperature, water was added, the product was extracted into toluene, and the organic layer was washed sequentially with water and a saturated aqueous solution of sodium chloride before being dried over anhydrous sodium sulfate. The crude product obtained by removal of the solvent by evaporation was purified by silica gel column chromatography (hexane) and 2-propyl-7-(3-fluoro-4-trifluoromethylphenyl)phenanthrene,
2-propyl-7-(3,5-difluoro-4-trifluoromethylphenyl)phenanthrene,
2-propyl-7-(4-chlorophenyl)phenanthrene,
2-propyl-7-(3-fluoro-4-chlorophenyl)phenanthrene, and
2-propyl-7-(3,5-difluoro-4-chlorophenyl)phenanthrene.

Example 10

Synthesis of 2-propyl-7-(3,4-difluorophenylethynyl)phenanthrene

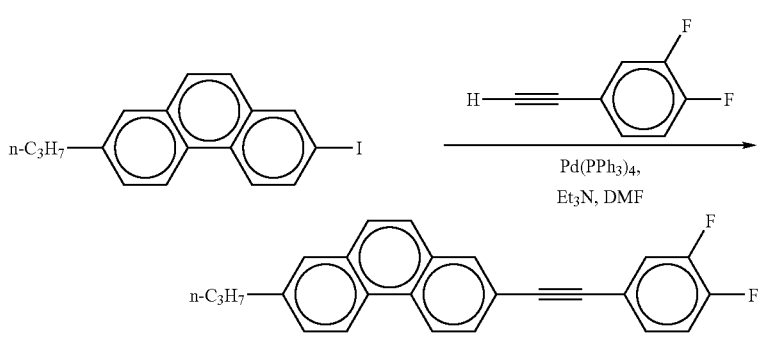

2-iodo-7-propyl-phenanthrene in dimethylformamide and triethylamine was reacted with 4-ethynyl-1,2-difluorobenzene in the presence of tetrakis(triphenylphosphine)palladium (0), and the product was purified by silica gel column chromatography (hexane) and then recrystallized from ethanol to yield 2-propyl-7-(3,4-difluorophenylethynyl)phenanthrene.

The compounds listed below can be produced in a similar manner.
2-propyl-7-(4-fluorophenylethynyl)phenanthrene,
2-propyl-7-(3,4-difluorophenylethynyl)phenanthrene,
2-propyl-7-(3,5-difluorophenylethynyl)phenanthrene,
2-propyl-7-(4-trifluoromethoxyphenylethynyl)phenanthrene,
2-propyl-7-(3-fluoro-4-trifluoromethoxyphenylethynyl) phenanthrene,
2-propyl-7-(3,5-difluoro-4-trifluoromethoxyphenylethynyl) phenanthrene,
2-propyl-7-(3,4,5-trifluorophenylethynyl)phenanthrene,
2-propyl-7-(4-difluoromethoxyphenylethynyl)phenanthrene,
2-propyl-7-(4-trifluoromethylphenylethynyl)phenanthrene,
2-propyl-7-(3-fluoro-4-trifluoromethylphenylethynyl) phenanthrene,
2-propyl-7-(3,5-difluoro-4-trifluoromethylphenylethynyl) phenanthrene,
2-propyl-7-(4-chlorophenylethynyl)phenanthrene,
2-propyl-7-(3-fluoro-4-chlorophenylethynyl)phenanthrene, and
2-propyl-7-(3,5-difluoro-4-chlorophenylethynyl)phenanthrene.

Example 11

Synthesis of 8-fluoro-2-propyl-7-(3,4,5-trifluorophenyl)phenanthrene and 6-fluoro-2-propyl-7-(3,4,5-trifluorophenyl)phenanthrene sulfate. The solvent was removed by evaporation and the whole crude product was dissolved in ethyl acetate, and 5% palladium/carbon (wet) was then added, and the mixture was stirred in an autoclave under a hydrogen pressure of 4 Kg/cm$^2$. After 5 hours stirring at room temperature, the catalyst was removed by filtration through celite, and the solvent was then removed by evaporation. The crude product was purified by silica gel column chromatography (hexane) and then recrystallized 3 times from ethanol to yield 8-fluoro-2-propyl-7-(3,4,5-trifluorophenyl)phenanthrene.

The compounds listed below can be produced in a similar manner.
8-fluoro-2-propyl-7-(4-fluorophenyl)phenanthrene,
8-fluoro-2-propyl-7-(3,4-difluorophenyl)phenanthrene,
8-fluoro-2-propyl-7-(3,5-difluorophenyl)phenanthrene,
8-fluoro-2-propyl-7-(3,4,5-trifluorophenyl)phenanthrene,
8-fluoro-2-propyl-7-(4-trifluoromethoxyphenyl)phenanthrene,
8-fluoro-2-propyl-7-(3-fluoro-4-trifluoromethoxyphenyl) phenanthrene,
8-fluoro-2-propyl-7-(3,5-difluoro-4-trifluoromethoxyphenyl)phenanthrene,
8-fluoro-2-propyl-7-(4-difluoromethoxyphenyl)phenanthrene,
8-fluoro-2-propyl-7-(4-trifluoromethylphenyl)phenanthrene,
8-fluoro-2-propyl-7-(3-fluoro-4-trifluoromethylphenyl) phenanthrene,
8-fluoro-2-propyl-7-(3,5-difluoro-4-trifluoromethylphenyl) phenanthrene,
8-fluoro-2-propyl-7-(4-chlorophenyl)phenanthrene,
8-fluoro-2-propyl-7-(3-fluoro-4-chlorophenyl)phenanthrene,
8-fluoro-2-propyl-7-(3,5-difluoro-4-chlorophenyl)phenanthrene,
6-fluoro-2-propyl-7-(4-fluorophenyl)phenanthrene,
6-fluoro-2-propyl-7-(3,4-difluorophenyl)phenanthrene,

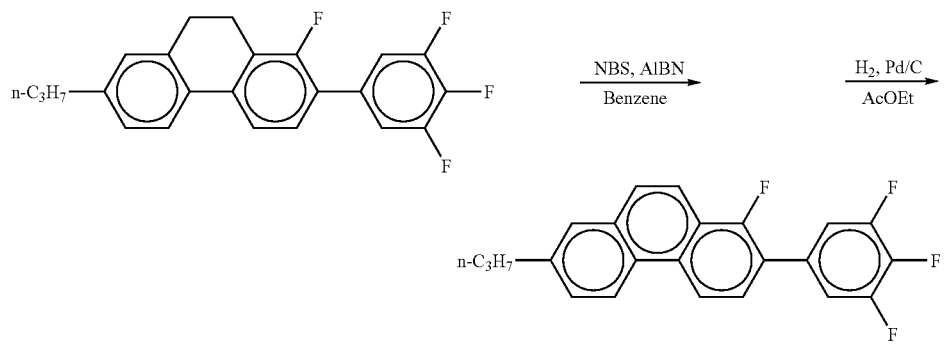

8-fluoro-2-propyl-7-(3,4,5-trifluorophenyl)-9,10-dihydrophenanthrene produced in Example 1 was dissolved in benzene, NBS (N-bromosuccinimide) and AIBN (2,2-azobis isobutyronitrile) were added, and the temperature was gradually raised to benzene reflux temperature. Stirring was then continued for a further 2 hours, before water was added and the reaction halted, and the organic layer was then separated. The aqueous layer was extracted with toluene and this extract was combined with the organic layer, which was then washed with water and a saturated aqueous solution of sodium chloride, before being dried over anhydrous sodium 6-fluoro-2-propyl-7-(3,5-difluorophenyl)phenanthrene,
6-fluoro-2-propyl-7-(3,4,5-trifluorophenyl)phenanthrene,
6-fluoro-2-propyl-7-(4-trifluoromethoxyphenyl)phenanthrene,
6-fluoro-2-propyl-7-(3-fluoro-4-trifluoromethoxyphenyl) phenanthrene,
6-fluoro-2-propyl-7-(3,5-difluoro-4-trifluoromethoxyphenyl)phenanthrene,
6-fluoro-2-propyl-7-(4-difluoromethoxyphenyl)phenanthrene, 6-fluoro-2-propyl-7-(4-trifluoromethylphenyl)phenanthrene,
6-fluoro-2-propyl-7-(3-fluoro-4-trifluoromethylphenyl)phenanthrene,
6-fluoro-2-propyl-7-(3,5-difluoro-4-trifluoromethylphenyl)phenanthrene,
6-fluoro-2-propyl-7-(4-chlorophenyl)phenanthrene,
6-fluoro-2-propyl-7-(3-fluoro-4-chlorophenyl)phenanthrene, and
6-fluoro-2-propyl-7-(3,5-difluoro-4-chlorophenyl)phenanthrene.

Example 12

Synthesis of 2-fluoro-4-(7-propylphenanthren2-yl)benzonitrile 2-fluoro-4-(3-fluoro-7-propylphenanthrene-2-yl)benzonitrile,
4-(3-fluoro-7-propylphenanthrene-2-yl)benzonitrile,
4-(1,3-difluoro-7-propylphenanthrene-2-yl)benzonitrile,
2-fluoro-4-(1,3-difluoro-7-propylphenanthrene-2-yl)benzonitrile,
2-fluoro-4-(1,3-difluoro-7-ethylphenanthrene-2-yl)benzonitrile,
4-(1,3-difluoro-7-ethylphenanthrene-2-yl)benzonitrile,
2-fluoro-4-(1,3-difluoro-7-butylphenanthrene-2-yl)benzonitrile,
4-(1,3-difluoro-7-butylphenanthrene-2-yl)benzonitrile,
2-fluoro-4-(1,3-difluoro-7-pentylphenanthrene-2-yl)benzonitrile,
4-(1,3-difluoro-7-pentylphenanthrene-2-yl)benzonitrile,

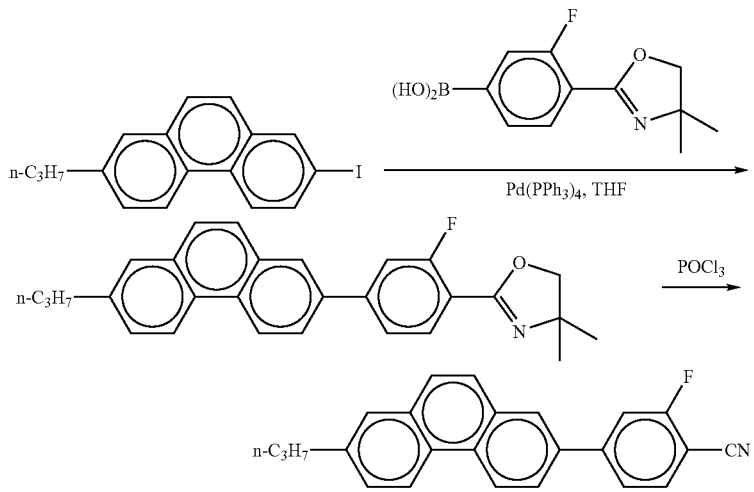

2-iodo-7-propylphenanthrene was reacted with 4-(4,4-dimethyl-4,5-dihydrooxazol-2-yl)-2-fluorophenylboric acid in the presence of tetrakis(triphenylphosphine)palladium, and subsequently reacted with phosphorus oxychloride to remove the cyano group protective group, and yielded 2-fluoro-4-(7-propylphenanthren-2-yl) benzonitrile.

The compounds listed below can be produced in a similar manner.
4-(7-propylphenanthrene-2-yl)benzonitrile,
2-fluoro-4-(1-fluoro-7-propylphenanthrene-2-yl)benzonitrile,
4-(1-fluoro-7-propylphenanthrene-2-yl)benzonitrile, 2-fluoro-4-(1,3-difluoro-7-hexylphenanthrene-2-yl)benzonitrile,
4-(1,3-difluoro-7-hexylphenanthrene-2-yl)benzonitrile,
2-fluoro-4-(1,3-difluoro-7-heptylphenanthrene-2-yl)benzonitrile, and
4-(1,3-difluoro-7-heptylphenanthrene-2-yl)benzonitrile.

Example 13

Synthesis of 2-fluoro-4-(1-fluoro-trans-7-propylphenanthrene-2-yl)benzonitrile

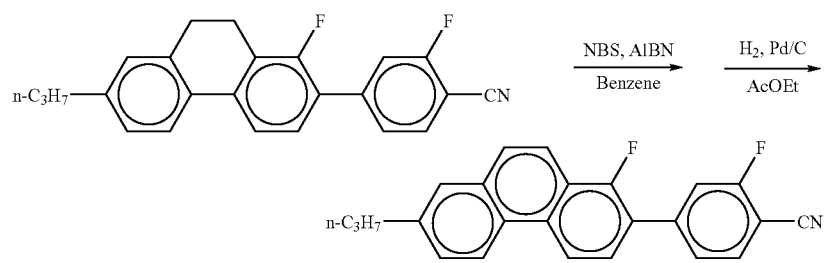

2-fluoro-4-(1-fluoro-7-propyl-9,10-dihydrophenanthren-2-yl)benzonitrile produced in Example 6 was dissolved in benzene, NBS (N-bromosuccinimide) and AIBN (2,2-azobis isobutyronitrile) were added, and the temperature was gradually raised to benzene reflux temperature. Stirring was then continued for a further 2 hours, before water was added and the reaction halted, and the organic layer was then separated. The aqueous layer was extracted with toluene and this extract was combined with the organic layer, which was then washed with water and a saturated aqueous solution of sodium chloride, before being dried over anhydrous sodium sulfate. The crude product was purified by silica gel column chromatography and then recrystallized 3 times from ethanol to yield 2-fluoro-4-(1-fluoro-trans-7-propylphenanthren-2-yl)benzonitrile.

The compounds listed below can be produced in a similar manner.

2-fluoro-4-(1-fluoro-trans-7-propylphenanthrene-trans-2-yl)benzonitrile,
4-(1-fluoro-trans-7-propylphenanthrene-trans-2-yl)benzonitrile,
2-fluoro-4-(1-fluoro-trans-7-ethylphenanthrene-trans-2-yl)benzonitrile,
4-(1-fluoro-trans-7-ethylphenanthrene-trans-2-yl)benzonitrile,
2-fluoro-4-(1-fluoro-trans-7-butylphenanthrene-trans-2-yl)benzonitrile,
4-(1-fluoro-trans-7-butylphenanthrene-trans-2-yl)benzonitrile,
2-fluoro-4-(1-fluoro-trans-7-pentylphenanthrene-trans-2-yl)benzonitrile,
4-(1-fluoro-trans-7-pentylphenanthrene-trans-2-yl)benzonitrile,
2-fluoro-4-(1-fluoro-trans-7-hexylphenanthrene-trans-2-yl)benzonitrile,
4-(1-fluoro-trans-7-hexylphenanthrene-trans-2-yl)benzonitrile,
2-fluoro-4-(1-fluoro-trans-7-heptylphenanthrene-trans-2-yl)benzonitrile,
4-(1-fluoro-trans-7-heptylphenanthrene-trans-2-yl)benzonitrile,
2-fluoro-4-(3-fluoro-trans-7-propylphenanthrene-trans-2-yl)benzonitrile,
4-(3-fluoro-trans-7-propylphenanthrene-trans-2-yl)benzonitrile,
2-fluoro-4-(3-fluoro-trans-7-ethylphenanthrene-trans-2-yl)benzonitrile,
4-(3-fluoro-trans-7-ethylphenanthrene-trans-2-yl)benzonitrile,
2-fluoro-4-(3-fluoro-trans-7-butylphenanthrene-trans-2-yl)benzonitrile,
4-(3-fluoro-trans-7-butylphenanthrene-trans-2-yl)benzonitrile,
2-fluoro-4-(3-fluoro-trans-7-pentylphenanthrene-trans-2-yl)benzonitrile,
4-(3-fluoro-trans-7-pentylphenanthrene-trans-2-yl)benzonitrile,
2-fluoro-4-(3-fluoro-trans-7-hexylphenanthrene-trans-2-yl)benzonitrile,
4-(3-fluoro-trans-7-hexylphenanthrene-trans-2-yl)benzonitrile,
2-fluoro-4-(3-fluoro-trans-7-heptylphenanthrene-trans-2-yl)benzonitrile, and
4-(3-fluoro-trans-7-heptylphenanthrene-trans-2-yl)benzonitrile.

Example 14

Synthesis of 2,6-difluoro-4-(1-fluoro-trans-7-propylphenanthrene-2-trans-yl)benzonitrile

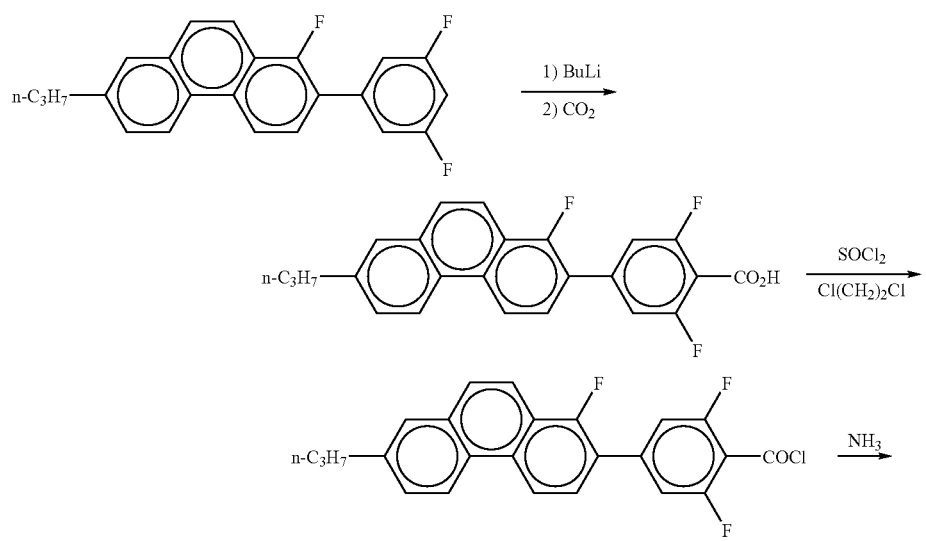

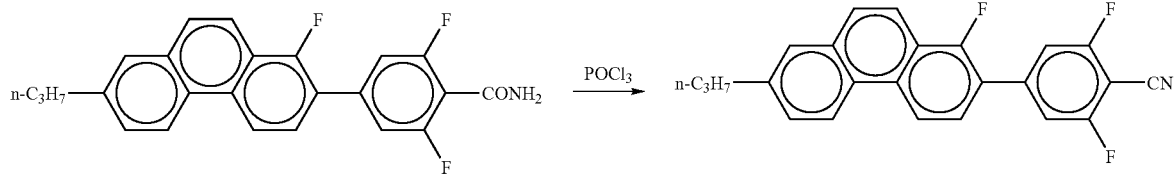

1-fluoro-trans-7-propyl-2-(3,5-difluorophenyl)phenanthrene produced using the same method as Example 11 was lithiated using a butyl lithium-hexane solution, and subsequently reacted with carbon dioxide gas to yield 2,6-difluoro-4-(1-fluoro-trans-7-propylphenanthren-trans-2-yl) benzoic acid. This compound was converted to an acid chloride with thionyl chloride, and then reacted with ammonia to yield 2,6-difluoro-4-(1-fluoro-trans-7-propylphenanthren-trans-2-yl)benzamide. Subsequent reaction with phosphorus oxychloride producing a dehydration yielded 2,6-difluoro-4-(1-fluoro-trans-7-propylphenanthren-trans-2-yl) benzonitrile.

The compounds listed below can be produced in a similar manner.

2,6-difluoro-4-(trans-7-ethylphenanthrene-trans-2-yl)benzonitrile,
2,6-difluoro-4-(trans-7-propylphenanthrene-trans-2-yl)benzonitrile,
2,6-difluoro-4-(trans-7-butylphenanthrene-trans-2-yl)benzonitrile,
2,6-difluoro-4-(trans-7-pentylphenanthrene-trans-2-yl)benzonitrile,
2,6-difluoro-4-(trans-7-hexylphenanthrene-trans-2-yl)benzonitrile,
2,6-difluoro-4-(trans-7-heptylphenanthrene-trans-2-yl)benzonitrile,
2,6-difluoro-4-(1,3-difluoro-trans-7-propylphenanthrene-trans-2-yl)benzonitrile,
2-fluoro-4-(1,3-difluoro-trans-7-propylphenanthrene-trans-2-yl)benzonitrile,
4-(1,3-difluoro-trans-7-propylphenanthrene-trans-2-yl)benzonitrile,
2,6-difluoro-4-(1,3-difluoro-trans-7-ethylphenanthrene-trans-2-yl)benzonitrile,
2-fluoro-4-(1,3-difluoro-trans-7-ethylphenanthrene-2-yl)benzonitrile,
4-(1,3-difluoro-trans-7-ethylphenanthrene-trans-2-yl)benzonitrile,
2,6-difluoro-4-(1,3-difluoro-trans-7-butylphenanthrene-trans-2-yl)benzonitrile,
2-fluoro-4-(1,3-difluoro-trans-7-butylphenanthrene-trans-2-yl)benzonitrile,
4-(1,3-difluoro-trans-7-butylphenanthrene-trans-2-yl)benzonitrile,
2,6-difluoro-4-(1,3-difluoro-trans-7-pentylphenanthrene-trans-2-yl)benzonitrile,
2-fluoro-4-(1,3-difluoro-trans-7-pentylphenanthrene-trans-2-yl)benzonitrile,
4-(1,3-difluoro-trans-7-pentylphenanthrene-trans-2-yl)benzonitrile,
2,6-difluoro-4-(1,3-difluoro-trans-7-hexylphenanthrene-trans-2-yl)benzonitrile,
2-fluoro-4-(1,3-difluoro-trans-7-hexylphenanthrene-trans-2-yl)benzonitrile,
4-(1,3-difluoro-trans-7-hexylphenanthrene-trans-2-yl)benzonitrile,
2,6-difluoro-4-(1,3-difluoro-trans-7-heptylphenanthrene-trans-2-yl)benzonitrile,
2-fluoro-4-(1,3-difluoro-trans-7-heptylphenanthrene-trans-2-yl)benzonitrile,
4-(1,3-difluoro-trans-7-heptylphenanthrene-trans-2-yl)benzonitrile,
2,6-difluoro-4-(1-fluoro-trans-7-ethylphenanthrene-trans-2-yl)benzonitrile,
2,6-difluoro-4-(1-fluoro-trans-7-butylphenanthrene-trans-2-yl)benzonitrile,
2,6-difluoro-4-(1-fluoro-trans-7-pentylphenanthrene-trans-2-yl)benzonitrile,
2,6-difluoro-4-(1-fluoro-trans-7-hexylphenanthrene-trans-2-yl)benzonitrile,
2,6-difluoro-4-(1-fluoro-trans-7-heptylphenanthrene-trans-2-yl)benzonitrile,
2,6-difluoro-4-(3-fluoro-trans-7-propylphenanthrene-trans-2-yl)benzonitrile,
2,6-difluoro-4-(3-fluoro-trans-7-ethylphenanthrene-trans-2-yl)benzonitrile,
2,6-difluoro-4-(3-fluoro-trans-7-butylphenanthrene-trans-2-yl)benzonitrile,
2,6-difluoro-4-(3-fluoro-trans-7-pentylphenanthrene-trans-2-yl)benzonitrile,
2,6-difluoro-4-(3-fluoro-trans-7-hexylphenanthrene-trans-2-yl)benzonitrile,
2,6-difluoro-4-(3-fluoro-trans-7-heptylphenanthrene-trans-2-yl)benzonitrile,
2,6-difluoro-4-(trans-7-ethylfluorene-trans-2-yl)benzonitrile,
2,6-difluoro-4-(trans-7-propylfluorene-trans-2-yl)benzonitrile,
2,6-difluoro-4-(trans-7-butylfluorene-trans-2-yl)benzonitrile,
2,6-difluoro-4-(trans-7-pentylfluorene-trans-2-yl)benzonitrile,
2,6-difluoro-4-(trans-7-hexylfluorene-trans-2-yl)benzonitrile,
2,6-difluoro-4-(trans-7-heptylfluorene-trans-2-yl)benzonitrile,
2,6-difluoro-4-(1,3-difluoro-trans-7-propylfluorene-trans-2-yl)benzonitrile,
2-fluoro-4-(1,3-difluoro-trans-7-propylfluorene-trans-2-yl)benzonitrile,
4-(1,3-difluoro-trans-7-propylfluorene-trans-2-yl)benzonitrile,
2,6-difluoro-4-(1,3-difluoro-trans-7-ethylfluorene-trans-2-yl)benzonitrile,
2-fluoro-4-(1,3-difluoro-trans-7-ethylfluorene-trans-2-yl)benzonitrile,
4-(1,3-difluoro-trans-7-ethylfluorene-trans-2-yl)benzonitrile, 2,6-difluoro-4-(1,3-difluoro-trans-7-butylfluorene-trans-2-yl)benzonitrile,
2-fluoro-4-(1,3-difluoro-trans-7-butylfluorene-trans-2-yl)benzonitrile,
4-(1,3-difluoro-trans-7-butylfluorene-trans-2-yl)benzonitrile,
2,6-difluoro-4-(1,3-difluoro-trans-7-pentylfluorenetrans-2-yl)benzonitrile,
2-fluoro-4-(1,3-difluoro-trans-7-pentylfluorene-trans-2-yl)benzonitrile,
4-(1,3-difluoro-trans-7-pentylfluorene-trans-2-yl)benzonitrile,
2,6-difluoro-4-(1,3-difluoro-trans-7-hexylfluorene-trans-2-yl)benzonitrile,
2-fluoro-4-(1,3-difluoro-trans-7-hexylfluorene-trans-2-yl)benzonitrile,
4-(1,3-difluoro-trans-7-hexylfluorene-trans-2-yl)benzonitrile,
2,6-difluoro-4-(1,3-difluoro-trans-7-heptylfluorene-trans-2-yl)benzonitrile,
2-fluoro-4-(1,3-difluoro-trans-7-heptylfluorene-trans-2-yl)benzonitrile,
4-(1,3-difluoro-trans-7-heptylfluorene-trans-2-yl)benzonitrile,
2,6-difluoro-4-(1-fluoro-trans-7-ethylfluorene-trans-2-yl)benzonitrile,
2,6-difluoro-4-(1-fluoro-trans-7-propylfluorene-trans-2-yl)benzonitrile,
2,6-difluoro-4-(1-fluoro-trans-7-butylfluorene-trans-2-yl)benzonitrile,
2,6-difluoro-4-(1-fluoro-trans-7-pentylfluorene-trans-2-yl)benzonitrile,
2,6-difluoro-4-(1-fluoro-trans-7-hexylfluorene-trans-2-yl)benzonitrile,
2,6-difluoro-4-(1-fluoro-trans-7-heptylfluorene-trans-2-yl)benzonitrile,
2,6-difluoro-4-(3-fluoro-trans-7-propylfluorene-trans-2-yl)benzonitrile,
2,6-difluoro-4-(3-fluoro-trans-7-ethylfluorene-trans-2-yl)benzonitrile,
2,6-difluoro-4-(3-fluoro-trans-7-butylfluorene-trans-2-yl)benzonitrile,
2,6-difluoro-4-(3-fluoro-trans-7-pentylfluorene-trans-2-yl)benzonitrile,
2,6-difluoro-4-(3-fluoro-trans-7-hexylfluorene-trans-2-yl)benzonitrile, and
2,6-difluoro-4-(3-fluoro-trans-7-heptylfluorene-trans-2-yl)benzonitrile.

Example 15

Synthesis of 4-cyano-3-fluorophenyl 7-propylphenanthrene-2-carboxylate

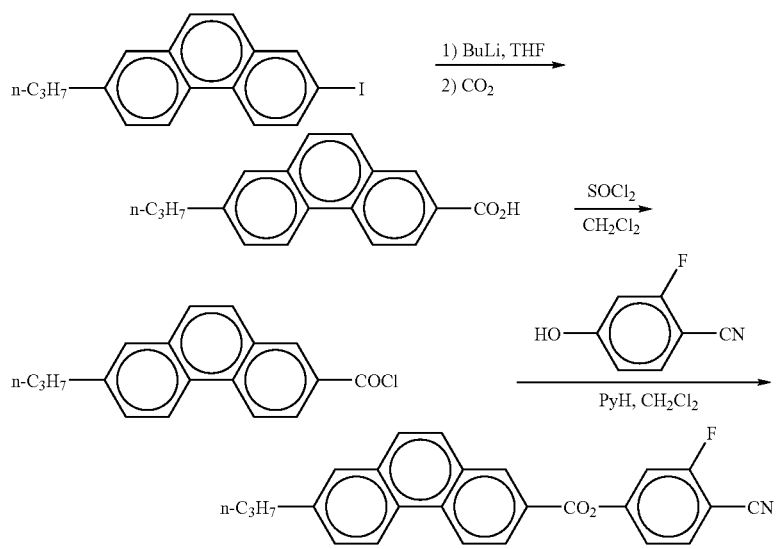

2-iodo-7-propylphenanthrene produced in Example 1 was reacted with oxalyl dichloride, and subsequently reacted with 2-fluoro-4-hydroxybenzonitrile to yield 4-cyano-3-fluorophenyl 7-propylphenanthrene-2-carboxylate The compounds listed below can be produced in a similar manner.

4-cyanophenyl 7-propylphenanthrene-2-carboxylate,
4-cyano-3,5-difluorophenyl 7-propylphenanthrene-2-carboxylate,
4-cyanophenyl 1-fluoro-7-propylphenanthrene-2-carboxylate,
4-cyano-3-fluorophenyl 1-fluoro-7-propylphenanthrene-2-carboxylate,
4-cyano-3,5-difluorophenyl 1-fluoro-7-propylphenanthrene-2-carboxylate,
4-cyanophenyl 1-fluoro-7-propylfluorene-2-carboxylate,
4-cyano-3-fluorophenyl 1-fluoro-7-propylfluorene-2-carboxylate,
4-cyano-3,5-difluorophenyl 1-fluoro-7-propylfluorene-2-carboxylate,
4-cyanophenyl 1,3-difluoro-7-propylphenanthrene-2-carboxylate, 4-cyano-3-fluorophenyl 1,3-difluoro-7-propylphenanthrene-2-carboxylate,
4-cyano-3,5-difluorophenyl 1,3-difluoro-7-propylphenanthrene-2-carboxylate,
4-cyanophenyl 1,3-difluoro-7-propylfluorene-2-carboxylate,
4-cyano-3-fluorophenyl 1,3-difluoro-7-propylfluorene-2-carboxylate, and
4-cyano-3,5-difluorophenyl 1,3-difluoro-7-propylfluorene-2-carboxylate.

Example 16

Synthesis of 1,9-difluoro-2-propyl-7-(3,4,5-trifluorophenyl)phenanthrene

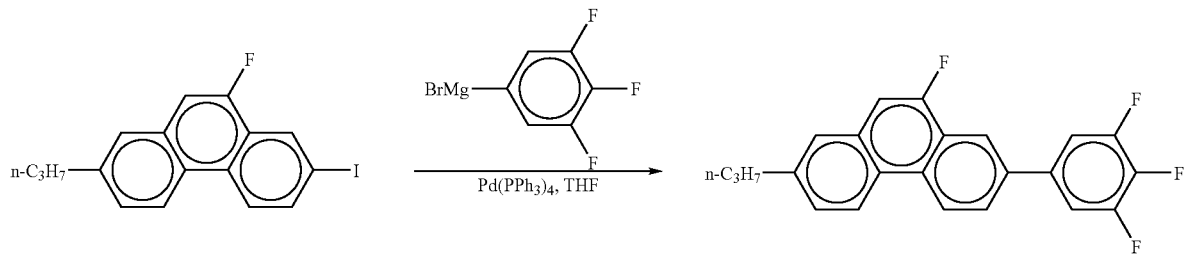

2-iodo-7-propylphenanthrene was fluorinated using xenon fluoride or the like, and column chromatography used to separate the isomers and obtain 2-iodo-1,9-difluoro-7-propylphenanthrene. To a solution of this compound in THF was added tetrakis(triphenylphosphine)palladium (0) and the reaction mixture was stirred at room temperature. This mixture was then reacted with a Grignard reagent prepared from 3,4,5-trifluorobromobenzene and magnesium. Following stirring for 2 hours at room temperature, the mixture was allowed to cool to room temperature, water was added, the product was extracted into toluene, and the organic layer was washed sequentially with water and a saturated aqueous solution of sodium chloride before being dried over anhydrous sodium sulfate. The crude product obtained by removal of the solvent by evaporation was purified by silica gel column chromatography (hexane) and then recrystallized 3 times from ethanol to yield crystals of 2-propyl-7-(3,4,5-trifluorophenyl)-9,10-dihydrophenanthrene.

The compounds listed below can be produced in a similar manner.

1,9-difluoro-2-propyl-7-(4-fluorophenyl)phenanthrene, 1,9-difluoro-2-propyl-7-(3,4-difluorophenyl)phenanthrene, 1,9-difluoro-2-propyl-7-(3,5-difluorophenyl)phenanthrene, 1,9-difluoro-2-propyl-7-(4-trifluoromethoxyphenyl)phenanthrene, 1,9-difluoro-2-propyl-7-(3-fluoro-4-trifluoromethoxyphenyl)phenanthrene, 1,9-difluoro-2-propyl-7-(3,5-difluoro-4-trifluoromethoxyphenyl)phenanthrene, 1,9-difluoro-2-propyl-7-(4-difluoromethoxyphenyl)phenanthrene, 1,9-difluoro-2-propyl-7-(4-trifluoromethylphenyl)phenanthrene, 1,9-difluoro-2-propyl-7-(3-fluoro-4-trifluoromethylphenyl)phenanthrene, 1,9-difluoro-2-propyl-7-(3,5-difluoro-4-trifluoromethylphenyl)phenanthrene, 1,9-difluoro-2-propyl-7-(4-chlorophenyl)phenanthrene, 1,9-difluoro-2-propyl-7-(3-fluoro-4-chlorophenyl)phenanthrene, 1,9-difluoro-2-propyl-7-(3,5-difluoro-4-chlorophenyl)phenanthrene, 1,9-difluoro-2-propyl-7-(4-fluorophenyl)phenanthrene, 1,9-difluoro-2-propyl-7-(3,4-difluorophenyl)phenanthrene, 1,9-difluoro-2-propyl-7-(3,5-difluorophenyl)phenanthrene, 1,9-difluoro-2-propyl-7-(4-trifluoromethoxyphenyl)phenanthrene, 1,9-difluoro-2-propyl-7-(3-fluoro-4-trifluoromethoxyphenyl)phenanthrene, 1,9-difluoro-2-propyl-7-(3,5-difluoro-4-trifluoromethoxyphenyl)phenanthrene, 1,9-difluoro-2-propyl-7-(4-difluoromethoxyphenyl)phenanthrene, 1,9-difluoro-2-propyl-7-(4-trifluoromethylphenyl)phenanthrene, 1,9-difluoro-2-propyl-7-(3-fluoro-4-trifluoromethylphenyl)phenanthrene, 1,9-difluoro-2-propyl-7-(3,5-difluoro-4-trifluoromethylphenyl)phenanthrene, 1,9-difluoro-2-propyl-7-(4-chlorophenyl)phenanthrene, 1,9-difluoro-2-propyl-7-(3-fluoro-4-chlorophenyl)phenanthrene, and 1,9-difluoro-2-propyl-7-(3,5-difluoro-4-chlorophenyl)phenanthrene.

Example 17

Synthesis of 2-propyl-7-(3,4,5-trifluorophenyl)-trans-tetradecahydrophenanthrene

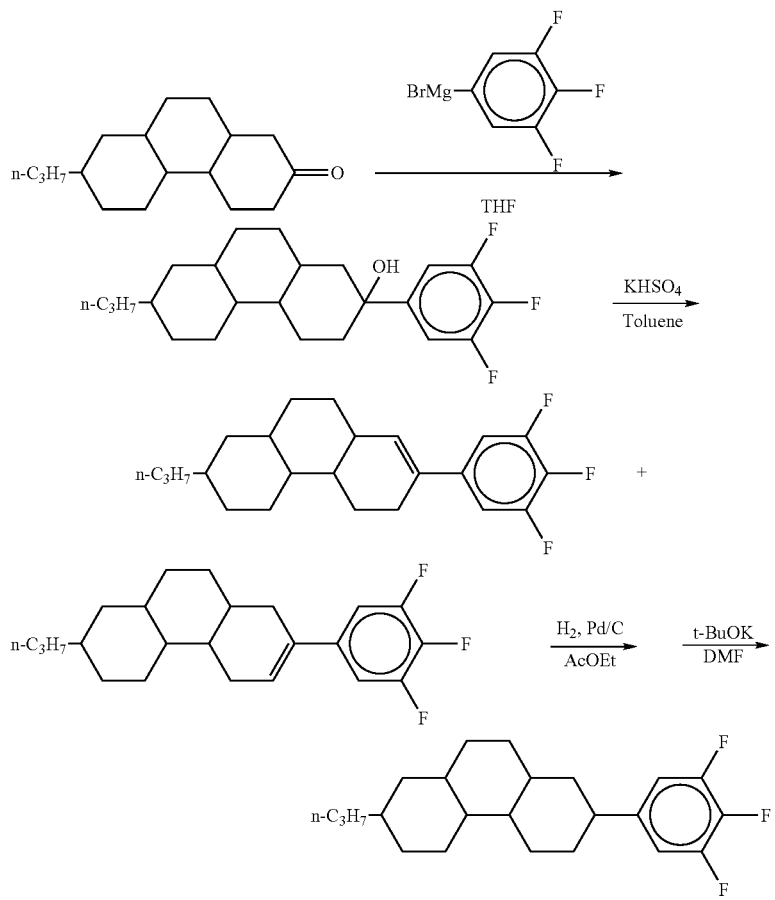

41.6 g of magnesium was suspended in 40 mL of THF, and a solution of 361 g of bromo-3,4,5-trifluorobenzene in 1.4 L of THF was then added dropwise to the suspension over an approximately one hour period at such a rate that the THF refluxed gently. The mixture was then stirred for a further 1 hour, and a solution of 354 g of trans-7-propyl-trans-dodecahydrophenanthren-2-one (synthesis of this compound was carried out using the method disclosed in D. Varech, L. Lacombe and J. Lacques, Nouv. J. Chim., 8, 445 (1984)) in 700 mL of THF was then added dropwise to the mixture over a one hour period. Following stirring for a further 1 hour, 10% hydrochloric acid was added and the reaction halted. Ethyl acetate was then added, the organic layer was separated, and the aqueous layer extracted with additional ethyl acetate which was combined with the organic layer. The combined organic extract was then washed with water, a saturated aqueous solution of sodium bicarbonate, and a saturated aqueous solution of sodium chloride, and was then dried over anhydrous sodium sulfate. The solvent was then removed by evaporation, 2.9 L of toluene and 13.6 g of p-toluenesulfonic acid monohydrate were added, and the mixture was heated at 110° C. with stirring while evaporated water was separated and removed. When the evaporation of water had ceased, the temperature was reduced to room temperature, water was added, and the organic layer was separated. The organic layer was washed with a saturated aqueous solution of sodium bicarbonate, water, and a saturated aqueous solution of sodium chloride, and was then dried over anhydrous sodium sulfate. The solvent was removed by evaporation, and the entire residue was dissolved in 2 L of ethyl acetate. 52 g of 5% palladium-carbon (wet) was then added, and the mixture was stirred in an autoclave under a hydrogen pressure of 4 Kg/cm$^2$. After stirring for 5 hours at room temperature, the catalyst was removed by filtration through celite, and the solvent was removed by evaporation. Following removal of the solvent, isomerization to the trans form was conducted using 16.5 g of potassium-t-butoxide in 2.2 L of ice cooled DMF, the product was recrystallized, and then recrystallized again from ethanol to yield 345 g of white crystals of 2-propyl-7-(3,4,5-trifluorophenyl)-trans-tetradecahydrophenan-threne. Measurement of the phase transition temperature revealed a transition from the crystalline phase to an isotropic liquid phase at 106° C. under rising temperature conditions, whereas the compound displayed a nematic phase at temperatures of 73° or greater under supercooling conditions.

NMR: δ=0.66 to 0.79 (m, 5H), δ=0.82 to 1.35 (m, 15H), δ=1.64 to 2.01 (m, 8H), δ=2.47 (m, 1H), δ=6.79 (dd, 2H, J=6.4 Hz, J=9.2 Hz)

MS: m/e=364 (M+)

The compounds listed below can be produced in a similar manner.

trans-2-propyl-trans-7-(4-fluorophenyl)-trans-tetradecahydrophenanthrene,

Example 18

Synthesis of trans-2-propyl-trans-7-[2-(3,4,5-trifluorophenyl)ethyl]-trans-tetradecahydrophenanthrene

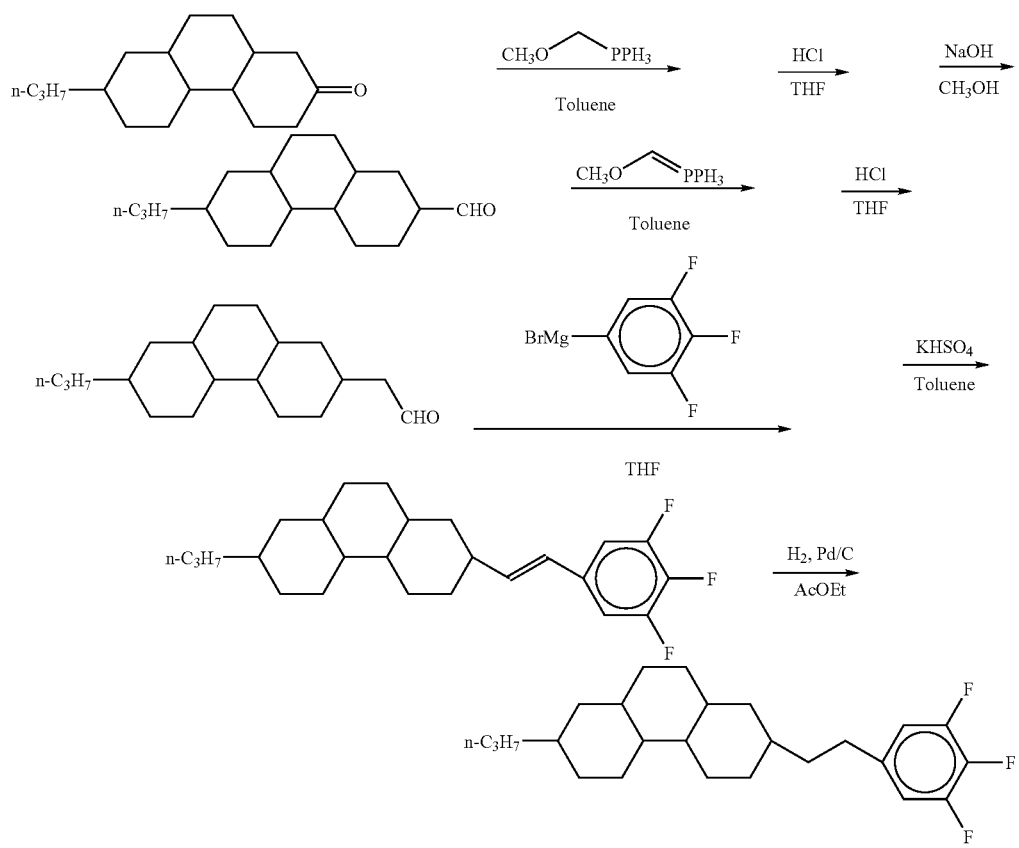

trans-2-propyl-trans-7-(3,4-difluorophenyl)-trans-tetradecahydrophenanthrene,
trans-2-propyl-trans-7-(3,5-difluorophenyl)-trans-tetradecahydrophenanthrene,
trans-2-propyl-trans-7-(4-trifluoromethoxyphenyl)-trans-tetradecahydrophenanthrene,
trans-2-propyl-trans-7-(3-fluoro-4-trifluoromethoxyphenyl)-trans-tetradecahydrophenanthrene,
trans-2-propyl-trans-7-(3,5-difluoro-4-trifluoromethoxyphenyl)-trans-tetradecahydrophenanthrene,
trans-2-propyl-trans-7-(4-difluoromethoxyphenyl)-trans-tetradecahydrophenanthrene,
trans-2-propyl-trans-7-(4-trifluoromethylphenyl)-trans-tetradecahydrophenanthrene,
trans-2-propyl-trans-7-(3-fluoro-4-trifluoromethylphenyl)-trans-tetradecahydrophenanthrene,
trans-2-propyl-trans-7-(3,5-difluoro-4-trifluoromethylphenyl)-trans-tetradecahydrophenanthrene,
trans-2-propyl-trans-7-(4-chlorophenyl)-trans-tetradecahydrophenanthrene,
trans-2-propyl-trans-7-(3-fluoro-4-chlorophenyl)-trans-tetradecahydrophenanthrene, and
trans-2-propyl-trans-7-(3,5-difluoro-4-chlorophenyl)-trans-tetradecahydrophenanthrene.

Trans-7-propyl-trans-dodecahydrophenanthren-2-one was reacted with a Wittig reagent prepared from methoxymethyltriphenylphosphonium chloride and potassium-t-butoxide, and the product enol ether was hydrolyzed using a 10% aqueous solution of hydrochloric acid in THF, and then isomerized using an aqueous solution of sodium hydroxide in methanol to yield trans-7-propyl-trans-tetradecahydrophenanthren-2-carbaldehyde. This compound was then further reacted with a Wittig reagent prepared from methoxymethyltriphenylphosphonium chloride and potassium t-butoxide, and the product enol ether was hydrolyzed using a 10% aqueous solution of hydrochloric acid in THF, to yield (trans-7-propyl-trans-tetradecahydrophenanthren-2-yl)acetoaldehyde. This compound was reacted with a Grignard reagent prepared from bromo-3,4,5-trifluorobenzene and magnesium, and a dehydration was then performed using p-toluenesulfonic acid monohydrate in toluene to yield trans-2-propyl-trans-7-[2-(3,4,5-trifluorophenyl)vinyl]-trans-tetradecahydrophenanthrene, which was subsequently reduced in the presence of a 5% palladium-carbon (wet) catalyst to yield trans-2-propyl-trans-7-[2-(3,4,5-trifluorophenyl)ethyl]-trans-tetradecahydrophenanthrene.

The compounds listed below can be produced in a similar manner.

trans-2-propyl-trans-7-[2-(4-fluorophenyl)ethyl]-trans-tetradecahydrophenanthrene,
trans-2-propyl-trans-7-[2-(3,4-difluorophenyl)ethyl]-trans-tetradecahydrophenanthrene,
trans-2-propyl-trans-7-[2-(3,5-difluorophenyl)ethyl]-trans-tetradecahydrophenanthrene,
trans-2-propyl-trans-7-[2-(4-trifluoromethoxyphenyl)ethyl]-trans-tetradecahydrophenanthrene,
trans-2-propyl-trans-7-[2-(3-fluoro-4-trifluoromethoxyphenyl)ethyl]-trans-tetradecahydrophenanthrene,
trans-2-propyl-trans-7-[2-(3,5-difluoro-4-trifluoromethoxyphenyl)ethyl]-trans-tetradecahydrophenanthrene,
trans-2-propyl-trans-7-[2-(4-difluoromethoxyphenyl)ethyl]-trans-tetradecahydrophenanthrene,
trans-2-propyl-trans-7-[2-(4-trifluoromethylphenyl)ethyl]-trans-tetradecahydrophenanthrene,
trans-2-propyl-trans-7-[2-(3-fluoro-4-trifluoromethylphenyl)ethyl]-trans-tetradecahydrophenanthrene,
trans-2-propyl-trans-7-[2-(3,5-difluoro-4-trifluoromethylphenyl)ethyl]-trans-tetradecahydrophenanthrene,
trans-2-propyl-trans-7-[2-(4-chlorophenyl)ethyl]-trans-tetradecahydrophenanthrene,
trans-2-propyl-trans-7-[2-(3-fluoro-4-chlorophenyl)ethyl]-trans-tetradecahydrophenanthrene, and
trans-2-propyl-trans-7-[2-(3,5-difluoro-4-chlorophenyl)ethyl]-trans-tetradecahydrophenanthrene.

Example 19

Synthesis of 2-fluoro-4-(trans-7-propyl-trans-tetradecahydrophenanthren-trans-2-yl)benzonitrile Trans-7-propyl-trans-dodecahydrophenanthren-2-one was reacted with a Grignard reagent prepared from 2-(4-bromo-2-fluorophenyl)-4,4-dimethyl-4,5-dihydrooxazole and magnesium, the cyano group protective group was then removed and the aromatic ring dehydrated by addition of phosphorus oxychloride, and a reduction was then performed in the presence of a Raney nickel catalyst to yield 2-fluoro-4-(trans-7-propyl-trans-tetradecahydrophenanthren-trans-2-yl)benzonitrile. Measurement of the phase transition temperature revealed a transition from the crystalline phase to an isotropic liquid phase at 173° C. under rising temperature conditions.

The compounds listed below can be produced in a similar manner.

4-(trans-7-propyl-trans-tetradecahydrophenanthrene-trans-2-yl)benzonitrile,
2-fluoro-4-(trans-7-ethyl-trans-tetradecahydrophenanthrene-trans-2-yl)benzonitrile,
4-(trans-7-ethyl-trans-tetradecahydrophenanthrene-trans-2-yl)benzonitrile,
2-fluoro-4-(trans-7-butyl-trans-tetradecahydrophenanthrene-trans-2-yl)benzonitrile,
4-(trans-7-butyl-trans-tetradecahydrophenanthrene-trans-2-yl)benzonitrile,
2-fluoro-4-(trans-7-pentyl-trans-tetradecahydrophenanthrene-trans-2-yl)benzonitrile,
4-(trans-7-pentyl-trans-tetradecahydrophenanthrene-trans-2-yl)benzonitrile,
2-fluoro-4-(trans-7-hexyl-trans-tetradecahydrophenanthrene-trans-2-yl)benzonitrile,
4-(trans-7-hexyl-trans-tetradecahydrophenanthrene-trans-2-yl)benzonitrile,
2-fluoro-4-(trans-7-heptyl-trans-tetradecahydrophenanthrene-trans-2-yl)benzonitrile, and
4-(trans-7-heptyl-trans-tetradecahydrophenanthrene-trans-2-yl)benzonitrile.

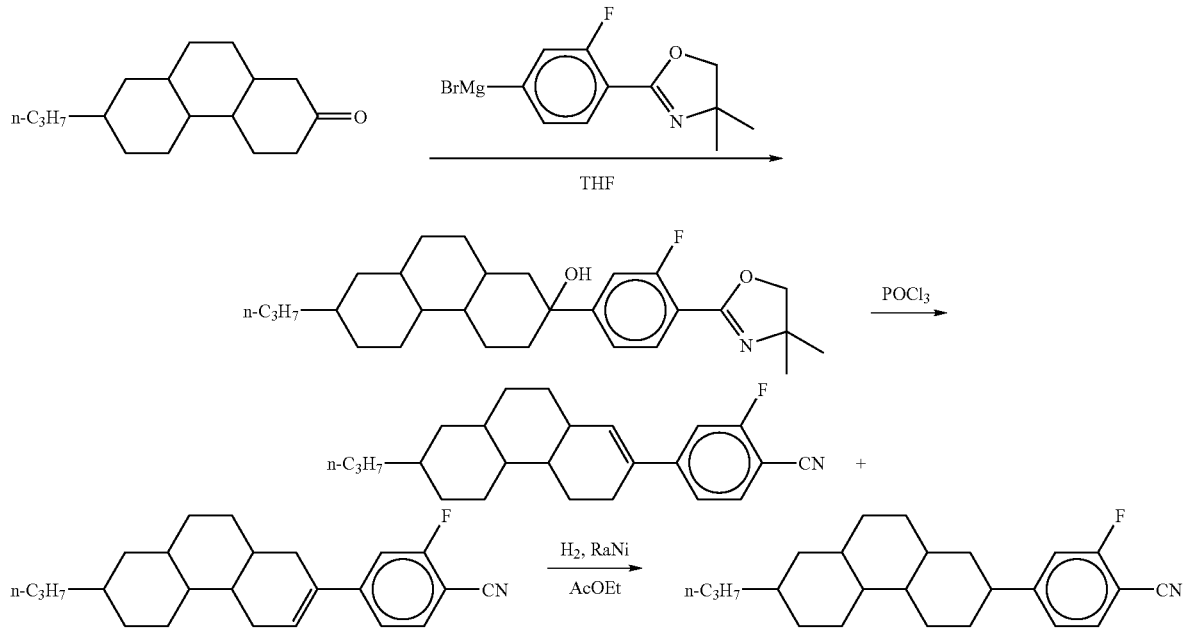

Example 20

Synthesis of 2,6-difluoro-4-(trans-7-propyl-trans-tetradecahydrophenanthren-trans-2-yl)benzonitrile

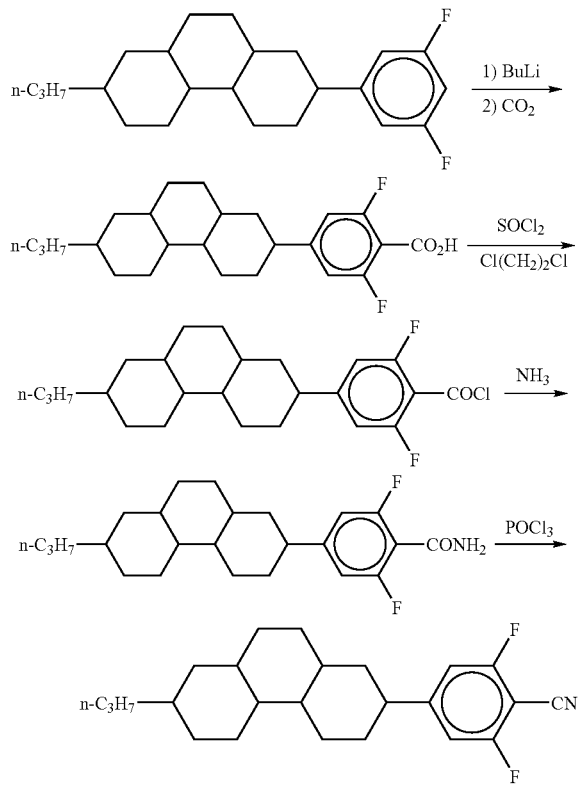

Trans-2-propyl-trans-7-(3,5-difluorophenyl)-trans-tetradecahydrophenanthrene produced using the same method as Example 1 was lithiated using a butyl lithium-hexane solution, and subsequently reacted with carbon dioxide gas to yield 2,5-difluoro-4-(trans-7-propyl-trans-tetradecahydrophenanthren-trans-2-yl)benzoic acid. This compound was converted to an acid chloride with thionyl chloride, and then reacted with ammonia to yield 2,5-difluoro-4-(trans-7-propyl-trans-tetradecahydrophenanthren-trans-2-yl)benzamide. Subsequent reaction with phosphorus oxychloride producing a dehydration yielded 2,5-difluoro-4-(trans-7-propyl-trans-tetradecahydrophenanthren-trans-2-yl) benzonitrile.

The compounds listed below can be produced in a similar manner.

2,6-difluoro-4-(trans-7-ethyl-trans-tetradecahydrophenanthrene-trans-2-yl)benzonitrile, 2,6-difluoro-4-(trans-7-butyl-trans-tetradecahydrophenanthrene-trans-2-yl)benzonitrile, 2,6-difluoro-4-(trans-7-pentyl-trans-tetradecahydrophenanthrene-trans-2-yl)benzonitrile, 2,6-difluoro-4-(trans-7-hexyl-trans-tetradecahydrophenanthrene-trans-2-yl)benzonitrile, and 2,6-difluoro-4-(trans-7-heptyl-trans-tetradecahydrophenanthrene-trans-2-yl)benzonitrile.

Example 21

Synthesis of 4-cyano-3-fluorophenyl trans-7-propyl-trans-tetradecahydrophenanthrene-2-carboxylate

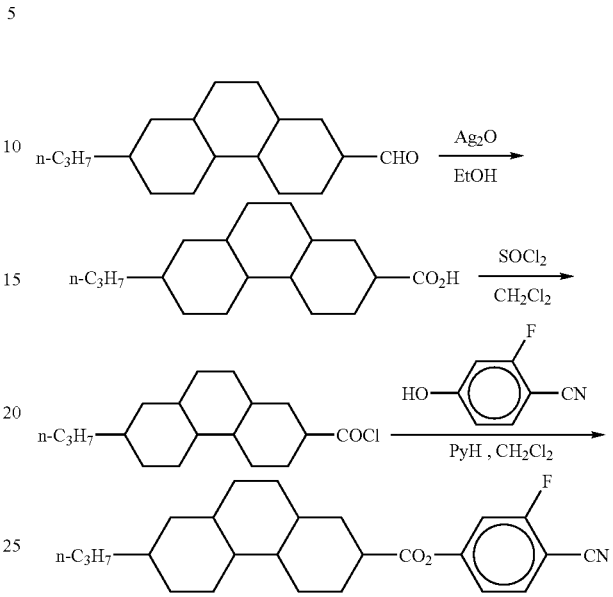

Trans-7-propyl-trans-tetradecahydrophenanthren-2-carbaldehyde produced in Example 18 was oxidized using silver oxide prepared from silver nitrate and sodium hydroxide and yielded trans-7-propyl-trans-tetradecahydrophenanthren-2-carboxylic acid. This compound was converted to an acid chloride using thionyl chloride, and then reacted with 2-fluoro-4-hydroxybenzonitrile to yield 4-cyano-3-fluorophenyl trans-7-propyl-trans-tetradecahydrophenanthrene-2-carboxylate.

The compounds listed below can be produced in a similar manner.

4-cyanophenyl trans-7-propyl-trans-tetradecahydrophenanthrene-2-carboxylate, 4-cyano-3,5-difluorophenyl trans-7-propyl-trans-tetradecahydrophenanthrene-2-carboxylate, 4-cyanophenyl trans-7-ethyl-trans-tetradecahydrophenanthrene-2-carboxylate, 4-cyano-3-fluorophenyl trans-7-ethyl-trans-tetradecahydrophenanthrene-2-carboxylate, 4-cyano-3,5-difluorophenyl trans-7-ethyl-trans-tetradecahydrophenanthrene-2-carboxylate, 4-cyanophenyl trans-7-butyl-trans-tetradecahydrophenanthrene-2-carboxylate, 4-cyano-3-fluorophenyl trans-7-butyl-trans-tetradecahydrophenanthrene-2-carboxylate, 4-cyano-3,5-difluorophenyl trans-7-butyl-trans-tetradecahydrophenanthrene-2-carboxylate, 4-cyanophenyl trans-7-pentyl-trans-tetradecahydrophenanthrene-2-carboxylate, 4-cyano-3-fluorophenyl trans-7-pentyl-trans-tetradecahydrophenanthrene-2-carboxylate, 4-cyano-3,5-difluorophenyl trans-7-pentyl-trans-tetradecahydrophenanthrene-2-carboxylate, 4-cyanophenyl trans-7-pentyl-trans-tetradecahydrophenanthrene-2-carboxylate, 4-cyano-3-fluorophenyl trans-7-pentyl-trans-tetradecahydrophenanthrene-2-carboxylate, 4-cyano-3,5-difluorophenyl trans-7-pentyl-trans-tetradecahydrophenanthrene-2-carboxylate, 4-cyanophenyl trans-7-heptyl-trans-tetradecahydrophenanthrene-2-carboxylate,
4-cyano-3-fluorophenyl trans-7-heptyl-trans-tetradecahydrophenanthrene-2-carboxylate, and
4-cyano-3,5-difluorophenyl trans-7-heptyl-trans-tetradecahydrophenanthrene-2-carboxylate.

Example 22

Synthesis of trans-2-(3,4,5-trifluorophenyl)-trans-7-vinyl-trans-tetrahydrophenanthrene bromo-3,4,5-trifluorobenzene and magnesium, and a dehydration was then performed using p-toluenesulfonic acid monohydrate in toluene to yield a mixture of trans-7-(3,4,5-trifluorophenyl)-3,4,4a,4b,5,6,8a,9,10,10a-trans-dodecahydro-1H-phenanthren-2-one ethylene acetal and trans-7-(3,4,5-trifluorophenyl)-3,4,4a,4b,5,8,8a,9,10,10a-trans-dodecahydro-1H-phenanthren-2-one ethylene acetal, which was subsequently reduced in the presence of a 5% palladium-carbon (wet) catalyst to yield trans-7-(3,4,5-trifluorophenyl)-trans-dodecahydrophenanthren-2-one ethylene acetal. Following removal of the carbonyl group pro-

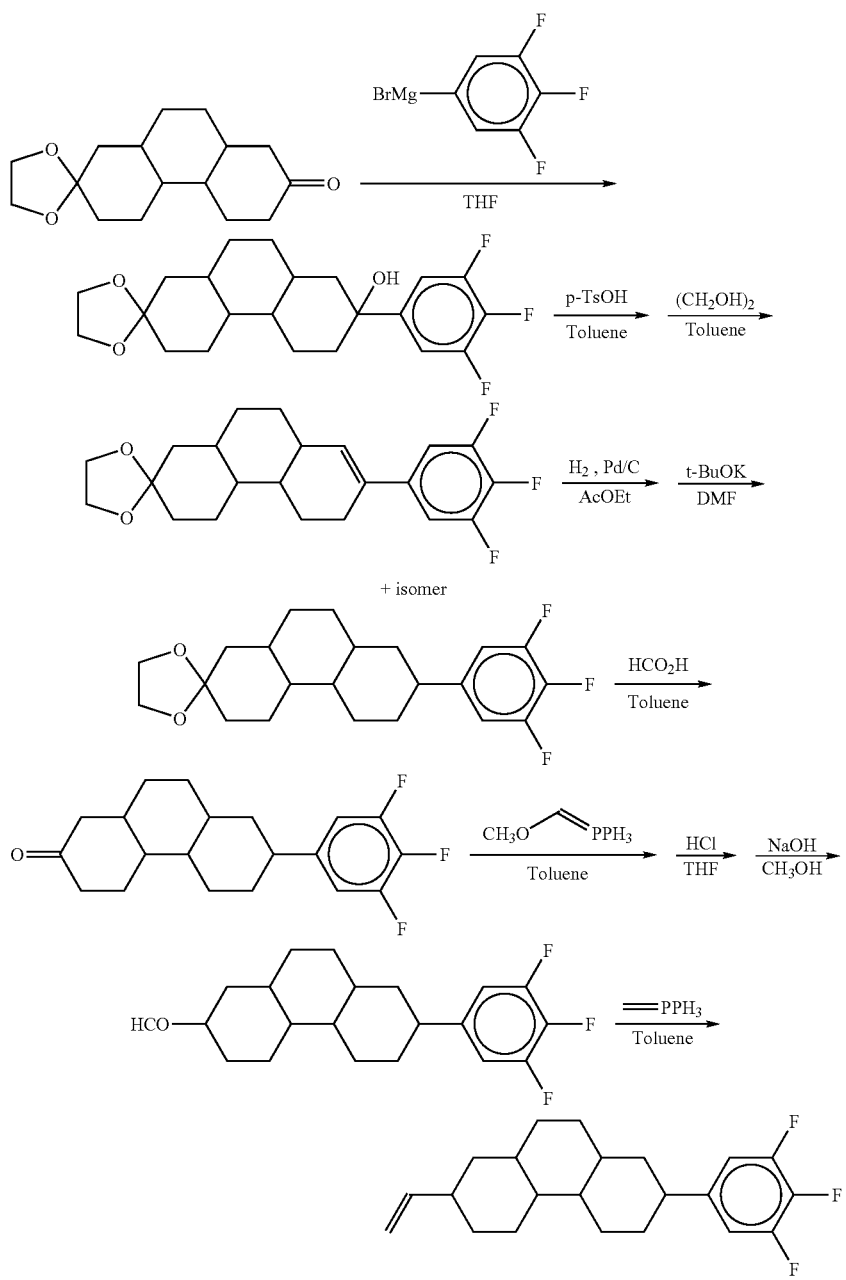

trans-dodecahydrophenanthren-2,7-dione monoethylene acetal was reacted with a Grignard reagent prepared from tective group, this compound was reacted with a Wittig reagent prepared from methoxymethyltriphenylphosphonium chloride and potassium-t-butoxide, and the product enol ether was hydrolyzed using a 10% aqueous solution of hydrochloric acid in THF, and then isomerized using an aqueous solution of sodium hydroxide in methanol to yield trans-7-(3,4,5-trifluorophenyl)-trans-tetrahydrophenanthren-trans-2-carbaldehyde. This compound was then reacted with a Wittig reagent prepared from methyltriphenylphosphonium bromide and potassium t-butoxide to yield trans-2-(3,4,5-trifluorophenyl)-trans-7-vinyl-trans-tetrahydrophenanthrene.

The compounds listed below can be produced by reacting trans-7-(3,4,5-trifluorophenyl)-trans-tetrahydrophenanthren-trans-2-carbaldehyde with a variety of Wittig reagents.

trans-2-(4-fluorophenyl)-trans-7-vinyl-trans-tetrahydrophenanthrene,
trans-2-(3,4-difluorophenyl)-trans-7-vinyl-trans-tetrahydrophenanthrene,
trans-2-(3,5-difluorophenyl)-trans-7-vinyl-trans-tetrahydrophenanthrene,
trans-2-(4-trifluoromethoxyphenyl)-trans-7-vinyl-trans-tetrahydrophenanthrene,
trans-2-(3-fluoro-4-trifluoromethoxyphenyl)-trans-7-vinyl-trans-tetrahydrophenanthrene,
trans-2-(3,5-difluoro-4-trifluoromethoxyphenyl)-trans-7-vinyl-trans-tetrahydrophenanthrene,
trans-2-(4-difluoromethoxyphenyl)-trans-7-vinyl-trans-tetrahydrophenanthrene,
trans-2-(4-trifluoromethylphenyl)-trans-7-vinyl-trans-tetrahydrophenanthrene,
trans-2-(3-fluoro-4-trifluoromethylphenyl)-trans-7-vinyl-trans-tetrahydrophenanthrene,
trans-2-(3,5-difluoro-4-trifluoromethylphenyl)-trans-7-vinyl-trans-tetrahydrophenanthrene,
trans-2-(4-chlorophenyl)-trans-7-vinyl-trans-tetrahydrophenanthrene,
trans-2-(3-fluoro-4-chlorophenyl)-trans-7-vinyl-trans-tetrahydrophenanthrene,
trans-2-(3,5-difluoro-4-chlorophenyl)-trans-7-vinyl-trans-tetrahydrophenanthrene,
trans-2-(trans-1-propenyl)-trans-7-(4-fluorophenyl)-trans-tetradecahydrophenanthrene,
trans-2-(trans-1-propenyl)-trans-7-(3,4-difluorophenyl)-trans-tetradecahydrophenanthrene,
trans-2-(trans-1-propenyl)-trans-7-(3,5-difluorophenyl)-trans-tetradecahydrophenanthrene,
trans-2-(trans-1-propenyl)-trans-7-(3,4,5-trifluorophenyl)-trans-tetradecahydrophenanthrene,
trans-2-(trans-1-propenyl)-trans-7-(4-trifluoromethoxyphenyl)-trans-tetradecahydrophenanthrene,
trans-2-(trans-1-propenyl)-trans-7-(3-fluoro-4-trifluoromethoxyphenyl)-trans-tetradecahydrophenanthrene,
trans-2-(trans-1-propenyl)-trans-7-(3,5-difluoro-4-trifluoromethoxyphenyl)-trans-tetradecahydrophenanthrene,
trans-2-(trans-1-propenyl)-trans-7-(4-difluoromethoxyphenyl)-trans-tetradecahydrophenanthrene,
trans-2-(trans-1-propenyl)-trans-7-(4-trifluoromethylphenyl)-trans-tetradecahydrophenanthrene,
trans-2-(trans-1-propenyl)-trans-7-(3-fluoro-4-trifluoromethylphenyl)-trans-tetradecahydrophenanthrene,
trans-2-(trans-1-propenyl)-trans-7-(3,5-difluoro-4-trifluoromethylphenyl)-trans-tetradecahydrophenanthrene,
trans-2-(trans-1-propenyl)-trans-7-(4-chlorophenyl)-trans-tetradecahydrophenanthrene,
trans-2-(trans-1-propenyl)-trans-7-(3-fluoro-4-chlorophenyl)-trans-tetradecahydrophenanthrene,
trans-2-(trans-1-propenyl)-trans-7-(3,5-difluoro-4-chlorophenyl)-trans-tetradecahydrophenanthrene,
trans-2-(trans-1-butenyl)-trans-7-(4-fluorophenyl)-trans-tetradecahydrophenanthrene,
trans-2-(trans-1-butenyl)-trans-7-(3,4-difluorophenyl)-trans-tetradecahydrophenanthrene,
trans-2-(trans-1-butenyl)-trans-7-(3,5-difluorophenyl)-trans-tetradecahydrophenanthrene,
trans-2-(trans-1-butenyl)-trans-7-(3,4,5-trifluorophenyl)-trans-tetradecahydrophenanthrene,
trans-2-(trans-1-butenyl)-trans-7-(4-trifluoromethoxyphenyl)-trans-tetradecahydrophenanthrene,
trans-2-(trans-1-butenyl)-trans-7-(3-fluoro-4-trifluoromethoxyphenyl)-trans-tetradecahydrophenanthrene,
trans-2-(trans-1-butenyl)-trans-7-(3,5-difluoro-4-trifluoromethoxyphenyl)-trans-tetradecahydrophenanthrene,
trans-2-(trans-1-butenyl)-trans-7-(4-difluoromethoxyphenyl)-trans-tetradecahydrophenanthrene,
trans-2-(trans-1-butenyl)-trans-7-(4-trifluoromethylphenyl)-trans-tetradecahydrophenanthrene,
trans-2-(trans-1-butenyl)-trans-7-(3-fluoro-4-trifluoromethylphenyl)-trans-tetradecahydrophenanthrene,
trans-2-(trans-1-butenyl)-trans-7-(3,5-difluoro-4-trifluoromethylphenyl)-trans-tetradecahydrophenanthrene,
trans-2-(trans-1-butenyl)-trans-7-(4-chlorophenyl)-trans-tetradecahydrophenanthrene,
trans-2-(trans-1-butenyl)-trans-7-(3-fluoro-4-chlorophenyl)-trans-tetradecahydrophenanthrene,
trans-2-(trans-1-butenyl)-trans-7-(3,5-difluoro-4-chlorophenyl)-trans-tetradecahydrophenanthrene,
trans-2-(trans-1-pentenyl)-trans-7-(4-fluorophenyl)-trans-tetradecahydrophenanthrene,
trans-2-(trans-1-pentenyl)-trans-7-(3,4-difluorophenyl)-trans-tetradecahydrophenanthrene,
trans-2-(trans-1-pentenyl)-trans-7-(3,5-difluorophenyl)-trans-tetradecahydrophenanthrene,
trans-2-(trans-1-pentenyl)-trans-7-(3,4,5-trifluorophenyl)-trans-tetradecahydrophenanthrene,
trans-2-(trans-1-pentenyl)-trans-7-(4-trifluoromethoxyphenyl)-trans-tetradecahydrophenanthrene,
trans-2-(trans-1-pentenyl)-trans-7-(3-fluoro-4-trifluoromethoxyphenyl)-trans-tetradecahydrophenanthrene,
trans-2-(trans-1-pentenyl)-trans-7-(3,5-difluoro-4-trifluoromethoxyphenyl)-trans-tetradecahydrophenanthrene,
trans-2-(trans-1-pentenyl)-trans-7-(4-difluoromethoxyphenyl)-trans-tetradecahydrophenanthrene,
trans-2-(trans-1-pentenyl)-trans-7-(4-trifluoromethylphenyl)-trans-tetradecahydrophenanthrene,
trans-2-(trans-1-pentenyl)-trans-7-(3-fluoro-4-trifluoromethylphenyl)-trans-tetradecahydrophenanthrene,
trans-2-(trans-1-pentenyl)-trans-7-(3,5-difluoro-4-trifluoromethylphenyl)-trans-tetradecahydrophenanthrene,
trans-2-(trans-1-pentenyl)-trans-7-(4-chlorophenyl)-trans-tetradecahydrophenanthrene,
trans-2-(trans-1-pentenyl)-trans-7-(3-fluoro-4-chlorophenyl)-trans-tetradecahydrophenanthrene,
trans-2-(trans-1-pentenyl)-trans-7-(3,5-difluoro-4-chlorophenyl)-trans-tetradecahydrophenanthrene,
trans-2-(trans-3-pentenyl)-trans-7-(4-fluorophenyl)-trans-tetradecahydrophenanthrene,
trans-2-(trans-3-pentenyl)-trans-7-(3,4-difluorophenyl)-trans-tetradecahydrophenanthrene,
trans-2-(trans-3-pentenyl)-trans-7-(3,5-difluorophenyl)-trans-tetradecahydrophenanthrene,
trans-2-(trans-3-pentenyl)-trans-7-(3,4,5-trifluorophenyl)-trans-tetradecahydrophenanthrene,
trans-2-(trans-3-pentenyl)-trans-7-(4-trifluoromethoxyphenyl)-trans-tetradecahydrophenanthrene, trans-2-(trans-3-pentenyl)-trans-7-(3-fluoro-4-trifluoromethoxyphenyl)-trans-tetradecahydrophenanthrene,
trans-2-(trans-3-pentenyl)-trans-7-(3,5-difluoro-4-trifluoromethoxyphenyl)-trans-tetradecahydrophenanthrene,
trans-2-(trans-3-pentenyl)-trans-7-(4-difluoromethoxyphenyl)-trans-tetradecahydrophenanthrene,
trans-2-(trans-3-pentenyl)-trans-7-(4-trifluoromethylphenyl)-trans-tetradecahydrophenanthrene,
trans-2-(trans-3-pentenyl)-trans-7-(3-fluoro-4-trifluoromethylphenyl)-trans-tetradecahydrophenanthrene,
trans-2-(trans-3-pentenyl)-trans-7-(3,5-difluoro-4-trifluoromethylphenyl)-trans-tetradecahydrophenanthrene,
trans-2-(trans-3-pentenyl)-trans-7-(4-chlorophenyl)-trans-tetradecahydrophenanthrene,
trans-2-(trans-3-pentenyl)-trans-7-(3-fluoro-4-chlorophenyl)-trans-tetradecahydrophenanthrene,
trans-2-(trans-3-pentenyl)-trans-7-(3,5-difluoro-4-chlorophenyl)-trans-tetradecahydrophenanthrene,
trans-2-(3-butenyl)-trans-7-(4-fluorophenyl)-trans-tetradecahydrophenanthrene,
trans-2-(3-butenyl)-trans-7-(3,4-difluorophenyl)-trans-tetradecahydrophenanthrene,
trans-2-(3-butenyl)-trans-7-(3,5-difluorophenyl)-trans-tetradecahydrophenanthrene,
trans-2-(3-butenyl)-trans-7-(3,4,5-trifluorophenyl)-trans-tetradecahydrophenanthrene,
trans-2-(3-butenyl)-trans-7-(4-trifluoromethoxyphenyl)-trans-tetradecahydrophenanthrene,
trans-2-(3-butenyl)-trans-7-(3-fluoro-4-trifluoromethoxyphenyl)-trans-tetradecahydrophenanthrene,
trans-2-(3-butenyl)-trans-7-(3,5-difluoro-4-trifluoromethoxyphenyl)-trans-tetradecahydrophenanthrene,
trans-2-(3-butenyl)-trans-7-(4-difluoromethoxyphenyl)-trans-tetradecahydrophenanthrene,
trans-2-(3-butenyl)-trans-7-(4-trifluoromethylphenyl)-trans-tetradecahydrophenanthrene,
trans-2-(3-butenyl)-trans-7-(3-fluoro-4-trifluoromethylphenyl)-trans-tetradecahydrophenanthrene,
trans-2-(3-butenyl)-trans-7-(3,5-difluoro-4-trifluoromethylphenyl)-trans-tetradecahydrophenanthrene,
trans-2-(3-butenyl)-trans-7-(4-chlorophenyl)-trans-tetradecahydrophenanthrene,
trans-2-(3-butenyl)-trans-7-(3-fluoro-4-chlorophenyl)-trans-tetradecahydrophenanthrene, and
trans-2-(3-butenyl)-trans-7-(3,5-difluoro-4-chlorophenyl)-trans-tetradecahydrophenanthrene.

Example 23

Synthesis of trans-2-propyl-7-(3,4,5-trifluorophenyl)-trans-1,2,3,4,4a,9,10,10a-octahydrophenanthrene

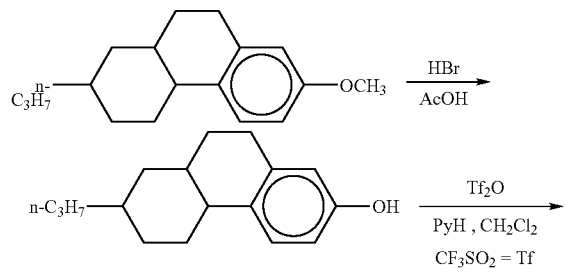

-continued

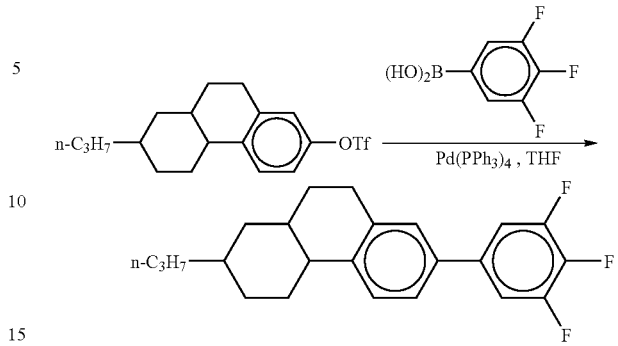

A mixture of 20 g of 7-methoxy-trans-2-propyl-trans-1,2,3,4,4a,9,10,10a-octahydrophenanthrene (synthesis of this compound was carried out using the method disclosed in D. Varech, L. Lacombe and J. Lacques, Nouv. J. Chim., 8, 445 (1984)), 80 mL of acetic acid and 80 mL of 40% hydrobromic acid was refluxed for 10 hours, and yielded 19.1 g of trans-7-propyl-trans-4b,5,6,7,8,8a,9,10-octahydrophenanthren-2-ol. The thus obtained crude product was dissolved in 100 mL of methylene chloride, a suspension was then formed by adding 15.8 mL of trifluoromethanesulfonic anhydride, and the suspension was then cooled to 5° C. With the mixture being stirred vigorously, 15 mL of pyridine was then added dropwise and the mixture stirred for a further one hour. 100 mL of water was then added, the reaction halted, and the organic layer was separated. The aqueous layer was extracted with 80 mL of dichloromethane and this extract was combined with the organic layer, which was subsequently washed with dilute hydrochloric acid, a saturated aqueous solution of sodium bicarbonate, water, and then a saturated aqueous solution of sodium chloride before being dried over anhydrous sodium sulfate. The solvent was removed by evaporation, and the product purified by silica gel column chromatography (hexane) to yield 24.5 g of trans-7-propyl-trans-4b,5,6,7,8,8a,9,10-octahydrophenanthren-2-yl trifluoromethanesulfonate. This compound was combined with 13.2 g of 3,4,5-trifluorophenylboric acid (which was produced by a reaction between a Grignard reagent prepared from 3,4,5-trifluorobromobenzene and magnesium, and trimethylborate, followed by hydrolysis with dilute hydrochloric acid), 1.5 g of tetrakis(triphenylphosphine)palladium (0) and 21.2 g of potassium phosphate in 120 mL of dimethylformamide solvent, and the reaction mixture was then stirred for 10 hours at 80° C. The reaction mixture was then cooled to room temperature, water was added, the mixture was extracted with toluene, and the resulting organic layer was washed sequentially with water and a saturated aqueous solution of sodium chloride, and then dried over anhydrous sodium sulfate. The crude product obtained by removal of the solvent by evaporation was purified by silica gel column chromatography (hexane) and then recrystallized 3 times from ethanol to yield 6.3 g of trans-2-propyl-7-(3,4,5-trifluorophenyl)-trans-1,2,3,4,4a,9,10,10a-octahydrophenanthrene.

NMR: δ=0.86 to 0.89 (m, 5H), δ=1.11 to 1.35 (m, 15H), δ=1.74 to 1.86 (m, 8H), δ=2.37 (m, 1H), δ=6.79 (dd, 2H, J=6.4 Hz, J=9.2 Hz)

MS: m/e=358 (M+)

The compounds listed below can be produced in a similar manner.

trans-2-propyl-trans-7-(4-fluorophenyl)-trans-1,2,3,4,4a,9,10,10a-octahydrophenanthrene,
trans-2-propyl-trans-7-(3,4-difluorophenyl)-trans-1,2,3,4,4a,9,10,10a-octahydrophenanthrene,
trans-2-propyl-trans-7-(3,5-difluorophenyl)-trans-1,2,3,4,4a,9,10,10a-octahydrophenanthrene,
trans-2-propyl-trans-7-(4-trifluoromethoxyphenyl)-trans-1,2,3,4,4a,9,10,10a-octahydrophenanthrene,
trans-2-propyl-trans-7-(3-fluoro-4-trifluoromethoxyphenyl)-trans-1,2,3,4,4a,9,10,10a-octahydrophenanthrene,
trans-2-propyl-trans-7-(3,5-difluoro-4-trifluoromethoxyphenyl)-trans-1,2,3,4,4a,9,10,10a-octahydrophenanthrene,
trans-2-propyl-trans-7-(4-difluoromethoxyphenyl)-trans-1,2,3,4,4a,9,10,10a-octahydrophenanthrene,
trans-2-propyl-trans-7-(4-trifluoromethylphenyl)-trans-1,2,3,4,4a,9,10,10a-octahydrophenanthrene,
trans-2-propyl-trans-7-(3-fluoro-4-trifluoromethylphenyl)-trans-1,2,3,4,4a,9,10,10a-octahydrophenanthrene,
trans-2-propyl-trans-7-(3,5-difluoro-4-trifluoromethylphenyl)-trans-1,2,3,4,4a,9,10,10a-octahydrophenanthrene,
trans-2-propyl-trans-7-(4-chlorophenyl)-trans-1,2,3,4,4a,9,10,10a-octahydrophenanthrene,
trans-2-propyl-trans-7-(3-fluoro-4-chlorophenyl)-trans-1,2,3,4,4a,9,10,10a-octahydrophenanthrene, and
trans-2-propyl-trans-7-(3,5-difluoro-4-chlorophenyl)-trans-1,2,3,4,4a,9,10,10a-octahydrophenanthrene.

Example 24

Synthesis of trans-2-propyl-7-(3,4-difluorophenylethynyl)-trans-1,2,3,4,4a,9,10,10a-octahydrophenanthrene

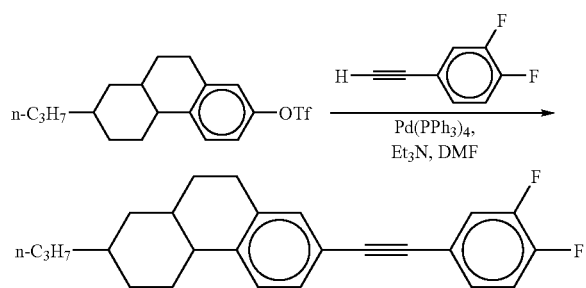

Trans-7-propyl-trans-4b,5,6,7,8,8a,9,10-octahydrophenanthren-2-yl in dimethylformamide and triethylamine was reacted with 4-ethynyl-1,2-difluorobenzene in the presence of tetrakis(triphenylphosphine)palladium (0), and the product was purified by silica gel column chromatography (hexane) and then recrystallized from ethanol to yield trans-2-propyl-7-(3,4-difluorophenylethynyl)-trans-1,2,3,4,4a,9,10,10a-octahydrophenanthrene.

The compounds listed below can be produced in a similar manner.
trans-2-propyl-trans-7-(4-fluorophenylethynyl)-trans-1,2,3,4,4a,9,10,10a-octahydrophenanthrene,
trans-2-propyl-trans-7-(3,4-difluorophenylethynyl)-trans-1,2,3,4,4a,9,10,10a-octahydrophenanthrene,
trans-2-propyl-trans-7-(3,5-difluorophenylethynyl)-trans-1,2,3,4,4a,9,10,10a-octahydrophenanthrene,
trans-2-propyl-trans-7-(4-trifluoromethoxyphenylethynyl)-trans-1,2,3,4,4a,9,10,10a-octahydrophenanthrene,
trans-2-propyl-trans-7-(3-fluoro-4-trifluoromethoxyphenylethynyl)-trans-1,2,3,4,4a,9,10,10a-octahydrophenanthrene,
trans-2-propyl-trans-7-(3,5-difluoro-4-trifluoromethoxyphenylethynyl)-trans-1,2,3,4,4a,9,10,10a-octahydrophenanthrene,
trans-2-propyl-trans-7-(4-difluoromethoxyphenylethynyl)-trans-1,2,3,4,4a,9,10,10a-octahydrophenanthrene,
trans-2-propyl-trans-7-(4-trifluoromethylphenylethynyl)-trans-1,2,3,4,4a,9,10,10a-octahydrophenanthrene,
trans-2-propyl-trans-7-(3-fluoro-4-trifluoromethylphenylethynyl)-trans-1,2,3,4,4a,9,10,10a-octahydrophenanthrene,
trans-2-propyl-trans-7-(3,5-difluoro-4-trifluoromethylphenylethynyl)-trans-1,2,3,4,4a,9,10,10a-octahydrophenanthrene,
trans-2-propyl-trans-7-(4-chlorophenylethynyl)-trans-1,2,3,4,4a,9,10,10a-octahydrophenanthrene,
trans-2-propyl-trans-7-(3-fluoro-4-chlorophenylethynyl)-trans-1,2,3,4,4a,9,10,10a-octahydrophenanthrene,
trans-2-propyl-trans-7-(3,5-difluoro-4-chlorophenylethynyl)-trans-1,2,3,4,4a,9,10,10a-octahydrophenanthrene,
trans-2-ethyl-trans-7-(4-fluorophenylethynyl)-trans-1,2,3,4,4a,9,10,10a-octahydrophenanthrene,
trans-2-ethyl-trans-7-(3,4-difluorophenylethynyl)-trans-1,2,3,4,4a,9,10,10a-octahydrophenanthrene,
trans-2-ethyl-trans-7-(3,5-difluorophenylethynyl)-trans-1,2,3,4,4a,9,10,10a-octahydrophenanthrene,
trans-2-ethyl-trans-7-(3,4,5-trifluorophenylethynyl)-trans-1,2,3,4,4a,9,10,10a-octahydrophenanthrene,
trans-2-ethyl-trans-7-(4-trifluoromethoxyphenylethynyl)-trans-1,2,3,4,4a,9,10,10a-octahydrophenanthrene,
trans-2-ethyl-trans-7-(3-fluoro-4-trifluoromethoxyphenylethynyl)-trans-1,2,3,4,4a,9,10,10a-octahydrophenanthrene,
trans-2-ethyl-trans-7-(3,5-difluoro-4-trifluoromethoxyphenylethynyl)-trans-1,2,3,4,4a,9,10,10a-octahydrophenanthrene,
trans-2-ethyl-trans-7-(4-difluoromethoxyphenylethynyl)-trans-1,2,3,4,4a,9,10,10a-octahydrophenanthrene,
trans-2-ethyl-trans-7-(4-trifluoromethylphenylethynyl)-trans-1,2,3,4,4a,9,10,10a-octahydrophenanthrene,
trans-2-ethyl-trans-7-(3-fluoro-4-trifluoromethylphenylethynyl)-trans-1,2,3,4,4a,9,10,10a-octahydrophenanthrene,
trans-2-ethyl-trans-7-(3,5-difluoro-4-trifluoromethylphenylethynyl)-trans-1,2,3,4,4a,9,10,10a-octahydrophenanthrene,
trans-2-ethyl-trans-7-(4-chlorophenylethynyl)-trans-1,2,3,4,4a,9,10,10a-octahydrophenanthrene,
trans-2-ethyl-trans-7-(3-fluoro-4-chlorophenylethynyl)-trans-1,2,3,4,4a,9,10,10a-octahydrophenanthrene,
trans-2-ethyl-trans-7-(3,5-difluoro-4-chlorophenylethynyl)-trans-1,2,3,4,4a,9,10,10a-octahydrophenanthrene,
trans-2-butyl-trans-7-(4-fluorophenylethynyl)-trans-1,2,3,4,4a,9,10,10a-octahydrophenanthrene,
trans-2-butyl-trans-7-(3,4-difluorophenylethynyl)-trans-1,2,3,4,4a,9,10,10a-octahydrophenanthrene,
trans-2-butyl-trans-7-(3,5-difluorophenylethynyl)-trans-1,2,3,4,4a,9,10,10a-octahydrophenanthrene,
trans-2-butyl-trans-7-(3,4,5-trifluorophenylethynyl)-trans-1,2,3,4,4a,9,10,10a-octahydrophenanthrene,
trans-2-butyl-trans-7-(4-trifluoromethoxyphenylethynyl)-trans-1,2,3,4,4a,9,10,10a-octahydrophenanthrene,
trans-2-butyl-trans-7-(3-fluoro-4-trifluoromethoxyphenylethynyl)-trans-1,2,3,4,4a,9,10,10a-octahydrophenanthrene, trans-2-butyl-trans-7-(3,5-difluoro-4-trifluoromethoxyphenylethynyl)-trans-1,2,3,4,4a,9,10,10a-octahydrophenanthrene,
trans-2-butyl-trans-7-(4-difluoromethoxyphenylethynyl)-trans-1,2,3,4,4a,9,10,10a-octahydrophenanthrene,
trans-2-butyl-trans-7-(4-trifluoromethylphenylethynyl)-trans-1,2,3,4,4a,9,10,10a-octahydrophenanthrene,
trans-2-butyl-trans-7-(3-fluoro-4-trifluoromethylphenylethynyl)-trans-1,2,3,4,4a,9,10,10a-octahydrophenanthrene,
trans-2-butyl-trans-7-(3,5-difluoro-4-trifluoromethylphenylethynyl)-trans-1,2,3,4,4a,9,10,10a-octahydrophenanthrene,
trans-2-butyl-trans-7-(4-chlorophenylethynyl)-trans-1,2,3,4,4a,9,10,10a-octahydrophenanthrene,
trans-2-butyl-trans-7-(3-fluoro-4-chlorophenylethynyl)-trans-1,2,3,4,4a,9,10,10a-octahydrophenanthrene,
trans-2-butyl-trans-7-(3,5-difluoro-4-chlorophenylethynyl)-trans-1,2,3,4,4a,9,10,10a-octahydrophenanthrene,
trans-2-pentyl-trans-7-(4-fluorophenylethynyl)-trans-1,2,3,4,4a,9,10,10a-octahydrophenanthrene,
trans-2-pentyl-trans-7-(3,4-difluorophenylethynyl)-trans-1,2,3,4,4a,9,10,10a-octahydrophenanthrene,
trans-2-pentyl-trans-7-(3,5-difluorophenylethynyl)-trans-1,2,3,4,4a,9,10,10a-octahydrophenanthrene,
trans-2-pentyl-trans-7-(3,4,5-trifluorophenylethynyl)-trans-1,2,3,4,4a,9,10,10a-octahydrophenanthrene,
trans-2-pentyl-trans-7-(4-trifluoromethoxyphenylethynyl)-trans-1,2,3,4,4a,9,10,10a-octahydrophenanthrene,
trans-2-pentyl-trans-7-(3-fluoro-4-trifluoromethoxyphenylethynyl)-trans-1,2,3,4,4a,9,10,10a-octahydrophenanthrene,
trans-2-pentyl-trans-7-(3,5-difluoro-4-trifluoromethoxyphenylethynyl)-trans-1,2,3,4,4a,9,10,10a-octahydrophenanthrene,
trans-2-pentyl-trans-7-(4-difluoromethoxyphenylethynyl)-trans-1,2,3,4,4a,9,10,10a-octahydrophenanthrene,
trans-2-pentyl-trans-7-(4-trifluoromethylphenylethynyl)-trans-1,2,3,4,4a,9,10,10a-octahydrophenanthrene,
trans-2-pentyl-trans-7-(3-fluoro-4-trifluoromethylphenylethynyl)-trans-1,2,3,4,4a,9,10,10a-octahydrophenanthrene,
trans-2-pentyl-trans-7-(3,5-difluoro-4-trifluoromethylphenylethynyl)-trans-1,2,3,4,4a,9,10,10a-octahydrophenanthrene,
trans-2-pentyl-trans-7-(4-chlorophenylethynyl)-trans-1,2,3,4,4a,9,10,10a-octahydrophenanthrene,
trans-2-pentyl-trans-7-(3-fluoro-4-chlorophenylethynyl)-trans-1,2,3,4,4a,9,10,10a-octahydrophenanthrene,
trans-2-pentyl-trans-7-(3,5-difluoro-4-chlorophenylethynyl)-trans-1,2,3,4,4a,9,10,10a-octahydrophenanthrene,
trans-2-hexyl-trans-7-(4-fluorophenylethynyl)-trans-1,2,3,4,4a,9,10,10a-octahydrophenanthrene,
trans-2-hexyl-trans-7-(3,4-difluorophenylethynyl)-trans-1,2,3,4,4a,9,10,10a-octahydrophenanthrene,
trans-2-hexyl-trans-7-(3,5-difluorophenylethynyl)-trans-1,2,3,4,4a,9,10,10a-octahydrophenanthrene,
trans-2-hexyl-trans-7-(3,4,5-trifluorophenylethynyl)-trans-1,2,3,4,4a,9,10,10a-octahydrophenanthrene,
trans-2-hexyl-trans-7-(4-trifluoromethoxyphenylethynyl)-trans-1,2,3,4,4a,9,10,10a-octahydrophenanthrene,
trans-2-hexyl-trans-7-(3-fluoro-4-trifluoromethoxyphenylethynyl)-trans-1,2,3,4,4a,9,10,10a-octahydrophenanthrene,
trans-2-hexyl-trans-7-(3,5-difluoro-4-trifluoromethoxyphenylethynyl)-trans-1,2,3,4,4a,9,10,10a-octahydrophenanthrene,
trans-2-hexyl-trans-7-(4-difluoromethoxyphenylethynyl)-trans-1,2,3,4,4a,9,10,10a-octahydrophenanthrene,
trans-2-hexyl-trans-7-(4-trifluoromethylphenylethynyl)-trans-1,2,3,4,4a,9,10,10a-octahydrophenanthrene,
trans-2-hexyl-trans-7-(3-fluoro-4-trifluoromethylphenylethynyl)-trans-1,2,3,4,4a,9,10,10a-octahydrophenanthrene,
trans-2-hexyl-trans-7-(3,5-difluoro-4-trifluoromethylphenylethynyl)-trans-1,2,3,4,4a,9,10,10a-octahydrophenanthrene,
trans-2-hexyl-trans-7-(4-chlorophenylethynyl)-trans-1,2,3,4,4a,9,10,10a-octahydrophenanthrene,
trans-2-hexyl-trans-7-(3-fluoro-4-chlorophenylethynyl)-trans-1,2,3,4,4a,9,10,10a-octahydrophenanthrene,
trans-2-hexyl-trans-7-(3,5-difluoro-4-chlorophenylethynyl)-trans-1,2,3,4,4a,9,10,10a-octahydrophenanthrene,
trans-2-heptyl-trans-7-(4-fluorophenylethynyl)-trans-1,2,3,4,4a,9,10,10a-octahydrophenanthrene,
trans-2-heptyl-trans-7-(3,4-difluorophenylethynyl)-trans-1,2,3,4,4a,9,10,10a-octahydrophenanthrene,
trans-2-heptyl-trans-7-(3,5-difluorophenylethynyl)-trans-1,2,3,4,4a,9,10,10a-octahydrophenanthrene,
trans-2-heptyl-trans-7-(3,4,5-trifluorophenylethynyl)-trans-1,2,3,4,4a,9,10,10a-octahydrophenanthrene,
trans-2-heptyl-trans-7-(4-trifluoromethoxyphenylethynyl)-trans-1,2,3,4,4a,9,10,10a-octahydrophenanthrene,
trans-2-heptyl-trans-7-(3-fluoro-4-trifluoromethoxyphenylethynyl)-trans-1,2,3,4,4a,9,10,10a-octahydrophenanthrene,
trans-2-heptyl-trans-7-(3,5-difluoro-4-trifluoromethoxyphenylethynyl)-trans-1,2,3,4,4a,9,10,10a-octahydrophenanthrene,
trans-2-heptyl-trans-7-(4-difluoromethoxyphenylethynyl)-trans-1,2,3,4,4a,9,10,10a-octahydrophenanthrene,
trans-2-heptyl-trans-7-(4-trifluoromethylphenylethynyl)-trans-1,2,3,4,4a,9,10,10a-octahydrophenanthrene,
trans-2-heptyl-trans-7-(3-fluoro-4-trifluoromethylphenylethynyl)-trans-1,2,3,4,4a,9,10,10a-octahydrophenanthrene,
trans-2-heptyl-trans-7-(3,5-difluoro-4-trifluoromethylphenylethynyl)-trans-1,2,3,4,4a,9,10,10a-octahydrophenanthrene,
trans-2-heptyl-trans-7-(4-chlorophenylethynyl)-trans-1,2,3,4,4a,9,10,10a-octahydrophenanthrene,
trans-2-heptyl-trans-7-(3-fluoro-4-chlorophenylethynyl)-trans-1,2,3,4,4a,9,10,10a-octahydrophenanthrene, and
trans-2-heptyl-trans-7-(3,5-difluoro-4-chlorophenylethynyl)-trans-1,2,3,4,4a,9,10,10a-octahydrophenanthrene.

Example 25

Synthesis of 8-fluoro-trans-2-propyl-7-(3,4,5-trifluorophenyl)-trans-1,2,3,4,4a,9,10,10a-octahydrophenanthrene and 6-fluoro-trans-2-propyl-7-(3,4,5-trifluorophenyl)-trans-1,2,3,4,4a,9,10,10a-octahydrophenanthrene

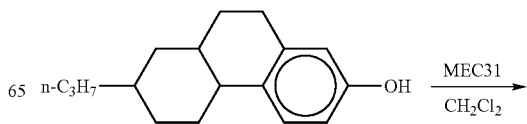

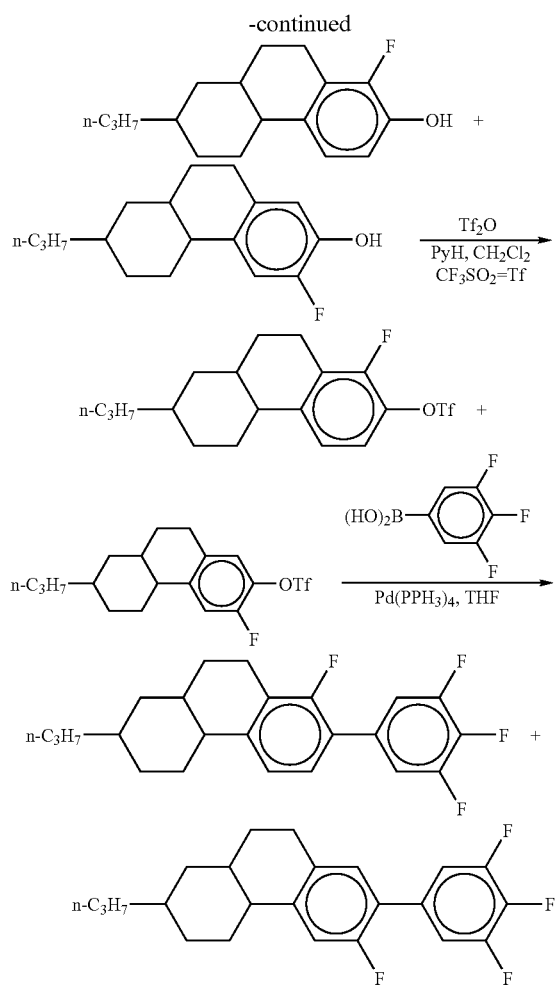

Trans-7-propyl-trans-4b,5,6,7,8,8a,9,10-octahydrophenanthren-2-ol obtained from Example 23 was dissolved in methylene chloride, and N,N'-difluoro-2,2'-bipyridinium bistetrafluoroborate (MEC-31) was added gradually, and following completion of the addition the mixture was stirred for 5 hours at room temperature. Water and a 10% aqueous solution of sodium hydroxide were then added, any residual fluorination agent was decomposed, and following the addition of sufficient dilute hydrochloric acid to return the reaction mixture to an acidic state, the organic layer was separated. The aqueous layer was extracted with dichloromethane and this extract was combined with the organic layer, which was subsequently washed with water and then a saturated aqueous solution of sodium chloride before being dried over anhydrous sodium sulfate. The crude product obtained by removal of the solvent by evaporation was separated and purified by silica gel column chromatography (hexane and toluene) to yield both 8-fluoro-trans-7-propyl-trans-4b,5,6,7,8,8a,9,10-octahydrophenanthren-2-ol and 6-fluoro-trans-7-propyl-trans-4b,5,6,7,8,8a,9,10-octahydrophenanthren-2-ol.

The thus obtained 8-fluoro-trans-7-propyl-trans-4b,5,6,7,8,8a,9,10-octahydrophenanthren-2-ol was dissolved in methylene chloride, a suspension was formed by adding trifluoromethanesulfonic anhydride, and the suspension was then cooled to 5° C. With the mixture being stirred vigorously, pyridine was then added dropwise and the mixture stirred for a further one hour. Water was then added, the reaction was halted, and the organic layer was separated. The aqueous layer was extracted with dichloromethane and this extract was combined with the organic layer, which was subsequently washed with dilute hydrochloric acid, a saturated aqueous solution of sodium bicarbonate, water, and then a saturated aqueous solution of sodium chloride before being dried over anhydrous sodium sulfate. The solvent was removed by evaporation, and the product purified by silica gel column chromatography (hexane) to yield 8-fluoro-trans-7-propyl-trans-4b,5,6,7,8,8a,9,10-octahydrophenanthren-2-yl trifluoromethanesulfonate. This compound was combined with 3,4,5-trifluorophenylboric acid (which was produced by a reaction between a Grignard reagent prepared from 3,4,5-trifluorobromobenzene and magnesium, and trimethylborate, followed by hydrolysis with dilute hydrochloric acid), tetrakis(triphenylphosphine)palladium (0) and potassium phosphate in a dimethylformamide solvent and was then stirred for 10 hours at 80° C. The reaction mixture was then cooled to room temperature, water was added, the mixture was extracted with toluene, and the resulting organic layer was washed sequentially with water and a saturated aqueous solution of sodium chloride, and then dried over anhydrous sodium sulfate. The crude product obtained by removal of the solvent by evaporation was purified by silica gel column chromatography (hexane) and then recrystallized 3 times from ethanol to yield 8-fluoro-trans-2-propyl-7-(3,4,5-trifluorophenyl)-trans-1,2,3,4,4a,9,10,10a-octahydrophenanthrene. The separated 6-fluoro-trans-7-propyl-trans-4b,5,6,7,8,8a,9,10-octahydrophenanthren-2-ol was also reacted in the same manner and yielded 6-fluoro-trans-2-propyl-7-(3,4,5-trifluorophenyl)-trans-1,2,3,4,4a,9,10,10a-octahydrophenanthrene.

The compounds listed below can be produced in a similar manner.

8-fluoro-trans-2-propyl-trans-7-(4-fluorophenyl)-trans-1,2,3,4,4a,9,10,10a-octahydrophenanthrene, 8-fluoro-trans-2-propyl-trans-7-(3,4-difluorophenyl)-trans-1,2,3,4,4a,9,10,10a-octahydrophenanthrene, 8-fluoro-trans-2-propyl-trans-7-(3,5-difluorophenyl)-trans-1,2,3,4,4a,9,10,10a-octahydrophenanthrene, 8-fluoro-trans-2-propyl-trans-7-(4-trifluoromethoxyphenyl)-trans-1,2,3,4,4a,9,10,10a-octahydrophenanthrene, 8-fluoro-trans-2-propyl-trans-7-(3-fluoro-4-trifluoromethoxyphenyl)-trans-1,2,3,4,4a,9,10,10a-octahydrophenanthrene, 8-fluoro-trans-2-propyl-trans-7-(3,5-difluoro-4-trifluoromethoxyphenyl)-trans-1,2,3,4,4a,9,10,10a-octahydrophenanthrene, 8-fluoro-trans-2-propyl-trans-7-(4-difluoromethoxyphenyl)-trans-1,2,3,4,4a,9,10,10a-octahydrophenanthrene, 8-fluoro-trans-2-propyl-trans-7-(4-trifluoromethylphenyl)-trans-1,2,3,4,4a,9,10,10a-octahydrophenanthrene, 8-fluoro-trans-2-propyl-trans-7-(3-fluoro-4-trifluoromethylphenyl)-trans-1,2,3,4,4a,9,10,10a-octahydrophenanthrene, 8-fluoro-trans-2-propyl-trans-7-(3,5-difluoro-4-trifluoromethylphenyl)-trans-1,2,3,4,4a,9,10,10a-octahydrophenanthrene, 8-fluoro-trans-2-propyl-trans-7-(4-chlorophenyl)-trans-1,2,3,4,4a,9,10,10a-octahydrophenanthrene, 8-fluoro-trans-2-propyl-trans-7-(3-fluoro-4-chlorophenyl)-trans-1,2,3,4,4a,9,10,10a-octahydrophenanthrene, 8-fluoro-trans-2-propyl-trans-7-(3,5-difluoro-4-chlorophenyl)-trans-1,2,3,4,4a,9,10,10a-octahydrophenanthrene, 6-fluoro-trans-2-propyl-trans-7-(4-fluorophenyl)-trans-1,2,3,4,4a,9,10,10a-octahydrophenanthrene, 6-fluoro-trans-2-propyl-trans-7-(3,4-difluorophenyl)-trans-1,2,3,4,4a,9,10,10a-octahydrophenanthrene, 6-fluoro-trans-2-propyl-trans-7-(3,5-difluorophenyl)-trans-1,2,3,4,4a,9,10,10a-octahydrophenanthrene, 6-fluoro-trans-2-propyl-trans-7-(4-trifluoromethoxyphenyl)-trans-1,2,3,4,4a,9,10,10a-octahydrophenanthrene, 6-fluoro-trans-2-propyl-trans-7-(3-fluoro-4-trifluoromethoxyphenyl)-trans-1,2,3,4,4a,9,10,10a-octahydrophenanthrene, 6-fluoro-trans-2-propyl-trans-7-(3,5-difluoro-4-trifluoromethoxyphenyl)-trans-1,2,3,4,4a,9,10,10a-octahydrophenanthrene, 6-fluoro-trans-2-propyl-trans-7-(4-difluoromethoxyphenyl)-trans-1,2,3,4,4a,9,10,10a-octahydrophenanthrene, 6-fluoro-trans-2-propyl-trans-7-(4-trifluoromethylphenyl)-trans-1,2,3,4,4a,9,10,10a-octahydrophenanthrene, 6-fluoro-trans-2-propyl-trans-7-(3-fluoro-4-trifluoromethylphenyl)-trans-1,2,3,4,4a,9,10,10a-octahydrophenanthrene, 6-fluoro-trans-2-propyl-trans-7-(3,5-difluoro-4-trifluoromethylphenyl)-trans-1,2,3,4,4a,9,10,10a-octahydrophenanthrene, 6-fluoro-trans-2-propyl-trans-7-(4-chlorophenyl)-trans-1,2,3,4,4a,9,10,10a-octahydrophenanthrene, 6-fluoro-trans-2-propyl-trans-7-(3-fluoro-4-chlorophenyl)-trans-1,2,3,4,4a,9,10,10a-octahydrophenanthrene, and 6-fluoro-trans-2-propyl-trans-7-(3,5-difluoro-4-chlorophenyl)-trans-1,2,3,4,4a,9,10,10a-octahydrophenanthrene.

Example 26

Synthesis of trans-2-propyl-7-(3,4,5-trifluorophenyl)-trans-1,2,3,4,4a,9,10,10a-octahydrophenanthrene

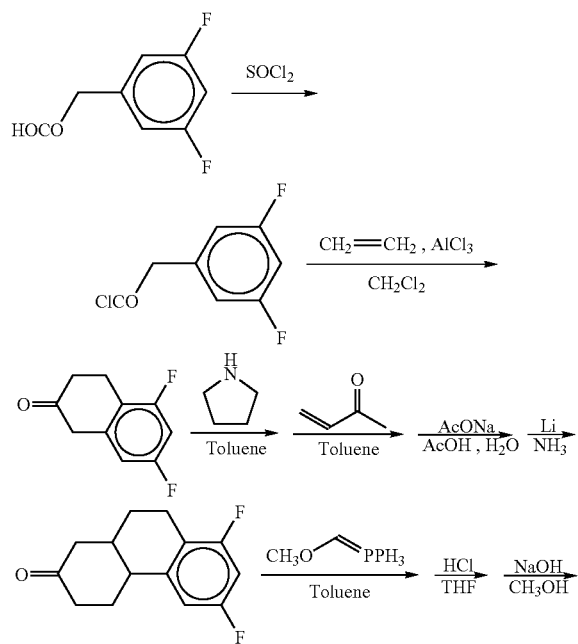

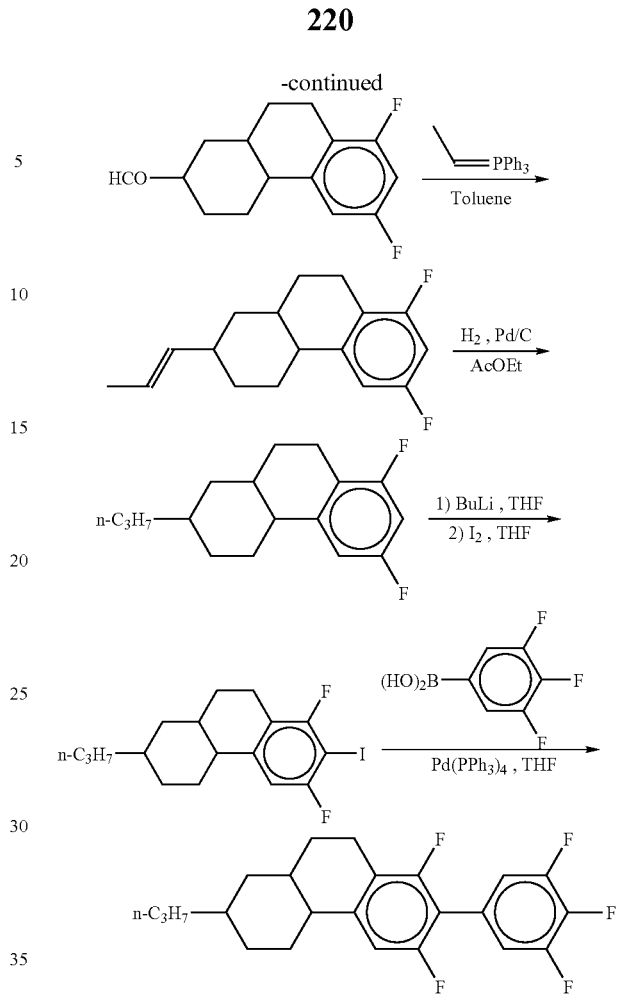

Following conversion of (3,5-difluorophenyl)-acetic acid to an acid chloride with thionyl chloride, subsequent reaction with ethylene gas at −10° C. using methylene chloride as the solvent and in the presence of aluminum chloride yielded 5,7-difluoro-3,4-dihydro-1H-naphthalen-2-one. A solution of pyrrolidine in toluene was then added and the mixture was heated for 3 hours, and any azeotropically distilled water was removed. Excess pyrrolidine was then removed by azeotropic distillation with toluene, to yield 1-(5,7-difluoro-1,4-dihydronaphthalen-2-yl)pyrrolidine.

The crude product was cooled, as is, to room temperature, more toluene was added, the mixture was cooled in a water bath, and methyl vinyl ketone was added dropwise over a period of 1 hour at a temperature of 25° C. or lower. Following completion of the addition, the mixture was immediately heated and refluxed under heat for 20 hours. The solution was then cooled to room temperature, a buffer solution of pH 5 prepared from sodium acetate, acetic acid and water was added, and the reflux was continued for a further 4 hours. After the solution had been cooled to room temperature, the organic layer was separated and washed with water and a saturated aqueous solution of sodium chloride. The organic layer was then dried over anhydrous sodium sulfate, and the solvent removed by evaporation to yield 6,8-difluoro-trans-4,4a,9,10-tetrahydro-3H-phenanthren-2-one.

At a temperature below −40° C., lithium was added gradually, in small portions, to liquid ammonia and dissolved. With the internal temperature maintained at a temperature from −30 to −40° C., a THF solution of 6,8-difluoro-trans-4,4a,9,10-tetrahydro-3H-phenanthren-2-one and t-butanol was then added dropwise. Following completion of the addition, stirring was continued for a further 30 minutes. Small quantities of solid ammonium chloride were added, and following oxidation of the lithium, the temperature was raised to room temperature, and the ammonia removed by evaporation. Water was then added, the mixture was extracted with toluene, and the organic layer was washed with a saturated aqueous solution of sodium chloride, and then dried over anhydrous magnesium sulfate. The solvent was then removed by evaporation, and vacuum distillation used to obtain 6,8-difluoro-trans-3,4,4a,9,10,10a-hexahydro-1H-phenanthren-2-one. This compound was subsequently reacted with a Wittig reagent prepared from methoxymethyltriphenylphosphonium chloride and potassium-t-butoxide, and the product enol ether was hydrolyzed using a 10% aqueous solution of hydrochloric acid in THF, and then isomerized using an aqueous solution of sodium hydroxide in methanol to yield 6,8-difluoro-trans-1,2,3,4,4a,9,10,10a-octahydrophenanthrene-trans-2-carbaldehyde. This compound was then reacted with a Wittig reagent prepared from ethyltriphenylphosphonium bromide and potassium t-butoxide to yield 6,8-difluoro-trans-2-propenyl-trans-1,2,3,4,4a,9,10,10a-octahydrophenanthrene, which was then reduced by hydrogen in the presence of a 5% palladium-carbon (wet) catalyst to yield 6,8-difluoro-trans-2-propyl-trans-1,2,3,4,4a,9,10,10a-octahydrophenanthrene. This compound was lithiated in an n-butyl lithium-hexane solution, and was then reacted with iodine to produce 6,8-difluoro-7-iodo-trans-2-propyl-trans-1,2,3,4,4a,9,10,10a-octahydrophenanthrene.

6,8-difluoro-7-iodo-trans-2-propyl-trans-1,2,3,4,4a,9,10,10a-octahydrophenanthrene was combined with 3,4,5-trifluorophenylboric acid (which was produced by a reaction between a Grignard reagent prepared from 3,4,5-trifluorobromobenzene and magnesium, and trimethylborate, followed by hydrolysis with dilute hydrochloric acid), tetrakis(triphenylphosphine)palladium (0) and potassium phosphate in a dimethylformamide solvent and was then stirred for 10 hours at 80° C. The reaction mixture was then cooled to room temperature, water was added, the mixture was extracted with toluene, and the resulting organic layer was washed sequentially with water and a saturated aqueous solution of sodium chloride, and then dried over anhydrous sodium sulfate. The crude product obtained by removal of the solvent by evaporation was purified by silica gel column chromatography (hexane) and then recrystallized 3 times from ethanol to yield 6,8-difluoro-trans-2-propyl-7-(3,4,5-trifluorophenyl)-trans-1,2,3,4,4a,9,10,10a-octahydrophenanthrene.

The compounds listed below can be produced in a similar manner.

6,8-difluoro-trans-2-propyl-(4-fluorophenyl)-trans-1,2,3,4,4a,9,10,10a-octahydrophenanthrene,
6,8-difluoro-trans-2-propyl-(3,4-difluorophenyl)-trans-1,2,3,4,4a,9,10,10a-octahydrophenanthrene,
6,8-difluoro-trans-2-propyl-(3,5-difluorophenyl)-trans-1,2,3,4,4a,9,10,10a-octahydrophenanthrene,
6,8-difluoro-trans-2-propyl-(4-trifluoromethoxyphenyl)-trans-1,2,3,4,4a,9,10,10a-octahydrophenanthrene,
6,8-difluoro-trans-2-propyl-(3-fluoro-4-trifluoromethoxyphenyl)-trans-1,2,3,4,4a,9,10,10a-octahydrophenanthrene,
6,8-difluoro-trans-2-propyl-(3,5-difluoro-4-trifluoromethoxyphenyl)-trans-1,2,3,4,4a,9,10,10a-octahydrophenanthrene,
6,8-difluoro-trans-2-propyl-(4-difluoromethoxyphenyl)-trans-1,2,3,4,4a,9,10,10a-octahydrophenanthrene,
6,8-difluoro-trans-2-propyl-(4-trifluoromethylphenyl)-trans-1,2,3,4,4a,9,10,10a-octahydrophenanthrene,
6,8-difluoro-trans-2-propyl-(3-fluoro-4-trifluoromethylphenyl)-trans-1,2,3,4,4a,9,10,10a-octahydrophenanthrene,
6,8-difluoro-trans-2-propyl-(3,5-difluoro-4-trifluoromethylphenyl)-trans-1,2,3,4,4a,9,10,10a-octahydrophenanthrene,
6,8-difluoro-trans-2-propyl-(4-chlorophenyl)-trans-1,2,3,4,4a,9,10,10a-octahydrophenanthrene,
6,8-difluoro-trans-2-propyl-(3-fluoro-4-chlorophenyl)-trans-1,2,3,4,4a,9,10,10a-octahydrophenanthrene, and
6,8-difluoro-trans-2-propyl-(3,5-difluoro-4-chlorophenyl)-trans-1,2,3,4,4a,9,10,10a-octahydrophenanthrene.

The following compounds can be obatained by reacting 6,8-difluoro-trans-1,2,3,4,4a,9,10,10a-octahydrophenanthrene-trans-2-carbaldehyde with various Wittig reagents and subsequently carrying out similar reactions.

6,8-difluoro-trans-2-vinyl-(4-fluorophenyl)-trans-1,2,3,4,4a,9,10,10a-octahydrophenanthrene,
6,8-difluoro-trans-2-vinyl-(3,4-difluorophenyl)-trans-1,2,3,4,4a,9,10,10a-octahydrophenanthrene,
6,8-difluoro-trans-2-vinyl-(3,5-difluorophenyl)-trans-1,2,3,4,4a,9,10,10a-octahydrophenanthrene,
6,8-difluoro-trans-2-vinyl-(3,4,5-trifluorophenyl)-trans-1,2,3,4,4a,9,10,10a-octahydrophenanthrene,
6,8-difluoro-trans-2-vinyl-(4-trifluoromethoxyphenyl)-trans-1,2,3,4,4a,9,10,10a-octahydrophenanthrene,
6,8-difluoro-trans-2-vinyl-(3-fluoro-4-trifluoromethoxyphenyl)-trans-1,2,3,4,4a,9,10,10a-octahydrophenanthrene,
6,8-difluoro-trans-2-vinyl-(3,5-difluoro-4-trifluoromethoxyphenyl)-trans-1,2,3,4,4a,9,10,10a-octahydrophenanthrene,
6,8-difluoro-trans-2-vinyl-(4-difluoromethoxyphenyl)-trans-1,2,3,4,4a,9,10,10a-octahydrophenanthrene,
6,8-difluoro-trans-2-vinyl-(4-trifluoromethylphenyl)-trans-1,2,3,4,4a,9,10,10a-octahydrophenanthrene,
6,8-difluoro-trans-2-vinyl-(3-fluoro-4-trifluoromethylphenyl)-trans-1,2,3,4,4a,9,10,10a-octahydrophenanthrene,
6,8-difluoro-trans-2-vinyl-(3,5-difluoro-4-trifluoromethylphenyl)-trans-1,2,3,4,4a,9,10,10a-octahydrophenanthrene,
6,8-difluoro-trans-2-vinyl-(4-chlorophenyl)-trans-1,2,3,4,4a,9,10,10a-octahydrophenanthrene,
6,8-difluoro-trans-2-vinyl-(3-fluoro-4-chlorophenyl)-trans-1,2,3,4,4a,9,10,10a-octahydrophenanthrene,
6,8-difluoro-trans-2-vinyl-(3,5-difluoro-4-chlorophenyl)-trans-1,2,3,4,4a,9,10,10a-octahydrophenanthrene,
6,8-difluoro-trans-2-(trans-1-propenyl)-(4-fluorophenyl)-trans-1,2,3,4,4a,9,10,10a-octahydrophenanthrene,
6,8-difluoro-trans-2-(trans-1-propenyl)-(3,4-difluorophenyl)-trans-1,2,3,4,4a,9,10,10a-octahydrophenanthrene,
6,8-difluoro-trans-2-(trans-1-propenyl)-(3,5-difluorophenyl)-trans-1,2,3,4,4a,9,10,10a-octahydrophenanthrene,
6,8-difluoro-trans-2-(trans-1-propenyl)-(3,4,5-trifluorophenyl)-trans-1,2,3,4,4a,9,10,10a-octahydrophenanthrene,
6,8-difluoro-trans-2-(trans-1-propenyl)-(4-trifluoromethoxyphenyl)-trans-1,2,3,4,4a,9,10,10a-octahydrophenanthrene,
6,8-difluoro-trans-2-(trans-1-propenyl)-(3-fluoro-4-trifluoromethoxyphenyl)-trans-1,2,3,4,4a,9,10,10a-octahydrophenanthrene,
6,8-difluoro-trans-2-(trans-1-propenyl)-(3,5-difluoro-4-trifluoromethoxyphenyl)-trans-1,2,3,4,4a,9,10,10a-octahydrophenanthrene, 6,8-difluoro-trans-2-(trans-1-propenyl)-(4-difluoromethoxyphenyl)-trans-1,2,3,4,4a,9,10,10a-octahydrophenanthrene,
6,8-difluoro-trans-2-(trans-1-propenyl)-(4-trifluoromethylphenyl)-trans-1,2,3,4,4a,9,10,10a-octahydrophenanthrene,
6,8-difluoro-trans-2-(trans-1-propenyl)-(3-fluoro-4-trifluoromethylphenyl)-trans-1,2,3,4,4a,9,10,10a-octahydrophenanthrene,
6,8-difluoro-trans-2-(trans-1-propenyl)-(3,5-difluoro-4-trifluoromethylphenyl)-trans-1,2,3,4,4a,9,10,10a-octahydrophenanthrene,
6,8-difluoro-trans-2-(trans-1-propenyl)-(4-chlorophenyl)-trans-1,2,3,4,4a,9,10,10a-octahydrophenanthrene,
6,8-difluoro-trans-2-(trans-1-propenyl)-(3-fluoro-4-chlorophenyl)-trans-1,2,3,4,4a,9,10,10a-octahydrophenanthrene,
6,8-difluoro-trans-2-(trans-1-propenyl)-(3,5-difluoro-4-chlorophenyl)-trans-1,2,3,4,4a,9,10,10a-octahydrophenanthrene,
6,8-difluoro-trans-2-(trans-1-butenyl)-(4-fluorophenyl)-trans-1,2,3,4,4a,9,10,10a-octahydrophenanthrene,
6,8-difluoro-trans-2-(trans-1-butenyl)-(3,4-difluorophenyl)-trans-1,2,3,4,4a,9,10,10a-octahydrophenanthrene,
6,8-difluoro-trans-2-(trans-1-butenyl)-(3,5-difluorophenyl)-trans-1,2,3,4,4a,9,10,10a-octahydrophenanthrene,
6,8-difluoro-trans-2-(trans-1-butenyl)-(3,4,5-trifluorophenyl)-trans-1,2,3,4,4a,9,10,10a-octahydrophenanthrene,
6,8-difluoro-trans-2-(trans-1-butenyl)-(4-trifluoromethoxyphenyl)-trans-1,2,3,4,4a,9,10,10a-octahydrophenanthrene,
6,8-difluoro-trans-2-(trans-1-butenyl)-(3-fluoro-4-trifluoromethoxyphenyl)-trans-1,2,3,4,4a,9,10,10a-octahydrophenanthrene,
6,8-difluoro-trans-2-(trans-1-butenyl)-(3,5-difluoro-4-trifluoromethoxyphenyl)-trans-1,2,3,4,4a,9,10,10a-octahydrophenanthrene,
6,8-difluoro-trans-2-(trans-1-butenyl)-(4-difluoromethoxyphenyl)-trans-1,2,3,4,4a,9,10,10a-octahydrophenanthrene,
6,8-difluoro-trans-2-(trans-1-butenyl)-(4-trifluoromethylphenyl)-trans-1,2,3,4,4a,9,10,10a-octahydrophenanthrene,
6,8-difluoro-trans-2-(trans-1-butenyl)-(3-fluoro-4-trifluoromethylphenyl)-trans-1,2,3,4,4a,9,10,10a-octahydrophenanthrene,
6,8-difluoro-trans-2-(trans-1-butenyl)-(3,5-difluoro-4-trifluoromethylphenyl)-trans-1,2,3,4,4a,9,10,10a-octahydrophenanthrene,
6,8-difluoro-trans-2-(trans-1-butenyl)-(4-chlorophenyl)-trans-1,2,3,4,4a,9,10,10a-octahydrophenanthrene,
6,8-difluoro-trans-2-(trans-1-butenyl)-(3-fluoro-4-chlorophenyl)-trans-1,2,3,4,4a,9,10,10a-octahydrophenanthrene,
6,8-difluoro-trans-2-(trans-1-butenyl)-(3,5-difluoro-4-chlorophenyl)-trans-1,2,3,4,4a,9,10,10a-octahydrophenanthrene,
6,8-difluoro-trans-2-(trans-1-pentenyl)-(4-fluorophenyl)-trans-1,2,3,4,4a,9,10,10a-octahydrophenanthrene,
6,8-difluoro-trans-2-(trans-1-pentenyl)-(3,4-difluorophenyl)-trans-1,2,3,4,4a,9,10,10a-octahydrophenanthrene,
6,8-difluoro-trans-2-(trans-1-pentenyl)-(3,5-difluorophenyl)-trans-1,2,3,4,4a,9,10,10a-octahydrophenanthrene,
6,8-difluoro-trans-2-(trans-1-pentenyl)-(3,4,5-trifluorophenyl)-trans-1,2,3,4,4a,9,10,10a-octahydrophenanthrene,
6,8-difluoro-trans-2-(trans-1-pentenyl)-(4-trifluoromethoxyphenyl)-trans-1,2,3,4,4a,9,10,10a-octahydrophenanthrene,
6,8-difluoro-trans-2-(trans-1-pentenyl)-(3-fluoro-4-trifluoromethoxyphenyl)-trans-1,2,3,4,4a,9,10,10a-octahydrophenanthrene,
6,8-difluoro-trans-2-(trans-1-pentenyl)-(3,5-difluoro-4-trifluoromethoxyphenyl)-trans-1,2,3,4,4a,9,10,10a-octahydrophenanthrene,
6,8-difluoro-trans-2-(trans-1-pentenyl)-(4-difluoromethoxyphenyl)-trans-1,2,3,4,4a,9,10,10a-octahydrophenanthrene,
6,8-difluoro-trans-2-(trans-1-pentenyl)-(4-trifluoromethylphenyl)-trans-1,2,3,4,4a,9,10,10a-octahydrophenanthrene,
6,8-difluoro-trans-2-(trans-1-pentenyl)-(3-fluoro-4-trifluoromethylphenyl)-trans-1,2,3,4,4a,9,10,10a-octahydrophenanthrene,
6,8-difluoro-trans-2-(trans-1-pentenyl)-(3,5-difluoro-4-trifluoromethylphenyl)-trans-1,2,3,4,4a,9,10,10a-octahydrophenanthrene,
6,8-difluoro-trans-2-(trans-1-pentenyl)-(4-chlorophenyl)-trans-1,2,3,4,4a,9,10,10a-octahydrophenanthrene,
6,8-difluoro-trans-2-(trans-1-pentenyl)-(3-fluoro-4-chlorophenyl)-trans-1,2,3,4,4a,9,10,10a-octahydrophenanthrene,
6,8-difluoro-trans-2-(trans-1-pentenyl)-(3,5-difluoro-4-chlorophenyl)-trans-1,2,3,4,4a,9,10,10a-octahydrophenanthrene,
6,8-difluoro-trans-2-(3-butenyl)-(4-fluorophenyl)-trans-1,2,3,4,4a,9,10,10a-octahydrophenanthrene,
6,8-difluoro-trans-2-(3-butenyl)-(3,4-difluorophenyl)-trans-1,2,3,4,4a,9,10,10a-octahydrophenanthrene,
6,8-difluoro-trans-2-(3-butenyl)-(3,5-difluorophenyl)-trans-1,2,3,4,4a,9,10,10a-octahydrophenanthrene,
6,8-difluoro-trans-2-(3-butenyl)-(3,4,5-trifluorophenyl)-trans-1,2,3,4,4a,9,10,10a-octahydrophenanthrene,
6,8-difluoro-trans-2-(3-butenyl)-(4-trifluoromethoxyphenyl)-trans-1,2,3,4,4a,9,10,10a-octahydrophenanthrene,
6,8-difluoro-trans-2-(3-butenyl)-(3-fluoro-4-trifluoromethoxyphenyl)-trans-1,2,3,4,4a,9,10,10a-octahydrophenanthrene,
6,8-difluoro-trans-2-(3-butenyl)-(3,5-difluoro-4-trifluoromethoxyphenyl)-trans-1,2,3,4,4a,9,10,10a-octahydrophenanthrene,
6,8-difluoro-trans-2-(3-butenyl)-(–4-difluoromethoxyphenyl)-trans-1,2,3,4,4a,9,10,10a-octahydrophenanthrene,
6,8-difluoro-trans-2-(3-butenyl)-(4-trifluoromethylphenyl)-trans-1,2,3,4,4a,9,10,10a-octahydrophenanthrene,
6,8-difluoro-trans-2-(3-butenyl)-(3-fluoro-4-trifluoromethylphenyl)-trans-1,2,3,4,4a,9,10,10a-octahydrophenanthrene,
6,8-difluoro-trans-2-(3-butenyl)-(3,5-difluoro-4-trifluoromethylphenyl)-trans-1,2,3,4,4a,9,10,10a-octahydrophenanthrene,
6,8-difluoro-trans-2-(3-butenyl)-(4-chlorophenyl)-trans-1,2,3,4,4a,9,10,10a-octahydrophenanthrene,
6,8-difluoro-trans-2-(3-butenyl)-(3-fluoro-4-chlorophenyl)-trans-1,2,3,4,4a,9,10,10a-octahydrophenanthrene,
6,8-difluoro-trans-2-(3-butenyl)-(3,5-difluoro-4-chlorophenyl)-trans-1,2,3,4,4a,9,10,10a-octahydrophenanthrene,
6,8-difluoro-trans-2-(trans-3-pentenyl)-(4-fluorophenyl)-trans-1,2,3,4,4a,9,10,10a-octahydrophenanthrene,
6,8-difluoro-trans-2-(trans-3-pentenyl)-(3,4-difluorophenyl)-trans-1,2,3,4,4a,9,10,10a-octahydrophenanthrene,
6,8-difluoro-trans-2-(trans-3-pentenyl)-(3,5-difluorophenyl)-trans-1,2,3,4,4a,9,10,10a-octahydrophenanthrene, 6,8-difluoro-trans-2-(trans-3-pentenyl)-(3,4,5-trifluorophenyl)-trans-1,2,3,4,4a,9,10,10a-octahydrophenanthrene,
6,8-difluoro-trans-2-(trans-3-pentenyl)-(4-trifluoromethoxyphenyl)-trans-1,2,3,4,4a,9,10,10a-octahydrophenanthrene,
6,8-difluoro-trans-2-(trans-3-pentenyl)-(3-fluoro-4-trifluoromethoxyphenyl)-trans-1,2,3,4,4a,9,10,10a-octahydrophenanthrene,
6,8-difluoro-trans-2-(trans-3-pentenyl)-(3,5-difluoro-4-trifluoromethoxyphenyl)-trans-1,2,3,4,4a,9,10,10a-octahydrophenanthrene,
6,8-difluoro-trans-2-(trans-3-pentenyl)-(4-difluoromethoxyphenyl)-trans-1,2,3,4,4a,9,10,10a-octahydrophenanthrene,
6,8-difluoro-trans-2-(trans-3-pentenyl)-(4-trifluoromethylphenyl)-trans-1,2,3,4,4a,9,10,10a-octahydrophenanthrene,
6,8-difluoro-trans-2-(trans-3-pentenyl)-(3-fluoro-4-trifluoromethylphenyl)-trans-1,2,3,4,4a,9,10,10a-octahydrophenanthrene,
6,8-difluoro-trans-2-(trans-3-pentenyl)-(3,5-difluoro-4-trifluoromethylphenyl)-trans-1,2,3,4,4a,9,10,10a-octahydrophenanthrene,
6,8-difluoro-trans-2-(trans-3-pentenyl)-(4-chlorophenyl)-trans-1,2,3,4,4a,9,10,10a-octahydrophenanthrene,
6,8-difluoro-trans-2-(trans-3-pentenyl)-(3-fluoro-4-chlorophenyl)-trans-1,2,3,4,4a,9,10,10a-octahydrophenanthrene, and
6,8-difluoro-trans-2-(trans-3-pentenyl)-(3,5-difluoro-4-chlorophenyl)-trans-1,2,3,4,4a,9,10,10a-octahydrophenanthrene.

Example 27

Synthesis of 2-fluoro-4-(trans-7-propyl-trans-4b,5,6,7,8,8a,9,10-octahydrophenanthren-2-yl)benzonitrile

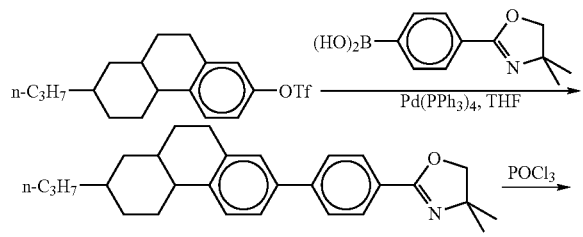

-continued

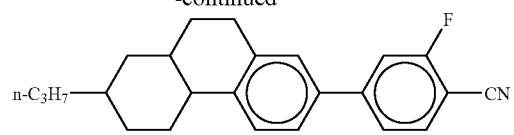

Trans-7-propyl-trans-4b,5,6,7,8,8a,9,10-octahydrophenanthren-2-yl trifluoromethanesulfonate produced in Example 23 was reacted with 4-(4,4-dimethyl-4,5-dihydrooxazol-2-yl)-2-fluorophenylboric acid in the presence of tetrakis(triphenylphosphine)palladium, and subsequently reacted with phosphorus oxychloride to remove the cyano group protective group, and yielded 2-fluoro-4-(trans-7-propyl-trans-4b,5,6,7,8,8a,9,10-octahydrophenanthren-2-yl)benzonitrile.

The compounds listed below can be produced in a similar manner.

4-(trans-7-propyl-trans-4b,5,6,7,8,8a,9,10-octahydrophenanthrene-trans-2-yl)benzonitrile,
2-fluoro-4-(trans-7-ethyl-trans-4b,5,6,7,8,8a,9,10-octahydrophenanthrene-trans-2-yl)benzonitrile,
4-(trans-7-ethyl-trans-4b,5,6,7,8,8a,9,10-octahydrophenanthrene-trans-2-yl)benzonitrile,
2-fluoro-4-(trans-7-butyl-trans-4b,5,6,7,8,8a,9,10-octahydrophenanthrene-trans-2-yl)benzonitrile,
4-(trans-7-butyl-trans-4b,5,6,7,8,8a,9,10-octahydrophenanthrene-trans-2-yl)benzonitrile,
2-fluoro-4-(trans-7-pentyl-trans-4b,5,6,7,8,8a,9,10-octahydrophenanthrene-trans-2-yl)benzonitrile,
4-(trans-7-pentyl-trans-4b,5,6,7,8,8a,9,10-octahydrophenanthrene-trans-2-yl)benzonitrile,
2-fluoro-4-(trans-7-hexyl-trans-4b,5,6,7,8,8a,9,10-octahydrophenanthrene-trans-2-yl)benzonitrile,
4-(trans-7-hexyl-trans-4b,5,6,7,8,8a,9,10-octahydrophenanthrene-trans-2-yl)benzonitrile,
2-fluoro-4-(trans-7-heptyl-trans-4b,5,6,7,8,8a,9,10-octahydrophenanthrene-trans-2-yl)benzonitrile, and
4-(trans-7-heptyl-trans-4b,5,6,7,8,8a,9,10-octahydrophenanthrene-trans-2-yl)benzonitrile.

Example 28

Synthesis of 2-fluoro-4-(1-fluoro-trans-7-propyl-trans-4b,5,6,7,8,8a,9,10-octahydrophenanthren-2-yl)benzonitrile

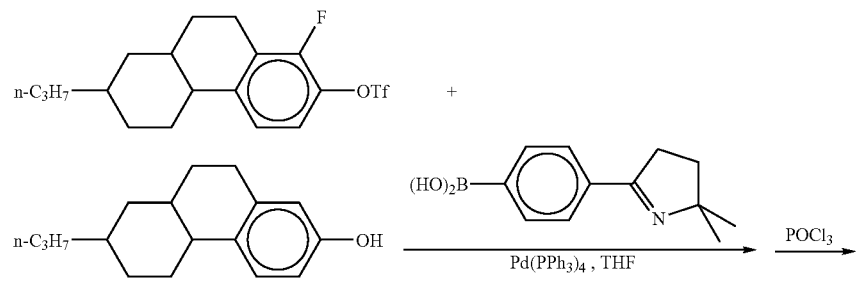

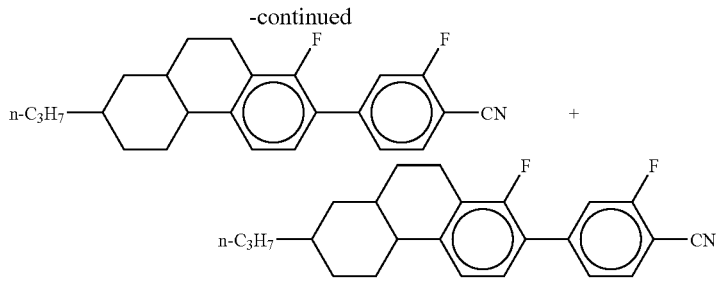

8-fluoro-trans-7-propyl-trans-4b,5,6,7,8,8a,9,10-octahydrophenanthren-2-yl trifluoromethanesulfonate produced in Example 25 was reacted with 4-(4,4-dimethyl-4,5-dihydrooxazol-2-yl)-2-fluorophenylboric acid in the presence of tetrakis(triphenylphosphine)palladium, and subsequently reacted with phosphorus oxychloride to remove the cyano group protective group, and yielded 2-fluoro-4-(1-fluoro-trans-7-propyl-trans-4b,5,6,7,8,8a,9,10-octahydrophenanthren-2-yl)benzonitrile.

The compounds listed below can be produced in a similar manner.

2-fluoro-4-(1-fluoro-trans-7-propyl-trans-4b,5,6,7,8,8a,9,10-octahydrophenanthrene-trans-2-yl)benzonitrile, 4-(1-fluoro-trans-7-propyl-trans-4b,5,6,7,8,8a,9,10-octahydrophenanthrene-trans-2-yl)benzonitrile, 2-fluoro-4-(3-fluoro-trans-7-propyl-trans-4b,5,6,7,8,8a,9,10-octahydrophenanthrene-trans-2-yl)benzonitrile, and 4-(3-fluoro-trans-7-propyl-trans-4b,5,6,7,8,8a,9,10-octahydrophenanthrene-trans-2-yl)benzonitrile.

Example 29

Synthesis of 2,6-difluoro-4-(1-fluoro-trans-7-propyl-trans-4b,5,6,7,8,8a,9,10-octahydrophenanthren-trans-2-yl)benzonitrile

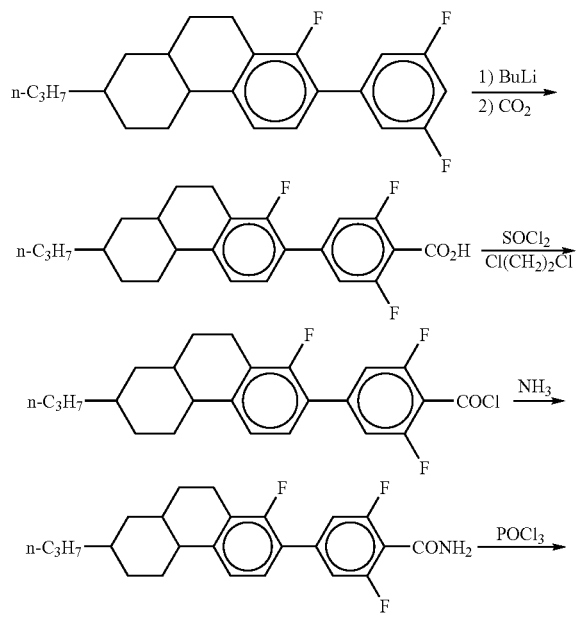

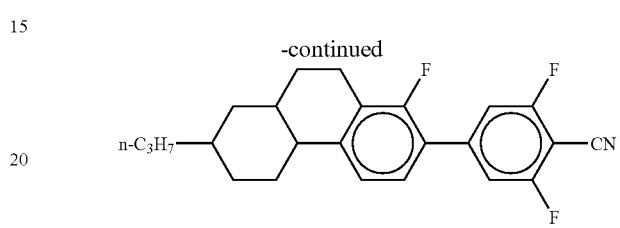

1-fluoro-trans-7-propyl-2-(3,5-difluorophenyl)-trans-4b,5,6,7,8,8a,9,10-octahydrophenanthrene produced using the same method as Example 25 was lithiated using a butyl lithium-hexane solution, and subsequently reacted with carbon dioxide gas to yield 2,6-difluoro-4-(1-fluoro-trans-7-propyl-trans-4b,5,6,7,8,8a,9,10-octahydrophenanthren-trans-2-yl)benzoic acid. This compound was converted to an acid chloride with thionyl chloride, and then reacted with ammonia to yield 2,6-difluoro-4-(1-fluoro-trans-7-propyl-trans-4b,5,6,7,8,8a,9,10-octahydrophenanthren-trans-2-yl) benzamide. Subsequent reaction with phosphorus oxychloride producing a dehydration yielded 2,6-difluoro-4-(1-fluoro-trans-7-propyl-trans-4b,5,6,7,8,8a,9,10-octahydrophenanthren-trans-2-yl) benzonitrile.

The compounds listed below can be produced in a similar manner.

2,6-difluoro-4-(trans-7-ethyl-trans-4b,5,6,7,8,8a,9,10-octahydrophenanthrene-trans-2-yl)benzonitrile, 2,6-difluoro-4-(trans-7-propyl-trans-4b,5,6,7,8,8a,9,10-octahydrophenanthrene-trans-2-yl)benzonitrile, 2,6-difluoro-4-(trans-7-butyl-trans-4b,5,6,7,8,8a,9,10-octahydrophenanthrene-trans-2-yl)benzonitrile, 2,6-difluoro-4-(trans-7-pentyl-trans-4b,5,6,7,8,8a,9,10-octahydrophenanthrene-trans-2-yl)benzonitrile, 2,6-difluoro-4-(trans-7-hexyl-trans-4b,5,6,7,8,8a,9,10-octahydrophenanthrene-trans-2-yl)benzonitrile, 2,6-difluoro-4-(trans-7-heptyl-trans-4b,5,6,7,8,8a,9,10-octahydrophenanthrene-trans-2-yl)benzonitrile, 2,6-difluoro-4-(1,3-difluoro-trans-7-propyl-trans-4b,5,6,7,8,8a,9,10-octahydrophenanthrene-trans-2-yl)benzonitrile, 2-fluoro-4-(1,3-difluoro-trans-7-propyl-trans-4b,5,6,7,8,8a,9,10-octahydrophenanthrene-trans-2-yl)benzonitrile, 4-(1,3-difluoro-trans-7-propyl-trans-4b,5,6,7,8,8a,9,10-octahydrophenanthrene-trans-2-yl)benzonitrile, 2,6-difluoro-4-(1,3-difluoro-trans-7-ethyl-trans-4b,5,6,7,8,8a,9,10-octahydrophenanthrene-trans-2-yl)benzonitrile, 2-fluoro-4-(1,3-difluoro-trans-7-ethyl-trans-4b,5,6,7,8,8a,9,10-octahydrophenanthrene-trans-2-yl)benzonitrile, 4-(1,3-difluoro-trans-7-ethyl-trans-4b,5,6,7,8,8a,9,10-octahydrophenanthrene-trans-2-yl)benzonitrile, 2,6-difluoro-4-(1,3-difluoro-trans-7-butyl-trans-4b,5,6,7,8,8a,9,10-octahydrophenanthrene-trans-2-yl)benzonitrile, 2-fluoro-4-(1,3-difluoro-trans-7-butyl-trans-4b,5,6,7,8,8a,9,10-octahydrophenanthrene-trans-2-yl)benzonitrile,
4-(1,3-difluoro-trans-7-butyl-trans-4b,5,6,7,8,8a,9,10-octahydrophenanthrene-trans-2-yl)benzonitrile,
2,6-difluoro-4-(1,3-difluoro-trans-7-pentyl-trans-4b,5,6,7,8,8a,9,10-octahydrophenanthrene-trans-2-yl)benzonitrile,
2-fluoro-4-(1,3-difluoro-trans-7-pentyl-trans-4b,5,6,7,8,8a,9,10-octahydrophenanthrene-trans-2-yl)benzonitrile,
4-(1,3-difluoro-trans-7-pentyl-trans-4b,5,6,7,8,8a,9,10-octahydrophenanthrene-trans-2-yl)benzonitrile,
2,6-difluoro-4-(1,3-difluoro-trans-7-hexyl-trans-4b,5,6,7,8,8a,9,10-octahydrophenanthrene-trans-2-yl)benzonitrile,
2-fluoro-4-(1,3-difluoro-trans-7-hexyl-trans-4b,5,6,7,8,8a,9,10-octahydrophenanthrene-trans-2-yl)benzonitrile,
4-(1,3-difluoro-trans-7-hexyl-trans-4b,5,6,7,8,8a,9,10-octahydrophenanthrene-trans-2-yl)benzonitrile,
2,6-difluoro-4-(1,3-difluoro-trans-7-heptyl-trans-4b,5,6,7,8,8a,9,10-octahydrophenanthrene-trans-2-yl)benzonitrile,
2-fluoro-4-(1,3-difluoro-trans-7-heptyl-trans-4b,5,6,7,8,8a,9,10-octahydrophenanthrene-trans-2-yl)benzonitrile,
4-(1,3-difluoro-trans-7-heptyl-trans-4b,5,6,7,8,8a,9,10-octahydrophenanthrene-trans-2-yl)benzonitrile,
2,6-difluoro-4-(1-fluoro-trans-7-ethyl-trans-4b,5,6,7,8,8a,9,10-octahydrophenanthrene-trans-2-yl)benzonitrile,
2,6-difluoro-4-(1-fluoro-trans-7-butyl-trans-4b,5,6,7,8,8a,9,10-octahydrophenanthrene-trans-2-yl)benzonitrile,
2,6-difluoro-4-(1-fluoro-trans-7-pentyl-trans-4b,5,6,7,8,8a,9,10-octahydrophenanthrene-trans-2-yl)benzonitrile,
2,6-difluoro-4-(1-fluoro-trans-7-hexyl-trans-4b,5,6,7,8,8a,9,10-octahydrophenanthrene-trans-2-yl)benzonitrile,
2,6-difluoro-4-(1-fluoro-trans-7-heptyl-trans-4b,5,6,7,8,8a,9,10-octahydrophenanthrene-trans-2-yl)benzonitrile,
2,6-difluoro-4-(3-fluoro-trans-7-propyl-trans-4b,5,6,7,8,8a,9,10-octahydrophenanthrene-trans-2-yl)benzonitrile,
2,6-difluoro-4-(3-fluoro-trans-7-ethyl-trans-4b,5,6,7,8,8a,9,10-octahydrophenanthrene-trans-2-yl)benzonitrile,
2,6-difluoro-4-(3-fluoro-trans-7-butyl-trans-4b,5,6,7,8,8a,9,10-octahydrophenanthrene-trans-2-yl)benzonitrile,
2,6-difluoro-4-(3-fluoro-trans-7-pentyl-trans-4b,5,6,7,8,8a,9,10-octahydrophenanthrene-trans-2-yl)benzonitrile,
2,6-difluoro-4-(3-fluoro-trans-7-hexyl-trans-4b,5,6,7,8,8a,9,10-octahydrophenanthrene-trans-2-yl)benzonitrile, and
2,6-difluoro-4-(3-fluoro-trans-7-heptyl-trans-4b,5,6,7,8,8a,9,10-octahydrophenanthrene-trans-2-yl)benzonitrile.

Example 30

Synthesis of trans-7-propyl-1,2,3,4-tetrahydrophenanthren-2-ol

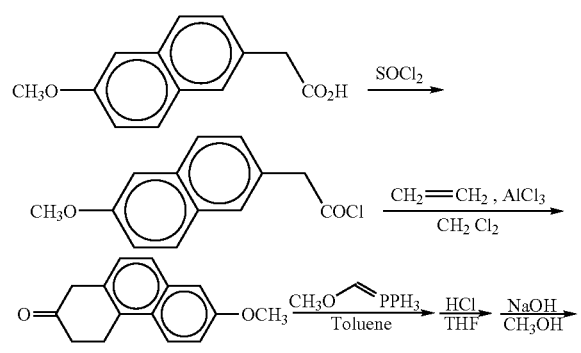

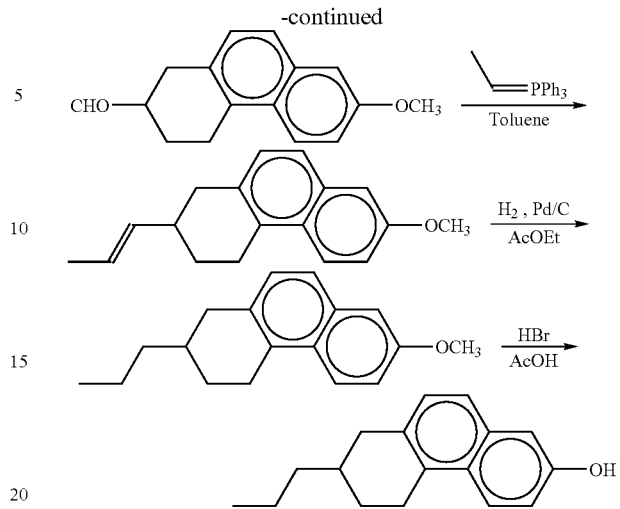

Following conversion of (6-methoxynaphthalen-2-yl)-acetic acid to an acid chloride with thionyl chloride, subsequent reaction with ethylene gas at −10° C. using methylene chloride as the solvent and in the presence of aluminum chloride yielded 7-methoxy-3,4-dihydro-1H-phenanthren-2-one. This compound was subsequently reacted with a Wittig reagent prepared from methoxymethyltriphenylphosphonium chloride and potassium-t-butoxide, and the product enol ether was hydrolyzed using a 10% aqueous solution of hydrochloric acid in THF, and then isomerized using an aqueous solution of sodium hydroxide in methanol to yield 7-methoxy-1,2,3,4-tetrahydrophenanthrene-trans-2-carbaldehyde. This compound was then reacted with a Wittig reagent prepared from ethyltriphenylphosphonium bromide and potassium t-butoxide to yield 7-methoxy-trans-2-propenyl-1,2,3,4-tetrahydrophenanthrene, which was then reduced by hydrogen in the presence of a 5% palladium-carbon (wet) catalyst to yield 7-methoxy-trans-2-propyl-trans-1,2,3,4-tetrahydrophenanthrene. This compound was lithiated in an n-butyl lithium-hexane solution, and was then reacted with iodine to produce trans-7-propyl-1,2,3,4-tetrahydrophenanthren-2-ol. This compound was reacted in the same manner as that described in Example 23 to Example 29, and yielded the compounds listed below.

trans-2-propyl-(4-fluorophenyl)-1,2,3,4-tetrahydrophenanthrene,
trans-2-propyl-(3,4-difluorophenyl)-1,2,3,4-tetrahydrophenanthrene,
trans-2-propyl-(3,5-difluorophenyl)-1,2,3,4-tetrahydrophenanthrene,
trans-2-propyl-(3,4,5-trifluorophenyl)-1,2,3,4-tetrahydrophenanthrene,
trans-2-propyl-(4-trifluoromethoxyphenyl)-1,2,3,4-tetrahydrophenanthrene,
trans-2-propyl-(3-fluoro-4-trifluoromethoxyphenyl)-1,2,3,4-tetrahydrophenanthrene,
trans-2-propyl-(3,5-difluoro-4-trifluoromethoxyphenyl)-1,2,3,4-tetrahydrophenanthrene,
trans-2-propyl-(4-difluoromethoxyphenyl)-1,2,3,4-tetrahydrophenanthrene,
trans-2-propyl-(4-trifluoromethylphenyl)-1,2,3,4-tetrahydrophenanthrene,
trans-2-propyl-(3-fluoro-4-trifluoromethylphenyl)-1,2,3,4-tetrahydrophenanthrene, trans-2-propyl-(3,5-difluoro-4-trifluoromethylphenyl)-1,2,3,4-tetrahydrophenanthrene,
trans-2-propyl-(4-chlorophenyl)-1,2,3,4-tetrahydrophenanthrene,
trans-2-propyl-(3-fluoro-4-chlorophenyl)-1,2,3,4-tetrahydrophenanthrene,
trans-2-propyl-(3,5-difluoro-4-chlorophenyl)-1,2,3,4-tetrahydrophenanthrene,
trans-2-propyl-(4-fluorophenylethynyl)-1,2,3,4-tetrahydrophenanthrene,
trans-2-propyl-(3,4-difluorophenylethynyl)-1,2,3,4-tetrahydrophenanthrene,
trans-2-propyl-(3,5-difluorophenylethynyl)-1,2,3,4-tetrahydrophenanthrene,
trans-2-propyl-(4-trifluoromethoxyphenylethynyl)-1,2,3,4-tetrahydrophenanthrene,
trans-2-propyl-(3-fluoro-4-trifluoromethoxyphenylethynyl)-1,2,3,4-tetrahydrophenanthrene,
trans-2-propyl-(3,5-difluoro-4-trifluoromethoxyphenylethynyl)-1,2,3,4-tetrahydrophenanthrene,
trans-2-propyl-(4-difluoromethoxyphenylethynyl)-1,2,3,4-tetrahydrophenanthrene,
trans-2-propyl-(4-trifluoromethylphenylethynyl)-1,2,3,4-tetrahydrophenanthrene,
trans-2-propyl-(3-fluoro-4-trifluoromethylphenylethynyl)-1,2,3,4-tetrahydrophenanthrene,
trans-2-propyl-(3,5-difluoro-4-trifluoromethylphenylethynyl)-1,2,3,4-tetrahydrophenanthrene,
trans-2-propyl-(4-chlorophenylethynyl)-1,2,3,4-tetrahydrophenanthrene,
trans-2-propyl-(3-fluoro-4-chlorophenylethynyl)-1,2,3,4-tetrahydrophenanthrene,
trans-2-propyl-(3,5-difluoro-4-chlorophenylethynyl)-1,2,3,4-tetrahydrophenanthrene,
8-fluoro-trans-2-propyl-(4-fluorophenyl)-1,2,3,4-tetrahydrophenanthrene,
8-fluoro-trans-2-propyl-(3,4-difluorophenyl)-1,2,3,4-tetrahydrophenanthrene,
8-fluoro-trans-2-propyl-(3,5-difluorophenyl)-1,2,3,4-tetrahydrophenanthrene,
8-fluoro-trans-2-propyl-(4-trifluoromethoxyphenyl)-1,2,3,4-tetrahydrophenanthrene,
8-fluoro-trans-2-propyl-(3-fluoro-4-trifluoromethoxyphenyl)-1,2,3,4-tetrahydrophenanthrene,
8-fluoro-trans-2-propyl-(3,5-difluoro-4-trifluoromethoxyphenyl)-1,2,3,4-tetrahydrophenanthrene,
8-fluoro-trans-2-propyl-(4-difluoromethoxyphenyl)-1,2,3,4-tetrahydrophenanthrene,
8-fluoro-trans-2-propyl-(4-trifluoromethylphenyl)-1,2,3,4-tetrahydrophenanthrene,
8-fluoro-trans-2-propyl-(3-fluoro-4-trifluoromethylphenyl)-1,2,3,4-tetrahydrophenanthrene,
8-fluoro-trans-2-propyl-(3,5-difluoro-4-trifluoromethylphenyl)-1,2,3,4-tetrahydrophenanthrene,
8-fluoro-trans-2-propyl-(4-chlorophenyl)-1,2,3,4-tetrahydrophenanthrene,
8-fluoro-trans-2-propyl-(3-fluoro-4-chlorophenyl)-1,2,3,4-tetrahydrophenanthrene,
8-fluoro-trans-2-propyl-(3,5-difluoro-4-chlorophenyl)-1,2,3,4-tetrahydrophenanthrene,
6-fluoro-trans-2-propyl-(4-fluorophenyl)-1,2,3,4-tetrahydrophenanthrene,
6-fluoro-trans-2-propyl-(3,4-difluorophenyl)-1,2,3,4-tetrahydrophenanthrene,
6-fluoro-trans-2-propyl-(3,5-difluorophenyl)-1,2,3,4-tetrahydrophenanthrene,
6-fluoro-trans-2-propyl-(4-trifluoromethoxyphenyl)-1,2,3,4-tetrahydrophenanthrene,
6-fluoro-trans-2-propyl-(3-fluoro-4-trifluoromethoxyphenyl)-1,2,3,4-tetrahydrophenanthrene,
6-fluoro-trans-2-propyl-(3,5-difluoro-4-trifluoromethoxyphenyl)-1,2,3,4-tetrahydrophenanthrene,
6-fluoro-trans-2-propyl-(4-difluoromethoxyphenyl)-1,2,3,4-tetrahydrophenanthrene,
6-fluoro-trans-2-propyl-(4-trifluoromethylphenyl)-1,2,3,4-tetrahydrophenanthrene,
6-fluoro-trans-2-propyl-(3-fluoro-4-trifluoromethylphenyl)-1,2,3,4-tetrahydrophenanthrene,
6-fluoro-trans-2-propyl-(3,5-difluoro-4-trifluoromethylphenyl)-1,2,3,4-tetrahydrophenanthrene,
6-fluoro-trans-2-propyl-(4-chlorophenyl)-1,2,3,4-tetrahydrophenanthrene,
6-fluoro-trans-2-propyl-(3-fluoro-4-chlorophenyl)-1,2,3,4-tetrahydrophenanthrene,
6-fluoro-trans-2-propyl-(3,5-difluoro-4-chlorophenyl)-1,2,3,4-tetrahydrophenanthrene,
4-(trans-7-propyl-5,6,7,8-tetrahydrophenanthrene-2-yl)benzonitrile,
2-fluoro-4-(trans-7-ethyl-5,6,7,8-tetrahydrophenanthrene-2-yl)benzonitrile,
4-(trans-7-ethyl-5,6,7,8-tetrahydrophenanthrene-2-yl)benzonitrile,
2-fluoro-4-(trans-7-butyl-5,6,7,8-tetrahydrophenanthrene-2-yl)benzonitrile,
4-(trans-7-butyl-5,6,7,8-tetrahydrophenanthrene-2-yl)benzonitrile,
2-fluoro-4-(trans-7-pentyl-5,6,7,8-tetrahydrophenanthrene-2-yl)benzonitrile,
4-(trans-7-pentyl-5,6,7,8-tetrahydrophenanthrene-2-yl)benzonitrile,
2-fluoro-4-(trans-7-hexyl-5,6,7,8-tetrahydrophenanthrene-2-yl)benzonitrile,
4-(trans-7-hexyl-5,6,7,8-tetrahydrophenanthrene-2-yl)benzonitrile,
2-fluoro-4-(trans-7-heptyl-5,6,7,8-tetrahydrophenanthrene-2-yl)benzonitrile,
4-(trans-7-heptyl-5,6,7,8-tetrahydrophenanthrene-2-yl)benzonitrile,
2-fluoro-4-(8-fluoro-trans-7-propyl-5,6,7,8-tetrahydrophenanthrene-2-yl)benzonitrile,
4-(8-fluoro-trans-7-propyl-5,6,7,8-tetrahydrophenanthrene-2-yl)benzonitrile,
2-fluoro-4-(8-fluoro-trans-7-ethyl-5,6,7,8-tetrahydrophenanthrene-2-yl)benzonitrile,
4-(8-fluoro-trans-7-ethyl-5,6,7,8-tetrahydrophenanthrene-2-yl)benzonitrile,
2-fluoro-4-(8-fluoro-trans-7-butyl-5,6,7,8-tetrahydrophenanthrene-2-yl)benzonitrile,
4-(8-fluoro-trans-7-butyl-5,6,7,8-tetrahydrophenanthrene-2-yl)benzonitrile,
2-fluoro-4-(8-fluoro-trans-7-pentyl-5,6,7,8-tetrahydrophenanthrene-2-yl)benzonitrile,
4-(8-fluoro-trans-7-pentyl-5,6,7,8-tetrahydrophenanthrene-2-yl)benzonitrile,
2-fluoro-4-(8-fluoro-trans-7-hexyl-5,6,7,8-tetrahydrophenanthrene-2-yl)benzonitrile,
4-(8-fluoro-trans-7-hexyl-5,6,7,8-tetrahydrophenanthrene-2-yl)benzonitrile,
2-fluoro-4-(8-fluoro-trans-7-heptyl-5,6,7,8-tetrahydrophenanthrene-2-yl)benzonitrile,
4-(8-fluoro-trans-7-heptyl-5,6,7,8-tetrahydrophenanthrene-2-yl)benzonitrile, 2-fluoro-4-(6-fluoro-trans-7-propyl-5,6,7,8-tetrahydro-phenanthrene-2-yl)benzonitrile,
4-(6-fluoro-trans-7-propyl-5,6,7,8-tetrahydrophenanthrene-2-yl)benzonitrile,
2-fluoro-4-(6-fluoro-trans-7-ethyl-5,6,7,8-tetrahydro-phenanthrene-2-yl)benzonitrile,
4-(6-fluoro-trans-7-ethyl-5,6,7,8-tetrahydrophenanthrene-2-yl)benzonitrile,
2-fluoro-4-(6-fluoro-trans-7-butyl-5,6,7,8-tetrahydro-phenanthrene-2-yl)benzonitrile,
4-(6-fluoro-trans-7-butyl-5,6,7,8-tetrahydrophenanthrene-2-yl)benzonitrile,
2-fluoro-4-(6-fluoro-trans-7-pentyl-5,6,7,8-tetrahydro-phenanthrene-2-yl)benzonitrile,
4-(6-fluoro-trans-7-pentyl-5,6,7,8-tetrahydrophenanthrene-2-yl)benzonitrile,
2-fluoro-4-(6-fluoro-trans-7-hexyl-5,6,7,8-tetrahydro-phenanthrene-2-yl)benzonitrile,
4-(6-fluoro-trans-7-hexyl-5,6,7,8-tetrahydrophenanthrene-2-yl)benzonitrile,
2-fluoro-4-(6-fluoro-trans-7-heptyl-5,6,7,8-tetrahydro-phenanthrene-2-yl)benzonitrile,
4-(6-fluoro-trans-7-heptyl-5,6,7,8-tetrahydrophenanthrene-2-yl)benzonitrile,
4-(6,8-difluoro-trans-7-propyl-5,6,7,8-tetrahydrophenan-threne-2-yl)benzonitrile,
2-fluoro-4-(6,8-difluoro-trans-7-propyl-5,6,7,8-tetrahydro-phenanthrene-2-yl)benzonitrile,
2-fluoro-4-(6,8-difluoro-trans-7-ethyl-5,6,7,8-tetrahydro-phenanthrene-2-yl)benzonitrile,
4-(6,8-difluoro-trans-7-ethyl-5,6,7,8-tetrahydrophenan-threne-2-yl)benzonitrile,
2-fluoro-4-(6,8-difluoro-trans-7-butyl-5,6,7,8-tetrahydro-phenanthrene-2-yl)benzonitrile,
4-(6,8-difluoro-trans-7-butyl-5,6,7,8-tetrahydrophenan-threne-2-yl)benzonitrile,
2-fluoro-4-(6,8-difluoro-trans-7-pentyl-5,6,7,8-tetrahydro-phenanthrene-2-yl)benzonitrile,
4-(6,8-difluoro-trans-7-pentyl-5,6,7,8-tetrahydrophenan-threne-2-yl)benzonitrile,
2-fluoro-4-(6,8-difluoro-trans-7-hexyl-5,6,7,8-tetrahydro-phenanthrene-2-yl)benzonitrile,
4-(6,8-difluoro-trans-7-hexyl-5,6,7,8-tetrahydrophenan-threne-2-yl)benzonitrile,
2-fluoro-4-(6,8-difluoro-trans-7-heptyl-5,6,7,8-tetrahydro-phenanthrene-2-yl)benzonitrile, and
4-(6,8-difluoro-trans-7-heptyl-5,6,7,8-tetrahydrophenan-threne-2-yl)benzonitrile.

Example 31

Synthesis of trans-7-propyl-3,4,5,6,7,8-tetrahydro-1H-phenanthren-2-one

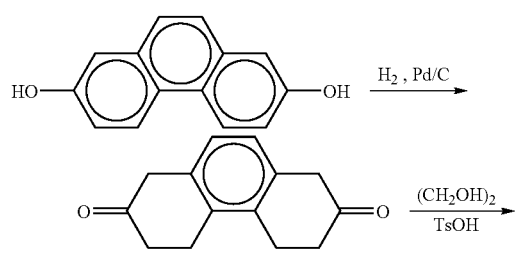

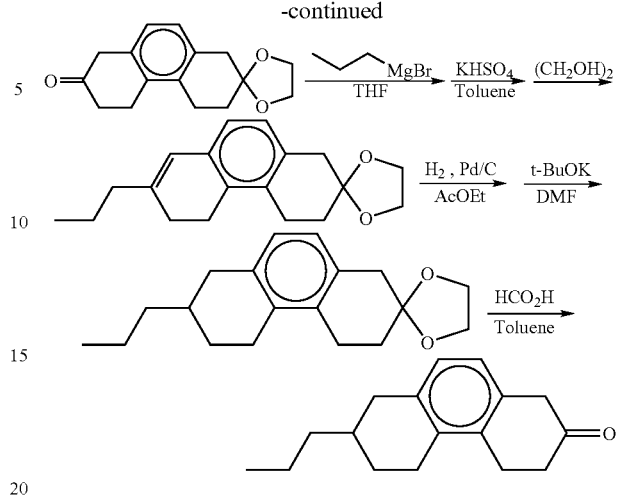

Phenanthren-2,7-diol was reduced with hydrogen in the presence of a 5% palladium-carbon (wet) catalyst, and then oxidized using a mixture of chromium trioxide, sulfuric acid and water to yield 1,3,4,5,6,8-hexahydrophenanthren-2,7-dione. One of the carbonyl groups of this compound was protected with an ethylene glycol, and the compound was then reacted with propylmagnesium bromide, dehydrated in the presence of an acid catalyst, and the partially deprotected group reformed to yield 7-propyl-3,4,5,6-tetrahydro-1H-phenanthren-2-one ethylene acetal. This compound was then reduced with hydrogen in the presence of a 5% palladium-carbon (wet) catalyst, and then isomerized using potassium-t-butoxide in DMF to yield trans-7-propyl-3,4,5,6,7,8-tetrahydro-1H-phenanthren-2-one. This compound was reacted in the same manner as that described in Example 17 to Example 22, and yielded the compounds listed below.

trans-2-propyl-trans-7-(4-fluorophenyl)-1,2,3,4,5,6,7,8-octahydrophenanthrene,
trans-2-propyl-trans-7-(3,4-difluorophenyl)-1,2,3,4,5,6,7,8-octahydrophenanthrene,
trans-2-propyl-trans-7-(3,5-difluorophenyl)-1,2,3,4,5,6,7,8-octahydrophenanthrene,
trans-2-propyl-trans-7-(3,4,5-trifluorophenyl)-1,2,3,4,5,6,7,8-octahydrophenanthrene,
trans-2-propyl-trans-7-(4-trifluoromethoxyphenyl)-1,2,3,4,5,6,7,8-octahydrophenanthrene,
trans-2-propyl-trans-7-(3-fluoro-4-trifluoromethoxyphenyl)-1,2,3,4,5,6,7,8-octahydrophenanthrene,
trans-2-propyl-trans-7-(3,5-difluoro-4-trifluoromethoxyphenyl)-1,2,3,4,5,6,7,8-octahydrophenanthrene,
trans-2-propyl-trans-7-(4-difluoromethoxyphenyl)-1,2,3,4,5,6,7,8-octahydrophenanthrene,
trans-2-propyl-trans-7-(4-trifluoromethylphenyl)-1,2,3,4,5,6,7,8-octahydrophenanthrene,
trans-2-propyl-trans-7-(3-fluoro-4-trifluoromethylphenyl)-1,2,3,4,5,6,7,8-octahydrophenanthrene,
trans-2-propyl-trans-7-(3,5-difluoro-4-trifluoromethylphenyl)-1,2,3,4,5,6,7,8-octahydrophenanthrene,
trans-2-propyl-trans-7-(4-chlorophenyl)-1,2,3,4,5,6,7,8-octahydrophenanthrene,
trans-2-propyl-trans-7-(3-fluoro-4-chlorophenyl)-1,2,3,4,5,6,7,8-octahydrophenanthrene,
trans-2-propyl-trans-7-(3,5-difluoro-4-chlorophenyl)-1,2,3,4,5,6,7,8-octahydrophenanthrene,
trans-2-propyl-trans-7-[2-(4-fluorophenyl)ethyl]-1,2,3,4,5,6,7,8-octahydrophenanthrene, trans-2-propyl-trans-7-[2-(3,4-difluorophenyl)ethyl]-1,2,3,
4,5,6,7,8-octahydrophenanthrene,
trans-2-propyl-trans-7-[2-(3,5-difluorophenyl)ethyl]-1,2,3,
4,5,6,7,8-octahydrophenanthrene,
trans-2-propyl-trans-7-[2-(3,4,5-trifluorophenyl)ethyl]-1,2,
3,4,5,6,7,8-octahydrophenanthrene,
trans-2-propyl-trans-7-[2-(4-trifluoromethoxyphenyl)
ethyl]-1,2,3,4,5,6,7,8-octahydrophenanthrene,
trans-2-propyl-trans-7-[2-(3-fluoro-4-trifluoromethoxyphe-
nyl)ethyl]-1,2,3,4,5,6,7,8-octahydrophenanthrene,
trans-2-propyl-trans-7-[2-(3,5-difluoro-4-trifluoromethox-
yphenyl)ethyl]-1,2,3,4,5,6,7,8-octahydrophenanthrene,
trans-2-propyl-trans-7-[2-(4-difluoromethoxyphenyl)ethyl]-
1,2,3,4,5,6,7,8-octahydrophenanthrene,
trans-2-propyl-trans-7-[2-(4-trifluoromethylphenyl)ethyl]-
1,2,3,4,5,6,7,8-octahydrophenanthrene,
trans-2-propyl-trans-7-[2-(3-fluoro-4-trifluoromethylphe-
nyl)ethyl]-1,2,3,4,5,6,7,8-octahydrophenanthrene,
trans-2-propyl-trans-7-[2-(3,5-difluoro-4-trifluorometh-
ylphenyl)ethyl]-1,2,3,4,5,6,7,8-octahydrophenanthrene,
trans-2-propyl-trans-7-[2-(4-chlorophenyl)ethyl]-1,2,3,4,5,
6,7,8-octahydrophenanthrene,
trans-2-propyl-trans-7-[2-(3-fluoro-4-chlorophenyl)ethyl]-
1,2,3,4,5,6,7,8-octahydrophenanthrene,
trans-2-propyl-trans-7-[2-(3,5-difluoro-4-chlorophenyl)
ethyl]-1,2,3,4,5,6,7,8-octahydrophenanthrene,
2-fluoro-4-(trans-7-propyl-1,2,3,4,5,6,7,8-octahydro-
phenanthrene-trans-2-yl)benzonitrile,
4-(trans-7-propyl-1,2,3,4,5,6,7,8-octahydrophenanthrene-
trans-2-yl)benzonitrile,
2-fluoro-4-(trans-7-ethyl-1,2,3,4,5,6,7,8-octahydrophenan-
threne-trans-2-yl)benzonitrile,
4-(trans-7-ethyl-1,2,3,4,5,6,7,8-octahydrophenanthrene-
trans-2-yl)benzonitrile,
2-fluoro-4-(trans-7-butyl-1,2,3,4,5,6,7,8-octahydrophenan-
threne-trans-2-yl)benzonitrile,
4-(trans-7-butyl-1,2,3,4,5,6,7,8-octahydrophenanthrene-
trans-2-yl)benzonitrile,
2-fluoro-4-(trans-7-pentyl-1,2,3,4,5,6,7,8-octahydro-
phenanthrene-trans-2-yl)benzonitrile,
4-(trans-7-pentyl-1,2,3,4,5,6,7,8-octahydrophenanthrene-
trans-2-yl)benzonitrile,
2-fluoro-4-(trans-7-hexyl-1,2,3,4,5,6,7,8-octahydrophenan-
threne-trans-2-yl)benzonitrile,
4-(trans-7-hexyl-1,2,3,4,5,6,7,8-octahydrophenanthrene-
trans-2-yl)benzonitrile,
2-fluoro-4-(trans-7-heptyl-1,2,3,4,5,6,7,8-octahydro-
phenanthrene-trans-2-yl)benzonitrile,
4-(trans-7-heptyl-1,2,3,4,5,6,7,8-octahydrophenanthrene-
trans-2-yl)benzonitrile,
2,5-difluoro-4-(trans-7-ethyl-1,2,3,4,5,6,7,8-octahydro-
phenanthrene-trans-2-yl)benzonitrile,
2,5-difluoro-4-(trans-7-propyl-1,2,3,4,5,6,7,8-octahydro-
phenanthrene-trans-2-yl)benzonitrile,
2,5-difluoro-4-(trans-7-butyl-1,2,3,4,5,6,7,8-octahydro-
phenanthrene-trans-2-yl)benzonitrile,
2,5-difluoro-4-(trans-7-pentyl-1,2,3,4,5,6,7,8-octahydro-
phenanthrene-trans-2-yl)benzonitrile,
2,5-difluoro-4-(trans-7-hexyl-1,2,3,4,5,6,7,8-octahydro-
phenanthrene-trans-2-yl)benzonitrile,
2,5-difluoro-4-(trans-7-heptyl-1,2,3,4,5,6,7,8-octahydro-
phenanthrene-trans-2-yl)benzonitrile,
4-cyanophenyl trans-7-propyl-1,2,3,4,5,6,7,8-octahydro-
phenanthrene-2-carboxylate,
4-cyano-3,5-difluorophenyl trans-7-propyl-1,2,3,4,5,6,7,8-
octahydrophenanthrene-2-carboxylate,
4-cyanophenyl trans-7-ethyl-1,2,3,4,5,6,7,8-octahydro-
phenanthrene-2-carboxylate,
4-cyano-3-fluorophenyl trans-7-ethyl-1,2,3,4,5,6,7,8-oc-
tahydrophenanthrene-2-carboxylate,
4-cyano-3,5-difluorophenyl trans-7-ethyl-1,2,3,4,5,6,7,8-
octahydrophenanthrene-2-carboxylate,
4-cyanophenyl trans-7-butyl-1,2,3,4,5,6,7,8-octahydro-
phenanthrene-2-carboxylate,
4-cyano-3-fluorophenyl trans-7-butyl-1,2,3,4,5,6,7,8-oc-
tahydrophenanthrene-2-carboxylate,
4-cyano-3,5-difluorophenyl trans-7-butyl-1,2,3,4,5,6,7,8-
octahydrophenanthrene-2-carboxylate,
4-cyanophenyl trans-7-pentyl-1,2,3,4,5,6,7,8-octahydro-
phenanthrene-2-carboxylate,
4-cyano-3-fluorophenyl trans-7-pentyl-1,2,3,4,5,6,7,8-oc-
tahydrophenanthrene-2-carboxylate,
4-cyano-3,5-difluorophenyl trans-7-pentyl-1,2,3,4,5,6,7,8-
octahydrophenanthrene-2-carboxylate,
4-cyanophenyl trans-7-pentyl-1,2,3,4,5,6,7,8-octahydro-
phenanthrene-2-carboxylate,
4-cyano-3-fluorophenyl trans-7-pentyl-1,2,3,4,5,6,7,8-oc-
tahydrophenanthrene-2-carboxylate,
4-cyano-3,5-difluorophenyl trans-7-pentyl-1,2,3,4,5,6,7,8-
octahydrophenanthrene-2-carboxylate,
4-cyanophenyl trans-7-heptyl-1,2,3,4,5,6,7,8-octahydro-
phenanthrene-2-carboxylate,
4-cyano-3-fluorophenyl trans-7-heptyl-1,2,3,4,5,6,7,8-oc-
tahydrophenanthrene-2-carboxylate,
4-cyano-3,5-difluorophenyl trans-7-heptyl-1,2,3,4,5,6,7,8-
octahydrophenanthrene-2-carboxylate,
trans-2-(4-fluorophenyl)-trans-7-vinyl-trans-tetrahydro-
phenanthrene,
trans-2-(3,4-difluorophenyl)-trans-7-vinyl-trans-tetrahydro-
phenanthrene,
trans-2-(3,5-difluorophenyl)-trans-7-vinyl-trans-tetrahydro-
phenanthrene,
trans-2-(4-trifluoromethoxyphenyl)-trans-7-vinyl-trans-tet-
rahydrophenanthrene,
trans-2-(3-fluoro-4-trifluoromethoxyphenyl)-trans-7-vinyl-
trans-tetrahydrophenanthrene,
trans-2-(3,5-difluoro-4-trifluoromethoxyphenyl)-trans-7-vi-
nyl-trans-tetrahydrophenanthrene,
trans-2-(4-difluoromethoxyphenyl)-trans-7-vinyl-trans-tet-
rahydrophenanthrene,
trans-2-(4-trifluoromethylphenyl)-trans-7-vinyl-trans-tet-
rahydrophenanthrene,
trans-2-(3-fluoro-4-trifluoromethylphenyl)-trans-7-vinyl-
trans-tetrahydrophenanthrene,
trans-2-(3,5-difluoro-4-trifluoromethylphenyl)-trans-7-vi-
nyl-trans-tetrahydrophenanthrene,
trans-2-(4-chlorophenyl)-trans-7-vinyl-trans-tetrahydro-
phenanthrene,
trans-2-(3-fluoro-4-chlorophenyl)-trans-7-vinyl-trans-tet-
rahydrophenanthrene,
trans-2-(3,5-difluoro-4-chlorophenyl)-trans-7-vinyl-trans-
tetrahydrophenanthrene,
trans-2-(trans-1-propenyl)-7-(4-fluorophenyl)-1,2,3,4,5,6,7,
8-octahydrophenanthrene,
trans-2-(trans-1-propenyl)-7-(3,4-difluorophenyl)-1,2,3,4,5,
6,7,8-octahydrophenanthrene,
trans-2-(trans-1-propenyl)-7-(3,5-difluorophenyl)-trans-1,2,
3,4,5,6,7,8-octahydrophenanthrene,
trans-2-(trans-1-propenyl)-7-(3,4,5-trifluorophenyl)-1,2,3,4,
5,6,7,8-octahydrophenanthrene,
trans-2-(trans-1-propenyl)-7-(4-trifluoromethoxyphenyl)-1,
2,3,4,5,6,7,8-octahydrophenanthrene, trans-2-(trans-1-propenyl)-7-(3-fluoro-4-trifluoromethoxyphenyl)-1,2,3,4,5,6,7,8-octahydrophenanthrene,
trans-2-(trans-1-propenyl)-7-(3,5-difluoro-4-trifluoromethoxyphenyl)-1,2,3,4,5,6,7,8-octahydrophenanthrene,
trans-2-(trans-1-propenyl)-7-(4-difluoromethoxyphenyl)-1,2,3,4,5,6,7,8-octahydrophenanthrene,
trans-2-(trans-1-propenyl)-7-(4-trifluoromethylphenyl)-1,2,3,4,5,6,7,8-octahydrophenanthrene,
trans-2-(trans-1-propenyl)-7-(3-fluoro-4-trifluoromethylphenyl)-1,2,3,4,5,6,7,8-octahydrophenanthrene,
trans-2-(trans-1-propenyl)-7-(3,5-difluoro-4-trifluoromethylphenyl)-1,2,3,4,5,6,7,8-octahydrophenanthrene,
trans-2-(trans-1-propenyl)-7-(4-chlorophenyl)-1,2,3,4,5,6,7,8-octahydrophenanthrene,
trans-2-(trans-1-propenyl)-7-(3-fluoro-4-chlorophenyl)-1,2,3,4,5,6,7,8-octahydrophenanthrene,
trans-2-(trans-1-propenyl)-7-(3,5-difluoro-4-chlorophenyl)-1,2,3,4,5,6,7,8-octahydrophenanthrene,
trans-2-(trans-1-butenyl)-7-(4-fluorophenyl)-1,2,3,4,5,6,7,8-octahydrophenanthrene,
trans-2-(trans-1-butenyl)-7-(3,4-difluorophenyl)-1,2,3,4,5,6,7,8-octahydrophenanthrene,
trans-2-(trans-1-butenyl)-7-(3,5-difluorophenyl)-trans-1,2,3,4,5,6,7,8-octahydrophenanthrene,
trans-2-(trans-1-butenyl)-7-(3,4,5-trifluorophenyl)-1,2,3,4,5,6,7,8-octahydrophenanthrene,
trans-2-(trans-1-butenyl)-7-(4-trifluoromethoxyphenyl)-1,2,3,4,5,6,7,8-octahydrophenanthrene,
trans-2-(trans-1-butenyl)-7-(3-fluoro-4-trifluoromethoxyphenyl)-1,2,3,4,5,6,7,8-octahydrophenanthrene,
trans-2-(trans-1-butenyl)-7-(3,5-difluoro-4-trifluoromethoxyphenyl)-1,2,3,4,5,6,7,8-octahydrophenanthrene,
trans-2-(trans-1-butenyl)-7-(4-difluoromethoxyphenyl)-1,2,3,4,5,6,7,8-octahydrophenanthrene,
trans-2-(trans-1-butenyl)-7-(4-trifluoromethylphenyl)-1,2,3,4,5,6,7,8-octahydrophenanthrene,
trans-2-(trans-1-butenyl)-7-(3-fluoro-4-trifluoromethylphenyl)-1,2,3,4,5,6,7,8-octahydrophenanthrene,
trans-2-(trans-1-butenyl)-7-(3,5-difluoro-4-trifluoromethylphenyl)-1,2,3,4,5,6,7,8-octahydrophenanthrene,
trans-2-(trans-1-butenyl)-7-(4-chlorophenyl)-1,2,3,4,5,6,7,8-octahydrophenanthrene,
trans-2-(trans-1-butenyl)-7-(3-fluoro-4-chlorophenyl)-1,2,3,4,5,6,7,8-octahydrophenanthrene,
trans-2-(trans-1-butenyl)-7-(3,5-difluoro-4-chlorophenyl)-1,2,3,4,5,6,7,8-octahydrophenanthrene,
trans-2-(trans-1-pentenyl)-7-(4-fluorophenyl)-1,2,3,4,5,6,7,8-octahydrophenanthrene,
trans-2-(trans-1-pentenyl)-7-(3,4-difluorophenyl)-1,2,3,4,5,6,7,8-octahydrophenanthrene,
trans-2-(trans-1-pentenyl)-7-(3,5-difluorophenyl)-trans-1,2,3,4,5,6,7,8-octahydrophenanthrene,
trans-2-(trans-1-pentenyl)-7-(3,4,5-trifluorophenyl)-1,2,3,4,5,6,7,8-octahydrophenanthrene,
trans-2-(trans-1-pentenyl)-7-(4-trifluoromethoxyphenyl)-1,2,3,4,5,6,7,8-octahydrophenanthrene,
trans-2-(trans-1-pentenyl)-7-(3-fluoro-4-trifluoromethoxyphenyl)-1,2,3,4,5,6,7,8-octahydrophenanthrene,
trans-2-(trans-1-pentenyl)-7-(3,5-difluoro-4-trifluoromethoxyphenyl)-1,2,3,4,5,6,7,8-octahydrophenanthrene,
trans-2-(trans-1-pentenyl)-7-(4-difluoromethoxyphenyl)-1,2,3,4,5,6,7,8-octahydrophenanthrene,
trans-2-(trans-1-pentenyl)-7-(4-trifluoromethylphenyl)-1,2,3,4,5,6,7,8-octahydrophenanthrene,
trans-2-(trans-1-pentenyl)-7-(3-fluoro-4-trifluoromethylphenyl)-1,2,3,4,5,6,7,8-octahydrophenanthrene,
trans-2-(trans-1-pentenyl)-7-(3,5-difluoro-4-trifluoromethylphenyl)-1,2,3,4,5,6,7,8-octahydrophenanthrene,
trans-2-(trans-1-pentenyl)-7-(4-chlorophenyl)-1,2,3,4,5,6,7,8-octahydrophenanthrene,
trans-2-(trans-1-pentenyl)-7-(3-fluoro-4-chlorophenyl)-1,2,3,4,5,6,7,8-octahydrophenanthrene,
trans-2-(trans-1-pentenyl)-7-(3,5-difluoro-4-chlorophenyl)-1,2,3,4,5,6,7,8-octahydrophenanthrene,
trans-2-(trans-3-pentenyl)-7-(4-fluorophenyl)-1,2,3,4,5,6,7,8-octahydrophenanthrene,
trans-2-(trans-3-pentenyl)-7-(3,4-difluorophenyl)-1,2,3,4,5,6,7,8-octahydrophenanthrene,
trans-2-(trans-3-pentenyl)-7-(3,5-difluorophenyl)-trans-1,2,3,4,5,6,7,8-octahydrophenanthrene,
trans-2-(trans-3-pentenyl)-7-(3,4,5-trifluorophenyl)-1,2,3,4,5,6,7,8-octahydrophenanthrene,
trans-2-(trans-3-pentenyl)-7-(4-trifluoromethoxyphenyl)-1,2,3,4,5,6,7,8-octahydrophenanthrene,
trans-2-(trans-3-pentenyl)-7-(3-fluoro-4-trifluoromethoxyphenyl)-1,2,3,4,5,6,7,8-octahydrophenanthrene,
trans-2-(trans-3-pentenyl)-7-(3,5-difluoro-4-trifluoromethoxyphenyl)-1,2,3,4,5,6,7,8-octahydrophenanthrene,
trans-2-(trans-3-pentenyl)-7-(4-difluoromethoxyphenyl)-1,2,3,4,5,6,7,8-octahydrophenanthrene,
trans-2-(trans-3-pentenyl)-7-(4-trifluoromethylphenyl)-1,2,3,4,5,6,7,8-octahydrophenanthrene,
trans-2-(trans-3-pentenyl)-7-(3-fluoro-4-trifluoromethylphenyl)-1,2,3,4,5,6,7,8-octahydrophenanthrene,
trans-2-(trans-3-pentenyl)-7-(3,5-difluoro-4-trifluoromethylphenyl)-1,2,3,4,5,6,7,8-octahydrophenanthrene,
trans-2-(trans-3-pentenyl)-7-(4-chlorophenyl)-1,2,3,4,5,6,7,8-octahydrophenanthrene,
trans-2-(trans-3-pentenyl)-7-(3-fluoro-4-chlorophenyl)-1,2,3,4,5,6,7,8-octahydrophenanthrene,
trans-2-(trans-3-pentenyl)-7-(3,5-difluoro-4-chlorophenyl)-1,2,3,4,5,6,7,8-octahydrophenanthrene,
trans-2-(3-butenyl)-7-(4-fluorophenyl)-1,2,3,4,5,6,7,8-octahydrophenanthrene,
trans-2-(3-butenyl)-7-(3,4-difluorophenyl)-1,2,3,4,5,6,7,8-octahydrophenanthrene,
trans-2-(3-butenyl)-7-(3,5-difluorophenyl)-trans-1,2,3,4,5,6,7,8-octahydrophenanthrene,
trans-2-(3-butenyl)-7-(3,4,5-trifluorophenyl)-1,2,3,4,5,6,7,8-octahydrophenanthrene,
trans-2-(3-butenyl)-7-(4-trifluoromethoxyphenyl)-1,2,3,4,5,6,7,8-octahydrophenanthrene,
trans-2-(3-butenyl)-7-(3-fluoro-4-trifluoromethoxyphenyl)-1,2,3,4,5,6,7,8-octahydrophenanthrene,
trans-2-(3-butenyl)-7-(3,5-difluoro-4-trifluoromethoxyphenyl)-1,2,3,4,5,6,7,8-octahydrophenanthrene,
trans-2-(3-butenyl)-7-(4-difluoromethoxyphenyl)-1,2,3,4,5,6,7,8-octahydrophenanthrene,
trans-2-(3-butenyl)-7-(4-trifluoromethylphenyl)-1,2,3,4,5,6,7,8-octahydrophenanthrene,
trans-2-(3-butenyl)-7-(3-fluoro-4-trifluoromethylphenyl)-1,2,3,4,5,6,7,8-octahydrophenanthrene,
trans-2-(3-butenyl)-7-(3,5-difluoro-4-trifluoromethylphenyl)-1,2,3,4,5,6,7,8-octahydrophenanthrene,
trans-2-(3-butenyl)-7-(4-chlorophenyl)-1,2,3,4,5,6,7,8-octahydrophenanthrene,
trans-2-(3-butenyl)-7-(3-fluoro-4-chlorophenyl)-1,2,3,4,5,6,7,8-octahydrophenanthrene, and
trans-2-(3-butenyl)-7-(3,5-difluoro-4-chlorophenyl)-1,2,3,4,5,6,7,8-octahydrophenanthrene.

Example 32

Synthesis of 2-(4-methylphenyl)-7-(n-propyl)-4aα, 4bβ,8aα,8bβ-tetradecahydrophenanthrene (II-A1)

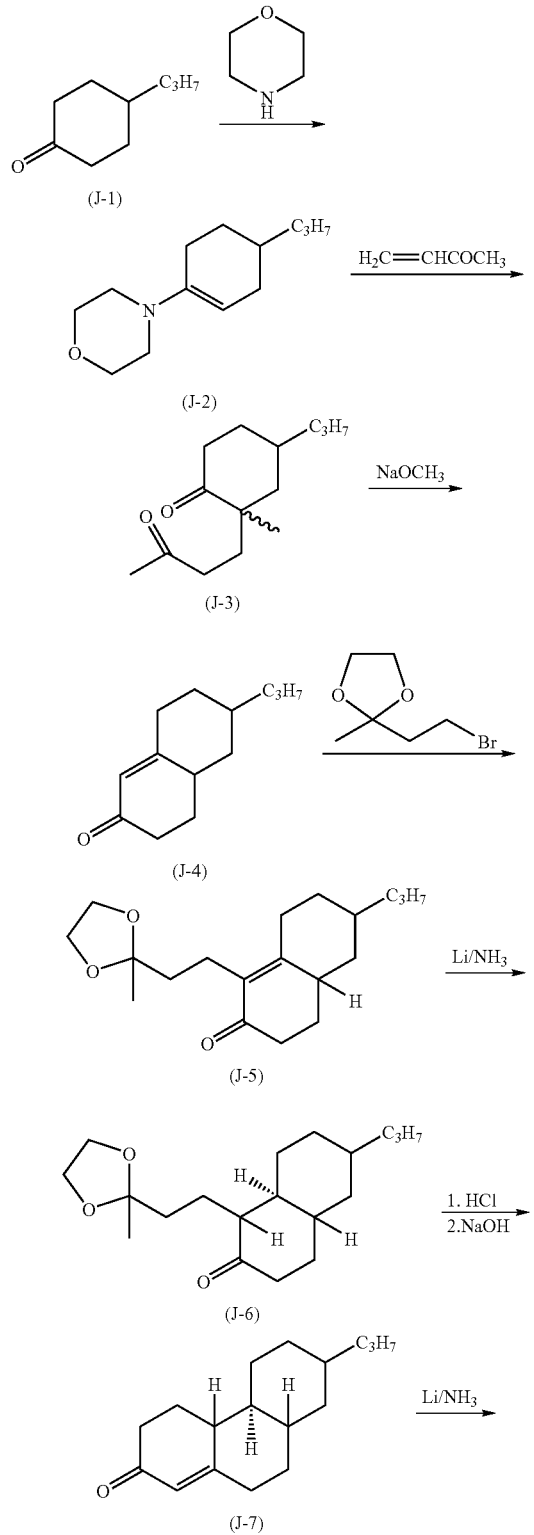

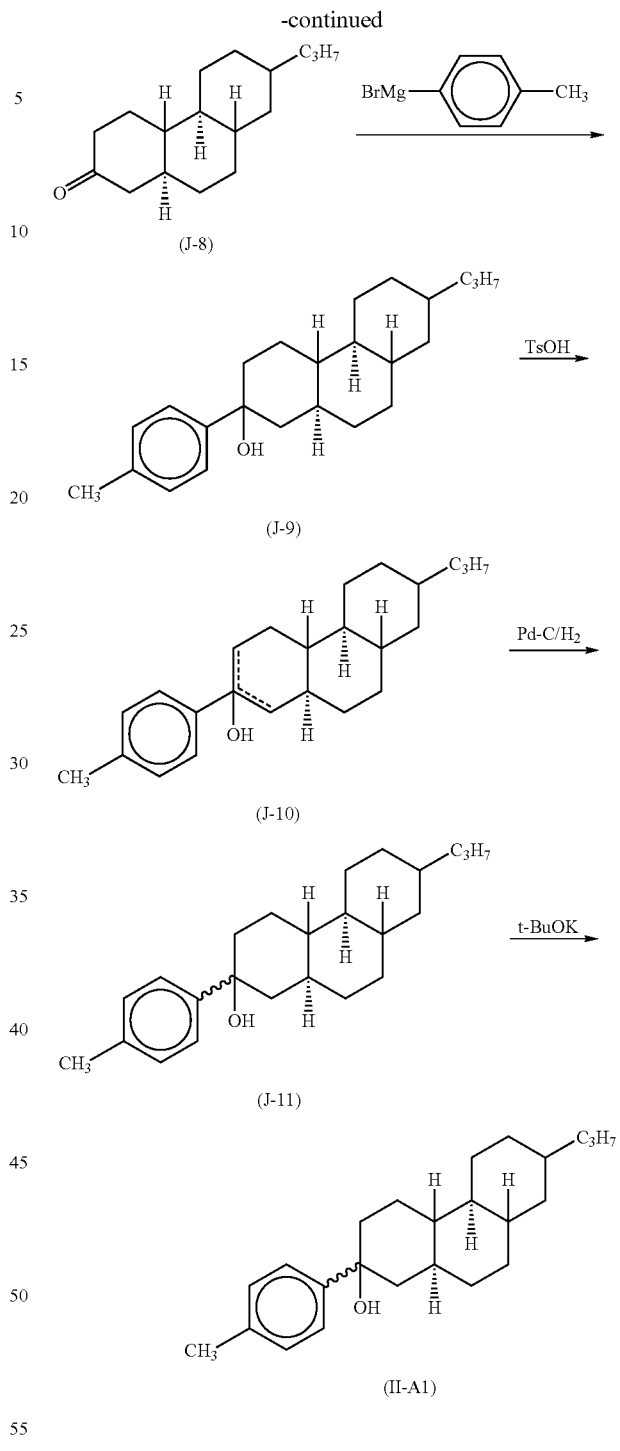

(1) Synthesis of 1-morpholine-4-n-propyl-1-cyclohexene (J-2)

A mixture of 44.9 g of 4-n-propylcyclohexanone (J-1), 33.2 g of morpholine and 0.32 g of p-toluenesulfonic acid was dissolved in 200 ml of toluene, and then using a water removal device, was refluxed under heat until water ceased to be produced, and the resulting product was vacuum distilled to yield 61.4 g of the enamine (J-2).

(2) Synthesis of 4-n-propyl-2-(3-oxobutyl)cyclohexanone (J-3)

29.3 g of the enamine (J-2) and 20 ml of 3-buten-2-one were dissolved in 150 ml of toluene, and then reacted for 4 hours at 100° C. The solution was then treated with 6N hydrochloric acid, washed with water, and dried, before being purified by silica gel chromatography (hexane:methylene chloride=1:1) to yield 21.5 g of the cyclohexanone (J-3).

(3) Synthesis of 6-n-propyl-4,4a,5,6,7,8-hexahydro-2 (3H)-naphthalenone (J-4)

21.5 g of the cyclohexanone (J-3) was dissolved in 250 ml of methanol, a sodium methoxide solution (4.6 g of sodium in 250 ml of methanol) was added, and the mixture was then refluxed under heat, under an atmosphere of nitrogen for 90 minutes. Following neutralization with hydrochloric acid, the methanol was removed by evaporation and the product extracted into toluene. The toluene extract was washed with water and dried, and then purified by silica gel chromatography (hexane:methylene chloride=1:1) to yield 13.7 g of the naphthalenone (J-4).

(4) Synthesis of 6-n-propyl-4,4a,5,6,7,8-hexahydro-1-[2-(2-methyl-1,3-dioxolan-2-yl)ethyl]-2 (3H)-naphthalenone (J-5)

Under an atmosphere of nitrogen, 2.2 g of sodium hydride (55% dispersion) was dispersed in 100 ml of dry dimethyl sulfoxide (DMSO) and was then heated for one hour at 65° C. The temperature was returned to room temperature, and a solution of 9.6 g of the naphthalenone (J-4) in DMSO (100 ml) was added, and the solution stirred for one hour. A solution of 9.8 g of 2-(2-bromomethyl)-2-methyl-1,3-dioxolane in DMSO (50 ml) was then added, and the resulting mixture was stirred for 19 hours. 250 ml of a saturated aqueous solution of ammonium chloride was added at 0° C., and the product was then extracted into toluene, dried, and purified by silica gel chromatography (hexane:methylene chloride=1:1) to yield 8.4 g of the naphthalenone (J-5).

(5) Synthesis of 6-n-propyloctahydro-1-[2-(2-methyl-1,3-dioxolan-2-yl)ethyl]-2 (1H)-naphthalenone (J-6)

A tetrahydrofuran (THF) solution (80 ml) of 6.2 g of the naphthalenone (J-5) was added dropwise to a liquid ammonia solution (approximately 600 ml) comprising 0.8 g of lithium. Following stirring for 90 minutes, 8.0 g of ammonium chloride was added, the ammonia was removed by evaporation, and the product was extracted into methylene chloride. The crude product was purified by silica gel chromatography (hexane:methylene chloride=1:1) to yield 3.7 g of the naphthalenone (J-6).

(6) Synthesis of 7-n-propyl-4,4a,4b,5,6,7,8,8a,9,10-decahydro-2(3H)-phenanthrenone (J-7)

To a solution of 3.7 g of the naphthalenone (J-6) in 100 ml of toluene was added 10 ml of 6N hydrochloric acid, and the reaction was allowed to proceed for 2 hours at 80° C. The organic layer was separated, 3 ml of 1N aqueous sodium hydroxide was added, and then using a water removal device, was refluxed under heat until water ceased to be produced. The crude product was washed sequentially with a saturated aqueous solution of sodium bicarbonate and a saturated aqueous solution of sodium chloride, and following drying was purified by silica gel chromatography (hexane:methylene chloride=1:1) to yield 2.4 g of the phenanthrenone (J-7).

(7) Synthesis of 7-n-propyl-tetradecahydro-2-phenanthrenone (J-8)

A tetrahydrofuran (THF) solution (40 ml) of 2.4 g of the phenanthrenone (J-7) was added dropwise to a liquid ammonia solution (approximately 300 ml) comprising 0.4 g of lithium. Following stirring for 90 minutes, 4.0 g of ammonium chloride was added, the ammonia was removed by evaporation, and the product was extracted into methylene chloride. The crude product was purified by silica gel chromatography (hexane:methylene chloride=1:1) to yield 1.5 g of the phenanthrenone (J-8).

(8) Synthesis of 2-(4-methylphenyl)-7-n-propyl-tetradecahydro-2-phenanthrenol (J-9)

8 ml of a Grignard reagent (1 mol/l/THF) prepared from 1.20 g of p-tolylbromide and 0.20 g of magnesium was added dropwise over a period of one hour to a THF (20 ml) solution of 1.5 g of the phenanthrenone (J-8). The mixture was stirred for a further 2 hours, cooled to room temperature, and 10 ml of a 10% aqueous solution of hydrochloric acid was then added and stirred. The product was extracted into toluene, and then washed sequentially with a saturated aqueous solution of sodium bicarbonate and a saturated aqueous solution of sodium chloride. Following drying, the solvent was removed by evaporation to yield 2.1 g of the phenanthrenol (J-9). This product was used without purification in the subsequent reaction.

(9) Synthesis of 2-(4-methylphenyl)-7-n-propyl-4,4a,4b,5,6,7,8,8a,9,10-decahydro-(3H and/or 1H)-phenanthrene (J-10)

2.1 g of the phenanthrenol (J-9) (crude product) was dissolved in 30 ml of toluene, 0.1 g of paratoluenesulfonic acid monohydrate was added, and then using a water removal device, the mixture was refluxed under heat until water ceased to be produced. The temperature was then returned to room temperature and 10 ml of water was added. The organic layer was separated and washed sequentially with a saturated aqueous solution of sodium bicarbonate and a saturated aqueous solution of sodium chloride. Following drying, the solvent was removed by evaporation to yield 2.0 g of the phenanthrene (J-10) (crude product). This product was used without purification in the subsequent reaction.

(10) Synthesis of 2-(4-methylphenyl)-7-n-propyl-tetradecahydrophenanthrene (J-11)

A solution of 2.0 g of the phenanthrene (J-10) (crude product) in 30 ml of ethyl acetate and 3 g of 5% palladium-carbon (wet) were placed in an autoclave, and stirred for 5 hours at room temperature under a hydrogen pressure of 4 Kg/cm$^2$. Following removal of the catalyst by filtration through celite, the solvent was removed by evaporation to yield 2.0 g of the phenanthrene (J-11) (crude product). This product was used without purification in the subsequent reaction.

(11) Synthesis of 2-(4-methylphenyl)-7-n-propyl-4-aα,4bβ,8aα,8bβ-tetradecahydrophenanthrene (II-A1)

2.0 g of the phenanthrene (J-11) (crude product) was dissolved in 30 ml of dimethylformamide (DMF). 0.7 g of potassium t-butoxide was then added and the mixture was refluxed under heat for 5 hours. The reaction mixture was then cooled to room temperature, 10 ml of water was added, and the mixture was extracted with two 50 ml portions of toluene. The organic layers were combined, and then washed sequentially with 200 mL portions of a 10% aqueous solution of hydrochloric acid, a saturated aqueous solution of sodium bicarbonate, and a saturated aqueous solution of sodium chloride. Following drying, the solvent was removed by evaporation, and the crude product purified by silica gel chromatography (toluene) to 20 yield 1.0 g of 2-(4-methylphenyl)-7-n-propyl-4aα,4bβ,8aαa,8bβ-tetradecahydrophenanthrene (II-A1).

Example 33

Synthesis of trans-2-propyl-7-trifluoromethoxy-8-fluoro-trans-1,2,3,4,4a,9,10,10a-octahydrophenanthrene (I-A1)

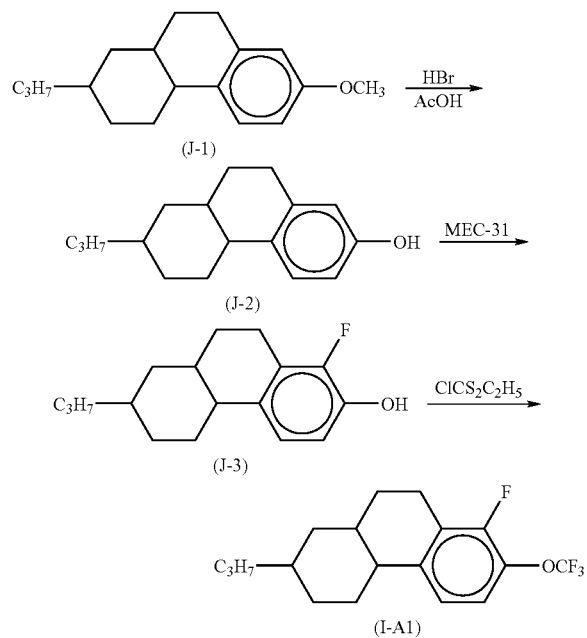

(1) Synthesis of trans-2-propyl-trans-4b,5,6,7,8,8a,9,10-octahydrophenanthren-7-ol (J-2)

A mixture of 20 g of 7-methoxy-trans-2-propyl-trans-1,2,3,4,4a,9,10,10a-octahydrophenanthrene (J-1) (synthesis of this compound was carried out using the method disclosed in D. Varech, L. Lacombe and J. Lacques, Nouv. J. Chim., 8, 445(1984)), 80 mL of acetic acid and 80 mL of 40% hydrobromic acid was refluxed under heat for 10 hours, and yielded 19.1 g of the octahydrophenanthren-2-ol (J-2).

(2) Synthesis of trans-1-fluoro-7-propyl-trans-4b,5,6,7,8,8a,9,10-octahydrophenanthren-2-ol (J-3)

12.2 g of the octahydrophenanthren-2-ol (J-2) was dissolved in 60 ml of methylene chloride, 0.9 g of sodium trifluoromethanesulfonate was added, and then with constant stirring, 10.7 g of MEC-31 was added in four separate portions at one hour intervals. Following subsequent stirring for 5 hours, 20 ml of water was added, the product was extracted into methylene chloride, and then washed sequentially with water and a saturated aqueous solution of sodium chloride, before being dried and the solvent removed by evaporation to yield 10.5 g of the compound (J-3). This product was used without purification in the subsequent reaction.

(3) Synthesis of trans-2-propyl-7-trifluoromethoxy-8-fluoro-trans-1,2,3,4,4a,9,10,10a-octahydrophenanthrene (I-A1)

A suspension was formed of 1.7 g of sodium hydride in 5 ml of tetrahydrofuran (THF), and a solution of 10.5 g of the compound (J-3) in 50 ml of THF was then added dropwise to the suspension. Following stirring for one hour, a solution of 8.1 g of S-ethyl chlorodithiocarbonate in 40 ml of THF was added dropwise to the reaction mixture. Following stirring for a further one hour, 20 ml of water was added and the mixture was extracted with 60 ml of ethyl acetate. The organic layer was washed with water, dried, and the solvent removed by evaporation to yield 12.5 g of S-ethyl-8-fluoro-2-propyl-trans-4b,5,6,7,8,8a,9,10-octahydrophenanthren-7-yl chlorodithiocarbonate. This compound was dissolved in 50 ml of methylene chloride, and then added dropwise to a cooled solution at 0° C. of 300 g of a hydrogen fluoride-melamine complex and 1,3-dibromo-5,5-dimethylhydantoin in 1 l of methylene chloride. Following stirring for 30 minutes, 200 ml of water was added, the organic layer was separated and washed with water, and following drying, the solvent was removed by evaporation to produce a reside, which was subsequently purified by silica gel chromatography (developing solvent: hexane). The purified product was dissolved in 50 ml of THF, and with the temperature at −78° C., 50 ml of a 1.6 M n-butyl lithium hexane solution was then added dropwise. Following stirring for 20 minutes, 10 ml of water was added, the organic layer was separated and washed with water, and following drying, the solvent was removed by evaporation to produce a reside, which was subsequently purified by silica gel chromatography (developing solvent: hexane/ethyl acetate=9/1), and then recrystallized from ethanol to yield 7.6 g of trans-2-propyl-7-trifluoromethoxy-8-fluoro-trans-1,2,3,4,4a,9,10,10a-octahydrophenanthrene (I-A1).

As follows is a description of specific examples of preferred compounds. In the description of these specific examples, the following abbreviations are used.

B10:

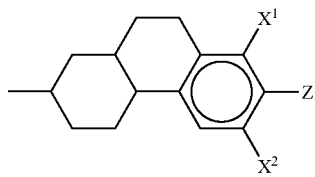

-continued
B20: 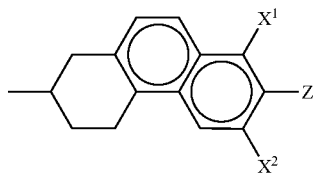
B21: 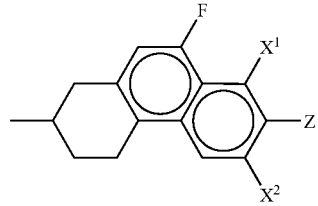
B30: 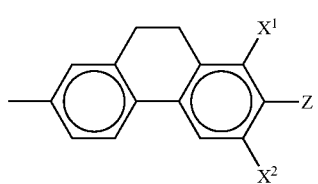
B31: 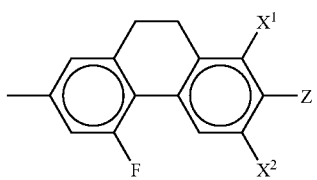
B40: 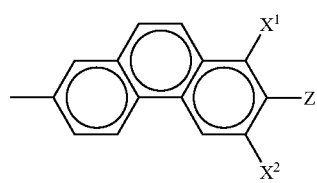
B41: 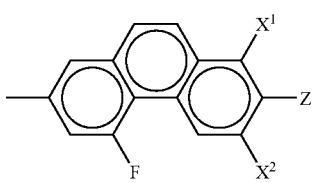
B42: 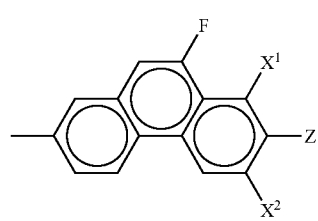
-continued
B43: 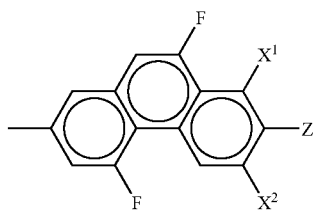
B50: 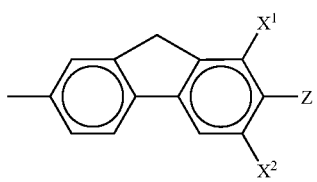
B51: 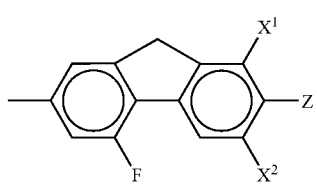
A10: 
A20: 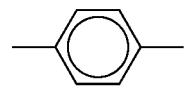
A30: 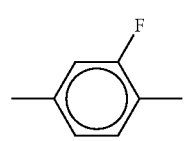
A40: 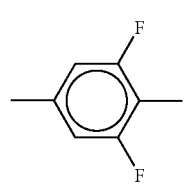

R: R0:CH₃
R02:Alky(C2–C5)
R03:CH₂=CH₂
R04:CH₂=CHCH₃
R05:CH₂CH=CH₂
R06:CH₂=CHCH₂CH₃
R07:CH₂CH=CHCH₃
R08:CH₂CH₂CH=CH₂
R09:CH₂=CHCH₂CH₂CH₃
R10:CH₂CH=CHCH₂CH₃
R11:CH₂CH₂CH=CHCH₃
R12:CH₂CH₂CH₂CH=CH₂

L: L10:CH₂CH₂

$X^1, X^2$: X00 = H
X10 = F

Z: Z00 = H
Z10 = F
Z20 = OCF₃
Z21 = OCHF₂
Z22 = OCH₂F
Z30 = CF₃
Z40 = CN

In the above, partial structures or accompanying items or symbols represent the same meaning as described in claim 1. Preferred compounds can be displayed by using combinations of the abbreviations for these partial structures. For example, the formula R05-A40-L10-B42-X10-X00-Z22 represents the compound shown below.

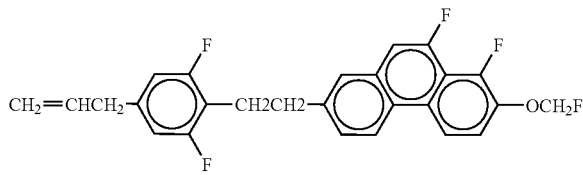

R05-A40-L10-B42-X10-X00-Z22

$X^1$, $X^2$ and Z are recorded in this order. Furthermore, the specific examples listed below represent only a portion of the possible sample compounds, and do not in any way limit the scope of the present invention.

| | | | |
|---|---|---|---|
| R02-B10-H-H-Z00 | R02-B10-H-H-Z10 | R02-B10-H-H-Z20 | R02-B10-H-H-Z30 |
| R02-B10-H-H-Z40 | R02-B10-H-F-Z00 | R02-B10-H-F-Z10 | R02-B10-H-F-Z20 |
| R02-B10-H-F-Z30 | R02-B10-H-F-Z40 | R02-B10-F-H-Z00 | R02-B10-F-H-Z10 |
| R02-B10-F-H-Z20 | R02-B10-F-H-Z30 | R02-B10-F-H-Z40 | R02-B10-F-H-Z40 |
| R02-B10-F-F-Z00 | R02-B10-F-F-Z10 | R02-B10-F-F-Z20 | R02-B10-F-F-Z30 |
| R02-B10-F-F-Z40 | R02-B20-H-H-Z00 | R02-B20-H-H-Z10 | R02-B20-H-H-Z20 |
| R02-B20-H-H-Z30 | R02-B20-H-H-Z40 | R02-B20-H-F-Z00 | R02-B20-H-F-Z10 |
| R02-B20-H-F-Z20 | R02-B20-H-F-Z30 | R02-B20-H-F-Z40 | R02-B20-F-H-Z00 |
| R02-B20-F-H-Z10 | R02-B20-F-H-Z20 | R02-B20-F-H-Z30 | R02-B20-F-H-Z40 |
| R02-B20-F-H-Z40 | R02-B20-F-F-Z00 | R02-B20-F-F-Z10 | R02-B20-F-F-Z20 |
| R02-B20-F-F-Z30 | R02-B20-F-F-Z40 | R02-B30-H-H-Z00 | R02-B30-H-H-Z10 |
| R02-B30-H-H-Z20 | R02-B30-H-H-Z30 | R02-B30-H-H-Z40 | R02-B30-H-F-Z00 |
| R02-B30-H-F-Z10 | R02-B30-H-F-Z20 | R02-B30-H-F-Z30 | R02-B30-H-F-Z40 |
| R02-B30-F-H-Z00 | R02-B30-F-H-Z10 | R02-B30-F-H-Z20 | R02-B30-F-H-Z30 |
| R02-B30-F-H-Z40 | R02-B30-F-H-Z40 | R02-B30-F-F-Z00 | R02-B30-F-F-Z10 |
| R02-B30-F-F-Z20 | R02-B30-F-F-Z30 | R02-B30-F-F-Z40 | R02-B40-H-H-Z00 |
| R02-B40-H-H-Z10 | R02-B40-H-H-Z20 | R02-B40-H-H-Z30 | R02-B40-H-H-Z40 |
| R02-B40-H-F-Z00 | R02-B40-H-F-Z10 | R02-B40-H-F-Z20 | R02-B40-H-F-Z30 |
| R02-B40-H-F-Z40 | R02-B40-F-H-Z00 | R02-B40-F-H-Z10 | R02-B40-F-H-Z20 |
| R02-B40-F-H-Z30 | R02-B40-F-H-Z40 | R02-B40-F-H-Z40 | R02-B40-F-F-Z00 |
| R02-B40-F-F-Z10 | R02-B40-F-F-Z20 | R02-B40-F-F-Z30 | R02-B40-F-F-Z40 |
| R02-B50-H-H-Z00 | R02-B50-H-H-Z10 | R02-B50-H-H-Z20 | R02-B50-H-H-Z30 |
| R02-B50-H-H-Z40 | R02-B50-H-F-Z00 | R02-B50-H-F-Z10 | R02-B50-H-F-Z20 |
| R02-B50-H-F-Z30 | R02-B50-H-F-Z40 | R02-B50-F-H-Z00 | R02-B50-F-H-Z10 |
| R02-B50-F-H-Z20 | R02-B50-F-H-Z30 | R02-B50-F-H-Z40 | R02-B50-F-H-Z40 |
| R02-B50-F-F-Z00 | R02-B50-F-F-Z10 | R02-B50-F-F-Z20 | R02-B50-F-F-Z30 |
| R02-B50-F-F-Z40 | | | |
| R03-B10-H-H-Z00 | R03-B10-H-H-Z10 | R03-B10-H-H-Z20 | R03-B10-H-H-Z30 |
| R03-B10-H-H-Z40 | R03-B10-H-F-Z00 | R03-B10-H-F-Z10 | R03-B10-H-F-Z20 |
| R03-B10-H-F-Z30 | R03-B10-H-F-Z40 | R03-B10-F-H-Z00 | R03-B10-F-H-Z10 |
| R03-B10-F-H-Z20 | R03-B10-F-H-Z30 | R03-B10-F-H-Z40 | R03-B10-F-H-Z40 |
| R03-B10-F-F-Z00 | R03-B10-F-F-Z10 | R03-B10-F-F-Z20 | R03-B10-F-F-Z30 |
| R03-B10-F-F-Z40 | R03-B20-H-H-Z00 | R03-B20-H-H-Z10 | R03-B20-H-H-Z20 |
| R03-B20-H-H-Z30 | R03-B20-H-H-Z40 | R03-B20-H-F-Z00 | R03-B20-H-F-Z10 |
| R03-B20-H-F-Z20 | R03-B20-H-F-Z30 | R03-B20-H-F-Z40 | R03-B20-F-H-Z00 |
| R03-B20-F-H-Z10 | R03-B20-F-H-Z20 | R03-B20-F-H-Z30 | R03-B20-F-H-Z40 |
| R03-B20-F-H-Z40 | R03-B20-F-F-Z00 | R03-B20-F-F-Z10 | R03-B20-F-F-Z20 |
| R03-B20-F-F-Z30 | R03-B20-F-F-Z40 | R03-B30-H-H-Z00 | R03-B30-H-H-Z10 |
| R03-B30-H-H-Z20 | R03-B30-H-H-Z30 | R03-B30-H-H-Z40 | R03-B30-H-F-Z00 |
| R03-B30-H-F-Z10 | R03-B30-H-F-Z20 | R03-B30-H-F-Z30 | R03-B30-H-F-Z40 |
| R03-B30-F-H-Z00 | R03-B30-F-H-Z10 | R03-B30-F-H-Z20 | R03-B30-F-H-Z30 |
| R03-B30-F-H-Z40 | R03-B30-F-H-Z40 | R03-B30-F-F-Z00 | R03-B30-F-F-Z10 |
| R03-B30-F-F-Z20 | R03-B30-F-F-Z30 | R03-B30-F-F-Z40 | R03-B40-H-H-Z00 |
| R03-B40-H-H-Z10 | R03-B40-H-H-Z20 | R03-B40-H-H-Z30 | R03-B40-H-H-Z40 |
| R03-B40-H-F-Z00 | R03-B40-H-F-Z10 | R03-B40-H-F-Z20 | R03-B40-H-F-Z30 |
| R03-B40-H-F-Z40 | R03-B40-F-H-Z00 | R03-B40-F-H-Z10 | R03-B40-F-H-Z20 |
| R03-B40-F-H-Z30 | R03-B40-F-H-Z40 | R03-B40-F-H-Z40 | R03-B40-F-F-Z00 |
| R03-B40-F-F-Z10 | R03-B40-F-F-Z20 | R03-B40-F-F-Z30 | R03-B40-F-F-Z40 |
| R03-B50-H-H-Z00 | R03-B50-H-H-Z10 | R03-B50-H-H-Z20 | R03-B50-H-H-Z30 |
| R03-B50-H-H-Z40 | R03-B50-H-F-Z00 | R03-B50-H-F-Z10 | R03-B50-H-F-Z20 |

-continued

| | | | |
|---|---|---|---|
| R03-B50-H-F-Z30 | R03-B50-H-F-Z40 | R03-B50-F-H-Z00 | R03-B50-F-H-Z10 |
| R03-B50-F-H-Z20 | R03-B50-F-H-Z30 | R03-B50-F-H-Z40 | R03-B50-F-H-Z40 |
| R03-B50-F-F-Z00 | R03-B50-F-F-Z10 | R03-B50-F-F-Z20 | R03-B50-F-F-Z30 |
| R03-B50-F-F-Z40 | | | |
| R05-B10-H-H-Z00 | R05-B10-H-H-Z10 | R05-B10-H-H-Z20 | R05-B10-H-H-Z30 |
| R05-B10-H-H-Z40 | R05-B10-H-F-Z00 | R05-B10-H-F-Z10 | R05-B10-H-F-Z20 |
| R05-B10-H-F-Z30 | R05-B10-H-F-Z40 | R05-B10-F-H-Z00 | R05-B10-F-H-Z10 |
| R05-B10-F-H-Z20 | R05-B10-F-H-Z30 | R05-B10-F-H-Z40 | R05-B10-F-H-Z40 |
| R05-B10-F-F-Z00 | R05-B10-F-F-Z10 | R05-B10-F-F-Z20 | R05-B10-F-F-Z30 |
| R05-B10-F-F-Z40 | R05-B20-H-H-Z00 | R05-B20-H-H-Z10 | R05-B20-H-H-Z20 |
| R05-B20-H-H-Z30 | R05-B20-H-H-Z40 | R05-B20-H-F-Z00 | R05-B20-H-F-Z10 |
| R05-B20-H-F-Z20 | R05-B20-H-F-Z30 | R05-B20-H-F-Z40 | R05-B20-F-H-Z00 |
| R05-B20-F-H-Z10 | R05-B20-F-H-Z20 | R05-B20-F-H-Z30 | R05-B20-F-H-Z40 |
| R05-B20-F-H-Z40 | R05-B20-F-F-Z00 | R05-B20-F-F-Z10 | R05-B20-F-F-Z20 |
| R05-B20-F-F-Z30 | R05-B20-F-F-Z40 | R05-B30-H-H-Z00 | R05-B30-H-H-Z10 |
| R05-B30-H-H-Z20 | R05-B30-H-H-Z30 | R05-B30-H-H-Z40 | R05-B30-H-F-Z00 |
| R05-B30-H-F-Z10 | R05-B30-H-F-Z20 | R05-B30-H-F-Z30 | R05-B30-H-F-Z40 |
| R05-B30-F-H-Z00 | R05-B30-F-H-Z10 | R05-B30-F-H-Z20 | R05-B30-F-H-Z30 |
| R05-B30-F-H-Z40 | R05-B30-F-H-Z40 | R05-B30-F-F-Z00 | R05-B30-F-F-Z10 |
| R05-B30-F-F-Z20 | R05-B30-F-F-Z30 | R05-B30-F-F-Z40 | R05-B40-H-H-Z00 |
| R05-B40-H-H-Z10 | R05-B40-H-H-Z20 | R05-B40-H-H-Z30 | R05-B40-H-H-Z40 |
| R05-B40-H-F-Z00 | R05-B40-H-F-Z10 | R05-B40-H-F-Z20 | R05-B40-H-F-Z30 |
| R05-B40-H-F-Z40 | R05-B40-F-H-Z00 | R05-B40-F-H-Z10 | R05-B40-F-H-Z20 |
| R05-B40-F-H-Z30 | R05-B40-F-H-Z40 | R05-B40-F-H-Z40 | R05-B40-F-F-Z00 |
| R05-B40-F-F-Z10 | R05-B40-F-F-Z20 | R05-B40-F-F-Z30 | R05-B40-F-F-Z40 |
| R05-B50-H-H-Z00 | R05-B50-H-H-Z10 | R05-B50-H-H-Z20 | R05-B50-H-H-Z30 |
| R05-B50-H-H-Z40 | R05-B50-H-F-Z00 | R05-B50-H-F-Z10 | R05-B50-H-F-Z20 |
| R05-B50-H-F-Z30 | R05-B50-H-F-Z40 | R05-B50-F-H-Z00 | R05-B50-F-H-Z10 |
| R05-B50-F-H-Z20 | R05-B50-F-H-Z30 | R05-B50-F-H-Z40 | R05-B50-F-H-Z40 |
| R05-B50-F-F-Z00 | R05-B50-F-F-Z10 | R05-B50-F-F-Z20 | R05-B50-F-F-Z30 |
| R05-B50-F-F-Z40 | | | |
| R06-B10-H-H-Z00 | R06-B10-H-H-Z10 | R06-B10-H-H-Z20 | R06-B10-H-H-Z30 |
| R06-B10-H-H-Z40 | R06-B10-H-F-Z00 | R06-B10-H-F-Z10 | R06-B10-H-F-Z20 |
| R06-B10-H-F-Z30 | R06-B10-H-F-Z40 | R06-B10-F-H-Z00 | R06-B10-F-H-Z10 |
| R06-B10-F-H-Z20 | R06-B10-F-H-Z30 | R06-B10-F-H-Z40 | R06-B10-F-H-Z40 |
| R06-B10-F-F-Z00 | R06-B10-F-F-Z10 | R06-B10-F-F-Z20 | R06-B10-F-F-Z30 |
| R06-B10-F-F-Z40 | R06-B20-H-H-Z00 | R06-B20-H-H-Z10 | R06-B20-H-H-Z20 |
| R06-B20-H-H-Z30 | R06-B20-H-H-Z40 | R06-B20-H-F-Z00 | R06-B20-H-F-Z10 |
| R06-B20-H-F-Z20 | R06-B20-H-F-Z30 | R06-B20-H-F-Z40 | R06-B20-F-H-Z00 |
| R06-B20-F-H-Z10 | R06-B20-F-H-Z20 | R06-B20-F-H-Z30 | R06-B20-F-H-Z40 |
| R06-B20-F-H-Z40 | R06-B20-F-F-Z00 | R06-B20-F-F-Z10 | R06-B20-F-F-Z20 |
| R06-B20-F-F-Z30 | R06-B20-F-F-Z40 | R06-B30-H-H-Z00 | R06-B30-H-H-Z10 |
| R06-B30-H-H-Z20 | R06-B30-H-H-Z30 | R06-B30-H-H-Z40 | R06-B30-H-F-Z00 |
| R06-B30-H-F-Z10 | R06-B30-H-F-Z20 | R06-B30-H-F-Z30 | R06-B30-H-F-Z40 |
| R06-B30-F-H-Z00 | R06-B30-F-H-Z10 | R06-B30-F-H-Z20 | R06-B30-F-H-Z30 |
| R06-B30-F-H-Z40 | R06-B30-F-H-Z40 | R06-B30-F-F-Z00 | R06-B30-F-F-Z10 |
| R06-B30-F-F-Z20 | R06-B30-F-F-Z30 | R06-B30-F-F-Z40 | R06-B40-H-H-Z00 |
| R06-B40-H-H-Z10 | R06-B40-H-H-Z20 | R06-B40-H-H-Z30 | R06-B40-H-H-Z40 |
| R06-B40-H-F-Z00 | R06-B40-H-F-Z10 | R06-B40-H-F-Z20 | R06-B40-H-F-Z30 |
| R06-B40-H-F-Z40 | R06-B40-F-H-Z00 | R06-B40-F-H-Z10 | R06-B40-F-H-Z20 |
| R06-B40-F-H-Z30 | R06-B40-F-H-Z40 | R06-B40-F-H-Z40 | R06-B40-F-F-Z00 |
| R06-B40-F-F-Z10 | R06-B40-F-F-Z20 | R06-B40-F-F-Z30 | R06-B40-F-F-Z40 |
| R06-B50-H-H-Z00 | R06-B50-H-H-Z10 | R06-B50-H-H-Z20 | R06-B50-H-H-Z30 |
| R06-B50-H-H-Z40 | R06-B50-H-F-Z00 | R06-B50-H-F-Z10 | R06-B50-H-F-Z20 |
| R06-B50-H-F-Z30 | R06-B50-H-F-Z40 | R06-B50-F-H-Z00 | R06-B50-F-H-Z10 |
| R06-B50-F-H-Z20 | R06-B50-F-H-Z30 | R06-B50-F-H-Z40 | R06-B50-F-H-Z40 |
| R06-B50-F-F-Z00 | R06-B50-F-F-Z10 | R06-B50-F-F-Z20 | R06-B50-F-F-Z30 |
| R06-B50-F-F-Z40 | | | |
| R10-B10-H-H-Z00 | R10-B10-H-H-Z10 | R10-B10-H-H-Z20 | R10-B10-H-H-Z30 |
| R10-B10-H-H-Z40 | R10-B10-H-F-Z00 | R10-B10-H-F-Z10 | R10-B10-H-F-Z20 |
| R10-B10-H-F-Z30 | R10-B10-H-F-Z40 | R10-B10-F-H-Z00 | R10-B10-F-H-Z10 |
| R10-B10-F-H-Z20 | R10-B10-F-H-Z30 | R10-B10-F-H-Z40 | R10-B10-F-H-Z40 |
| R10-B10-F-F-Z00 | R10-B10-F-F-Z10 | R10-B10-F-F-Z20 | R10-B10-F-F-Z30 |
| R10-B10-F-F-Z40 | R10-B20-H-H-Z00 | R10-B20-H-H-Z10 | R10-B20-H-H-Z20 |
| R10-B20-H-H-Z30 | R10-B20-H-H-Z40 | R10-B20-H-F-Z00 | R10-B20-H-F-Z10 |
| R10-B20-H-F-Z20 | R10-B20-H-F-Z30 | R10-B20-H-F-Z40 | R10-B20-F-H-Z00 |
| R10-B20-F-H-Z10 | R10-B20-F-H-Z20 | R10-B20-F-H-Z30 | R10-B20-F-H-Z40 |
| R10-B20-F-H-Z40 | R10-B20-F-F-Z00 | R10-B20-F-F-Z10 | R10-B20-F-F-Z20 |
| R10-B20-F-F-Z30 | R10-B20-F-F-Z40 | R10-B30-H-H-Z00 | R10-B30-H-H-Z10 |
| R10-B30-H-H-Z20 | R10-B30-H-H-Z30 | R10-B30-H-H-Z40 | R10-B30-H-F-Z00 |
| R10-B30-H-F-Z10 | R10-B30-H-F-Z20 | R10-B30-H-F-Z30 | R10-B30-H-F-Z40 |
| R10-B30-F-H-Z00 | R10-B30-F-H-Z10 | R10-B30-F-H-Z20 | R10-B30-F-H-Z30 |
| R10-B30-F-H-Z40 | R10-B30-F-H-Z40 | R10-B30-F-F-Z00 | R10-B30-F-F-Z10 |
| R10-B30-F-F-Z20 | R10-B30-F-F-Z30 | R10-B30-F-F-Z40 | R10-B40-H-H-Z00 |
| R10-B40-H-H-Z10 | R10-B40-H-H-Z20 | R10-B40-H-H-Z30 | R10-B40-H-H-Z40 |
| R10-B40-H-F-Z00 | R10-B40-H-F-Z10 | R10-B40-H-F-Z20 | R10-B40-H-F-Z30 |
| R10-B40-H-F-Z40 | R10-B40-F-H-Z00 | R10-B40-F-H-Z10 | R10-B40-F-H-Z20 |
| R10-B40-F-H-Z30 | R10-B40-F-H-Z40 | R10-B40-F-H-Z40 | R10-B40-F-F-Z00 |
| R10-B40-F-F-Z10 | R10-B40-F-F-Z20 | R10-B40-F-F-Z30 | R10-B40-F-F-Z40 |

-continued

| | | | |
|---|---|---|---|
| R10-B50-H-H-Z00 | R10-B50-H-H-Z10 | R10-B50-H-H-Z20 | R10-B50-H-H-Z30 |
| R10-B50-H-H-Z40 | R10-B50-H-F-Z00 | R10-B50-H-F-Z10 | R10-B50-H-F-Z20 |
| R10-B50-H-F-Z30 | R10-B50-H-F-Z40 | R10-B50-F-H-Z00 | R10-B50-F-H-Z10 |
| R10-B50-F-H-Z20 | R10-B50-F-H-Z30 | R10-B50-F-H-Z40 | R10-B50-F-H-Z40 |
| R10-B50-F-F-Z00 | R10-B50-F-F-Z10 | R10-B50-F-F-Z20 | R10-B50-F-F-Z30 |
| R10-B50-F-F-Z40 | | | |

| | | |
|---|---|---|
| R02-A10-B10-H-H-Z00 | R02-A10-B10-H-H-Z10 | R02-A10-B10-H-H-Z20 |
| R02-A10-B10-H-H-Z30 | R02-A10-B10-H-H-Z40 | R02-A10-B10-H-F-Z00 |
| R02-A10-B10-H-F-Z10 | R02-A10-B10-H-F-Z20 | R02-A10-B10-H-F-Z30 |
| R02-A10-B10-H-F-Z40 | R02-A10-B10-F-H-Z00 | R02-A10-B10-F-H-Z10 |
| R02-A10-B10-F-H-Z20 | R02-A10-B10-F-H-Z30 | R02-A10-B10-F-H-Z40 |
| R02-A10-B10-F-F-Z00 | R02-A10-B10-F-F-Z10 | R02-A10-B10-F-F-Z20 |
| R02-A10-B10-F-F-Z30 | R02-A10-B10-F-F-Z40 | R02-A10-B20-H-H-Z00 |
| R02-A10-B20-H-H-Z10 | R02-A10-B20-H-H-Z20 | R02-A10-B20-H-H-Z30 |
| R02-A10-B20-H-H-Z40 | R02-A10-B20-H-F-Z00 | R02-A10-B20-H-F-Z10 |
| R02-A10-B20-H-F-Z20 | R02-A10-B20-H-F-Z30 | R02-A10-B20-H-F-Z40 |
| R02-A10-B20-F-H-Z00 | R02-A10-B20-F-H-Z10 | R02-A10-B20-F-H-Z20 |
| R02-A10-B20-F-H-Z30 | R02-A10-B20-F-H-Z40 | R02-A10-B20-F-F-Z00 |
| R02-A10-B20-F-F-Z10 | R02-A10-B20-F-F-Z20 | R02-A10-B20-F-F-Z30 |
| R02-A10-B20-F-F-Z40 | R02-A10-B40-H-H-Z00 | R02-A10-B40-H-H-Z10 |
| R02-A10-B40-H-H-Z20 | R02-A10-B40-H-H-Z30 | R02-A10-B40-H-H-Z40 |
| R02-A10-B40-H-F-Z00 | R02-A10-B40-H-F-Z10 | R02-A10-B40-H-F-Z20 |
| R02-A10-B40-H-F-Z30 | R02-A10-B40-H-F-Z40 | R02-A10-B40-F-H-Z00 |
| R02-A10-B40-F-H-Z10 | R02-A10-B40-F-H-Z20 | R02-A10-B40-F-H-Z30 |
| R02-A10-B40-F-H-Z40 | R02-A10-B40-F-F-Z00 | R02-A10-B40-F-F-Z10 |
| R02-A10-B40-F-F-Z20 | R02-A10-B40-F-F-Z30 | R02-A10-B40-F-F-Z40 |
| R02-A10-B50-H-H-Z00 | R02-A10-B50-H-H-Z10 | R02-A10-B50-H-H-Z20 |
| R02-A10-B50-H-H-Z30 | R02-A10-B50-H-H-Z40 | R02-A10-B50-H-F-Z00 |
| R02-A10-B50-H-F-Z10 | R02-A10-B50-H-F-Z20 | R02-A10-B50-H-F-Z30 |
| R02-A10-B50-H-F-Z40 | R02-A10-B50-F-H-Z00 | R02-A10-B50-F-H-Z10 |
| R02-A10-B50-F-H-Z20 | R02-A10-B50-F-H-Z30 | R02-A10-B50-F-H-Z40 |
| R02-A10-B50-F-F-Z00 | R02-A10-B50-F-F-Z10 | R02-A10-B50-F-F-Z20 |
| R02-A10-B50-F-F-Z30 | R02-A10-B50-F-F-Z40 | |
| R02-A20-B10-H-H-Z00 | R02-A20-B10-H-H-Z10 | R02-A20-B10-H-H-Z20 |
| R02-A20-B10-H-H-Z30 | R02-A20-B10-H-H-Z40 | R02-A20-B10-H-F-Z00 |
| R02-A20-B10-H-F-Z10 | R02-A20-B10-H-F-Z20 | R02-A20-B10-H-F-Z30 |
| R02-A20-B10-H-F-Z40 | R02-A20-B10-F-H-Z00 | R02-A20-B10-F-H-Z10 |
| R02-A20-B10-F-H-Z20 | R02-A20-B10-F-H-Z30 | R02-A20-B10-F-H-Z40 |
| R02-A20-B10-F-F-Z00 | R02-A20-B10-F-F-Z10 | R02-A20-B10-F-F-Z20 |
| R02-A20-B10-F-F-Z30 | R02-A20-B10-F-F-Z40 | R02-A20-B20-H-H-Z00 |
| R02-A20-B20-H-H-Z10 | R02-A20-B20-H-H-Z20 | R02-A20-B20-H-H-Z30 |
| R02-A20-B20-H-H-Z40 | R02-A20-B20-H-F-Z00 | R02-A20-B20-H-F-Z10 |
| R02-A20-B20-H-F-Z20 | R02-A20-B20-H-F-Z30 | R02-A20-B20-H-F-Z40 |
| R02-A20-B20-F-H-Z00 | R02-A20-B20-F-H-Z10 | R02-A20-B20-F-H-Z20 |
| R02-A20-B20-F-H-Z30 | R02-A20-B20-F-H-Z40 | R02-A20-B20-F-F-Z00 |
| R02-A20-B20-F-F-Z10 | R02-A20-B20-F-F-Z20 | R02-A20-B20-F-F-Z30 |
| R02-A20-B20-F-F-Z40 | R02-A20-B40-H-H-Z00 | R02-A20-B40-H-H-Z10 |
| R02-A20-B40-H-H-Z20 | R02-A20-B40-H-H-Z30 | R02-A20-B40-H-H-Z40 |
| R02-A20-B40-H-F-Z00 | R02-A20-B40-H-F-Z10 | R02-A20-B40-H-F-Z20 |
| R02-A20-B40-H-F-Z30 | R02-A20-B40-H-F-Z40 | R02-A20-B40-F-H-Z00 |
| R02-A20-B40-F-H-Z10 | R02-A20-B40-F-H-Z20 | R02-A20-B40-F-H-Z30 |
| R02-A20-B40-F-H-Z40 | R02-A20-B40-F-F-Z00 | R02-A20-B40-F-F-Z10 |
| R02-A20-B40-F-F-Z20 | R02-A20-B40-F-F-Z30 | R02-A20-B40-F-F-Z40 |
| R02-A20-B50-H-H-Z00 | R02-A20-B50-H-H-Z10 | R02-A20-B50-H-H-Z20 |
| R02-A20-B50-H-H-Z30 | R02-A20-B50-H-H-Z40 | R02-A20-B50-H-F-Z00 |
| R02-A20-B50-H-F-Z10 | R02-A20-B50-H-F-Z20 | R02-A20-B50-H-F-Z30 |
| R02-A20-B50-H-F-Z40 | R02-A20-B50-F-H-Z00 | R02-A20-B50-F-H-Z10 |
| R02-A20-B50-F-H-Z20 | R02-A20-B50-F-H-Z30 | R02-A20-B50-F-H-Z40 |
| R02-A20-B50-F-F-Z00 | R02-A20-B50-F-F-Z10 | R02-A20-B50-F-F-Z20 |
| R02-A20-B50-F-F-Z30 | R02-A20-B50-F-F-Z40 | |
| R02-A30-B10-H-H-Z00 | R02-A30-B10-H-H-Z10 | R02-A30-B10-H-H-Z20 |
| R02-A30-B10-H-H-Z30 | R02-A30-B10-H-H-Z40 | R02-A30-B10-H-F-Z00 |
| R02-A30-B10-H-F-Z10 | R02-A30-B10-H-F-Z20 | R02-A30-B10-H-F-Z30 |
| R02-A30-B10-H-F-Z40 | R02-A30-B10-F-H-Z00 | R02-A30-B10-F-H-Z10 |
| R02-A30-B10-F-H-Z20 | R02-A30-B10-F-H-Z30 | R02-A30-B10-F-H-Z40 |
| R02-A30-B10-F-F-Z00 | R02-A30-B10-F-F-Z10 | R02-A30-B10-F-F-Z20 |
| R02-A30-B10-F-F-Z30 | R02-A30-B10-F-F-Z40 | R02-A30-B20-H-H-Z00 |
| R02-A30-B20-H-H-Z10 | R02-A30-B20-H-H-Z20 | R02-A30-B20-H-H-Z30 |
| R02-A30-B20-H-H-Z40 | R02-A30-B20-H-F-Z00 | R02-A30-B20-H-F-Z10 |
| R02-A30-B20-H-F-Z20 | R02-A30-B20-H-F-Z30 | R02-A30-B20-H-F-Z40 |
| R02-A30-B20-F-H-Z00 | R02-A30-B20-F-H-Z10 | R02-A30-B20-F-H-Z20 |
| R02-A30-B20-F-F-Z30 | R02-A30-B20-F-H-Z40 | R02-A30-B20-F-F-Z00 |
| R02-A30-B20-F-F-Z10 | R02-A30-B20-F-F-Z20 | R02-A30-B20-F-F-Z30 |

-continued

| | | |
|---|---|---|
| R02-A30-B20-F-F-Z40 | R02-A30-B40-H-H-Z00 | R02-A30-B40-H-H-Z10 |
| R02-A30-B40-H-H-Z20 | R02-A30-B40-H-H-Z30 | R02-A30-B40-H-H-Z40 |
| R02-A30-B40-H-F-Z00 | R02-A30-B40-H-F-Z10 | R02-A30-B40-H-F-Z20 |
| R02-A30-B40-H-F-Z30 | R02-A30-B40-H-F-Z40 | R02-A30-B40-F-H-Z00 |
| R02-A30-B40-F-H-Z10 | R02-A30-B40-F-H-Z20 | R02-A30-B40-F-H-Z30 |
| R02-A30-B40-F-H-Z40 | R02-A30-B40-F-F-Z00 | R02-A30-B40-F-F-Z10 |
| R02-A30-B40-F-F-Z20 | R02-A30-B40-F-F-Z30 | R02-A30-B40-F-F-Z40 |
| R02-A30-B50-H-H-Z00 | R02-A30-B50-H-H-Z10 | R02-A30-B50-H-H-Z20 |
| R02-A30-B50-H-H-Z30 | R02-A30-B50-H-H-Z40 | R02-A30-B50-H-F-Z00 |
| R02-A30-B50-H-F-Z10 | R02-A30-B50-H-F-Z20 | R02-A30-B50-H-F-Z30 |
| R02-A30-B50-H-F-Z40 | R02-A30-B50-F-H-Z00 | R02-A30-B50-F-H-Z10 |
| R02-A30-B50-F-H-Z20 | R02-A30-B50-F-H-Z30 | R02-A30-B50-F-H-Z40 |
| R02-A30-B50-F-F-Z00 | R02-A30-B50-F-F-Z10 | R02-A30-B50-F-F-Z20 |
| R02-A30-B50-F-F-Z30 | R02-A30-B50-F-F-Z40 | |
| R02-A40-B10-H-H-Z00 | R02-A40-B10-H-H-Z10 | R02-A40-B10-H-H-Z20 |
| R02-A40-B10-H-H-Z30 | R02-A40-B10-H-H-Z40 | R02-A40-B10-H-F-Z00 |
| R02-A40-B10-H-F-Z10 | R02-A40-B10-H-F-Z20 | R02-A40-B10-H-F-Z30 |
| R02-A40-B10-H-F-Z40 | R02-A40-B10-F-H-Z00 | R02-A40-B10-F-H-Z10 |
| R02-A40-B10-F-H-Z20 | R02-A40-B10-F-H-Z30 | R02-A40-B10-F-H-Z40 |
| R02-A40-B10-F-F-Z00 | R02-A40-B10-F-F-Z10 | R02-A40-B10-F-F-Z20 |
| R02-A40-B10-F-F-Z30 | R02-A40-B10-F-F-Z40 | R02-A40-B20-H-H-Z00 |
| R02-A40-B20-H-H-Z10 | R02-A40-B20-H-H-Z20 | R02-A40-B20-H-H-Z30 |
| R02-A40-B20-H-H-Z40 | R02-A40-B20-H-F-Z00 | R02-A40-B20-H-F-Z10 |
| R02-A40-B20-H-F-Z20 | R02-A40-B20-H-F-Z30 | R02-A40-B20-H-F-Z40 |
| R02-A40-B20-F-H-Z00 | R02-A40-B20-F-H-Z10 | R02-A40-B20-F-H-Z20 |
| R02-A40-B20-F-H-Z30 | R02-A40-B20-F-H-Z40 | R02-A40-B20-F-F-Z00 |
| R02-A40-B20-F-F-Z10 | R02-A40-B20-F-F-Z20 | R02-A40-B20-F-F-Z30 |
| R02-A40-B20-F-F-Z40 | R02-A40-B40-H-H-Z00 | R02-A40-B40-H-H-Z10 |
| R02-A40-B40-H-H-Z20 | R02-A40-B40-H-H-Z30 | R02-A40-B40-H-H-Z40 |
| R02-A40-B40-H-F-Z00 | R02-A40-B40-H-F-Z10 | R02-A40-B40-H-F-Z20 |
| R02-A40-B40-H-F-Z30 | R02-A40-B40-H-F-Z40 | R02-A40-B40-F-H-Z00 |
| R02-A40-B40-F-H-Z10 | R02-A40-B40-F-H-Z20 | R02-A40-B40-F-H-Z30 |
| R02-A40-B40-F-H-Z40 | R02-A40-B40-F-F-Z00 | R02-A40-B40-F-F-Z10 |
| R02-A40-B40-F-F-Z20 | R02-A40-B40-F-F-Z30 | R02-A40-B40-F-F-Z40 |
| R02-A40-B50-H-H-Z00 | R02-A40-B50-H-H-Z10 | R02-A40-B50-H-H-Z20 |
| R02-A40-B50-H-H-Z30 | R02-A40-B50-H-H-Z40 | R02-A40-B50-H-F-Z00 |
| R02-A40-B50-H-F-Z10 | R02-A40-B50-H-F-Z20 | R02-A40-B50-H-F-Z30 |
| R02-A40-B50-H-F-Z40 | R02-A40-B50-F-H-Z00 | R02-A40-B50-F-H-Z10 |
| R02-A40-B50-F-H-Z20 | R02-A40-B50-F-H-Z30 | R02-A40-B50-F-H-Z40 |
| R02-A40-B50-F-F-Z00 | R02-A40-B50-F-F-Z10 | R02-A40-B50-F-F-Z20 |
| R02-A40-B50-F-F-Z30 | R02-A40-B50-F-F-Z40 | |
| R03-A10-B10-H-H-Z00 | R03-A10-B10-H-H-Z10 | R03-A10-B10-H-H-Z20 |
| R03-A10-B10-H-H-Z30 | R03-A10-B10-H-H-Z40 | R03-A10-B10-H-F-Z00 |
| R03-A10-B10-H-F-Z10 | R03-A10-B10-H-F-Z20 | R03-A10-B10-H-F-Z30 |
| R03-A10-B10-H-F-Z40 | R03-A10-B10-F-H-Z00 | R03-A10-B10-F-H-Z10 |
| R03-A10-B10-F-H-Z20 | R03-A10-B10-F-H-Z30 | R03-A10-B10-F-H-Z40 |
| R03-A10-B10-F-F-Z00 | R03-A10-B10-F-F-Z10 | R03-A10-B10-F-F-Z20 |
| R03-A10-B10-F-F-Z30 | R03-A10-B10-F-F-Z40 | R03-A10-B20-H-H-Z00 |
| R03-A10-B20-H-H-Z10 | R03-A10-B20-H-H-Z20 | R03-A10-B20-H-H-Z30 |
| R03-A10-B20-H-H-Z40 | R03-A10-B20-H-F-Z00 | R03-A10-B20-H-F-Z10 |
| R03-A10-B20-H-F-Z20 | R03-A10-B20-H-F-Z30 | R03-A10-B20-H-F-Z40 |
| R03-A10-B20-F-H-Z00 | R03-A10-B20-F-H-Z10 | R03-A10-B20-F-H-Z20 |
| R03-A10-B20-F-H-Z30 | R03-A10-B20-F-H-Z40 | R03-A10-B20-F-F-Z00 |
| R03-A10-B20-F-F-Z10 | R03-A10-B20-F-F-Z20 | R03-A10-B20-F-F-Z30 |
| R03-A10-B20-F-F-Z40 | R03-A10-B40-H-H-Z00 | R03-A10-B40-H-H-Z10 |
| R03-A10-B40-H-H-Z20 | R03-A10-B40-H-H-Z30 | R03-A10-B40-H-H-Z40 |
| R03-A10-B40-H-F-Z00 | R03-A10-B40-H-F-Z10 | R03-A10-B40-H-F-Z20 |
| R03-A10-B40-H-F-Z30 | R03-A10-B40-H-F-Z40 | R03-A10-B40-F-H-Z00 |
| R03-A10-B40-F-H-Z10 | R03-A10-B40-F-H-Z20 | R03-A10-B40-F-H-Z30 |
| R03-A10-B40-F-H-Z40 | R03-A10-B40-F-F-Z00 | R03-A10-B40-F-F-Z10 |
| R03-A10-B40-F-F-Z20 | R03-A10-B40-F-F-Z30 | R03-A10-B40-F-F-Z40 |
| R03-A10-B50-H-H-Z00 | R03-A10-B50-H-H-Z10 | R03-A10-B50-H-H-Z20 |
| R03-A10-B50-H-H-Z30 | R03-A10-B50-H-H-Z40 | R03-A10-B50-H-F-Z00 |
| R03-A10-B50-H-F-Z10 | R03-A10-B50-H-F-Z20 | R03-A10-B50-H-F-Z30 |
| R03-A10-B50-H-F-Z40 | R03-A10-B50-F-H-Z00 | R03-A10-B50-F-H-Z10 |
| R03-A10-B50-F-H-Z20 | R03-A10-B50-F-H-Z30 | R03-A10-B50-F-H-Z40 |
| R03-A10-B50-F-F-Z00 | R03-A10-B50-F-F-Z10 | R03-A10-B50-F-F-Z20 |
| R03-A10-B50-F-F-Z30 | R03-A10-B50-F-F-Z40 | |
| R03-A20-B10-H-H-Z00 | R03-A20-B10-H-H-Z10 | R03-A20-B10-H-H-Z20 |
| R03-A20-B10-H-H-Z30 | R03-A20-B10-H-H-Z40 | R03-A20-B10-H-F-Z00 |
| R03-A20-B10-H-F-Z10 | R03-A20-B10-H-F-Z20 | R03-A20-B10-H-F-Z30 |
| R03-A20-B10-H-F-Z40 | R03-A20-B10-F-H-Z00 | R03-A20-B10-F-H-Z10 |
| R03-A20-B10-F-H-Z20 | R03-A20-B10-F-H-Z30 | R03-A20-B10-F-H-Z40 |
| R03-A20-B10-F-F-Z00 | R03-A20-B10-F-F-Z10 | R03-A20-B10-F-F-Z20 |
| R03-A20-B10-F-F-Z30 | R03-A20-B10-F-F-Z40 | R03-A20-B20-H-H-Z00 |
| R03-A20-B20-H-H-Z10 | R03-A20-B20-H-H-Z20 | R03-A20-B20-H-H-Z30 |
| R03-A20-B20-H-H-Z40 | R03-A20-B20-H-F-Z00 | R03-A20-B20-H-F-Z10 |
| R03-A20-B20-H-F-Z20 | R03-A20-B20-H-F-Z30 | R03-A20-B20-H-F-Z40 |
| R03-A20-B20-F-H-Z00 | R03-A20-B20-F-H-Z10 | R03-A20-B20-F-H-Z20 |

-continued

| | | |
|---|---|---|
| R03-A20-B20-F-H-Z30 | R03-A20-B20-F-H-Z40 | R03-A20-B20-F-F-Z00 |
| R03-A20-B20-F-F-Z10 | R03-A20-B20-F-F-Z20 | R03-A20-B20-F-F-Z30 |
| R03-A20-B20-F-F-Z40 | R03-A20-B40-H-H-Z00 | R03-A20-B40-H-H-Z10 |
| R03-A20-B40-H-H-Z20 | R03-A20-B40-H-H-Z30 | R03-A20-B40-H-H-Z40 |
| R03-A20-B40-H-F-Z00 | R03-A20-B40-H-F-Z10 | R03-A20-B40-H-F-Z20 |
| R03-A20-B40-H-F-Z30 | R03-A20-B40-H-F-Z40 | R03-A20-B40-F-H-Z00 |
| R03-A20-B40-F-H-Z10 | R03-A20-B40-F-H-Z20 | R03-A20-B40-F-H-Z30 |
| R03-A20-B40-F-H-Z40 | R03-A20-B40-F-F-Z00 | R03-A20-B40-F-F-Z10 |
| R03-A20-B40-F-F-Z20 | R03-A20-B40-F-F-Z30 | R03-A20-B40-F-F-Z40 |
| R03-A20-B50-H-H-Z00 | R03-A20-B50-H-H-Z10 | R03-A20-B50-H-H-Z20 |
| R03-A20-B50-H-H-Z30 | R03-A20-B50-H-H-Z40 | R03-A20-B50-H-F-Z00 |
| R03-A20-B50-H-F-Z10 | R03-A20-B50-H-F-Z20 | R03-A20-B50-H-F-Z30 |
| R03-A20-B50-H-F-Z40 | R03-A20-B50-F-H-Z00 | R03-A20-B50-F-H-Z10 |
| R03-A20-B50-F-H-Z20 | R03-A20-B50-F-H-Z30 | R03-A20-B50-F-H-Z40 |
| R03-A20-B50-F-F-Z00 | R03-A20-B50-F-F-Z10 | R03-A20-B50-F-F-Z20 |
| R03-A20-B50-F-F-Z30 | R03-A20-B50-F-F-Z40 | |
| R03-A30-B10-H-H-Z00 | R03-A30-B10-H-H-Z10 | R03-A30-B10-H-H-Z20 |
| R03-A30-B10-H-H-Z30 | R03-A30-B10-H-H-Z40 | R03-A30-B10-H-F-Z00 |
| R03-A30-B10-H-F-Z10 | R03-A30-B10-H-F-Z20 | R03-A30-B10-H-F-Z30 |
| R03-A30-B10-H-F-Z40 | R03-A30-B10-F-H-Z00 | R03-A30-B10-F-H-Z10 |
| R03-A30-B10-F-H-Z20 | R03-A30-B10-F-H-Z30 | R03-A30-B10-F-H-Z40 |
| R03-A30-B10-F-F-Z00 | R03-A30-B10-F-F-Z10 | R03-A30-B10-F-F-Z20 |
| R03-A30-B10-F-F-Z30 | R03-A30-B10-F-F-Z40 | R03-A30-B20-H-H-Z00 |
| R03-A30-B20-H-H-Z10 | R03-A30-B20-H-H-Z20 | R03-A30-B20-H-H-Z30 |
| R03-A30-B20-H-H-Z40 | R03-A30-B20-H-F-Z00 | R03-A30-B20-H-F-Z10 |
| R03-A30-B20-H-F-Z20 | R03-A30-B20-H-F-Z30 | R03-A30-B20-H-F-Z40 |
| R03-A30-B20-F-H-Z00 | R03-A30-B20-F-H-Z10 | R03-A30-B20-F-H-Z20 |
| R03-A30-B20-F-H-Z30 | R03-A30-B20-F-H-Z40 | R03-A30-B20-F-F-Z00 |
| R03-A30-B20-F-F-Z10 | R03-A30-B20-F-F-Z20 | R03-A30-B20-F-F-Z30 |
| R03-A30-B20-F-F-Z40 | R03-A30-B40-H-H-Z00 | R03-A30-B40-H-H-Z10 |
| R03-A30-B40-H-H-Z20 | R03-A30-B40-H-H-Z30 | R03-A30-B40-H-H-Z40 |
| R03-A30-B40-H-F-Z00 | R03-A30-B40-H-F-Z10 | R03-A30-B40-H-F-Z20 |
| R03-A30-B40-H-F-Z30 | R03-A30-B40-H-F-Z40 | R03-A30-B40-F-H-Z00 |
| R03-A30-B40-F-H-Z10 | R03-A30-B40-F-H-Z20 | R03-A30-B40-F-H-Z30 |
| R03-A30-B40-F-H-Z40 | R03-A30-B40-F-F-Z00 | R03-A30-B40-F-F-Z10 |
| R03-A30-B40-F-F-Z20 | R03-A30-B40-F-F-Z30 | R03-A30-B40-F-F-Z40 |
| R03-A30-B50-H-H-Z00 | R03-A30-B50-H-H-Z10 | R03-A30-B50-H-H-Z20 |
| R03-A30-B50-H-H-Z30 | R03-A30-B50-H-H-Z40 | R03-A30-B50-H-F-Z00 |
| R03-A30-B50-H-F-Z10 | R03-A30-B50-H-F-Z20 | R03-A30-B50-H-F-Z30 |
| R03-A30-B50-H-F-Z40 | R03-A30-B50-F-H-Z00 | R03-A30-B50-F-H-Z10 |
| R03-A30-B50-F-H-Z20 | R03-A30-B50-F-H-Z30 | R03-A30-B50-F-H-Z40 |
| R03-A30-B50-F-F-Z00 | R03-A30-B50-F-F-Z10 | R03-A30-B50-F-F-Z20 |
| R03-A30-B50-F-F-Z30 | R03-A30-B50-F-F-Z40 | |
| R03-A40-B10-H-H-Z00 | R03-A40-B10-H-H-Z10 | R03-A40-B10-H-H-Z20 |
| R03-A40-B10-H-H-Z30 | R03-A40-B10-H-H-Z40 | R03-A40-B10-H-F-Z00 |
| R03-A40-B10-H-F-Z10 | R03-A40-B10-H-F-Z20 | R03-A40-B10-H-F-Z30 |
| R03-A40-B10-H-F-Z40 | R03-A40-B10-F-H-Z00 | R03-A40-B10-F-H-Z10 |
| R03-A40-B10-F-H-Z20 | R03-A40-B10-F-H-Z30 | R03-A40-B10-F-H-Z40 |
| R03-A40-B10-F-F-Z00 | R03-A40-B10-F-F-Z10 | R03-A40-B10-F-F-Z20 |
| R03-A40-B10-F-F-Z30 | R03-A40-B10-F-F-Z40 | R03-A40-B20-H-H-Z00 |
| R03-A40-B20-H-H-Z10 | R03-A40-B20-H-H-Z20 | R03-A40-B20-H-H-Z30 |
| R03-A40-B20-H-H-Z40 | R03-A40-B20-H-F-Z00 | R03-A40-B20-H-F-Z10 |
| R03-A40-B20-H-F-Z20 | R03-A40-B20-H-F-Z30 | R03-A40-B20-H-F-Z40 |
| R03-A40-B20-F-H-Z00 | R03-A40-B20-F-H-Z10 | R03-A40-B20-F-H-Z20 |
| R03-A40-B20-F-H-Z30 | R03-A40-B20-F-H-Z40 | R03-A40-B20-F-F-Z00 |
| R03-A40-B20-F-F-Z10 | R03-A40-B20-F-F-Z20 | R03-A40-B20-F-F-Z30 |
| R03-A40-B20-F-F-Z40 | R03-A40-B40-H-H-Z00 | R03-A40-B40-H-H-Z10 |
| R03-A40-B40-H-H-Z20 | R03-A40-B40-H-H-Z30 | R03-A40-B40-H-H-Z40 |
| R03-A40-B40-H-F-Z00 | R03-A40-B40-H-F-Z10 | R03-A40-B40-H-F-Z20 |
| R03-A40-B40-H-F-Z30 | R03-A40-B40-H-F-Z40 | R03-A40-B40-F-H-Z00 |
| R03-A40-B40-F-H-Z10 | R03-A40-B40-F-H-Z20 | R03-A40-B40-F-H-Z30 |
| R03-A40-B40-F-H-Z40 | R03-A40-B40-F-F-Z00 | R03-A40-B40-F-F-Z10 |
| R03-A40-B40-F-F-Z20 | R03-A40-B40-F-F-Z30 | R03-A40-B40-F-F-Z40 |
| R03-A40-B50-H-H-Z00 | R03-A40-B50-H-H-Z10 | R03-A40-B50-H-H-Z20 |
| R03-A40-B50-H-H-Z30 | R03-A40-B50-H-H-Z40 | R03-A40-B50-H-F-Z00 |
| R03-A40-B50-H-F-Z10 | R03-A40-B50-H-F-Z20 | R03-A40-B50-H-F-Z30 |
| R03-A40-B50-H-F-Z40 | R03-A40-B50-F-H-Z00 | R03-A40-B50-F-H-Z10 |
| R03-A40-B50-F-H-Z20 | R03-A40-B50-F-H-Z30 | R03-A40-B50-F-H-Z40 |
| R03-A40-B50-F-F-Z00 | R03-A40-B50-F-F-Z10 | R03-A40-B50-F-F-Z20 |
| R03-A40-B50-F-F-Z30 | R03-A40-B50-F-F-Z40 | |
| R04-A10-B10-H-H-Z00 | R04-A10-B10-H-H-Z10 | R04-A10-B10-H-H-Z20 |
| R04-A10-B10-H-H-Z30 | R04-A10-B10-H-H-Z40 | R04-A10-B10-H-F-Z00 |
| R04-A10-B10-H-F-Z10 | R04-A10-B10-H-F-Z20 | R04-A10-B10-H-F-Z30 |
| R04-A10-B10-H-F-Z40 | R04-A10-B10-F-H-Z00 | R04-A10-B10-F-H-Z10 |
| R04-A10-B10-F-H-Z20 | R04-A10-B10-F-H-Z30 | R04-A10-B10-F-H-Z40 |
| R04-A10-B10-F-F-Z00 | R04-A10-B10-F-F-Z10 | R04-A10-B10-F-F-Z20 |
| R04-A10-B10-F-F-Z30 | R04-A10-B10-F-F-Z40 | R04-A10-B20-H-H-Z00 |
| R04-A10-B20-H-H-Z10 | R04-A10-B20-H-H-Z20 | R04-A10-B20-H-H-Z30 |
| R04-A10-B20-H-H-Z40 | R04-A10-B20-H-F-Z00 | R04-A10-B20-H-F-Z10 |

-continued

| | | |
|---|---|---|
| R04-A10-B20-H-F-Z20 | R04-A10-B20-H-F-Z30 | R04-A10-B20-H-F-Z40 |
| R04-A10-B20-F-H-Z00 | R04-A10-B20-F-H-Z10 | R04-A10-B20-F-H-Z20 |
| R04-A10-B20-F-H-Z30 | R04-A10-B20-F-H-Z40 | R04-A10-B20-F-F-Z00 |
| R04-A10-B20-F-F-Z10 | R04-A10-B20-F-F-Z20 | R04-A10-B20-F-F-Z30 |
| R04-A10-B20-F-F-Z40 | R04-A10-B40-H-H-Z00 | R04-A10-B40-H-H-Z10 |
| R04-A10-B40-H-H-Z20 | R04-A10-B40-H-H-Z30 | R04-A10-B40-H-H-Z40 |
| R04-A10-B40-H-F-Z00 | R04-A10-B40-H-F-Z10 | R04-A10-B40-H-F-Z20 |
| R04-A10-B40-H-F-Z30 | R04-A10-B40-H-F-Z40 | R04-A10-B40-F-H-Z00 |
| R04-A10-B40-F-H-Z10 | R04-A10-B40-F-H-Z20 | R04-A10-B40-F-H-Z30 |
| R04-A10-B40-F-H-Z40 | R04-A10-B40-F-F-Z00 | R04-A10-B40-F-F-Z10 |
| R04-A10-B40-F-F-Z20 | R04-A10-B40-F-F-Z30 | R04-A10-B40-F-F-Z40 |
| R04-A10-B50-H-H-Z00 | R04-A10-B50-H-H-Z10 | R04-A10-B50-H-H-Z20 |
| R04-A10-B50-H-H-Z30 | R04-A10-B50-H-H-Z40 | R04-A10-B50-H-F-Z00 |
| R04-A10-B50-H-F-Z10 | R04-A10-B50-H-F-Z20 | R04-A10-B50-H-F-Z30 |
| R04-A10-B50-H-F-Z40 | R04-A10-B50-F-H-Z00 | R04-A10-B50-F-H-Z10 |
| R04-A10-B50-F-H-Z20 | R04-A10-B50-F-H-Z30 | R04-A10-B50-F-H-Z40 |
| R04-A10-B50-F-F-Z00 | R04-A10-B50-F-F-Z10 | R04-A10-B50-F-F-Z20 |
| R04-A10-B50-F-F-Z30 | R04-A10-B50-F-F-Z40 | |
| R04-A20-B10-H-H-Z00 | R04-A20-B10-H-H-Z10 | R04-A20-B10-H-H-Z20 |
| R04-A20-B10-H-H-Z30 | R04-A20-B10-H-H-Z40 | R04-A20-B10-H-F-Z00 |
| R04-A20-B10-H-F-Z10 | R04-A20-B10-H-F-Z20 | R04-A20-B10-H-F-Z30 |
| R04-A20-B10-H-F-Z40 | R04-A20-B10-F-H-Z00 | R04-A20-B10-F-H-Z10 |
| R04-A20-B10-F-H-Z20 | R04-A20-B10-F-H-Z30 | R04-A20-B10-F-H-Z40 |
| R04-A20-B10-F-F-Z00 | R04-A20-B10-F-F-Z10 | R04-A20-B10-F-F-Z20 |
| R04-A20-B10-F-F-Z30 | R04-A20-B10-F-F-Z40 | R04-A20-B20-H-H-Z00 |
| R04-A20-B20-H-H-Z10 | R04-A20-B20-H-H-Z20 | R04-A20-B20-H-H-Z30 |
| R04-A20-B20-H-H-Z40 | R04-A20-B20-H-F-Z00 | R04-A20-B20-H-F-Z10 |
| R04-A20-B20-H-F-Z20 | R04-A20-B20-H-F-Z30 | R04-A20-B20-H-F-Z40 |
| R04-A20-B20-F-H-Z00 | R04-A20-B20-F-H-Z10 | R04-A20-B20-F-H-Z20 |
| R04-A20-B20-F-H-Z30 | R04-A20-B20-F-H-Z40 | R04-A20-B20-F-F-Z00 |
| R04-A20-B20-F-F-Z10 | R04-A20-B20-F-F-Z20 | R04-A20-B20-F-F-Z30 |
| R04-A20-B20-F-F-Z40 | R04-A20-B40-H-H-Z00 | R04-A20-B40-H-H-Z10 |
| R04-A20-B40-H-H-Z20 | R04-A20-B40-H-H-Z30 | R04-A20-B40-H-H-Z40 |
| R04-A20-B40-H-F-Z00 | R04-A20-B40-H-F-Z10 | R04-A20-B40-H-F-Z20 |
| R04-A20-B40-H-F-Z30 | R04-A20-B40-H-F-Z40 | R04-A20-B40-F-H-Z00 |
| R04-A20-B40-F-H-Z10 | R04-A20-B40-F-H-Z20 | R04-A20-B40-F-H-Z30 |
| R04-A20-B40-F-H-Z40 | R04-A20-B40-F-F-Z00 | R04-A20-B40-F-F-Z10 |
| R04-A20-B40-F-F-Z20 | R04-A20-B40-F-F-Z30 | R04-A20-B40-F-F-Z40 |
| R04-A20-B50-H-H-Z00 | R04-A20-B50-H-H-Z10 | R04-A20-B50-H-H-Z20 |
| R04-A20-B50-H-H-Z30 | R04-A20-B50-H-H-Z40 | R04-A20-B50-H-F-Z00 |
| R04-A20-B50-H-F-Z10 | R04-A20-B50-H-F-Z20 | R04-A20-B50-H-F-Z30 |
| R04-A20-B50-H-F-Z40 | R04-A20-B50-F-H-Z00 | R04-A20-B50-F-H-Z10 |
| R04-A20-B50-F-H-Z20 | R04-A20-B50-F-H-Z30 | R04-A20-B50-F-H-Z40 |
| R04-A20-B50-F-F-Z00 | R04-A20-B50-F-F-Z10 | R04-A20-B50-F-F-Z20 |
| R04-A20-B50-F-F-Z30 | R04-A20-B50-F-F-Z40 | |
| R04-A30-B10-H-H-Z00 | R04-A30-B10-H-H-Z10 | R04-A30-B10-H-H-Z20 |
| R04-A30-B10-H-H-Z30 | R04-A30-B10-H-H-Z40 | R04-A30-B10-H-F-Z00 |
| R04-A30-B10-H-F-Z10 | R04-A30-B10-H-F-Z20 | R04-A30-B10-H-F-Z30 |
| R04-A30-B10-H-F-Z40 | R04-A30-B10-F-H-Z00 | R04-A30-B10-F-H-Z10 |
| R04-A30-B10-F-H-Z20 | R04-A30-B10-F-H-Z30 | R04-A30-B10-F-H-Z40 |
| R04-A30-B10-F-F-Z00 | R04-A30-B10-F-F-Z10 | R04-A30-B10-F-F-Z20 |
| R04-A30-B10-F-F-Z30 | R04-A30-B10-F-F-Z40 | R04-A30-B20-H-H-Z00 |
| R04-A30-B20-H-H-Z10 | R04-A30-B20-H-H-Z20 | R04-A30-B20-H-H-Z30 |
| R04-A30-B20-H-H-Z40 | R04-A30-B20-H-F-Z00 | R04-A30-B20-H-F-Z10 |
| R04-A30-B20-H-F-Z20 | R04-A30-B20-H-F-Z30 | R04-A30-B20-H-F-Z40 |
| R04-A30-B20-F-H-Z00 | R04-A30-B20-F-H-Z10 | R04-A30-B20-F-H-Z20 |
| R04-A30-B20-F-H-Z30 | R04-A30-B20-F-H-Z40 | R04-A30-B20-F-F-Z00 |
| R04-A30-B20-F-F-Z10 | R04-A30-B20-F-F-Z20 | R04-A30-B20-F-F-Z30 |
| R04-A30-B20-F-F-Z40 | R04-A30-B40-H-H-Z00 | R04-A30-B40-H-H-Z10 |
| R04-A30-B40-H-H-Z20 | R04-A30-B40-H-H-Z30 | R04-A30-B40-H-H-Z40 |
| R04-A30-B40-H-F-Z00 | R04-A30-B40-H-F-Z10 | R04-A30-B40-H-F-Z20 |
| R04-A30-B40-H-F-Z30 | R04-A30-B40-H-F-Z40 | R04-A30-B40-F-H-Z00 |
| R04-A30-B40-F-H-Z10 | R04-A30-B40-F-H-Z20 | R04-A30-B40-F-H-Z30 |
| R04-A30-B40-F-H-Z40 | R04-A30-B40-F-F-Z00 | R04-A30-B40-F-F-Z10 |
| R04-A30-B40-F-F-Z20 | R04-A30-B40-F-F-Z30 | R04-A30-B40-F-F-Z40 |
| R04-A30-B50-H-H-Z00 | R04-A30-B50-H-H-Z10 | R04-A30-B50-H-H-Z20 |
| R04-A30-B50-H-H-Z30 | R04-A30-B50-H-H-Z40 | R04-A30-B50-H-F-Z00 |
| R04-A30-B50-H-F-Z10 | R04-A30-B50-H-F-Z20 | R04-A30-B50-H-F-Z30 |
| R04-A30-B50-H-F-Z40 | R04-A30-B50-F-H-Z00 | R04-A30-B50-F-H-Z10 |
| R04-A30-B50-F-H-Z20 | R04-A30-B50-F-H-Z30 | R04-A30-B50-F-H-Z40 |
| R04-A30-B50-F-F-Z00 | R04-A30-B50-F-F-Z10 | R04-A30-B50-F-F-Z20 |
| R04-A30-B50-F-F-Z30 | R04-A30-B50-F-F-Z40 | |
| R04-A40-B10-H-H-Z00 | R04-A40-B10-H-H-Z10 | R04-A40-B10-H-H-Z20 |
| R04-A40-B10-H-H-Z30 | R04-A40-B10-H-H-Z40 | R04-A40-B10-H-F-Z00 |
| R04-A40-B10-H-F-Z10 | R04-A40-B10-H-F-Z20 | R04-A40-B10-H-F-Z30 |
| R04-A40-B10-H-F-Z40 | R04-A40-B10-F-H-Z00 | R04-A40-B10-F-H-Z10 |
| R04-A40-B10-F-H-Z20 | R04-A40-B10-F-H-Z30 | R04-A40-B10-F-H-Z40 |
| R04-A40-B10-F-F-Z00 | R04-A40-B10-F-F-Z10 | R04-A40-B10-F-F-Z20 |
| R04-A40-B10-F-F-Z30 | R04-A40-B10-F-F-Z40 | R04-A40-B20-H-H-Z00 |

-continued

| | | |
|---|---|---|
| R04-A40-B20-H-H-Z10 | R04-A40-B20-H-H-Z20 | R04-A40-B20-H-H-Z30 |
| R04-A40-B20-H-H-Z40 | R04-A40-B20-H-F-Z00 | R04-A40-B20-H-F-Z10 |
| R04-A40-B20-H-F-Z20 | R04-A40-B20-H-F-Z30 | R04-A40-B20-H-F-Z40 |
| R04-A40-B20-F-H-Z00 | R04-A40-B20-F-H-Z10 | R04-A40-B20-F-H-Z20 |
| R04-A40-B20-F-H-Z30 | R04-A40-B20-F-H-Z40 | R04-A40-B20-F-F-Z00 |
| R04-A40-B20-F-F-Z10 | R04-A40-B20-F-F-Z20 | R04-A40-B20-F-F-Z30 |
| R04-A40-B20-F-F-Z40 | R04-A40-B40-H-H-Z00 | R04-A40-B40-H-H-Z10 |
| R04-A40-B40-H-H-Z20 | R04-A40-B40-H-H-Z30 | R04-A40-B40-H-H-Z40 |
| R04-A40-B40-H-F-Z00 | R04-A40-B40-H-F-Z10 | R04-A40-B40-H-F-Z20 |
| R04-A40-B40-H-F-Z30 | R04-A40-B40-H-F-Z40 | R04-A40-B40-F-H-Z00 |
| R04-A40-B40-F-H-Z10 | R04-A40-B40-F-H-Z20 | R04-A40-B40-F-H-Z30 |
| R04-A40-B40-F-H-Z40 | R04-A40-B40-F-F-Z00 | R04-A40-B40-F-F-Z10 |
| R04-A40-B40-F-F-Z20 | R04-A40-B40-F-F-Z30 | R04-A40-B40-F-F-Z40 |
| R04-A40-B50-H-H-Z00 | R04-A40-B50-H-H-Z10 | R04-A40-B50-H-H-Z20 |
| R04-A40-B50-H-H-Z30 | R04-A40-B50-H-H-Z40 | R04-A40-B50-H-F-Z00 |
| R04-A40-B50-H-F-Z10 | R04-A40-B50-H-F-Z20 | R04-A40-B50-H-F-Z30 |
| R04-A40-B50-H-F-Z40 | R04-A40-B50-F-H-Z00 | R04-A40-B50-F-H-Z10 |
| R04-A40-B50-F-H-Z20 | R04-A40-B50-F-H-Z30 | R04-A40-B50-F-H-Z40 |
| R04-A40-B50-F-F-Z00 | R04-A40-B50-F-F-Z10 | R04-A40-B50-F-F-Z20 |
| R04-A40-B50-F-F-Z30 | R04-A40-B50-F-F-Z40 | |
| R10-A20-B10-H-H-Z00 | R10-A20-B10-H-H-Z10 | R10-A20-B10-H-H-Z20 |
| R10-A20-B10-H-H-Z30 | R10-A20-B10-H-H-Z40 | R10-A20-B10-H-F-Z00 |
| R10-A20-B10-H-F-Z10 | R10-A20-B10-H-F-Z20 | R10-A20-B10-H-F-Z30 |
| R10-A20-B10-H-F-Z40 | R10-A20-B10-F-H-Z00 | R10-A20-B10-F-H-Z10 |
| R10-A20-B10-F-H-Z20 | R10-A20-B10-F-H-Z30 | R10-A20-B10-F-H-Z40 |
| R10-A20-B10-F-F-Z00 | R10-A20-B10-F-F-Z10 | R10-A20-B10-F-F-Z20 |
| R10-A20-B10-F-F-Z30 | R10-A20-B10-F-F-Z40 | R10-A20-B20-H-H-Z00 |
| R10-A20-B20-H-H-Z10 | R10-A20-B20-H-H-Z20 | R10-A20-B20-H-H-Z30 |
| R10-A20-B20-H-H-Z40 | R10-A20-B20-H-F-Z00 | R10-A20-B20-H-F-Z10 |
| R10-A20-B20-H-F-Z20 | R10-A20-B20-H-F-Z30 | R10-A20-B20-H-F-Z40 |
| R10-A20-B20-F-H-Z00 | R10-A20-B20-F-H-Z10 | R10-A20-B20-F-H-Z20 |
| R10-A20-B20-F-H-Z30 | R10-A20-B20-F-H-Z40 | R10-A20-B20-F-F-Z00 |
| R10-A20-B20-F-F-Z10 | R10-A20-B20-F-F-Z20 | R10-A20-B20-F-F-Z30 |
| R10-A20-B20-F-F-Z40 | R10-A20-B40-H-H-Z00 | R10-A20-B40-H-H-Z10 |
| R10-A20-B40-H-H-Z20 | R10-A20-B40-H-H-Z30 | R10-A20-B40-H-H-Z40 |
| R10-A20-B40-H-F-Z00 | R10-A20-B40-H-F-Z10 | R10-A20-B40-H-F-Z20 |
| R10-A20-B40-H-F-Z30 | R10-A20-B40-H-F-Z40 | R10-A20-B40-F-H-Z00 |
| R10-A20-B40-F-H-Z10 | R10-A20-B40-F-H-Z20 | R10-A20-B40-F-H-Z30 |
| R10-A20-B40-F-H-Z40 | R10-A20-B40-F-F-Z00 | R10-A20-B40-F-F-Z10 |
| R10-A20-B40-F-F-Z20 | R10-A20-B40-F-F-Z30 | R10-A20-B40-F-F-Z40 |
| R10-A20-B50-H-H-Z00 | R10-A20-B50-H-H-Z10 | R10-A20-B50-H-H-Z20 |
| R10-A20-B50-H-H-Z30 | R10-A20-B50-H-H-Z40 | R10-A20-B50-H-F-Z00 |
| R10-A20-B50-H-F-Z10 | R10-A20-B50-H-F-Z20 | R10-A20-B50-H-F-Z30 |
| R10-A20-B50-H-F-Z40 | R10-A20-B50-F-H-Z00 | R10-A20-B50-F-H-Z10 |
| R10-A20-B50-F-H-Z20 | R10-A20-B50-F-H-Z30 | R10-A20-B50-F-H-Z40 |
| R10-A20-B50-F-F-Z00 | R10-A20-B50-F-F-Z10 | R10-A20-B50-F-F-Z20 |
| R10-A20-B50-F-F-Z30 | R10-A20-B50-F-F-Z40 | |
| R10-A30-B10-H-H-Z00 | R10-A30-B10-H-H-Z10 | R10-A30-B10-H-H-Z20 |
| R10-A30-B10-H-H-Z30 | R10-A30-B10-H-H-Z40 | R10-A30-B10-H-F-Z00 |
| R10-A30-B10-H-F-Z10 | R10-A30-B10-H-F-Z20 | R10-A30-B10-H-F-Z30 |
| R10-A30-B10-H-F-Z40 | R10-A30-B10-F-H-Z00 | R10-A30-B10-F-H-Z10 |
| R10-A30-B10-F-H-Z20 | R10-A30-B10-F-H-Z30 | R10-A30-B10-F-H-Z40 |
| R10-A30-B10-F-F-Z00 | R10-A30-B10-F-F-Z10 | R10-A30-B10-F-F-Z20 |
| R10-A30-B10-F-F-Z30 | R10-A30-B10-F-F-Z40 | R10-A30-B20-H-H-Z00 |
| R10-A30-B20-H-H-Z10 | R10-A30-B20-H-H-Z20 | R10-A30-B20-H-H-Z30 |
| R10-A30-B20-H-H-Z40 | R10-A30-B20-H-F-Z00 | R10-A30-B20-H-F-Z10 |
| R10-A30-B20-H-F-Z20 | R10-A30-B20-H-F-Z30 | R10-A30-B20-H-F-Z40 |
| R10-A30-B20-F-H-Z00 | R10-A30-B20-F-H-Z10 | R10-A30-B20-F-H-Z20 |
| R10-A30-B20-F-H-Z30 | R10-A30-B20-F-H-Z40 | R10-A30-B20-F-F-Z00 |
| R10-A30-B20-F-F-Z10 | R10-A30-B20-F-F-Z20 | R10-A30-B20-F-F-Z30 |
| R10-A30-B20-F-F-Z40 | R10-A30-B40-H-H-Z00 | R10-A30-B40-H-H-Z10 |
| R10-A30-B40-H-H-Z20 | R10-A30-B40-H-H-Z30 | R10-A30-B40-H-H-Z40 |
| R10-A30-B40-H-F-Z00 | R10-A30-B40-H-F-Z10 | R10-A30-B40-H-F-Z20 |
| R10-A30-B40-H-F-Z30 | R10-A30-B40-H-F-Z40 | R10-A30-B40-F-H-Z00 |
| R10-A30-B40-F-H-Z10 | R10-A30-B40-F-H-Z20 | R10-A30-B40-F-H-Z30 |
| R10-A30-B40-F-H-Z40 | R10-A30-B40-F-F-Z00 | R10-A30-B40-F-F-Z10 |
| R10-A30-B40-F-F-Z20 | R10-A30-B40-F-F-Z30 | R10-A30-B40-F-F-Z40 |
| R10-A30-B50-H-H-Z00 | R10-A30-B50-H-H-Z10 | R10-A30-B50-H-H-Z20 |
| R10-A30-B50-H-H-Z30 | R10-A30-B50-H-H-Z40 | R10-A30-B50-H-F-Z00 |
| R10-A30-B50-H-F-Z10 | R10-A30-B50-H-F-Z20 | R10-A30-B50-H-F-Z30 |
| R10-A30-B50-H-F-Z40 | R10-A30-B50-F-H-Z00 | R10-A30-B50-F-H-Z10 |
| R10-A30-B50-F-H-Z20 | R10-A30-B50-F-H-Z30 | R10-A30-B50-F-H-Z40 |
| R10-A30-B50-F-F-Z00 | R10-A30-B50-F-F-Z10 | R10-A30-B50-F-F-Z20 |
| R10-A30-B50-F-F-Z30 | R10-A30-B50-F-F-Z40 | |
| R10-A40-B10-H-H-Z00 | R10-A40-B10-H-H-Z10 | R10-A40-B10-H-H-Z20 |
| R10-A40-B10-H-H-Z30 | R10-A40-B10-H-H-Z40 | R10-A40-B10-H-F-Z00 |
| R10-A40-B10-H-F-Z10 | R10-A40-B10-H-F-Z20 | R10-A40-B10-H-F-Z30 |
| R10-A40-B10-H-F-Z40 | R10-A40-B10-F-H-Z00 | R10-A40-B10-F-H-Z10 |
| R10-A40-B10-F-H-Z20 | R10-A40-B10-F-H-Z30 | R10-A40-B10-F-H-Z40 |

-continued

| | | |
|---|---|---|
| R10-A40-B10-F-F-Z00 | R10-A40-B10-F-F-Z10 | R10-A40-B10-F-F-Z20 |
| R10-A40-B10-F-F-Z30 | R10-A40-B10-F-F-Z40 | R10-A40-B20-H-H-Z00 |
| R10-A40-B20-H-H-Z10 | R10-A40-B20-H-H-Z20 | R10-A40-B20-H-H-Z30 |
| R10-A40-B20-H-H-Z40 | R10-A40-B20-H-F-Z00 | R10-A40-B20-H-F-Z10 |
| R10-A40-B20-H-F-Z20 | R10-A40-B20-H-F-Z30 | R10-A40-B20-H-F-Z40 |
| R10-A40-B20-F-H-Z00 | R10-A40-B20-F-H-Z10 | R10-A40-B20-F-H-Z20 |
| R10-A40-B20-F-H-Z30 | R10-A40-B20-F-H-Z40 | R10-A40-B20-F-F-Z00 |
| R10-A40-B20-F-F-Z10 | R10-A40-B20-F-F-Z20 | R10-A40-B20-F-F-Z30 |
| R10-A40-B20-F-F-Z40 | R10-A40-B40-H-H-Z00 | R10-A40-B40-H-H-Z10 |
| R10-A40-B40-H-H-Z20 | R10-A40-B40-H-H-Z30 | R10-A40-B40-H-H-Z40 |
| R10-A40-B40-H-F-Z00 | R10-A40-B40-H-F-Z10 | R10-A40-B40-H-F-Z20 |
| R10-A40-B40-H-F-Z30 | R10-A40-B40-H-F-Z40 | R10-A40-B40-F-H-Z00 |
| R10-A40-B40-F-H-Z10 | R10-A40-B40-F-H-Z20 | R10-A40-B40-F-H-Z30 |
| R10-A40-B40-F-H-Z40 | R10-A40-B40-F-F-Z00 | R10-A40-B40-F-F-Z10 |
| R10-A40-B40-F-F-Z20 | R10-A40-B40-F-F-Z30 | R10-A40-B40-F-F-Z40 |
| R10-A40-B50-H-H-Z00 | R10-A40-B50-H-H-Z10 | R10-A40-B50-H-H-Z20 |
| R10-A40-B50-H-H-Z30 | R10-A40-B50-H-H-Z40 | R10-A40-B50-H-F-Z00 |
| R10-A40-B50-H-F-Z10 | R10-A40-B50-H-F-Z20 | R10-A40-B50-H-F-Z30 |
| R10-A40-B50-H-F-Z40 | R10-A40-B50-F-H-Z00 | R10-A40-B50-F-H-Z10 |
| R10-A40-B50-F-H-Z20 | R10-A40-B50-F-H-Z30 | R10-A40-B50-F-H-Z40 |
| R10-A40-B50-F-F-Z00 | R10-A40-B50-F-F-Z10 | R10-A40-B50-F-F-Z20 |
| R10-A40-B50-F-F-Z30 | R10-A40-B50-F-F-Z40 | |

Example 34

Synthesis of 7-(4-methylphenyl)-2-(n-propyl)-1,8-difluorofluorene (II-I1)

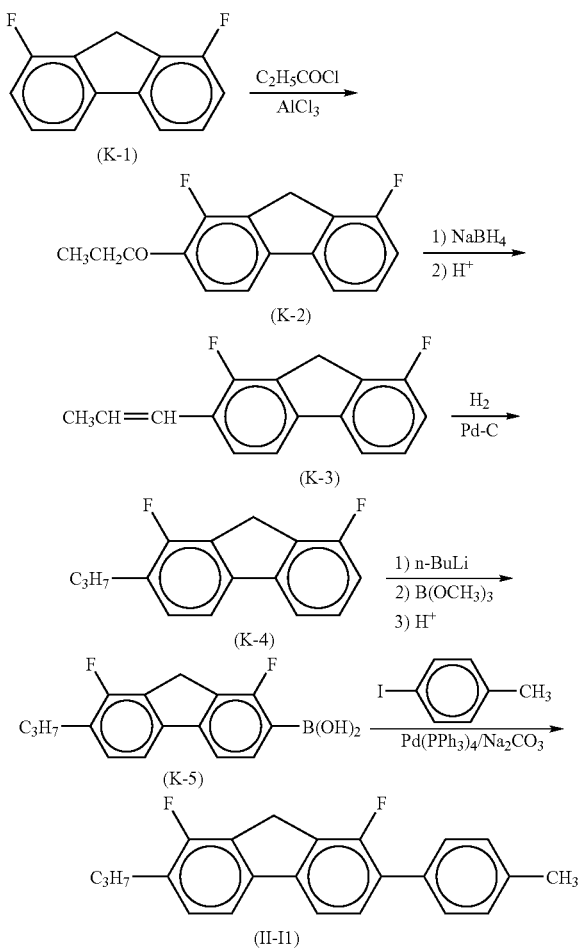

(1) Synthesis of 2-propionyl-1,8-difluorofluorene (K-2)

50.5 g of 1,8-difluorofluorene (K-1) was dissolved in 150 ml of carbon disulfide, and the temperature was lowered to −10° C. With the temperature maintained at this level, 30 g of anhydrous aluminum chloride was added, and with the temperature still held at −10° C., 25.4 g of propionyl chloride was added dropwise over a period of 30 minutes, and the mixture was then stirred at the same temperature for 2 hours. Following completion of the stirring, the reaction mixture was poured into 200 ml of cooled 1N dilute hydrochloric acid, and was then extracted with 250 ml of toluene. The thus obtained organic layer was washed twice with 100 ml portions of water. Following drying, the solvent was removed by evaporation and the product purified by silica gel chromatography (toluene) to yield 20.5 g of 2-propionyl-1,8-difluorofluorene (K-2).

(2) Synthesis of 2-(propen-1-yl)-1,8-difluorofluorene (K-3)

1.5 g of sodium borohydride was added to a mixture of 20.5 g of 2-propionyl-1,8-difluorofluorene (K-2) and 100 ml of methanol at a temperature of −10° C., and the temperature was gradually raised, and then held at 0° C. for two hours to allow the reaction to proceed. Following completion of the reaction, 30 ml of 1N dilute hydrochloric acid was added to the cooled reaction mixture, and the methanol was then removed by evaporation under reduced pressure. The residue was then extracted into 100 ml of toluene. The organic layer was washed with 100 ml of water. Following drying, 1.0 g of p-toluenesulfonic acid monohydrate was added, and the mixture was refluxed under heat for one hour. The reaction mixture was then cooled to room temperature, 7 ml of a 1N aqueous solution of sodium bicarbonate was added to neutralize the mixture, and the mixture was then washed with 100 ml of water. Following drying, the solvent was removed by evaporation to yield 19.3 g (crude product) of 2-(propen-1-yl)-1,8-difluorofluorene (K-3). This product was used without purification in the subsequent reaction.

(3) Synthesis of 2-propyl-1,8-difluorofluorene (K-4)

A mixture of 19.3 g of 2-(propen-1-yl)-1,8-difluorofluorene (K-3) (crude product), 1.5 g of 5% palladium-carbon, 80 ml of ethanol and 80 ml of toluene was hydrogenated over an 8 hour period at room temperature and under atmospheric pressure, with constant stirring. The palladium-carbon was removed by filtration, the solvent was removed from the filtrate by evaporation under reduced pressure, and the residue was then purified by silica gel column chromatography (hexane) to yield 8.5 g of 2-propyl-1,8-difluorofluorene (K-4).

(4) Synthesis of 7-(2-propyl-1,8-difluorofluorenyl) boric acid (K-5)

25 ml of a 1.60 M n-butyl lithium hexane solution was added dropwise, over a 30 minute period and at a temperature of −78° C., to a mixture of 8.5 g of 2-propyl-1,8-difluorofluorene (K-4) and 50 ml of THF, and the resulting mixture was then stirred for one hour. With the temperature maintained at this level, a solution of 5.2 g of trimethylborate in 20 ml of THF was added dropwise to the reaction mixture over a 30 minute period, and the temperature was then gradually raised to room temperature, and the mixture stirred for a further 2 hours. Following completion of the reaction, the reaction mixture was poured into 80 ml of 2N dilute hydrochloric acid, and then extracted with 300 ml of toluene. The thus obtained organic layer was washed with water, dried, and the solvent removed by evaporation under reduced pressure. The residue was then washed with hexane to yield 8.2 g of 7-(2-propyl-1,8-difluorofluorenyl)boric acid (K-5).

(5) Synthesis of 7-(4-methylphenyl)-2-(n-propyl)-1,8-difluorofluorene (II-I1)

To 200 ml of toluene was added 8.2 g of (2-propyl-1,8-difluorofluorenyl)boric acid (K-5), 7.4 g of p-iodotoluene, 31 ml of 2M aqueous sodium carbonate, 0.5 ml of ethanol and 1.0 g of tetrakis(triphenylphosphine)palladium, and the mixture was refluxed under heat for 20 hours. The reaction mixture was then washed sequentially with water and a saturated aqueous solution of sodium chloride, dried, and then purified by silica gel chromatography to yield 7.1 g of 7-(4-methylphenyl)-2-(n-propyl)-1,8-difluorofluorene (II-I1).

Example 35

Preparation 1 of a Liquid Crystal Composition

A host liquid crystal composition (H-1) of the composition shown below was prepared.

(H-1)

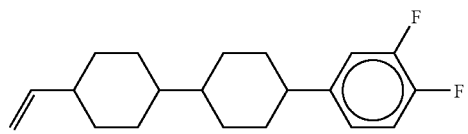
50%

-continued

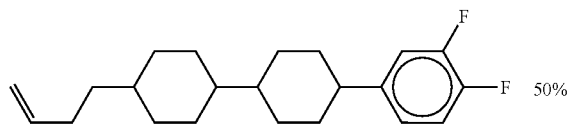
50%

The physical properties of this composition (H-1) are as shown below.

| | |
|---|---|
| Nematic phase upper limit temperature ($T_{N-I}$): | 116.7° C. |
| Solid phase or smectic phase to nematic phase transition temperature ($T \rightarrow_N$): | 11° C. |
| Threshold voltage (Vth): | 2.14 V |
| Dielectric anisotropy ($\Delta\epsilon$): | 4.8 |
| Birefringence ($\Delta n$): | 0.090 |

Measured at 20° C.

When a liquid crystal composition (M-1) was prepared from 80% of the above host liquid crystal (H-1) and 20% of the compound (Igc-1) produced in Example 1, (Igc-1)

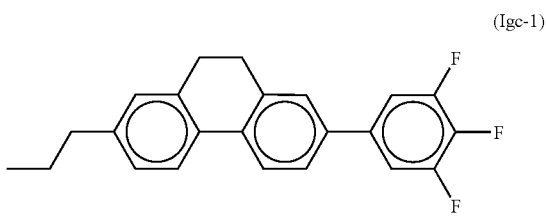

the physical properties of the composition (M-1) were as shown below.

| | |
|---|---|
| Nematic phase upper limit temperature ($T_{N-I}$): | 101.2° C. |
| Solid phase or smectic phase to nematic phase transition temperature ($T \rightarrow_N$): | 17° C. |
| Threshold voltage (Vth): | 1.91 V |
| Dielectric anisotropy ($\Delta\epsilon$): | 5.5 |
| Birefringence ($\Delta n$): | 0.116 |

From these results it is evident that the compound of the formula (Igc-1) is able to effectively reduce the threshold voltage without significantly reducing the liquid crystal phase temperature range, and furthermore Δn also increases.

Example 36

Preparation 2 of a Liquid Crystal Composition

When a liquid crystal composition (M-2) was prepared from 80% of the above host liquid crystal composition (H-1) and 20% of the compound (Ijc-1) produced in Example 1,

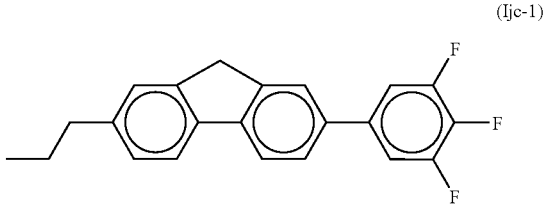

(Ijc-1)

the physical properties of the composition (M-2) were as shown below.

| | |
|---|---|
| Nematic phase upper limit temperature ($T_{N-I}$): | 103.2° C. |
| Solid phase or smectic phase to nematic phase transition temperature ($T \rightarrow_N$): | 27° C. |
| Threshold voltage (Vth): | 1.89 V |
| Dielectric anisotropy ($\Delta\epsilon$): | 5.9 |
| Birefringence ($\Delta n$): | 0.119 |

From these results it is evident that the compound of the formula (Ijc-1) is able to effectively reduce the threshold voltage even further without significantly reducing the liquid crystal phase temperature range, and furthermore Δn also increases.

Comparative Example 1

When 30% by weight of a compound (R-1) with a structure similar to the compound (Iac-1) was added to the composition (H-1),

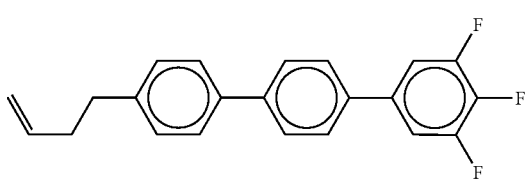

(R-1)

the physical properties of the thus obtained liquid crystal composition (MR-1) were as shown below.

| | |
|---|---|
| Nematic phase upper limit temperature ($T_{N-I}$): | 102.4° C. |
| Solid phase or smectic phase to nematic phase transition temperature ($T \rightarrow_N$): | 39° C. |
| Threshold voltage (Vth): | 2.09 V |
| Dielectric anisotropy ($\Delta\epsilon$): | 7.7 |
| Birefringence ($\Delta n$): | 0.133 |

When (R-1) was added to (H-1), because the amount of added (R-1) was large the increase in the value of Δn was large, but it is also evident that even though the amount added was large, the threshold voltage reducing effect largely disappeared.

Example 37

Preparation 3 of a Liquid Crystal Composition

A host liquid crystal composition (H-2) of the composition shown below was prepared.

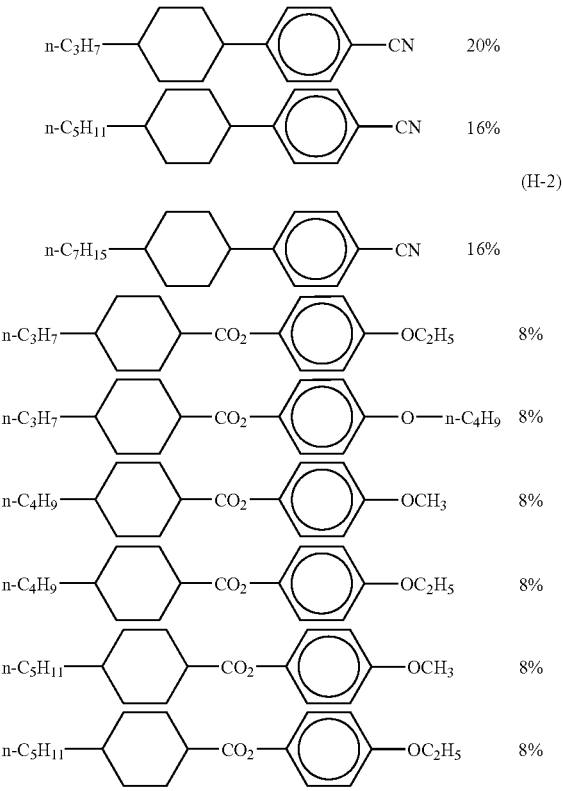

(H-2)

The physical properties of this composition (H-2) are as shown below.

| | |
|---|---|
| Nematic phase upper limit temperature ($T_{N-I}$): | 54.5° C. |
| Solid phase or smectic phase to nematic phase transition temperature ($T \rightarrow_N$): | −40° C. |
| Threshold voltage (Vth): | 1.60 V |
| Dielectric anisotropy ($\Delta\epsilon$): | 6.7 |
| Birefringence ($\Delta n$) : | 0.092 |

Measured at 20° C.

When a liquid crystal composition (M-3) was prepared from 80% of the above host liquid crystal (H-2) and 20% of the compound (Iic-1) produced in Example 7,

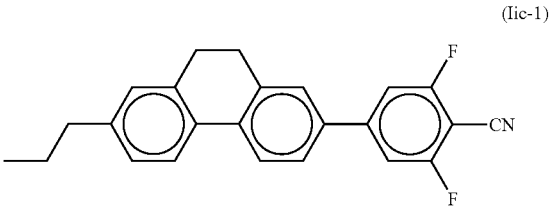

(Iic-1)

the physical properties of the composition (M-3) were as shown below.

| | |
|---|---|
| Nematic phase upper limit temperature ($T_{N-I}$): | 63.6° C. |
| Solid phase or smectic phase to nematic phase transition temperature ($T \to_N$): | −70° C. |
| Threshold voltage (Vth): | 1.23 V |
| Dielectric anisotropy ($\Delta\epsilon$): | 8.8 |
| Birefringence ($\Delta n$): | 0.129 |

From these results it is evident that the compound of the formula (Iic-1) also possesses a threshold voltage reducing effect.

Comparative Example 2

When the same amount (20% by weight) of a compound (R-2) with a structure similar to the compound (Iic-1) was added to the composition (H-2),

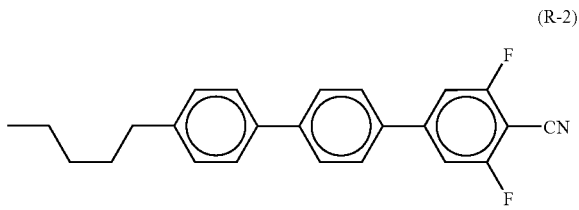
(R-2)

the physical properties of the thus obtained liquid crystal composition (MR-2) were as shown below.

| | |
|---|---|
| Nematic phase upper limit temperature ($T_{N-I}$): | 69.2° C. |
| Solid phase or smectic phase to nematic phase transition temperature ($T \to_N$): | −70° C. |
| Threshold voltage (Vth): | 1.29 V |
| Dielectric anisotropy ($\Delta\epsilon$): | 9.8 |
| Birefringence ($\Delta n$): | 0.134 |

It is evident that the threshold voltage reducing effect of (R-2) is inferior to that of (Iic-1).

Example 38

Preparation 4 of a Liquid Crystal Composition

When a liquid crystal composition (M-4) was prepared from 80% of the above host liquid crystal (H-1) and 20% of the compound (Iac-1) produced in Example 17,

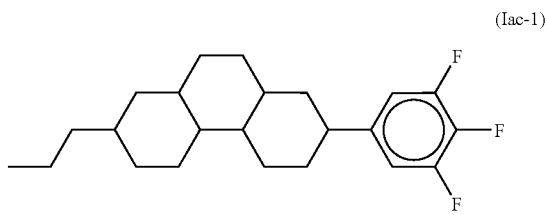
(Iac-1)

the physical properties of the composition (M-4) were as shown below.

| | |
|---|---|
| Nematic phase upper limit temperature ($T_{N-I}$): | 107.9° C. |
| Solid phase or smectic phase to nematic phase transition temperature ($T \to_N$): | −13° C. |
| Threshold voltage (Vth): | 1.92 V |
| Dielectric anisotropy ($\Delta\epsilon$): | 4.5 |
| Birefringence ($\Delta n$): | 0.085 |

From these results, it is evident that the compound of the formula (Iac-1) reduces the threshold voltage, and is also able to effectively reduce the value of $T_{\to N}$ without significantly affecting the other properties.

Comparative Example 3

When the same amount (20% by weight) of a compound (R-3) with a structure similar to the compound (Iac-1) was added to the composition (H-1),

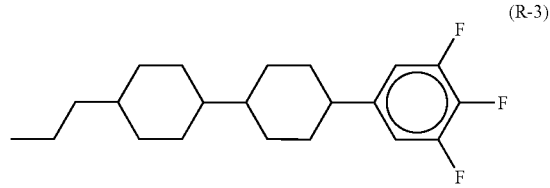
(R-3)

the physical properties of the thus obtained liquid crystal composition (MR-3) were as shown below.

| | |
|---|---|
| Nematic phase upper limit temperature ($T_{N-I}$): | 109.4° C. |
| Solid phase or smectic phase to nematic phase transition temperature ($T \to_N$): | 15° C. |
| Threshold voltage (Vth): | 1.79 V |
| Dielectric anisotropy ($\Delta\epsilon$): | 7.0 |
| Birefringence ($\Delta n$): | 0.087 |

When (R-3) was added to (H-1), the reducing effect on the threshold voltage was extremely large, but it is evident that the reducing effect on $T_{\to N}$ is inferior.

Example 39

Preparation 5 of a Liquid Crystal Composition

When a liquid crystal composition (M-5) was prepared from 80% of the above host liquid crystal (H-2) and 20% of the compound (Iah-1) produced in Example 19,

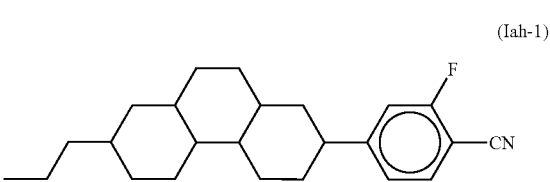
(Iah-1)

the physical properties of the composition (M-5) were as shown below.

| | |
|---|---|
| Nematic phase upper limit temperature ($T_{N-I}$): | 64.5° C. |
| Solid phase or smectic phase to nematic phase transition temperature ($T \rightarrow_N$): | −60° C. |
| Threshold voltage (Vth): | 1.49 V |
| Dielectric anisotropy ($\Delta\epsilon$): | 8.2 |

From these results it is evident that the compound of the formula (Iah-1) also possesses a $T_{\rightarrow N}$ reducing effect.

Comparative Example 4

When the same amount (20% by weight) of a compound (R-4) with a structure similar to the compound (Iac-1) was added to the composition (H-2),

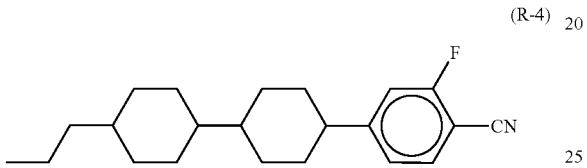

(R-4)

the physical properties of the thus obtained liquid crystal composition (MR-4) were as shown below.

| | |
|---|---|
| Nematic phase upper limit temperature ($T_{N-I}$): | 67.2° C. |
| Solid phase or smectic phase to nematic phase transition temperature ($T \rightarrow_N$): | −40° C. |
| Threshold voltage (Vth): | 1.44 V |
| Dielectric anisotropy ($\Delta\epsilon$): | 9.1 |

When (R-4) was added to (H-2), the reducing effect on the threshold voltage was extremely large, but it is evident that the reducing effect on $T_{\rightarrow N}$ is almost non-existent.

Example 40

Preparation 6 of a Liquid Crystal Composition

A host liquid crystal composition (H-3) of the composition shown below was prepared.

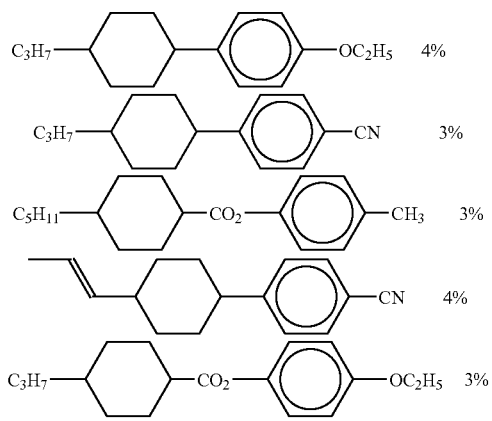

(H-3)

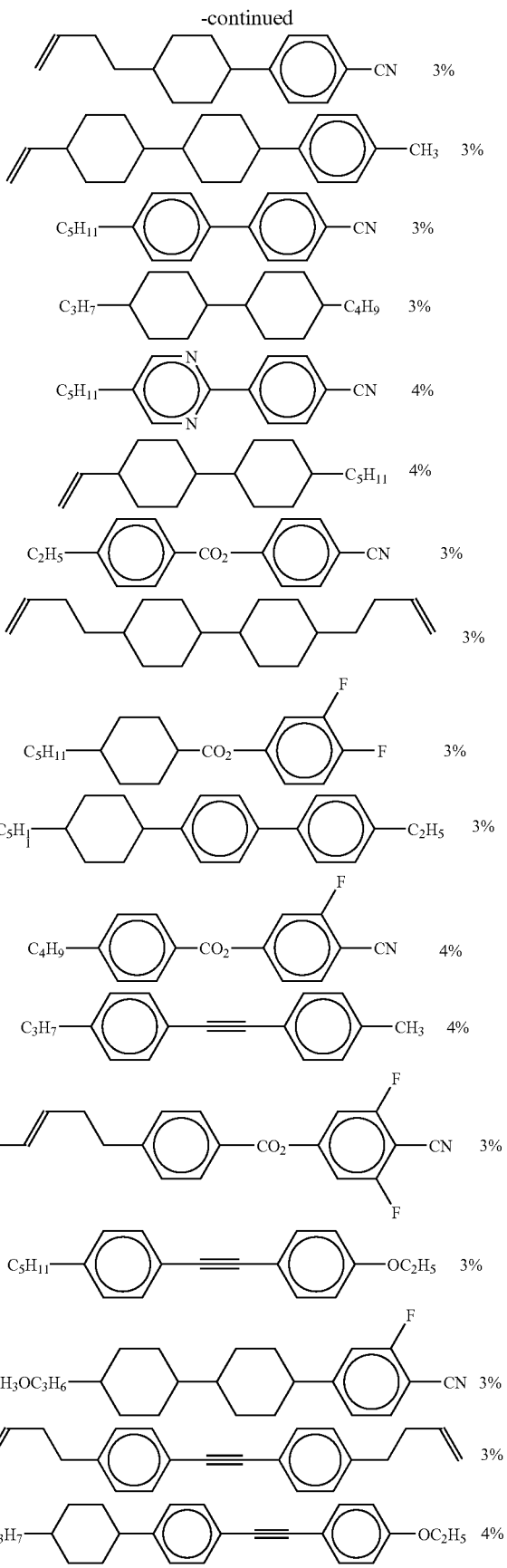

-continued

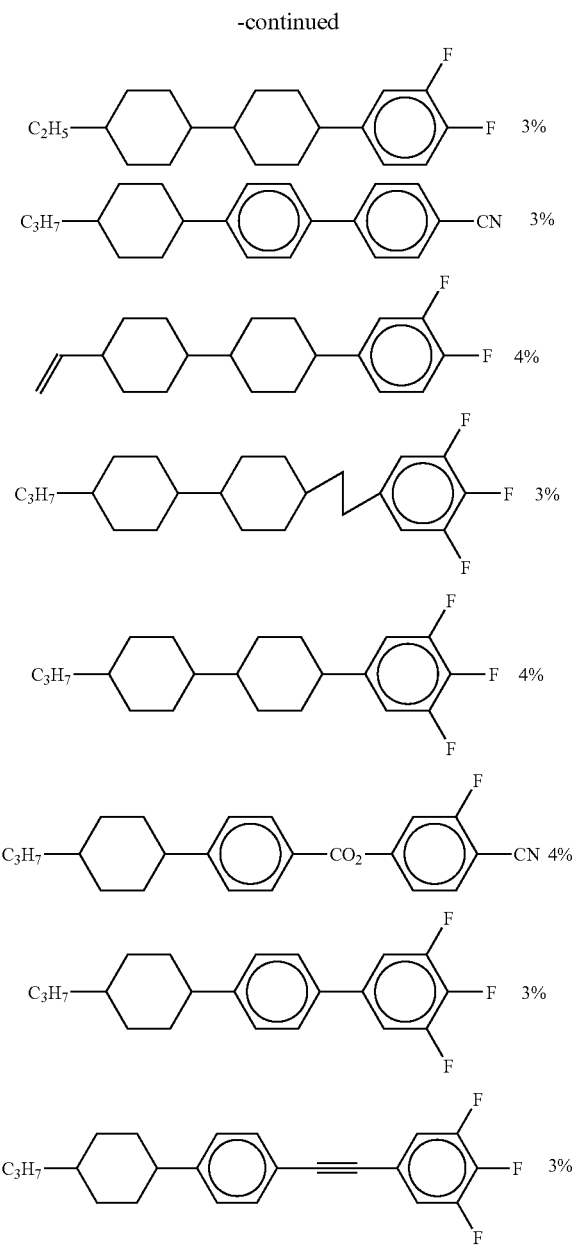

The physical properties of this composition (H-3) are as shown below.

| | |
|---|---|
| Nematic phase upper limit temperature ($T_{N-I}$): | 75.0° C. |
| Solid phase or smectic phase to nematic phase transition temperature ($T \to_N$): | −70° C. |
| Threshold voltage (Vth): | 1.49 V |
| Dielectric anisotropy ($\Delta\epsilon$): | 10.3 |
| Birefringence ($\Delta n$): | 0.142 |

A liquid crystal composition (M-6) was prepared from 90% of this host liquid crystal (H-3) and 10% of the compound (Iac-1) produced in Example 17.

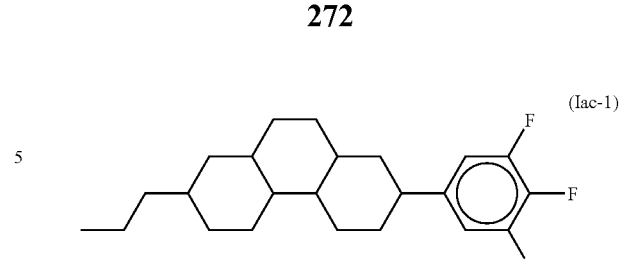

This composition also displayed favorable low temperature stability, and the compound (Iac-1) displays superior compatibility with a wide range of liquid crystal materials.

Example 41

Preparation 7 of a Liquid Crystal Composition

A liquid crystal composition (M-7) was prepared from 90% of the above host liquid crystal (H-3) and 10% of the compound (Ijc-1) produced in Example 1.

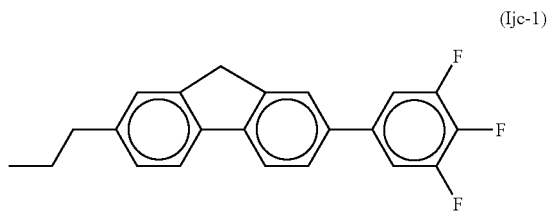

The physical properties of the composition (M-7) are shown below.

| | |
|---|---|
| Nematic phase upper limit temperature ($T_{N-I}$): | 72.6° C. |
| Solid phase or smectic phase to nematic phase transition temperature ($T \to_N$): | −70° C. |
| Threshold voltage (Vth): | 1.47 V |
| Dielectric anisotropy ($\Delta\epsilon$): | 10.4 |
| Birefringence ($\Delta n$): | 0.151 |

From the fact that there is no variation in the value of $T_{\to N}$ it is evident that the compound (Ijc-1) displays superior compatibility with a wide range of liquid crystal materials.

Example 42

Preparation 8 of a Liquid Crystal Composition

A liquid crystal composition was prepared from 90% of the above host liquid crystal (H-3) and 10% of the compound (II-A1) produced in Example 32.

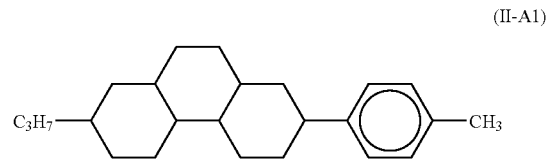

When a liquid crystal element was formed in a similar manner, and the electro-optical characteristics were measured, $T_{N-I}$ was 82.5° C. and $\Delta n$ was 0.134.

Example 43

Preparation 9 of a Liquid Crystal Composition

A liquid crystal composition was prepared from 90% of the above host liquid crystal (H-3) and 10% of the compound (I-A1) produced in Example 33.

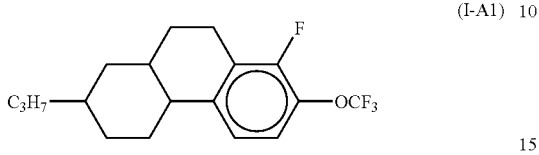
(I-A1)

When a liquid crystal element was formed in a similar manner, and the electro-optical characteristics were measured, $T_{N-I}$ was 68.5° C. and Δn was 0.137.

INDUSTRIAL APPLICABILITY

A compound represented by the general formula (I) according to the present invention, can be produced industrially extremely easily, as shown in the examples, displays superior compatibility with current general purpose host liquid crystals as a nematic phase, and also shows little crystal precipitation at low temperatures. Moreover, by addition of a small amount of a compound of the present invention to a host liquid crystal, the liquid crystal temperature range at low temperatures can be effectively widened without any significant worsening of the various characteristics of the liquid crystal material. Consequently, a compound of the present invention is an extremely useful liquid crystal material which is suitable for the various liquid crystal display elements which require a broad operating temperature range.

The invention claimed is:

1. A fused ring compound represented by a general formula (I)

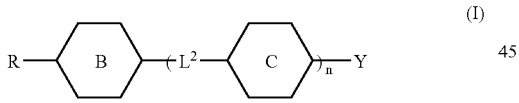
(I)

(wherein, R represents an alkyl group or alkoxyl group of 1 to 16 carbon atoms, an alkenyl group of 2 to 16 carbon atoms, an alkenyloxy group of 3 to 16 carbon atoms, or an alkyl group of 1 to 12 carbon atoms substituted with an alkoxyl group of 1 to 10 carbon atoms, and said groups may be substituted with a halogen, and in cases in which an asymmetric carbon arises due to substitution or branching, may be either one of optically active and a racemic mixture; ring C represents any one of a trans-1,4-cyclohexylene group in which one $CH_2$ structure within said group or two or more non-adjacent $CH_2$ structures within said group may be replaced with —O— and/or —S—, a 1,4-phenylene group in which one CH structure within said group or two or more non-adjacent CH structures within said group may be replaced with —N=, a 1,4-cyclohexenylene group, a 1,4-bicyclo(2.2.2)octylene group, a piperidine-1,4-diyl group, a naphthalene-2,6-diyl group, a trans-decahydronaphthalene-trans-2,6-diyl group, and a 1,2,3,4-tetrahydronaphthalene-2,6-diyl group, and said groups may be substituted with either one of a cyano group and a halogen; ring B represents any one of general formulas (I-1) to (I-10):

(I-1)

(I-2)

(I-3)

(I-4)

(I-5)

(I-6)

(I-7)

(I-8)

(I-9)

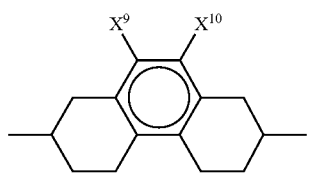

(I-10)

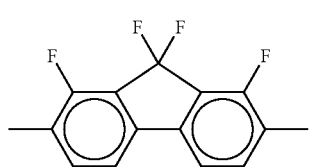

(wherein, $X^1$, $X^3$, $X^4$, $X^5$, $X^6$, $X^8$, $X^9$ and $X^{10}$ each represent, independently, any one of a hydrogen atom, a chlorine atom and a fluorine atom, provided that conditions described below are satisfied:

a. in (I-1), in a case in which at least one of $X^3$, $X^4$, $X^5$ and $X^6$ represents a fluorine atom, and a remainder represent hydrogen atoms, then at least one of $X^1$, $X^8$, $X^9$ and $X^{10}$ represents either one of a chlorine atom and a fluorine atom, b. in (I-1), in a case in which at least one of $X^1$, $X^8$, $X^9$ and $X^{10}$ represents a fluorine atom, and a remainder represent hydrogen atoms, then at least one of $X^3$, $X^4$, $X^5$ and $X^6$ represents either one of a chlorine atom and a fluorine atom, c. in (I-2), ring B represents any one of general formulas as follows:

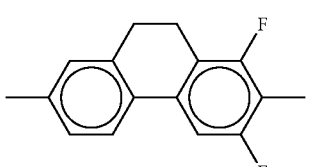

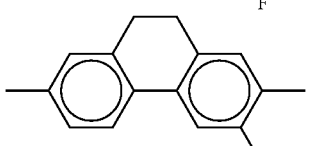

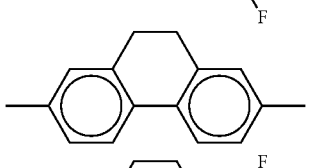

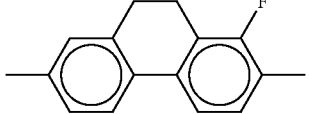

and in place of (I-3), ring B represents any one of general formulas as follows:

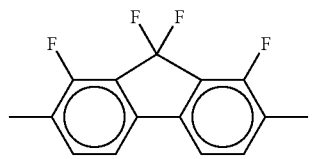

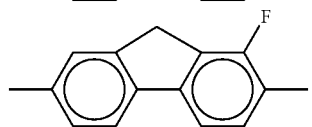

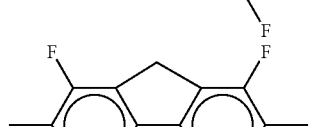

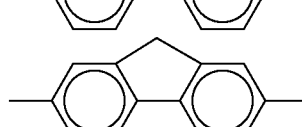

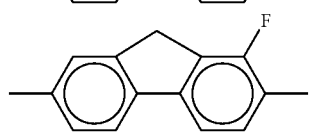

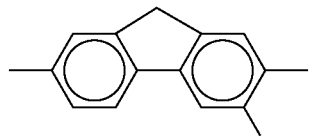

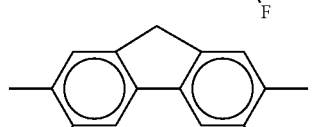

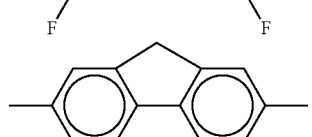

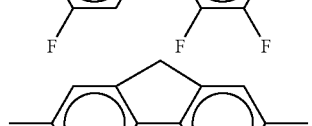

$L^2$ represents any one of —CH$_2$CH$_2$—, —C≡C—, —(CH$_2$)$_4$—, —CF=CF—, —OCH$_2$—, —CH$_2$O—, —OCF$_2$—, —CF$_2$O—, —CO$_2$—, —OCO—, —CH=N—N=CH—, —CH=CH—CH$_2$—CH$_2$—, —CH$_2$—CH$_2$—CH=CH— and a single bond; n represents 0 or 1; Y represents any one of a hydrogen atom, a fluorine atom, a chlorine atom, a trifluoromethoxy group, a difluoromethoxy group, a trifluoromethyl group, a 3,3,3-trifluoroethoxy group, a cyano group, a straight chain alkyl group of 1 to 16 carbon atoms, a straight chain alkenyl group of 2 to 16 carbon atoms, a straight chain alkyloxy group of 1 to 12 carbon atoms, and a straight chain alkenyloxy group of 2 to 16 carbon atoms, provided that cases described below are excluded:

i. a case in which ring B represents (I-2), n represents 0, R represents an alkyl group and Y represents an alkyl group,
ii. a case in which ring B represents (I-3), n represents 0, R represents an alkyl group and Y represents an alkoxy group,
iii. a case in which ring B represents (I-4), n represents 0, R represents an alkyl group and Y represents either one of an alkyl group and a cyano group,
iv. a case in which ring B represents (I-8), n represents 0, R represents an alkyl group and Y represents an alkyl group,
v. a case in which ring B represents (I-4), n represents 1, ring C represents a 1,4-phenylene group, $L^2$ represents —$CO_2$—, R represents an alkyl group and Y represents any one of an alkyl group, an alkoxy group and a cyano group,
vi. a case in which ring B represents (I-4), n represents 1, ring C represents a 1,4-phenylene group, $L^2$ represents —OCO—, R represents an alkyl group and Y represents an alkoxy group,
vii. a case in which ring B represents (I-2), n represents 1, ring C represents a 1,4-cyclohexylene group, $L^2$ represents —$CO_2$—, R represents an alkyl group and Y represents an alkyl group,
viii. a case in which ring B represents (I-1), and $X^9$ and $X^{10}$ represent fluorine atoms, and
ix. a case in which ring B represents (I-3), and $X^3$, $X^4$, $X^5$ and $X^6$ simultaneously represent fluorine atoms, and
x. a case in which ring B represents (I-1), Y does not represent a fluorine atom when n=0, $X^1$, $X^3$, $X^4$=F and R=Me).

2. A compound according to claim 1, wherein ring C represents a 1,4-phenylene group or a trans-1,4-cyclohexylene group which may be substituted with at least one fluorine atom.

3. A compound according to claim 1, wherein $L^2$ represents any one of —OCO—, —$CO_2$—, —$CH_2CH_2$— and a single bond.

4. A compound according to claim 1, wherein $L^2$ represents a single bond.

5. A compound according to claim 1, wherein ring B represents (I-3) or (I-4).

6. A compound according to claim 1, wherein ring C represents a 1,4-phenylene group or a trans-1,4-cyclohexylene group which may be substituted with at least one fluorine atom, and ring B represents any one of (I-1), (I-2), (I-3) and (I-4).

7. A compound according to claim 1, wherein ring C represents a 1,4-phenylene group or a trans-1,4-cyclohexylene group which may be substituted with at least one fluorine atom, ring B represents any one of (I-1), (I-2), (I-3) and (I-4), and $L^2$ represents a single bond.

8. A compound according to claim 1, wherein ring C represents a 1,4-phenylene group or a trans-1,4-cyclohexylene group which may be substituted with at least one fluorine atom, ring B represents any one of (I-1), (I-2), (I-3) and (I-4), n represents 1, and $L^2$ represents a single bond.

9. A compound according to claim 1, wherein R represents either one of a straight chain alkyl group of 1 to 12 carbon atoms and a straight chain alkenyl group of 2 to 12 carbon atoms, and Y represents any one of a fluorine atom, a chlorine atom, a trifluoromethoxy group, a trifluoromethyl group, a difluoromethoxy group, a 3,3,3-trifluoroethoxy group and a cyano group.

10. A liquid crystal composition incorporating at least one compound according to claims 1, 2, 3, 5, 6, 9, 10, 11 or 13.

11. A liquid crystal display element utilizing a liquid crystal composition according to claim 10.

12. An active matrix driven liquid crystal display element utilizing a liquid crystal composition according to claim 10.

13. A supertwisted nematic liquid crystal display element utilizing a liquid crystal composition according to claim 10.

14. A fused ring compound represented by a general formula (I)

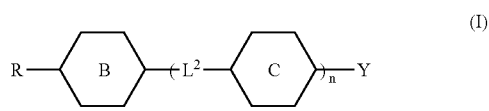

(wherein, R represents an alkyl group or an alkyl group of 1 to 12 carbon atoms substituted with an alkoxyl group of 1 to 10 carbon atoms, and said groups may be substituted with a halogen, and in cases in which an asymmetric carbon arises due to substitution or branching, may be either one of optically active and a racemic mixture; ring C represents any one of a trans-1,4-cyclohexylene group in which one $CH_2$ structure within said group or two or more non-adjacent $CH_2$ structures within said group may be replaced with —O— and/or —S—, a 1,4-phenylene group in which one CH structure within said group or two or more non-adjacent CH structures within said group may be replaced with —N=, a 1,4-cyclohexenylene group, a 1,4-bicyclo(2.2.2)octylene group, a piperidine-1,4-diyl group, a naphthalene-2,6-diyl group, a trans-decahydronaphthalene-trans-2,6-diyl group, and a 1,2,3,4-tetrahydronaphthalene-2,6-diyl group, and said groups may be substituted with either one of a cyano group and a halogen; ring B represents any one of general formulas (I-1) to (I-4)

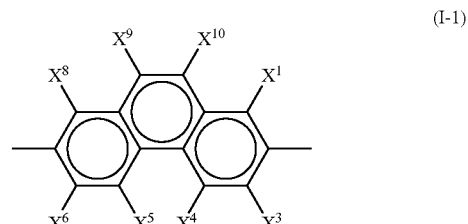

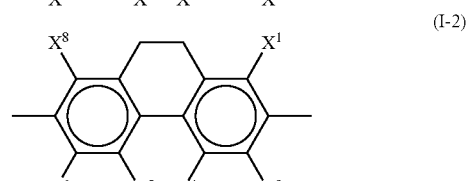

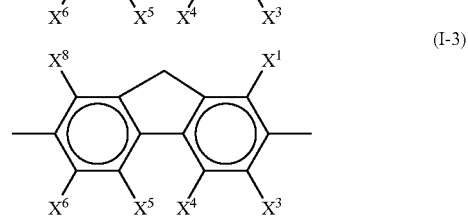

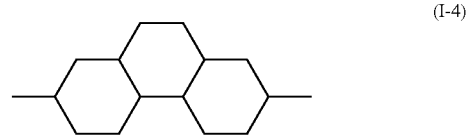

(wherein, $X^1$, $X^3$, $X^4$, $X^5$, $X^6$, $X^8$, $X^9$ and $X^{10}$ each represent, independently, any one of a hydrogen atom, a chlorine atom and a fluorine atom, provided that conditions described below are satisfied:

a. in (I-1) and (I-2), in a case in which at least one of $X^3$, $X^4$, $X^5$ and $X^6$ represents a fluorine atom, and a remainder represent hydrogen atoms, then at least one of $X^1$, $X^8$, $X^9$ and $X^{10}$ represents either one of a chlorine atom and a fluorine atom, and b. in (I-1) and (I-2), in a case in which at least one of $X^1$, $X^8$, $X^9$ and $X^{10}$ represents a fluorine atom, and a remainder represent hydrogen atoms, then at least one of $X^3$, $X^4$, $X^5$ and $X^6$ represents either one of a chlorine atom and a fluorine atom); and n represents 1, then $L^2$ when present, represents a single bond; and Y represents a fluorine atom.

15. A fused ring compound represented by a general formula (I)

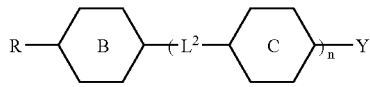
(I)

(wherein, R represents an alkyl group or alkoxyl group of 1 to 16 carbon atoms, an alkenyl group of 2 to 16 carbon atoms, an alkenyloxy group of 3 to 16 carbon atoms, or an alkyl group of 1 to 12 carbon atoms substituted with an alkoxyl group of 1 to 10 carbon atoms, and said groups may be substituted with a halogen, and in cases in which an asymmetric carbon arises due to substitution or branching, may be either one of optically active and a racemic mixture; ring C represents a trans-1,4-cyclohexylene group which may be substituted with a fluorine atom, or a 1,4-phenylene; and ring B represents any one of general formulas (I-1) to (I-4)

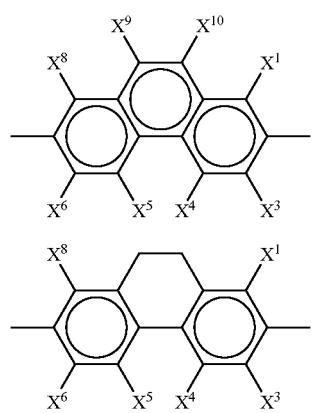
(I-1)
(I-2)

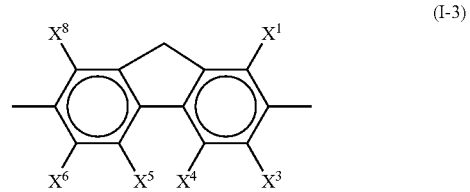
(I-3)

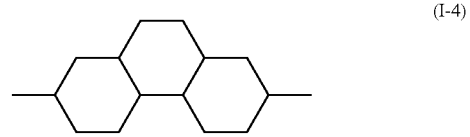
(I-4)

(wherein, $X^1$, $X^3$, $X^4$, $X^5$, $X^6$, $X^8$, $X^9$ and $X^{10}$ each represent, independently, any one of a hydrogen atom, a chlorine atom and a fluorine atom, provided that conditions described below are satisfied:

a. in (I-1) and (I-2), in a case in which at least one of $X^3$, $X^4$, $X^5$ and $X^6$ represents a fluorine atom, and a remainder represent hydrogen atoms, then at least one of $X^1$, $X^8$, $X^9$ and $X^{10}$ represents either one of a chlorine atom and a fluorine atom, and b. in (I-1) and (I-2), in a case in which at least one of $X^1$, $X^8$, $X^9$ and $X^{10}$ represents a fluorine atom, and a remainder represent hydrogen atoms, then at least one of $X^3$, $X^4$, $X^5$ and $X^6$ represents either one of a chlorine atom and a fluorine atom);

$L^2$ represents a single bond; n represents 1; and

Y represents any one of a hydrogen atom, a fluorine atom, a chlorine atom, a trifluoromethoxy group, a difluoromethoxy group, a trifluoromethyl group, a 3,3,3-trifluoroethoxy group, a cyano group, a straight chain alkyl group of 1 to 16 carbon atoms, a straight chain alkenyl group of 2 to 16 carbon atoms, a straight chain alkyloxy group of 1 to 12 carbon atoms, and a straight chain alkenyloxy group of 2 to 16 carbon atoms, provided that cases described below are excluded:

viii. a case in which ring B represents (I-1), and $X^9$ and $X^{10}$ represent fluorine atoms, and ix. a case in which ring B represents (I-3), and $X^3$, $X^4$, $X^5$ and $X^6$ simultaneously represent fluorine atoms.

* * * * *